United States Patent
Bhagwat et al.

(10) Patent No.: US 10,851,058 B2
(45) Date of Patent: Dec. 1, 2020

(54) HISTONE DEACETYLASE INHIBITORS

(71) Applicant: BIOMARIN PHARMACEUTICAL INC., Novato, CA (US)

(72) Inventors: Shripad Bhagwat, Novato, CA (US); Gregory Luedtke, Royal Oaks, CA (US); Alexander Bridges, Saline, MI (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 250 days.

(21) Appl. No.: 15/740,437

(22) PCT Filed: Jul. 1, 2016

(86) PCT No.: PCT/US2016/040705
§ 371 (c)(1),
(2) Date: Dec. 28, 2017

(87) PCT Pub. No.: WO2017/004522
PCT Pub. Date: Jan. 5, 2017

(65) Prior Publication Data
US 2019/0382342 A1    Dec. 19, 2019

Related U.S. Application Data

(60) Provisional application No. 62/188,139, filed on Jul. 2, 2015.

(51) Int. Cl.
| | |
|---|---|
| *C07D 223/08* | (2006.01) |
| *C07D 223/12* | (2006.01) |
| *C07D 451/04* | (2006.01) |
| *C07D 451/06* | (2006.01) |
| *C07D 205/04* | (2006.01) |
| *C07D 207/12* | (2006.01) |
| *C07D 207/14* | (2006.01) |
| *C07D 211/46* | (2006.01) |
| *C07D 211/58* | (2006.01) |
| *A61P 25/28* | (2006.01) |
| *C07D 211/54* | (2006.01) |
| *C07D 451/02* | (2006.01) |

(52) U.S. Cl.
CPC .......... *C07D 211/46* (2013.01); *A61P 25/28* (2018.01); *C07D 205/04* (2013.01); *C07D 207/12* (2013.01); *C07D 207/14* (2013.01); *C07D 211/54* (2013.01); *C07D 211/58* (2013.01); *C07D 223/08* (2013.01); *C07D 223/12* (2013.01); *C07D 451/02* (2013.01); *C07D 451/04* (2013.01); *C07D 451/06* (2013.01)

(58) Field of Classification Search
CPC .. C07D 223/08; C07D 223/12; C07D 451/04; C07D 451/06; C07D 205/04; C07D 207/12; C07D 207/14; C07D 211/46; C07D 211/58
See application file for complete search history.

(56) References Cited

FOREIGN PATENT DOCUMENTS

| | | |
|---|---|---|
| CN | 102477001 A | 5/2012 |
| JP | 2005508905 A | 4/2005 |
| JP | 2005533011 A | 11/2005 |
| JP | 2007530459 A | 11/2007 |
| JP | 2009536615 A | 10/2009 |
| JP | 2010539206 A | 12/2010 |
| RU | 2453536 C2 | 6/2012 |
| WO | WO-2008/109994 A1 | 9/2008 |
| WO | WO-2009/002534 A1 | 12/2008 |

OTHER PUBLICATIONS

Alberini, Transcription factors in long-term memory and synaptic plasticity, Physiol. Rev., 89(1):121-45 (2009).
Andrews et al., Anti-malarial effect of histone deacetylation inhibitors and mammalian tumour cytodifferentiating agents, Int. J. Parasitol., 30(6):761-8 (2000).
Andrews et al., Potent antimalarial activity of histone deacetylase inhibitor analogues, Antimicrob. Agents Chemother., 52(4):1454-61 (2008).
Archin et al., Administration of vorinostat disrupts HIV-1 latency in patients on antiretroviral therapy, Nature, 487(7408):482-5 (2012).
Blazkova et al., Effect of histone deacetylase inhibitors on HIV production in latently infected, resting CD4(+) T cells from infected individuals receiving effective antiretroviral therapy, J. Infect. Dis., 206(5):765-9 (2012).
Campuzano et al., Friedreich's ataxia: autosomal recessive disease caused by an intronic GAA triplet repeat expansion, Science, 271(5254):1423-7 (1996).
De Ruijter et al., Histone deacetylases (HDACs): characterization of the classical HDAC family, Biochem. J., 370(Pt. 3):737-49 (2003).
Dokmanovic et al., Histone deacetylase inhibitors: overview and perspectives, Mol. Cancer Res., 5(10):981-9 (2007).
Finnin et al., Structures of a histone deacetylase homologue bound to the TSA and SAHA inhibitors, Nature, 401(6749):188-93 (1999).
Guan et al., HDAC2 negatively regulates memory formation and synaptic plasticity, Nature, 459(7243):55-60 (2009).
Herman et al., Histone deacetylase inhibitors reverse gene silencing in Friedreich's ataxia, Nat. Chem. Biol., 2(10):551-8 (2006).
International Application No. PCT/US2016/040705, International Preliminary Report on Patentability, dated Jan. 2, 2018.
International Application No. PCT/US2016/040705, International Search Report and Written Opinion, dated Oct. 14, 2016.
Khan et al., Determination of the class and isoform selectivity of small-molecule histone deacetylase inhibitors, Biochem. J., 409(2):581-9 (2008).
McQuown et al., HDAC3 is a critical negative regulator of long-term memory formation, J. Neurosci., 31(2):764-74 (2011).
Raeppel et al., SAR and biological evaluation of analogues of a small molecule histone deacetylase inhibitor N-(2-aminophenyl)-4-((4-(pyridin-3-yl)pyrimidin-2-ylamino)methyl)benzamide (MGCD0103), Bioorg. Med. Chem. Lett., 19(3):644-9 (2009).

(Continued)

*Primary Examiner* — Bruck Kifle
(74) *Attorney, Agent, or Firm* — Marshall, Gerstein & Borun LLP

(57) ABSTRACT

Provided herein are compounds and methods for inhibiting histone deacetylase ("HDAC") enzymes (e.g., HDAC1, HDAC2, and HDAC3).

18 Claims, No Drawings

Specification includes a Sequence Listing.

(56) References Cited

OTHER PUBLICATIONS

Schroeder et al., A selective HDAC 1/2 inhibitor modulates chromatin and gene expression in brain and alters mouse behavior in two mood-related tests, PLoS One, 8(8):e71323 (2013).

Stefanko et al., Modulation of long-term memory for object recognition via HDAC inhibition, Proc. Natl. Acad. Sci. USA, 106(23):9447-52 (2009).

Thomas et al., The HDAC inhibitor 4b ameliorates the disease phenotype and transcriptional abnormalities in Huntington's disease transgenic mice, Proc. Natl. Acad. Sci. USA, 105(40):15564-9 (2008).

Wang et al., Immunomodulatory effects of deacetylase inhibitors: therapeutic targeting of FOXP3+ regulatory T cells, Nat. Rev. Drug Discov., 8(12):969-81 (2009).

Wilen et al., Tetrahedron Report No. 38: Strategies in optical resolutions, Tetrahedron, 33:2725-36 (1977).

SEQUENCE LISTING

<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1
agaggaaacg ctggactct                                      19

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
agccagattt gcttgtttgg                                     20

HISTONE DEACETYLASE INHIBITORS

TECHNICAL FIELD

Provided herein are compounds and methods of inhibiting histone deacetylase ("HDAC") enzymes (e.g., HDAC1, HDAC2, and HDAC3).

BACKGROUND

To date, 18 HDAC enzymes have been identified in humans and there is increasing evidence that the 18 HDAC enzymes in humans are not redundant in function. HDAC enzymes are classified into three main groups based on their homology to yeast proteins. Class I includes HDAC1, HDAC2, HDAC3, and HDAC8 and have homology to yeast RPD3. HDAC4, HDAC5, HDAC7, and HDAC9 belong to class IIa and have homology to yeast HDAC1. HDAC6 and HDAC10 contain two catalytic sites and are classified as class IIb, whereas HDAC11 has conserved residues in its catalytic center that are shared by both class I and class II deacetylases and is placed in class IV. These HDAC enzymes contain zinc in their catalytic site and are inhibited by compounds like trichostatin A (TSA) and vorinostat [suberoylanilide hydroxamic acid (SAHA)]. Class III HDAC enzymes are known as sirtuins. They have homology to yeast Sir2, require $NAD^+$ as cofactor, and do not contain zinc in the catalytic site. In general, HDAC inhibitors of zinc-dependent HDAC enzymes include a Zn-binding group, as well as a surface recognition domain.

HDAC enzymes are involved in the regulation of a number of cellular processes. Histone acetyltransferases (HATs) and HDAC enzymes acetylate and deacetylate lysine residues on the N termini of histone proteins thereby affecting transcriptional activity. They have also been shown to regulate post-translational acetylation of at least 50 non-histone proteins such as α-tubulin (see for example Kahn, N et al Biochem J 409 (2008) 581, Dokmanovic, M., et al Mol Cancer Res 5 (2007) 981).

Altering gene expression through chromatin modification can be accomplished by inhibiting HDAC enzymes. There is evidence that histone acetylation and deacetylation are mechanisms by which transcriptional regulation in a cell—a major event in cell differentiation, proliferation, and apoptosis—is achieved. It has been hypothesized that these effects occur through changes in the structure of chromatin by altering the affinity of histone proteins for coiled DNA in the nucleosome. Hypoacetylation of histone proteins is believed to increase the interaction of the histone with the DNA phosphate backbone. Tighter binding between the histone protein and DNA can render the DNA inaccessible to transcriptional regulatory elements and machinery. HDAC enzymes have been shown to catalyze the removal of acetyl groups from the ε-amino groups of lysine residues present within the N-terminal extension of core histones, thereby leading to hypoacetylation of the histones and blocking of the transcriptional machinery and regulatory elements.

Inhibition of HDAC, therefore can lead to histone deacetylase-mediated transcriptional derepression of tumor suppressor genes. For example, cells treated in culture with HDAC inhibitors have shown a consistent induction of the kinase inhibitor p21, which plays an important role in cell cycle arrest. HDAC inhibitors are thought to increase the rate of transcription of p21 by propagating the hyperacetylated state of histones in the region of the p21 gene, thereby making the gene accessible to transcriptional machinery. Further, non-histone proteins involved in the regulation of cell death and cell-cycle also undergo lysine acetylation and deacetylation by HDAC enzymes and histone acetyl transferase (HATs).

This evidence supports the use of HDAC inhibitors in treating various types of cancers. For example, vorinostat (suberoylanilide hydroxamic acid (SAHA)) has been approved by the FDA to treat cutaneous T-cell lymphoma and is being investigated for the treatment of solid and hematological tumors. Further, other HDAC inhibitors are in development for the treatment of acute myelogenous leukemia, Hodgkin's disease, myelodysplastic syndromes and solid tumor cancers.

HDAC inhibitors have also been shown to inhibit pro-inflammatory cytokines, such as those involved in autoimmune and inflammatory disorders (e.g. TNF-α). For example, the HDAC inhibitor MS275 was shown to slow disease progression and joint destruction in collagen-induced arthritis in rat and mouse models. Other HDAC inhibitors have been shown to have efficacy in treating or ameliorating inflammatory disorders or conditions in in vivo models or tests for disorders such as Crohn's disease, colitis, and airway inflammation and hyper-responsiveness. HDAC inhibitors have also been shown to ameliorate spinal cord inflammation, demyelination, and neuronal and axonal loss in experimental autoimmune encephalomyelitis (see for example Wanf, L., et al, Nat Rev Drug Disc 8 (2009) 969).

Triplet repeat expansion in genomic DNA is associated with many neurological conditions (e.g., neurodegenerative and neuromuscular diseases) including myotonic dystrophy, spinal muscular atrophy, fragile X syndrome, Huntington's disease, spinocerebellar ataxias, amyotrophic lateral sclerosis, Kennedy's disease, spinal and bulbar muscular atrophy, Friedreich's ataxia and Alzheimer's disease. Triplet repeat expansion may cause disease by altering gene expression. For example, in Huntington's disease, spinocerebellar ataxias, fragile X syndrome, and myotonic dystrophy, expanded repeats lead to gene silencing. In Friedreich's ataxia, the DNA abnormality found in 98% of FRDA patients is an unstable hyper-expansion of a GAA triplet repeat in the first intron of the frataxin gene (see Campuzano, et al., Science 271:1423 (1996)), which leads to frataxin insufficiency resulting in a progressive spinocerebellar neurodegeneration. Since they can affect transcription and potentially correct transcriptional dysregulation, HDAC inhibitors have been tested and have been shown to positively affect neurodegenerative diseases (see Herman, D., et al, Nat Chem Bio 2 551 (2006) for Friedreich's ataxia, Thomas, E. A., et al, Proc Natl Acad Sci USA 105 15564 (2008) for Huntington's disease).

HDAC inhibitors may also play a role in cognition-related conditions and diseases. It has indeed become increasingly evident that transcription is likely a key element for long-term memory processes (Alberini, C. M., Physiol Rev 89 121 (2009)) thus highlighting another role for CNS-penetrant HDAC inhibitors. Although studies have shown that treatment with non-specific HDAC inhibitors such as sodium butyrate can lead to long-term memory formation (Stefanko, D. P., et al, Proc Natl Acad Sci USA 106 9447 (2009)), little is known about the role of specific isoforms. A limited number of studies have shown that, within class I HDAC enzymes, main target of sodium butyrate, the prototypical inhibitor used in cognition studies, HDAC2 (Guan, J-S., et al, Nature 459 55 (2009)) and HDAC3 (McQuown, S. C., et al, J Neurosci 31 764 (2011)) have been shown to regulate memory processes and as such are interesting targets for memory enhancement or extinction in memory-affecting conditions such as, but not limited to, Alzheimer's disease, post-traumatic stress disorder or drug addiction.

HDAC inhibitors may also be useful to treat infectious disease such as viral infections. For example, treatment of HIV infected cells with HDAC inhibitors and anti-retroviral drugs can eradicate virus from treated cells (Blazkova, J., et al J Infect Dis. 2012 Sep. 1; 206(5):765-9; Archin, N. M., et al Nature 2012 Jul. 25, 487(7408):482-5).

Some prior disclosed HDAC inhibitors include a moiety of

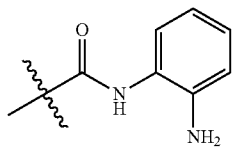

which can metabolize under physiological conditions to provide a metabolite OPD (ortho-phenylenediamine)

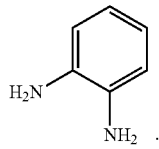

OPD is a toxic material. Thus, the need exists for HDAC inhibitors comprising a moiety of

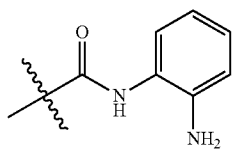

which, under physiological conditions, produce lower amounts, or substantially no amounts, of OPD.

SUMMARY

Provided herein are compounds of formula (I), or a pharmaceutically acceptable salt thereof, and methods of using compounds of formula (I), e.g., for inhibiting HDAC (e.g., one or more of HDAC1, HDAC2, and HDAC3):

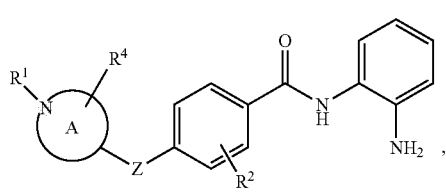

wherein ring A is a 4-7 membered heterocycloalkyl ring containing one nitrogen ring atom or a 7-9 membered bicyclic heterocycloalkyl ring containing one nitrogen ring atom; Z is O, $NR^3$, S, SO, or $SO_2$; $R^1$ is H, $C_{1-6}$alkyl, $C_{1-6}$hydroxyalkyl, $C(O)C_{1-6}$alkyl, $C_{0-3}$alkylene-$C_{3-10}$cycloalkyl, or $C_{0-3}$alkylene-$C_{2-5}$heterocycloalkyl having 1 or 2 heteroatoms selected from O, S, N, and $N(C_{1-4}$alkyl); $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl.

Further provided herein are compounds of formula (II), or a pharmaceutically acceptable salt thereof:

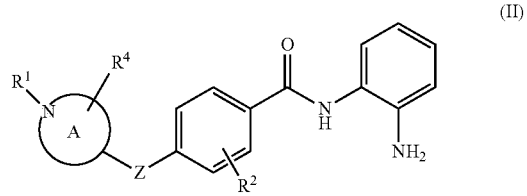

wherein ring A is selected from the group consisting of:

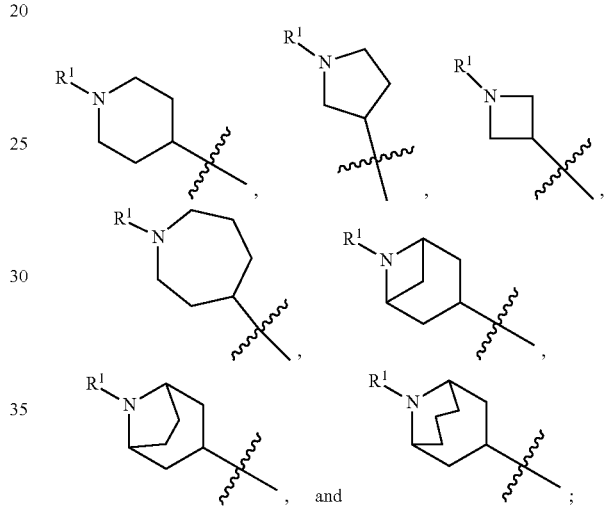

Z is O, $NR^3$, S, SO, or $SO_2$; $R^1$ is selected from the group consisting of H, $CH_3$, $C(O)CH_3$,

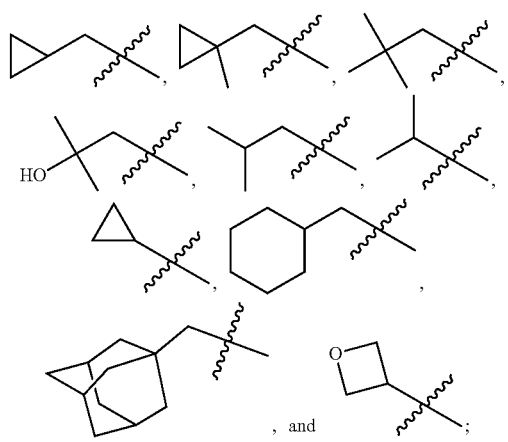

$R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl.

Also provided herein are compounds of formula (III), or a pharmaceutically acceptable salt thereof:

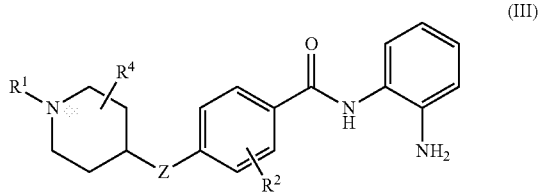

(III)

wherein Z is O, NR³, S, SO, or SO₂; R¹ is selected from the group consisting of H, CH₃, C(O)CH₃,

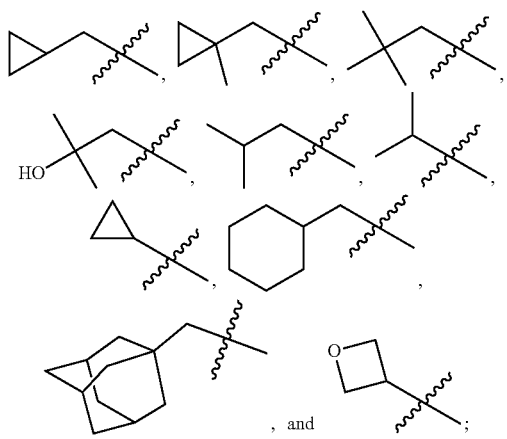

$R^2$ is H, F, Cl, or CH₃; $R^3$ is H, $C_{1-6}$alkyl, $C_{1-6}$haloalkyl, $C_{0-3}$alkylene-$C_{3-7}$cycloalkyl, C(O)$C_{1-6}$alkyl, or C(O)$C_{0-3}$alkylene-$C_{3-7}$cycloalkyl; and $R^4$ is H or $C_{1-3}$alkyl.

Also provided herein are pharmaceutical compositions comprising a compound as disclosed herein, or pharmaceutically acceptable salt thereof, and a pharmaceutically acceptable carrier.

Further provided are methods of using the compounds as disclosed herein to inhibit HDAC (e.g., one or more of HDAC1, HDAC2, and HDAC3) and methods of treating conditions associated with aberrant HDAC activity by administering a compound disclosed herein to a subject suffering from such a condition.

DETAILED DESCRIPTION

Provided herein are compounds of formula (I), pharmaceutical compositions thereof, and methods of using compounds of formula (I), e.g., for inhibiting HDAC (e.g., one or more of HDAC1, HDAC2, and HDAC3):

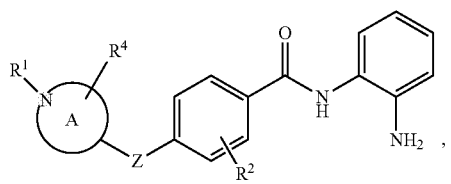

(I)

wherein ring A, Z, R¹, R², R³, and R⁴ are defined herein.

The compounds provided herein are capable of forming low amounts of OPD under physiological conditions (e.g., a pH of about 7.2 and 37° C.). Physiological conditions as disclosed herein are intended to include a temperature of about 35 to 40° C., and a pH of about 7.0 to about 7.4 and more typically include a pH of 7.2 to 7.4 and a temperature of 36 to 38° C. in an aqueous environment. By "low amounts" of OPD, as used herein, it is intended to mean that the compounds disclosed herein generate OPD under physiological conditions for 24 hours at an amount of 30% or less. In some embodiments, the amount of OPD generated at physiological conditions for 24 hours is 25% or less, or 20% or less, or 15% or less, or 10% or less, or 5% or less, or 1% or less. The amount of OPD generated can be measured indirectly by measuring the amount of resulting acid from the amide hydrolysis of the compound. In some embodiments, the measurement of OPD generated can be performed by administration of the compound as disclosed herein to a subject, collection of plasma samples over 24 hours, and determining the amount of ODP and/or the relevant acid over that 24 hours.

Definitions

The following definitions are used, unless otherwise described. Specific and general values listed below for radicals, substituents, and ranges, are for illustration only; they do not exclude other defined values or other values within defined ranges for the radicals and substituents.

As used herein, the term "alkyl," employed alone or in combination with other terms, refers to a saturated hydrocarbon group that may be straight-chain or branched. In some embodiments, the alkyl group contains 1 to 12, 1 to 8, or 1 to 6 carbon atoms.

As used herein, the term "alkylene" employed alone or in combination with other terms, refers to a divalent radical formed by removal of a hydrogen atom from alkyl.

In some embodiments, alkyl includes methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, n-heptyl, n-octyl, and the like. In some embodiments, the alkyl moiety is methyl, ethyl, n-propyl, isopropyl, n-butyl, isobutyl, tert-butyl, n-pentyl, isopentyl, neopentyl, n-hexyl, or 2,4,4-trimethylpentyl.

As used herein, the term "cycloalkyl," employed alone or in combination with other terms, refers to a saturated, cyclic hydrocarbon moiety of 3 to 10 carbon atoms. Cycloalkyl includes saturated or partially unsaturated rings, but does not contain an aromatic ring. Cycloalkyl includes fused, bridged and spiro rings. In some embodiments, the cycloalkyl group contains 3 to 7, or 3 to 6 carbon ring atoms. In some embodiments, cycloalkyl groups include cyclopropyl, cyclobutyl, cyclopentyl, cyclohexyl, and cycloheptyl. In some embodiments, cycloalkyl includes cyclopropyl, cyclopentyl, and cyclohexyl. In some embodiments, cycloalkyl includes cyclopropyl; or it includes cyclopentyl; or it includes cyclohexyl. In certain embodiments, cycloalkyl includes a bicyclic ring system of 8 to 10 carbon atoms. In certain embodiments, cycloalkyl includes a bridged ring system of 7 to 10 carbon atoms. In certain embodiments, cycloalkyl groups include pinenyl, adamantanyl, bicyclo[2.2.1]heptyl, and bicyclo[2.2.2]octyl.

As used herein, the term "haloalkyl" and the like employed alone or in combination with other terms, refers to an alkyl group having at least one halogen atom. In some embodiments, the halogen atoms are fluoro atoms. In some embodiments, the haloalkyl is CH₂CF₃.

As used herein, the term "heterocycloalkyl" employed alone or in combination with other terms, refers to a saturated ring system, which has carbon ring atoms and at least one heteroatom ring atom selected from nitrogen, sulfur, and oxygen (independently selected when more than one is present), unless specified otherwise. Heterocycloalkyl includes saturated or partially unsaturated rings, but does not contain an aromatic ring. Heterocycloalkyl includes fused, bridged and spiro rings. When the heterocycloalkyl group contains more than one heteroatom, the heteroatoms may be the same or different. Heterocycloalkyl groups can include mono- or bicyclic (e.g., having 2 fused rings) ring systems. Heterocycloalkyl groups can also include bridgehead heterocycloalkyl groups. As used herein, "bridgehead heterocycloalkyl group" refers to a heterocycloalkyl moiety containing at least one bridgehead heteroatom (e.g., nitrogen or carbon). The moiety "$C_{2-5}$heterocycloalkyl" and the like refer to heterocycloalkyl rings having at least 2 to 5 ring carbon atoms in addition to at least 1 heteroatom. For example, a $C_2$ heterocycloalkyl can be a three-membered ring with 1 heteroatom in the ring and 2 carbon ring atoms, or a four-membered ring, where there are 2 carbon ring atoms and 2 heteroatoms in the ring, or a five-membered ring, where there are 2 carbon ring atoms and 3 heteroatoms in the ring.

In certain embodiments, heterocycloalkyl includes a monocyclic ring of 3 to 6 ring atoms. In certain embodiments, heterocycloalkyl includes a bicyclic ring system of 8 to 10 ring atoms. In certain embodiments, heterocycloalkyl includes a bridged ring system of 7 to 10 ring atoms. In certain embodiments, heterocycloalkyl includes 1, 2, or 3 nitrogen ring atoms; or 1 or 2 nitrogen ring atoms; or 1 nitrogen ring atom. In certain embodiments, heterocycloalkyl includes 1 or 2 nitrogen ring atoms and 1 oxygen ring atom; or 1 nitrogen ring atom and 1 oxygen ring atom. In certain embodiments, heterocycloalkyl includes 1 or 2 oxygen ring atoms (where the 2 oxygen atoms are not adjacent to each other on the ring); or 1 oxygen ring atom; or 1 or 2 sulfur ring atoms (where the 2 sulfur atoms are not adjacent to each other on the ring); or 1 sulfur ring atom.

In certain embodiments, heterocycloalkyl includes azetidinyl, pyrrolidinyl, 2-oxopyrrolidinyl, 2,5-dihydro-1H-pyrrolinyl, 2,5-dioxo-1H-pyrrolyl, 2,5-dioxo-pyrrolidinyl, 2,5-dihydro-1H-pyrrolyl, piperidinyl, 2-oxopiperidinyl, 4-piperidonyl, morpholinyl, piperazinyl, 2-oxopiperazinyl, dioxopiperazinyl, pyranyl, tetrahydropyranyl, tetrahydrothiopyranyl, 1,3-dioxinyl, 1,3-dioxanyl, 1,4-dioxinyl, 1,4-dioxanyl, thiomorpholinyl, thiamorpholinyl, perhydroazepinyl, pyrazolidinyl, imidazolinyl, imidazolidinyl, 2,4-dioxo-imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, 2-azaspiro[3.3]heptanyl, 7-azabicyclo[2.2.1]heptanyl, and 8-azabicyclo[3.2.1]octanyl.

As used herein, the term "hydroxyalkyl" and the like employed alone or in combination with other terms, refers to an alkyl group having at least one hydroxy group.

The term "subject" refers to a mammal, such as a mouse, guinea pig, rat, dog, or human. In certain embodiments, the subject is a human; or the subject is a human adult; or the subject is a human child.

Although methods and materials similar or equivalent to those described herein can be used in practice or testing, suitable methods and materials are described below. All publications, patent applications, patents, and other references mentioned herein are incorporated by reference in their entirety. In embodiment of conflict, the present specification, including definitions, will control.

Compounds of Formula (I)

Compounds of formula (I) are provided herein:

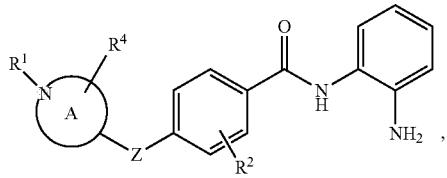

(I)

wherein ring A (i.e., the

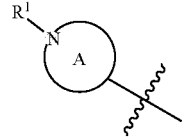

moiety) is a 4-7 membered heterocycloalkyl ring containing one nitrogen ring atom or a 7-9 membered bicyclic heterocycloalkyl ring containing one nitrogen ring atom; Z is O, $NR^3$, S, SO, or $SO_2$; $R^1$ is H, $C_{1-6}$alkyl, $C_{1-6}$hydroxyalkyl, $C(O)C_{1-6}$alkyl, $C_{0-3}$alkylene-$C_{3-10}$cycloalkyl, or $C_{0-3}$alkylene-$C_{2-5}$heterocycloalkyl having 1 or 2 heteroatoms selected from O, S, N, and $N(C_{1-4}$alkyl); $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl. In some embodiments, ring A is a 4-7 membered heterocycloalkyl ring containing one nitrogen ring atom or a 7-9 membered bicyclic heterocycloalkyl ring containing one nitrogen ring atom; Z is O or $NR^3$; $R^1$ is H, $C_{1-6}$alkyl, $C_{1-6}$hydroxyalkyl, $C(O)C_{1-6}$alkyl, $C_{0-3}$alkylene-$C_{3-10}$cycloalkyl, or $C_{0-3}$alkylene-$C_{2-5}$heterocycloalkyl having 1 or 2 heteroatoms selected from O, S, N, and $N(C_{1-6}$alkyl); $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl. In some embodiments, ring A is a 4-7 membered heterocycloalkyl ring containing one nitrogen ring atom or a 7-9 membered bicyclic heterocycloalkyl ring containing one nitrogen ring atom; Z is O, $NR^3$, S, SO, or $SO_2$; R1 is H, $C_{1-6}$alkyl, $C_{1-6}$hydroxyalkyl, $C(O)C_{1-6}$alkyl, or $C_{0-3}$alkylene-$C_{3-10}$cycloalkyl; $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl. In some embodiments, compounds of formula (I) also include those where ring A is a 4-7 membered heterocycloalkyl ring containing one nitrogen ring atom or a 7-9 membered bicyclic heterocycloalkyl ring containing one nitrogen ring atom; Z is O, $NR^3$, S, SO, or $SO_2$; $R^1$ is $C_{0-3}$alkylene-$C_{2-5}$heterocycloalkyl having 1 or 2 heteroatoms selected from O, S, N, and $N(C_{1-4}$alkyl); $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl.

In some embodiments, compounds of formula (I) are those where ring A is a 4-7 membered heterocycloalkyl ring containing one nitrogen ring atom or a 7-9 membered bicyclic heterocycloalkyl ring containing one nitrogen ring atom; Z is O, $NR^3$, S, or $SO_2$; $R^1$ is $C_{1-6}$alkyl, $C_{1-6}$hydroxyalkyl, or $C_{0-3}$alkylene-$C_{3-7}$cycloalkyl; $R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, C(O)C$_{1-6}$alkyl, or C(O)C$_{0-3}$alkylene-C$_{3-7}$cycloalkyl; and R$^4$ is H or C$_{1-3}$alkyl. In some embodiments, compounds of formula (I) also include those where ring A is a 4-7 membered heterocycloalkyl ring containing one nitrogen ring atom or a 7-9 membered bicyclic heterocycloalkyl ring containing one nitrogen ring atom; Z is O, NR$^3$, S, SO, or SO$_2$; R$^1$ is C$_{0-3}$alkylene-C$_{2-5}$heterocycloalkyl having 1 or 2 heteroatoms selected from O, S, N, and N(C$_{1-4}$alkyl); R$^2$ is H, F, Cl, or CH$_3$; R$^3$ is H, C$_{1-6}$alkyl, C$_{1-6}$haloalkyl, C$_{0-3}$alkylene-C$_{3-7}$cycloalkyl, C(O)C$_{1-6}$alkyl, or C(O)C$_{0-3}$alkylene-C$_{3-7}$cycloalkyl; and R$^4$ is H or C$_{1-3}$alkyl. In some embodiments, ring A is

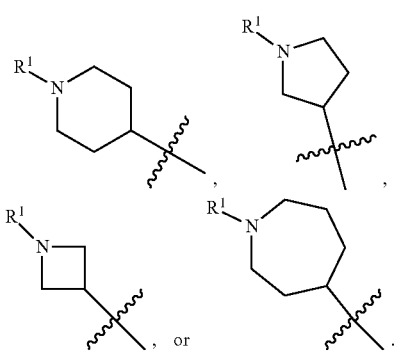

In other embodiments, ring A is

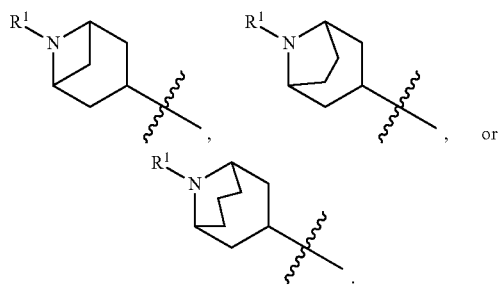

In other embodiments, ring A is

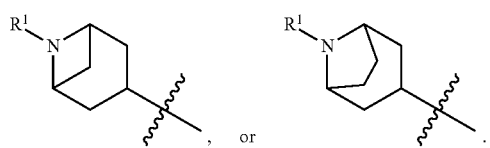

In other embodiments, ring A is

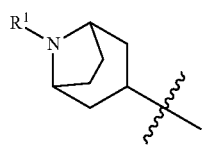

In various embodiments, Z is O or NR$^3$. In some embodiments, Z is O. In some embodiments, Z is S, SO, or SO$_2$. In some embodiments, Z is S. In some embodiments, Z is SO. In some embodiments, Z is SO$_2$. In some embodiments, Z is NR$^3$. In some embodiments, R$^3$ can be H, C$_{1-6}$alkyl, or C$_{0-3}$alkylene-C$_{3-6}$cycloalkyl. In some embodiments, R$^3$ can be H, C$_{1-6}$alkyl, or C$_{3-6}$cycloalkyl. In some embodiments, R$^3$ can be H, C$_{1-6}$alkyl, or C$_{1-3}$alkylene-C$_{3-6}$cycloalkyl. In some embodiments, R$^3$ can be H. In some embodiments, R$^3$ can be C$_{1-6}$alkyl; or R$^3$ can be methyl, ethyl, or propyl; or R$^3$ can be methyl or ethyl; or R$^3$ can be methyl. In some embodiments, R$^3$ can be H, methyl, ethyl, or CH$_2$cyclopropyl. In some embodiments, R$^3$ can be H, methyl, or CH$_2$cyclopropyl. In some embodiments, R$^3$ is C$_{1-6}$haloalkyl. In some embodiments, R$^3$ is C$_{0-3}$alkylene-C$_{3-7}$cycloalkyl, for example C$_0$alkylene-C$_{3-7}$cycloalkyl (i.e., C$_{3-7}$cycloalkyl) or C$_{1-3}$alkylene-C$_{3-7}$cycloalkyl. In various embodiments, the cycloalkyl group is cyclopropyl, cyclobutyl, or cyclohexyl. In some embodiments, R$^3$ is cyclopropyl; or R$^3$ is CH$_2$cyclopropyl. In some embodiments, R$^3$ is C(O)C$_{1-6}$alkyl. In some embodiments, R$^3$ is C(O)C$_{0-3}$alkylene-C$_{3-7}$cycloalkyl, for example C(O)C$_0$alkylene-C$_{3-7}$cycloalkyl (i.e., C(O)C$_{3-7}$cycloalkyl) or C(O)C$_{1-3}$alkylene-C$_{3-7}$cycloalkyl.

In various embodiments, R$^1$ is H. In some embodiments, R$^1$ is a C$_{1-6}$alkyl, or more specifically can be methyl, isopropyl, sec-butyl, or CH$_2$C(CH$_3$)$_3$; or R$^1$ is isopropyl, sec-butyl, or CH$_2$C(CH$_3$)$_3$. In some embodiments, R$^1$ is C$_{1-6}$hydroxyalkyl. In some embodiments, R$^1$ is

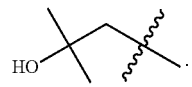

In some embodiments, R$^1$ is C$_{0-3}$alkylene-C$_{3-7}$cycloalkyl, or more specifically, R$^1$ is C$_0$alkylene-C$_{3-7}$cycloalky (i.e., C$_{3-7}$cycloalky) or is CH$_2$—C$_{3-7}$cycloalkyl. In some embodiments, R$^1$ is cyclopropyl, cyclobutyl, or cyclohexyl. In some embodiments, R$^1$ is cyclopropyl. In some embodiments, R$^1$ is CH$_2$cyclopropyl, CH$_2$cyclobutyl, or CH$_2$cyclohexyl. In some embodiments, R$^1$ is CH$_2$cyclopropyl. In some embodiments, R$^1$ is C$_{0-3}$alkylene-C$_{10}$cycloalkyl, or more specifically, R$^1$ is C$_0$alkylene-C$_{10}$cycloalky (i.e., C$_{10}$cycloalkyl) or is CH$_2$—C$_{10}$cycloalkyl. In some embodiments, R$^1$ is C$_{0-3}$alkylene-adamantanyl, or more specifically, R$^1$ is C$_0$alkylene-adamantanyl (i.e., adamantanyl) or is CH$_2$-adamantanyl. In some embodiments, R$^1$ is C$_{0-3}$alkylene-C$_{2-5}$heterocycloalkyl having 1 or 2 heteroatoms selected from O, S, N, and N(C$_{1-4}$alkyl), or more specifically, R$^1$ is C$_0$alkylene-C$_{2-5}$heterocycloalkyl having 1 or 2 heteroatoms selected from O, S, N, and N(C$_{1-4}$alkyl) (i.e. (C$_{2-5}$heterocycloalkyl)), or is CH$_2$—C$_{2-5}$heterocycloalkyl. In some embodiments, the C$_{2-5}$heterocycloalkyl is azetidinyl, pyrrolidinyl, piperidinyl, piperazinyl, oxetanyl, tetrahydrofuranyl, tetrahydropyranyl, or morpholinyl. In some embodiments, the C$_{2-5}$heterocycloalkyl is azetidinyl, pyrrolidinyl, piperidinyl, or piperazinyl. In some embodiments, the C$_{2-5}$heterocycloalkyl is oxetanyl, tetrahydrofuranyl, or tetrahydropyranyl. In some embodiments, the C$_{2-5}$heterocycloalkyl is oxetanyl.

In various embodiments, R$^4$ is H. In some embodiments, R$^4$ is C$_{1-3}$alkyl. In some embodiments, R$^4$ is methyl.

In various embodiments, R$^2$ is H. In some embodiments, R$^2$ is F. In some embodiments, R$^2$ is Cl. In some embodiments, R$^2$ is CH$_3$.

In various embodiments, ring A is selected from the group consisting of

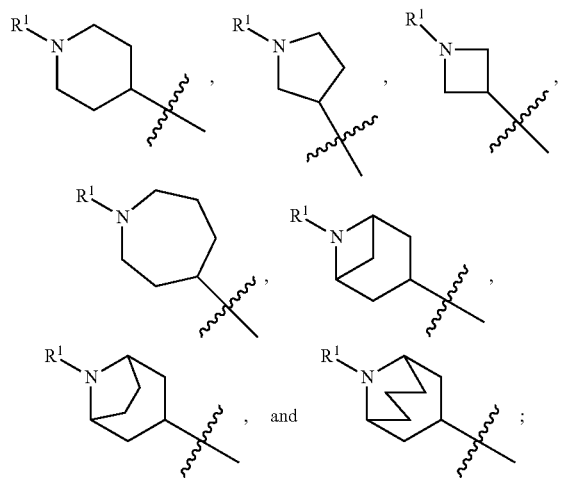

and $R^1$ is selected from the group consisting of

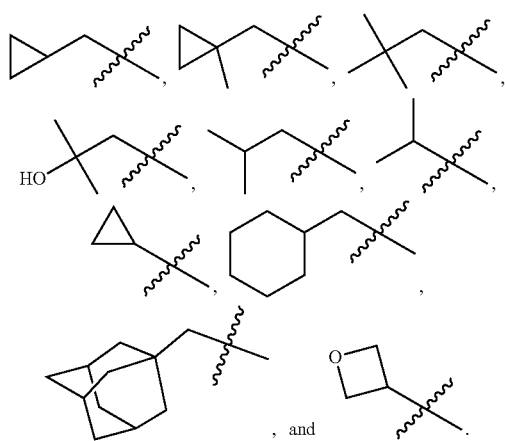

In various embodiments, ring A is selected from the group consisting of

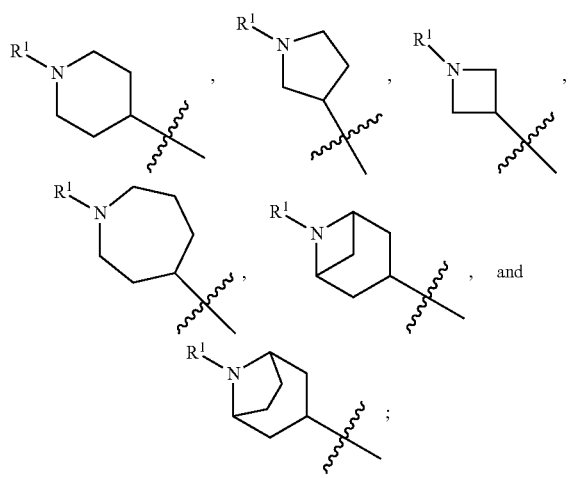

$Z$ is O or $NR^3$; and $R^1$ is selected from the group consisting of

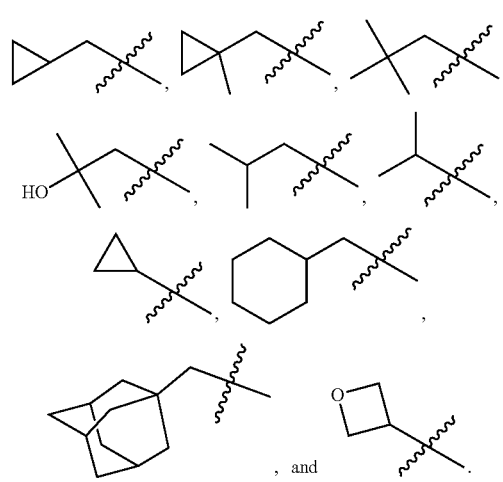

In various embodiments, ring A is selected from the group consisting of

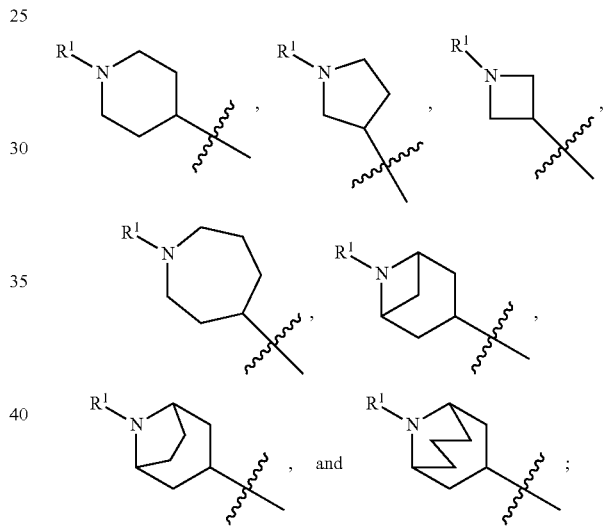

$Z$ is O, $NR^3$, S, or $SO_2$; and $R^1$ is selected from the group consisting of

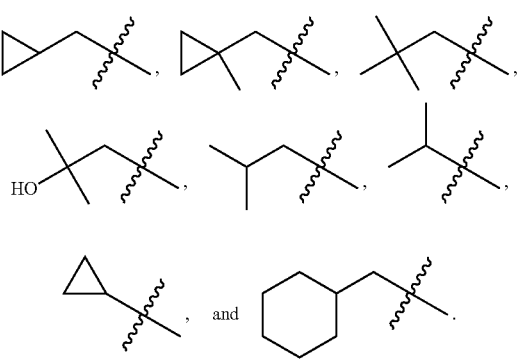

In various embodiments, ring A is selected from the group consisting of

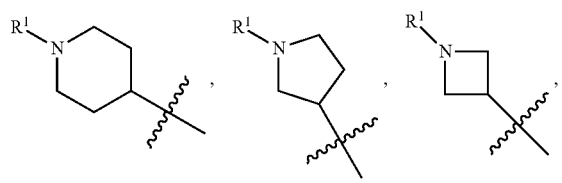

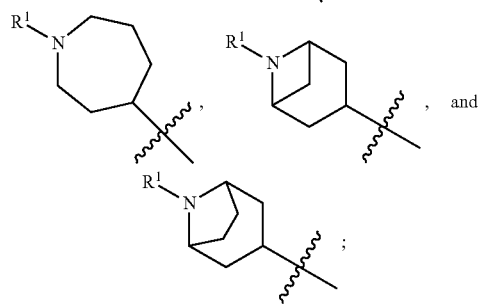

Z is O or NR³; and R¹ is selected from the group consisting of

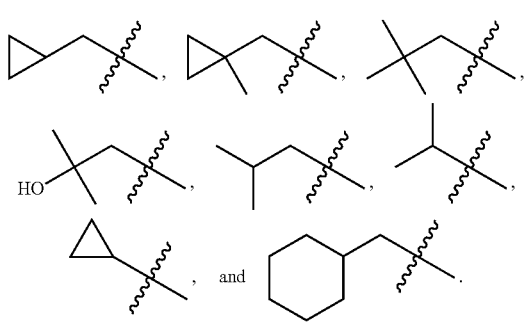

In some embodiments, the compound of formula (I) is a compound of formula (II):

(II)

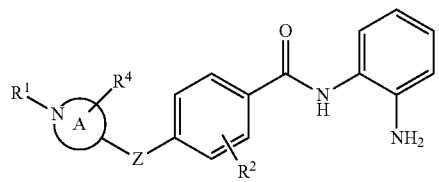

wherein ring A is selected from the group consisting of

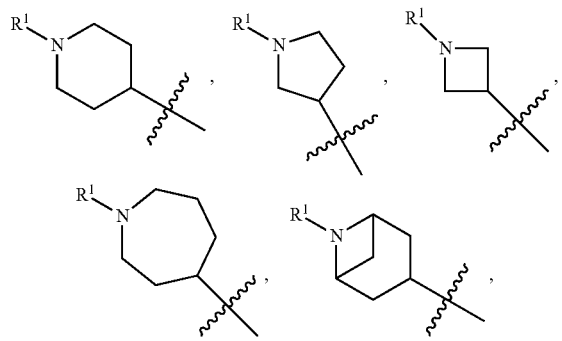

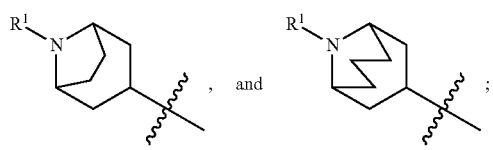

Z is O, NR³, S, or SO₂; R¹ is selected from the group consisting of

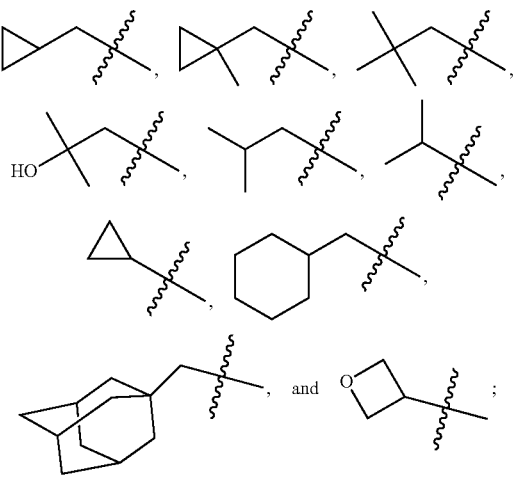

R² is H, F, Cl, or CH₃; R³ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and R⁴ is H or $C_{1-3}$alkyl. In other embodiments, R³ is H, $C_{1-6}$alkyl, or $C_{0-3}$alkylene-$C_{3-6}$cycloalkyl; and R⁴ is H. In other embodiments, R³ is H, methyl, ethyl, or CH₂($C_{3-6}$cycloalkyl); and R⁴ is H. In other embodiments, R³ is H, methyl, ethyl, or CH₂(cyclopropyl); and R⁴ is H.

In some embodiments, the compound of formula (II) is that where ring A is selected from the group consisting of

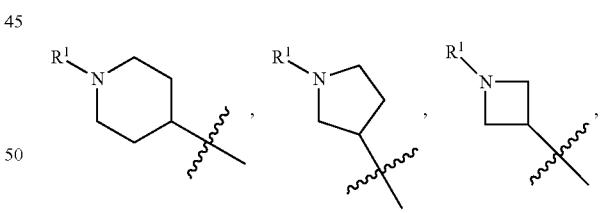

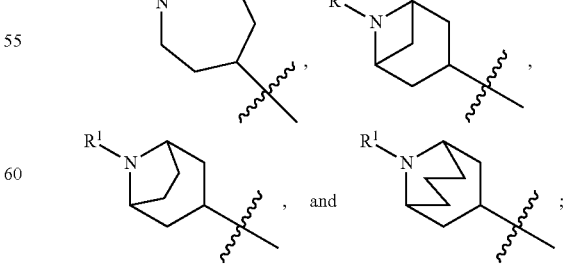

Z is O, NR³, S, or SO₂; R¹ is selected from the group consisting of

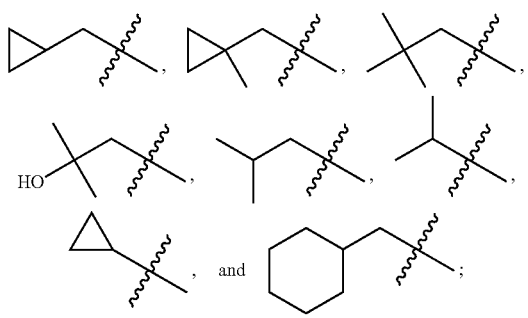

$R^2$ is H, F, Cl, or $CH_3$; $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl; and $R^4$ is H or $C_{1-3}$alkyl. In other embodiments, $R^3$ is H, $C_{1-6}$alkyl, or $C_{0-3}$alkylene-$C_{3-6}$cycloalkyl; and $R^4$ is H. In other embodiments, $R^3$ is H, methyl, ethyl, or $CH_2(C_{3-6}$cycloalkyl); and $R^4$ is H. In other embodiments, $R^3$ is H, methyl, ethyl, or $CH_2$(cyclopropyl); and $R^4$ is H.

In some embodiments, for compounds of formula (II), ring A is 4-7 membered heterocycloalkyl ring consisting of

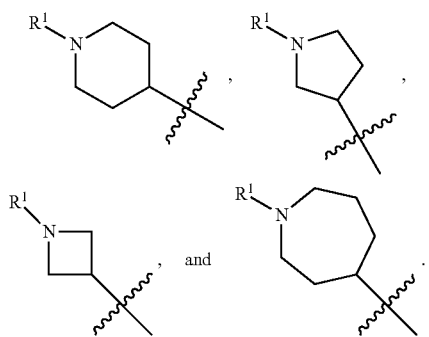

In other embodiments, ring A 7-9 membered bicyclic heterocycloalkyl ring consisting of

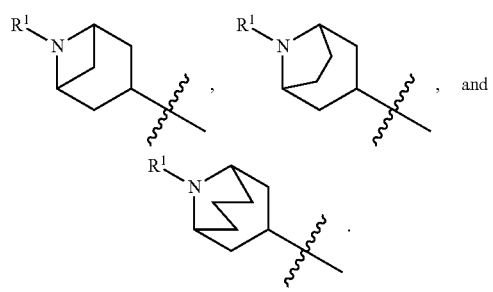

In some embodiments, the compound of formula (I) is a compound of formula (IIa):

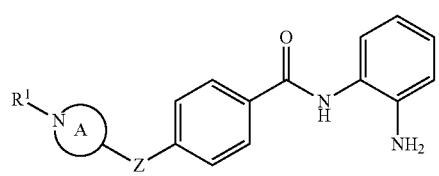

(IIa)

wherein ring A is selected from the group consisting of

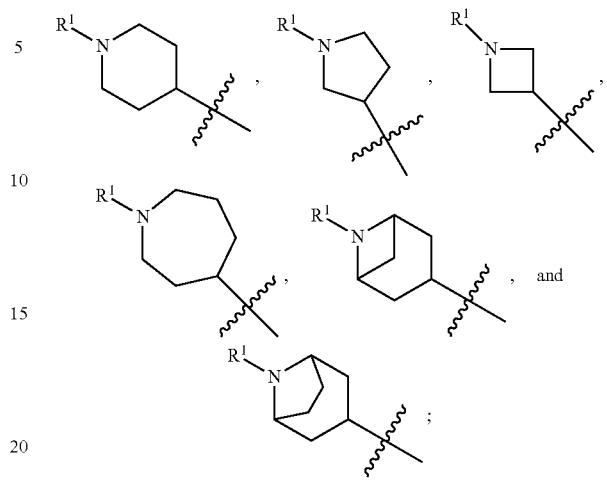

Z is O, $NR^3$, S, SO, or $SO_2$; $R^1$ is selected from the group consisting of H, $CH_3$, $C(O)CH_3$,

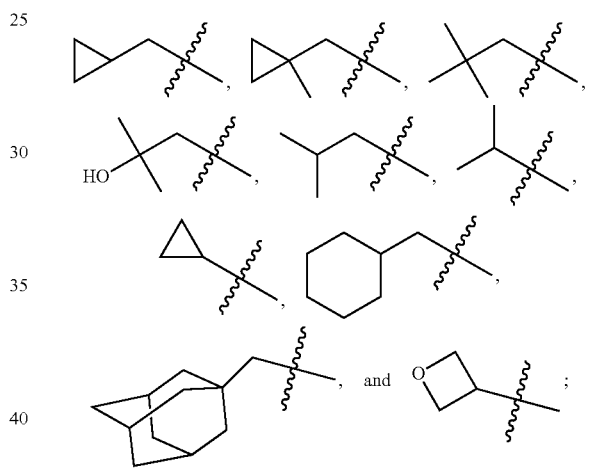

and $R^3$ is H, $C_{1-6}$alkyl, $C_{1-6}$haloalkyl, $C_{0-3}$alkylene-$C_{3-7}$cycloalkyl, $C(O)C_{1-6}$alkyl, or $C(O)C_{0-3}$alkylene-$C_{3-7}$cycloalkyl. In other embodiments, $R^3$ is H, $C_{1-6}$alkyl, or $C_{0-3}$alkylene-$C_{3-6}$cycloalkyl. In other embodiments, $R^3$ is H, methyl, ethyl, or $CH_2(C_{3-6}$cycloalkyl). In other embodiments, $R^3$ is H, methyl, ethyl, or $CH_2$(cyclopropyl).

In some embodiments, the compound of formula (IIa) is that wherein ring A is selected from the group consisting of

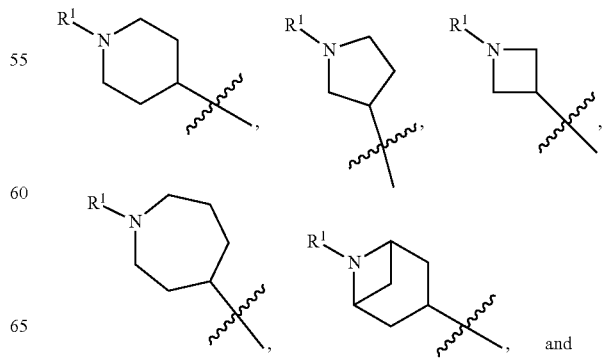

-continued

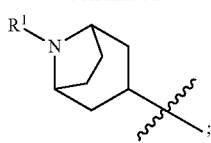

Z is O or NR³; R¹ is selected from the group consisting of H, CH₃, CH₃C(O),

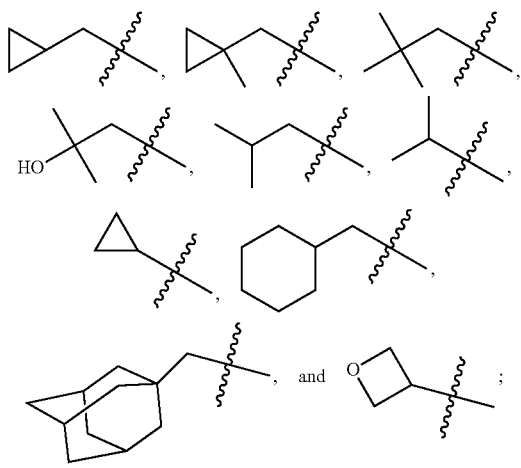

and R³ is H, $C_{1-6}$alkyl, $C_{1-6}$haloalkyl, $C_{0-3}$alkylene-$C_{3-7}$cycloalkyl, C(O)$C_{1-6}$alkyl, or C(O)$C_{0-3}$alkylene-$C_{3-7}$cycloalkyl. In other embodiments, R³ is H, $C_{1-6}$alkyl, or $C_{0-3}$alkylene-$C_{3-6}$cycloalkyl. In other embodiments, R³ is H, methyl, ethyl, or CH₂($C_{3-6}$cycloalkyl). In other embodiments, R³ is H, methyl, ethyl, or CH₂(cyclopropyl).

In various embodiments, the compound of formula (I) is a compound of formula (III):

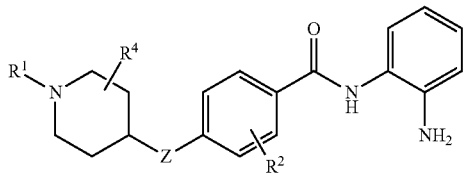

(III)

wherein Z is O, NR³, S, or SO₂; R¹ is selected from the group consisting of

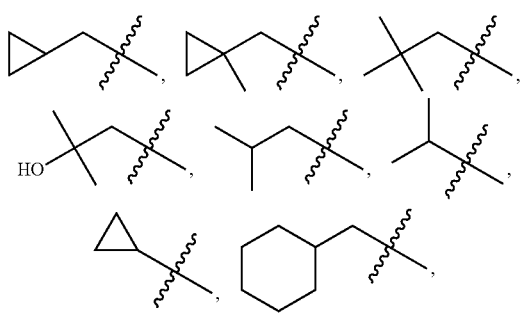

-continued

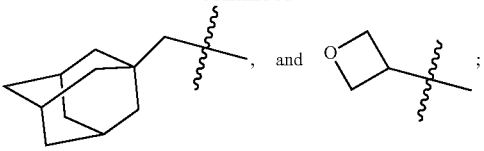

R² is H, F, Cl, or CH₃; R³ is H, $C_{1-6}$alkyl, $C_{1-6}$haloalkyl, $C_{0-3}$alkylene-$C_{3-7}$cycloalkyl, C(O)$C_{1-6}$alkyl, or C(O)$C_{0-3}$alkylene-$C_{3-7}$cycloalkyl; and R⁴ is H or $C_{1-3}$alkyl. In other embodiments, R³ is H, $C_{1-6}$alkyl, or $C_{0-3}$alkylene-$C_{3-6}$cycloalkyl; and R⁴ is H. In other embodiments, R³ is H, methyl, ethyl, or CH₂($C_{3-6}$cycloalkyl); and R⁴ is H. In other embodiments, R³ is H, methyl, ethyl, or CH₂(cyclopropyl); and R⁴ is H.

In various embodiments, the compound of formula (III) is where Z is O, NR³, S, or SO₂; R¹ is selected from the group consisting of

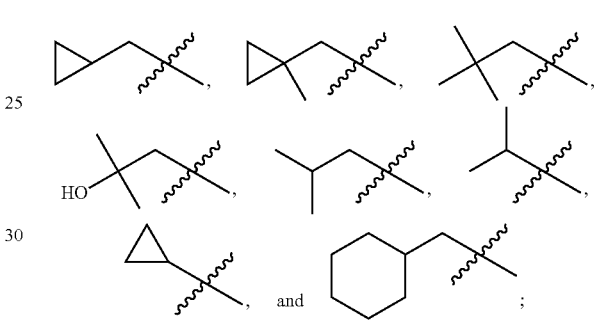

R² is H, F, Cl, or CH₃; R³ is H, $C_{1-6}$alkyl, $C_{1-6}$haloalkyl, $C_{0-3}$alkylene-$C_{3-7}$cycloalkyl, C(O)$C_{1-6}$alkyl, or C(O)$C_{0-3}$alkylene-$C_{3-7}$cycloalkyl; and R⁴ is H or $C_{1-3}$alkyl.

In various embodiments, the compound of formula (I) is a compound of formula (IIIa):

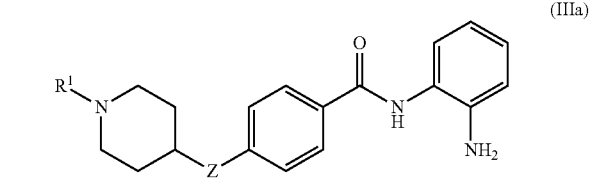

(IIIa)

wherein Z is O or NR³; R¹ is selected from the group consisting of H, CH₃, C(O)CH₃,

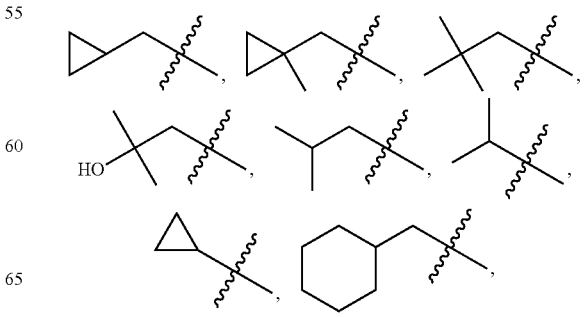

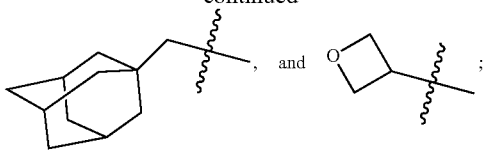

and $R^3$ is H, $C_{1-6}$alkyl, $C_{1-6}$haloalkyl, $C_{0-3}$alkylene-$C_{3-7}$cycloalkyl, C(O)$C_{1-6}$alkyl, or C(O)$C_{0-3}$alkylene-$C_{3-7}$cycloalkyl. In other embodiments, $R^3$ is H, $C_{1-6}$alkyl, or $C_{0-3}$alkylene-$C_{3-6}$cycloalkyl. In other embodiments, $R^3$ is H, methyl, ethyl, or $CH_2$($C_{3-6}$cycloalkyl). In other embodiments, $R^3$ is H, methyl, ethyl, or $CH_2$(cyclopropyl).

Compounds of formula (I) described herein may contain one or more asymmetric centers and thus occur as racemates and racemic mixtures, single enantiomers, individual diastereomers and diastereomeric mixtures. While shown without respect to the stereochemistry in formula (I), the present disclosure includes such optical isomers (enantiomers) and diastereomers; as well as the racemic and resolved, enantiomerically pure R and S stereoisomers; as well as other mixtures of the R and S stereoisomers and pharmaceutically acceptable salts thereof. The use of these compounds is intended to cover the racemic mixture or either of the chiral enantiomers.

One skilled in the art will also recognize that it is possible for tautomers to exist for the compounds described herein. The disclosure includes all such tautomers even though not shown in the formulas herein. All such isomeric forms of such compounds are expressly included in the present disclosure.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this disclosure encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds described herein also include the various hydrate and solvate forms of the compounds.

Compounds described herein can also include all isotopes of atoms occurring in the intermediates or final compounds. Isotopes include those atoms having the same atomic number but different mass numbers. For example, isotopes of hydrogen include tritium and deuterium, preferably deuterium.

Specific compounds contemplated include:

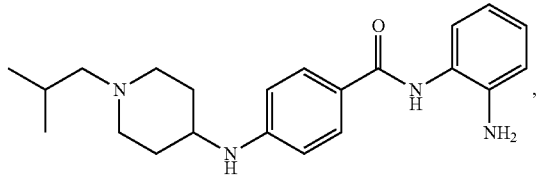

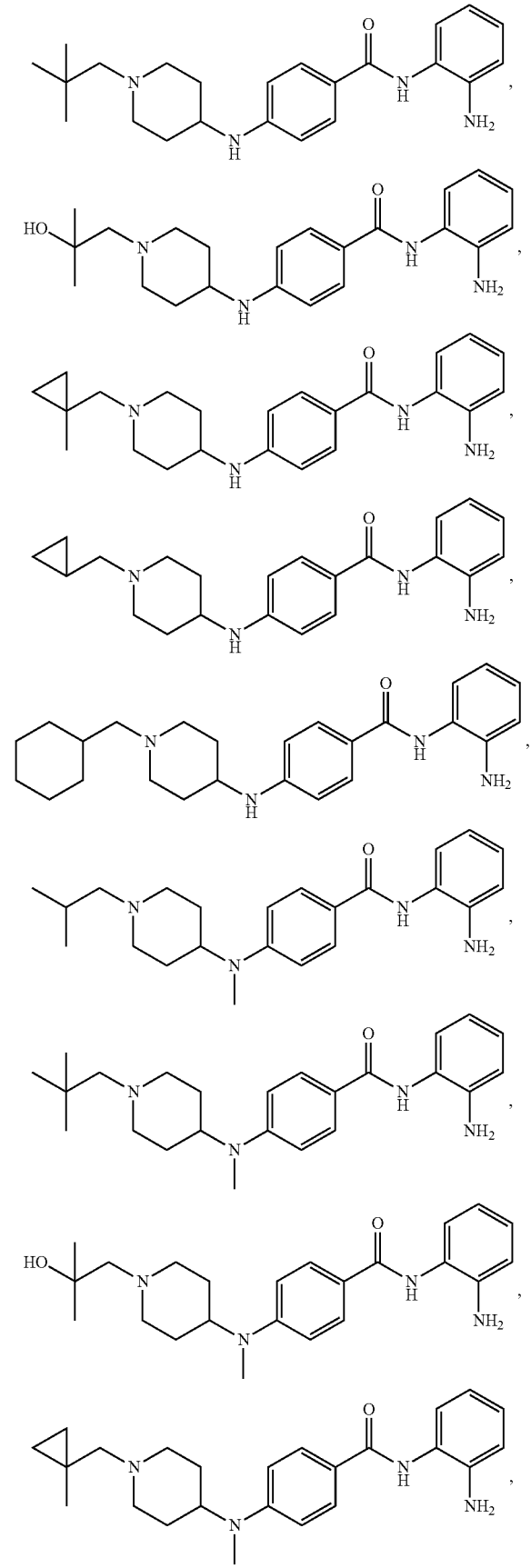

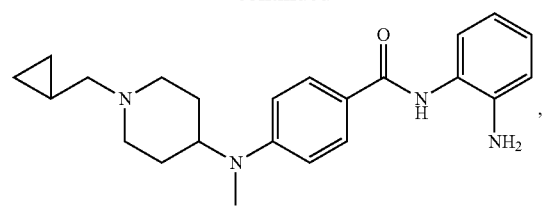
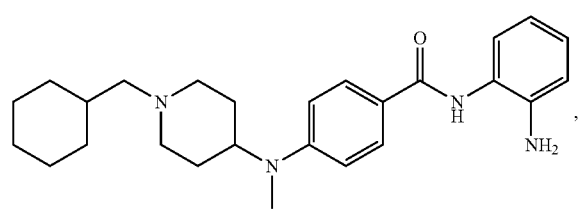
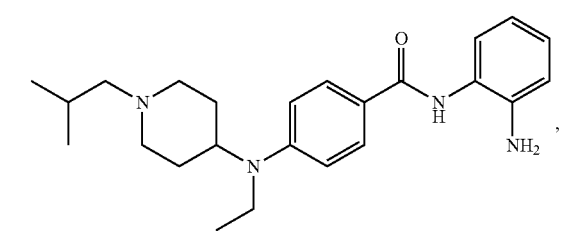
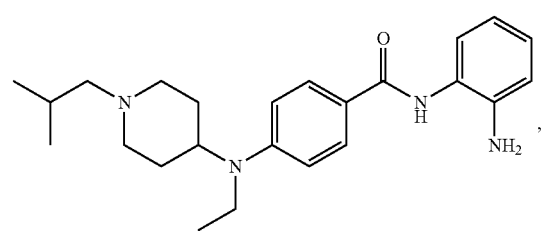
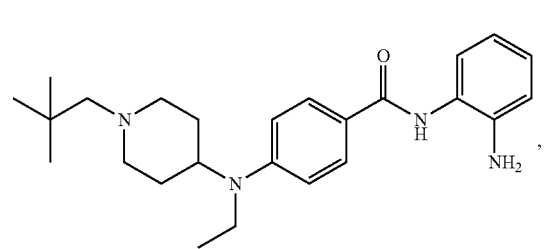
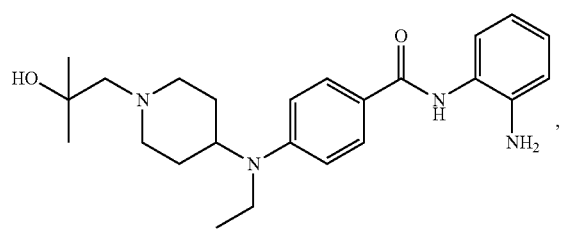
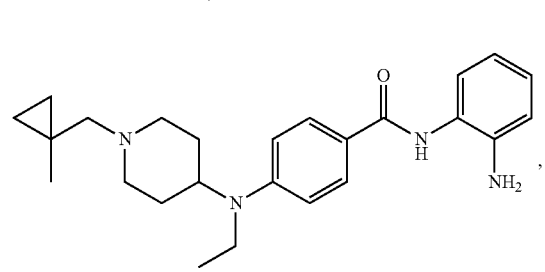
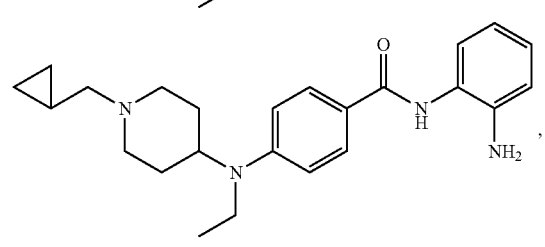
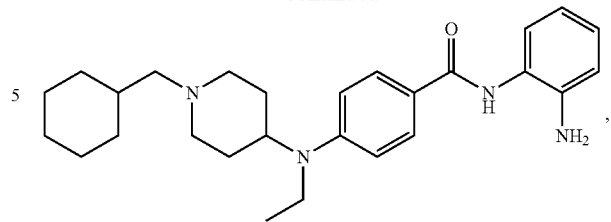
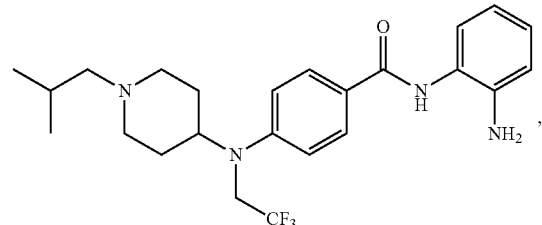
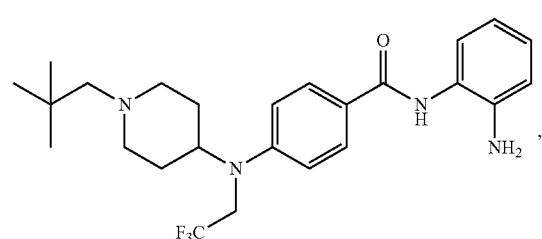
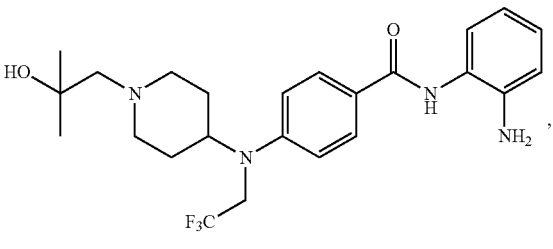
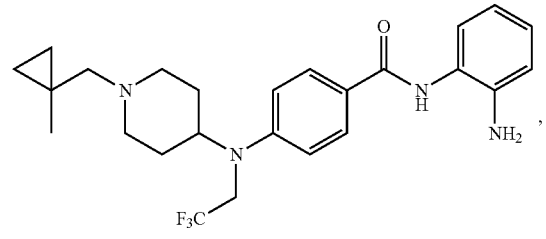
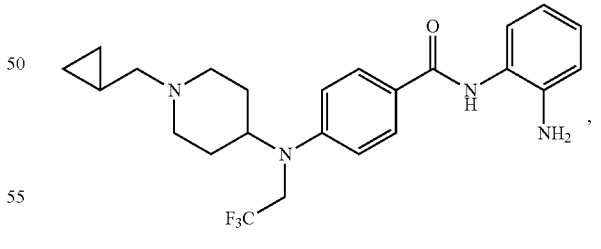
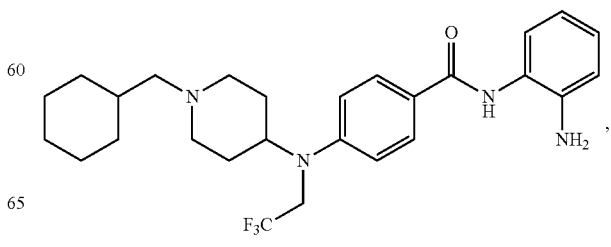

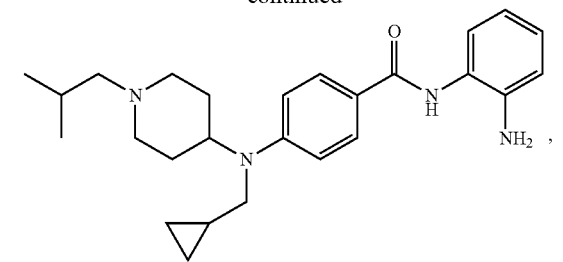
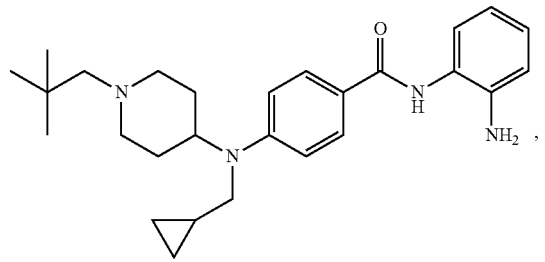
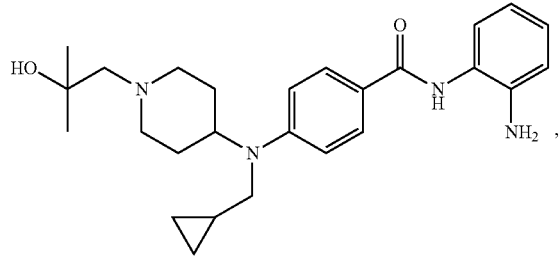
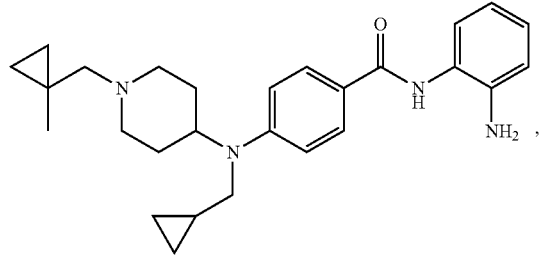
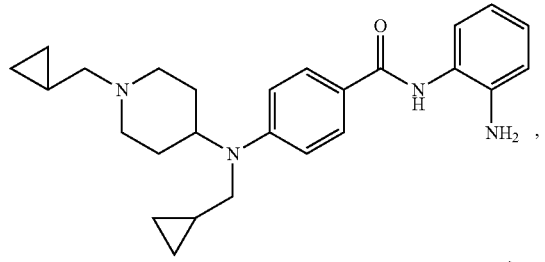
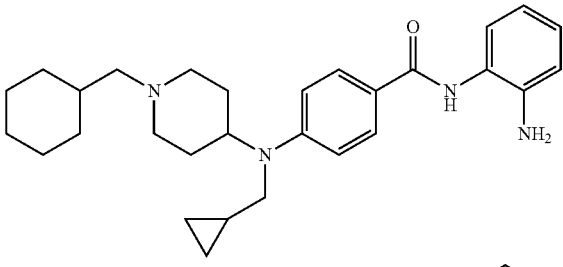
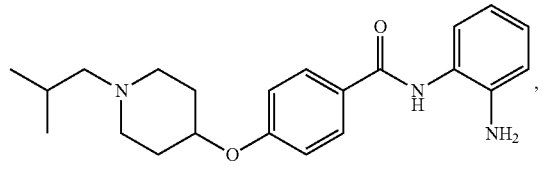
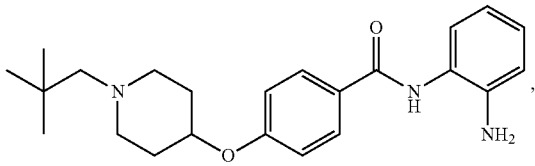
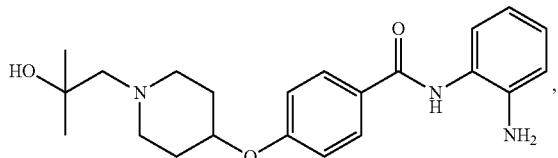
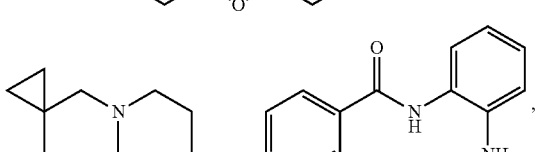
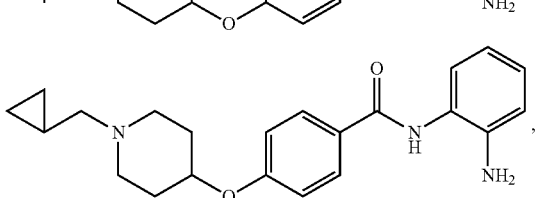
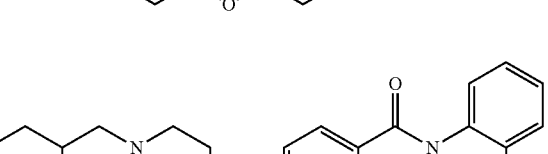
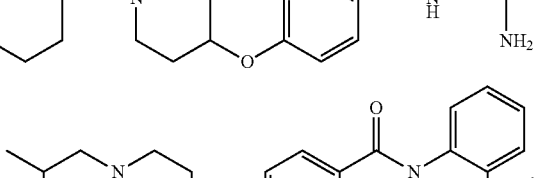
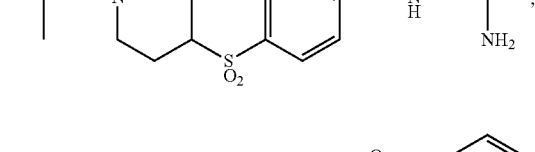
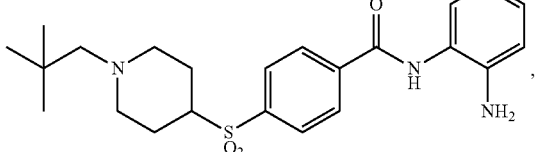
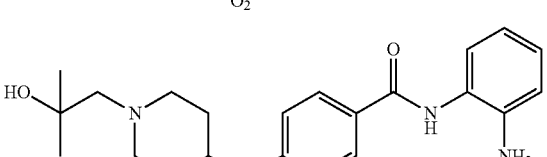
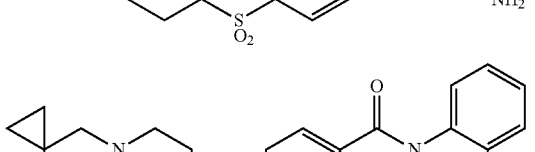

25
-continued

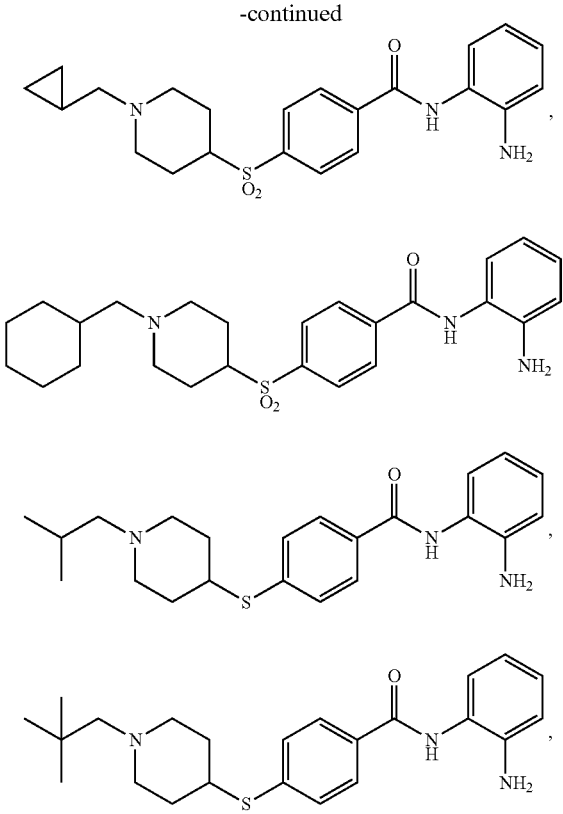

26
-continued

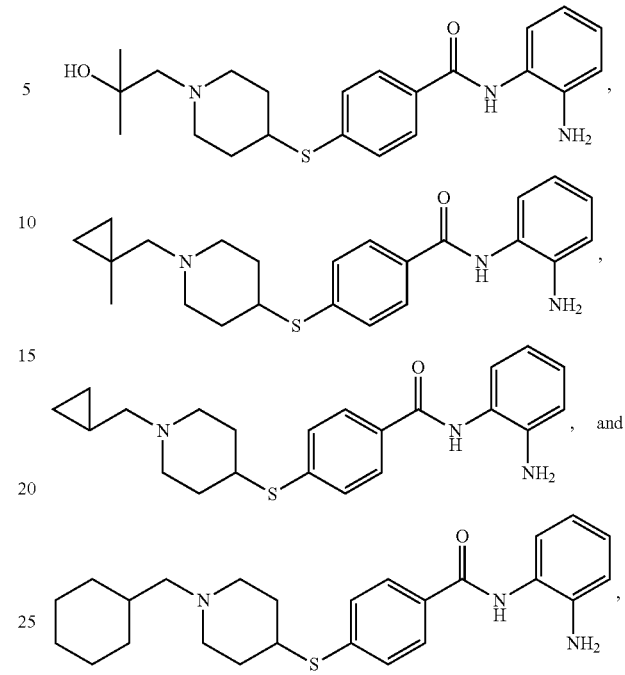

or a pharmaceutically acceptable salt thereof.

Other specific compounds contemplated include those as listed in the following table.

| Ex No | Structure | Name |
|---|---|---|
| 1 | 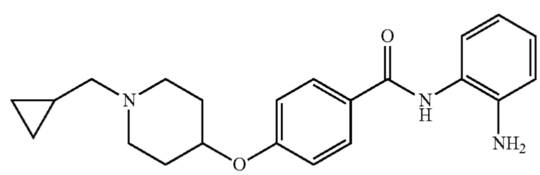 [SMILES: Nc1ccccc1NC(=O)c1ccc(OC2CCN(CC3CC3)CC2)cc1] | N-(2-aminophenyl)-4-((1-(cyclopropylmethyl)piperidin-4-yl)oxy)benzamide |
| 2 | 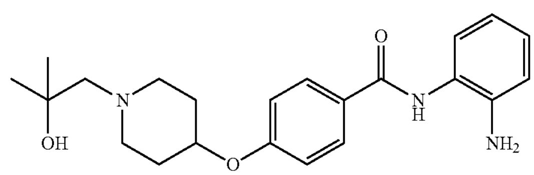 [SMILES: CC(C)(O)CN1CCC(Oc2ccc(C(=O)Nc3ccccc3N)cc2)CC1] | N-(2-aminophenyl)-4-((1-(2-hydroxy-2-methylpropyl)piperidin-4-yl)oxy)benzamide |
| 3 | 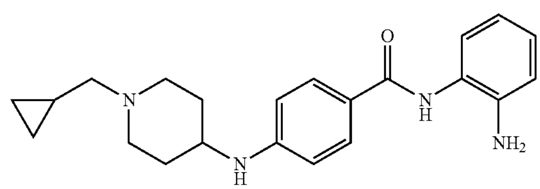 [SMILES: Nc1ccccc1NC(=O)c1ccc(NC2CCN(CC3CC3)CC2)cc1] | N-(2-aminophenyl)-4-((1-(cyclopropylmethyl)piperidin-4-yl)amino)benzamide |
| 4 | 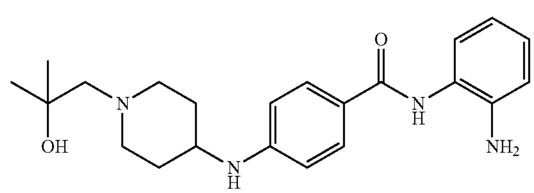 [SMILES: CC(C)(O)CN1CCC(Nc2ccc(C(=O)Nc3ccccc3N)cc2)CC1] | N-(2-aminophenyl)-4-((1-(2-hydroxy-2-methylpropyl)piperidin-4-yl)amino)benzamide |

-continued

| Ex No | Structure | Name |
|---|---|---|
| 5 | 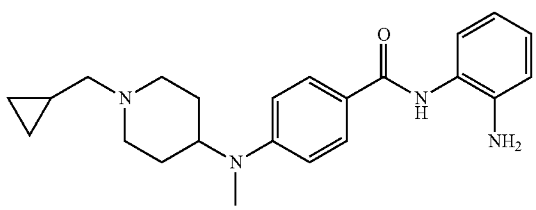 [SMILES: CN(c1ccc(C(=O)Nc2ccccc2N)cc1)C1CCN(CC2CC2)CC1] | N-(2-aminophenyl)-4-((1-(cyclopropylmethyl)piperidin-4-yl)(methyl)amino)benzamide |
| 6 | 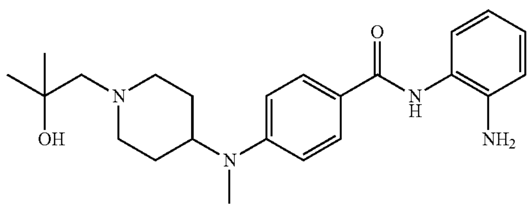 [SMILES: CN(c1ccc(C(=O)Nc2ccccc2N)cc1)C1CCN(CC(C)(C)O)CC1] | N-(2-aminophenyl)-4-((1-(2-hydroxy-2-methylpropyl)piperidin-4-yl)(methyl)amino) benzamide |
| 26 | 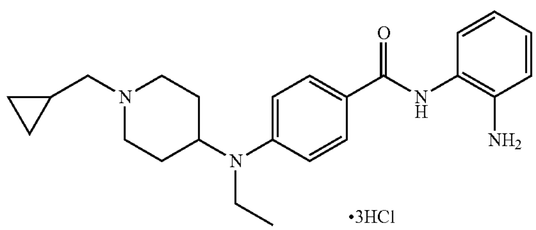 [SMILES: CCN(c1ccc(C(=O)Nc2ccccc2N)cc1)C1CCN(CC2CC2)CC1 ; "·3HCl"] | N-(2-aminophenyl)-4-((1-(cyclopropylmethyl)piperidin-4-yl)(ethyl)amino)benzamide trihydrochloride |
| 27 | 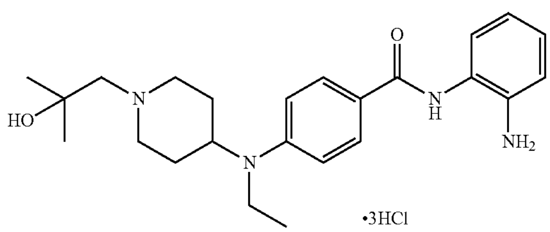 [SMILES: CCN(c1ccc(C(=O)Nc2ccccc2N)cc1)C1CCN(CC(C)(C)O)CC1 ; "·3HCl"] | N-(2-aminophenyl)-4-(ethyl(1-(2-hydroxy-2-methylpropyl)piperidin-4-yl)amino) benzamide trihydrochloride |
| 29 | 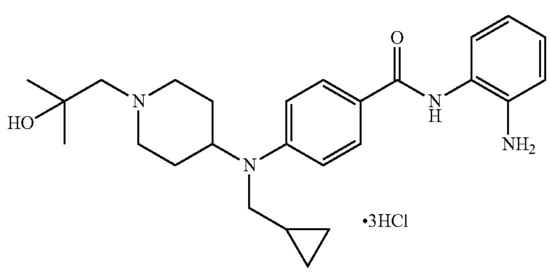 [SMILES: CC(C)(O)CN1CCC(N(CC2CC2)c2ccc(C(=O)Nc3ccccc3N)cc2)CC1 ; "·3HCl"] | N-(2-aminophenyl)-4-((cyclopropylmethyl)(1-(2-hydroxy-2-methylpropyl)piperidin-4-yl)amino) benzamide trihydrochloride |
| 28 | 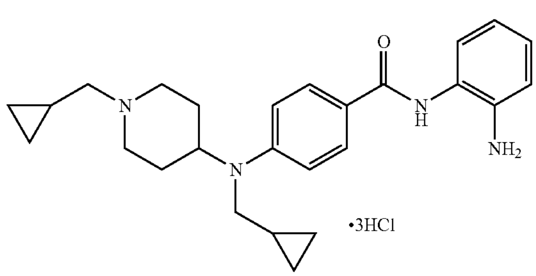 [SMILES: Nc1ccccc1NC(=O)c1ccc(N(CC2CC2)C2CCN(CC3CC3)CC2)cc1 ; "·3HCl"] | N-(2-aminophenyl)-4-((cyclopropylmethyl)(1-(cyclopropylmethyl)piperidin-4-yl)amino) benzamide trihydrochloride |

-continued

| Ex No | Structure | Name |
|---|---|---|
| 30 | 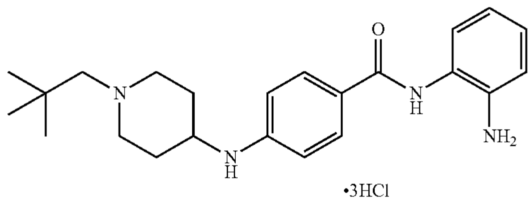 [SMILES: CC(C)(C)CN1CCC(Nc2ccc(C(=O)Nc3ccccc3N)cc2)CC1 ; "·3HCl"] | N-(2-aminophenyl)-4-((1-neopentylpiperidin-4-yl)amino)benzamide trihydrochloride |
| 35 | 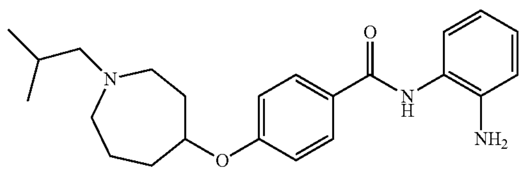 | N-(2-aminophenyl)-4-((1-isobutylazepan-4-yl)oxy)benzamide dihydrochloride |
| 38 | 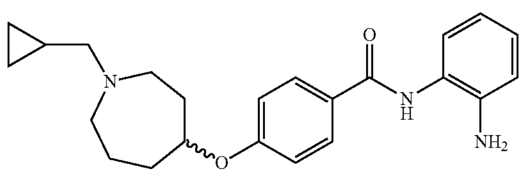 | N-(2-aminophenyl)-4-((1-(cyclopropylmethyl)azepan-4-yl) oxy)benzamide dihydrochloride |
| 40 | 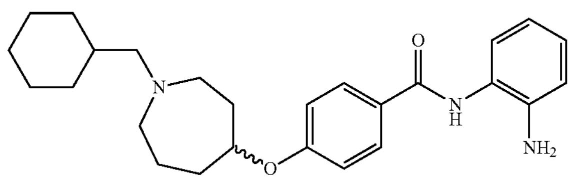 | N-(2-aminophenyl)-4-((1-(cyclohexylmethyl)azepan-4-yl)oxy)benzamide dihydrochloride |
| 41 | 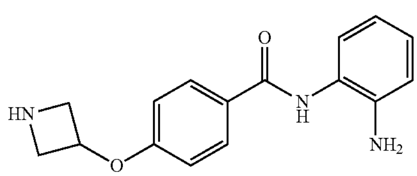 | N-(2-aminophenyl)-4-(azetidin-3-yloxy)benzamide hydrochloride |
| 44 | 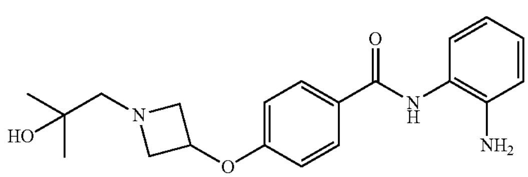 | N-(2-aminophenyl)-4-((1-(2-hydroxy-2-methylpropyl)azetidin-3-yl)oxy)benzamide dihydrochloride |
| 46 | 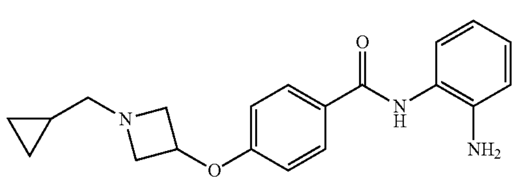 | N-(2-aminophenyl)-4-((1-(cyclopropylmethyl)azetidin-3-yl)oxy)benzamide dihydrochloride |

| Ex No | Structure | Name |
|---|---|---|
| 48 | 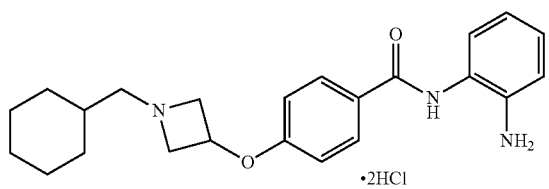 [SMILES: Nc1ccccc1NC(=O)c1ccc(OC2CN(CC3CCCCC3)C2)cc1 ; "·2HCl"] | N-(2-aminophenyl)-4-((1-(cyclohexylmethyl)azetidin-3-yl)oxy)benzamide dihydrochloride |
| 49 | 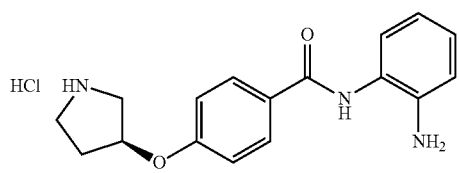 [SMILES: Cl ; Nc1ccccc1NC(=O)c1ccc(O[C@H]2CCNC2)cc1] | (S)-N-(2-aminophenyl)-4-(pyrrolidin-3-yloxy)benzamide hydrochloride |
| 51 | 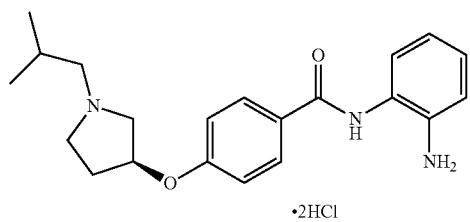 [SMILES: CC(C)CN1CC[C@H](Oc2ccc(C(=O)Nc3ccccc3N)cc2)C1 ; "·2HCl"] | (S)-N-(2-aminophenyl)-4-((1-isobutylpyrrolidin-3-yl)oxy)benzamide dihydrochloride |
| 52 | 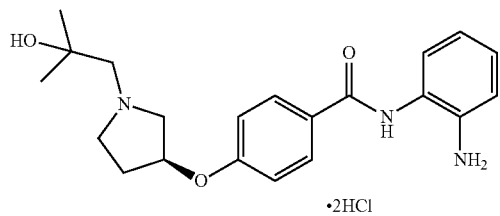 [SMILES: CC(C)(O)CN1CC[C@H](Oc2ccc(C(=O)Nc3ccccc3N)cc2)C1 ; "·2HCl"] | (S)-N-(2-aminophenyl)-4-((1-(2-hydroxy-2-methylpropyl)pyrrolidin-3-yl)oxy)benzamide dihydrochloride |
| 54 | 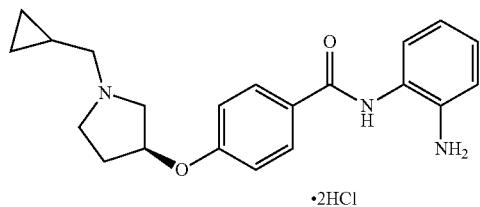 [SMILES: Nc1ccccc1NC(=O)c1ccc(O[C@H]2CCN(CC3CC3)C2)cc1 ; "·2HCl"] | (S)-N-(2-aminophenyl)-4-((1-(cyclopropylmethyl)pyrrolidin-3-yl)oxy)benzamide dihydrochloride |
| 33 | 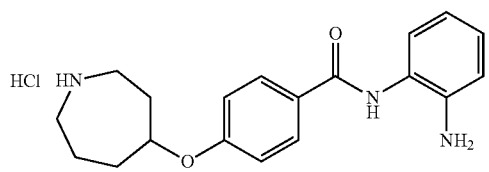 [SMILES: Cl ; Nc1ccccc1NC(=O)c1ccc(OC2CCCNCC2)cc1] | N-(2-aminophenyl)-4-(azepan-4-yloxy)benzamide hydrochloride |
| 36 | 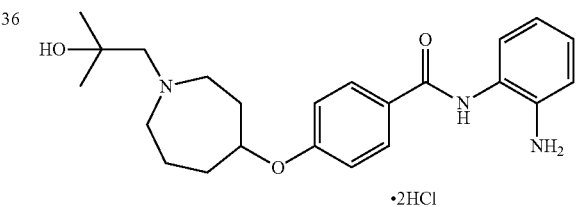 | N-(2-aminophenyl)-4-((1-(2-hydroxy-2-methylpropyl)azepan-4-yl)oxy)benzamide dihydrochloride |

| Ex No | Structure | Name |
|---|---|---|
| 43 | 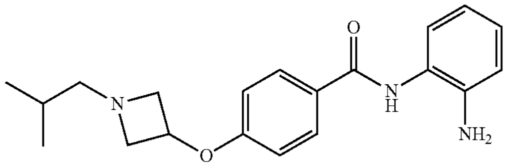 | N-(2-aminophenyl)-4-((1-isobutylazetidin-3-yl)oxy)benzamide dihydrochloride |
| 64 | 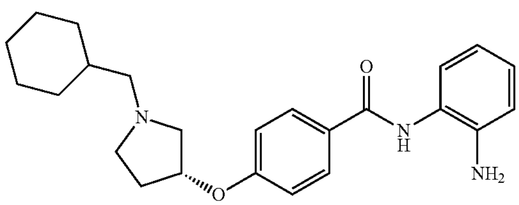 | (R)-N-(2-aminophenyl)-4-((1-(cyclohexylmethyl)pyrrolidin-3-yl)oxy)benzamide dihydrochloride |
| 62 | 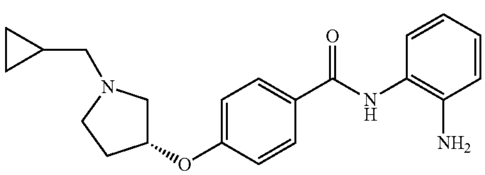 | (R)-N-(2-aminophenyl)-4-((1-(cyclopropylmethyl)pyrrolidin-3-yl)oxy)benzamide dihydrochloride |
| 58 | 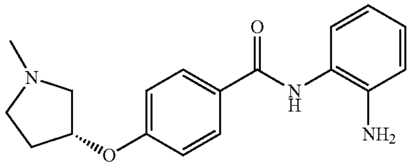 [SMILES: CN1CC[C@@H](Oc2ccc(C(=O)Nc3ccccc3N)cc2)C1] | (R)-N-(2-aminophenyl)-4-((1-methylpyrrolidin-3-yl)oxy)benzamide |
| 59 | 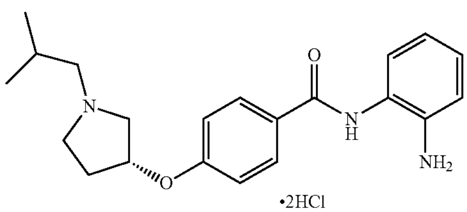 [SMILES: CC(C)CN1CC[C@@H](Oc2ccc(C(=O)Nc3ccccc3N)cc2)C1 ; "·2HCl"] | (R)-N-(2-aminophenyl)-4-((1-isobutylpyrrolidin-3-yl)oxy)benzamide dihydrochloride |
| 60 | 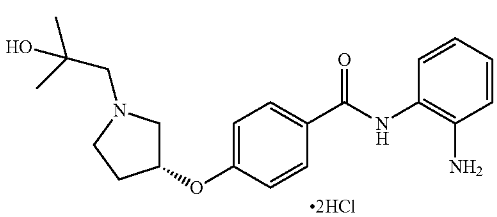 [SMILES: CC(C)(O)CN1CC[C@@H](Oc2ccc(C(=O)Nc3ccccc3N)cc2)C1 ; "·2HCl"] | (R)-N-(2-aminophenyl)-4-((1-(2-hydroxy-2-methylpropyl)pyrrolidin-3-yl)oxy)benzamide dihydrochloride |
| 56 | 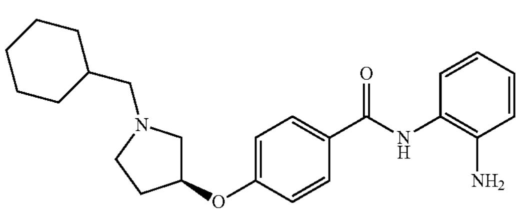 | (S)-N-(2-aminophenyl)-4-((1-(cyclohexylmethyl)pyrrolidin-3-yl)oxy)benzamide dihydrochloride |

-continued

| Ex No | Structure | Name |
|---|---|---|
| 57 | 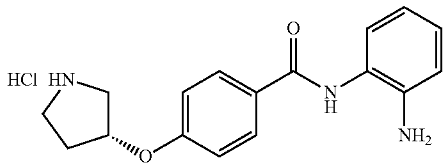 [SMILES: Cl ; Nc1ccccc1NC(=O)c1ccc(O[C@@H]2CCNC2)cc1] | (R)-N-(2-aminophenyl)-4-(pyrrolidin-3-yloxy)benzamide hydrochloride |
| 42 | 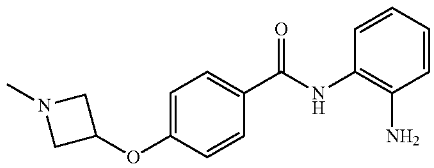 [SMILES: CN1CC(Oc2ccc(C(=O)Nc3ccccc3N)cc2)C1] | N-(2-aminophenyl)-4-((1-methylazetidin-3-yl)oxy)benzamide |
| 50 | 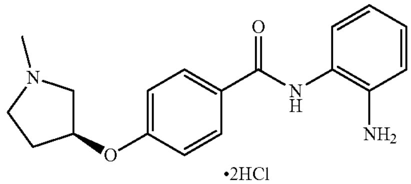 [SMILES: CN1CC[C@H](Oc2ccc(C(=O)Nc3ccccc3N)cc2)C1 ; "·2HCl"] | (S)-N-(2-aminophenyl)-4-((1-methylpyrrolidin-3-yl)oxy)benzamide dihydrochloride |
| 65 | 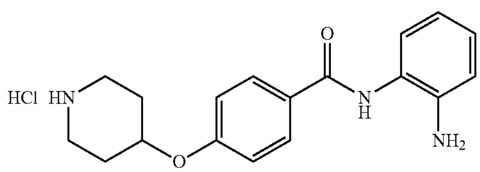 [SMILES: Cl ; Nc1ccccc1NC(=O)c1ccc(OC2CCNCC2)cc1] | N-(2-aminophenyl)-4-(piperidin-4-yloxy)benzamide hydrochloride |
| 66 | 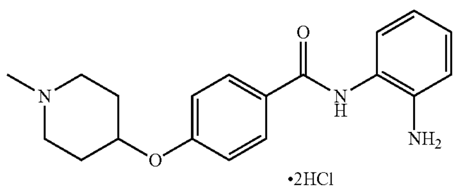 [SMILES: CN1CCC(Oc2ccc(C(=O)Nc3ccccc3N)cc2)CC1 ; "·2HCl"] | N-(2-aminophenyl)-4-((1-methylpiperidin-4-yl)oxy)benzamide dihydrochloride |
| 69 | 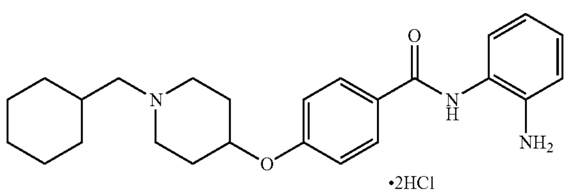 [SMILES: Nc1ccccc1NC(=O)c1ccc(OC2CCN(CC3CCCCC3)CC2)cc1 ; "·2HCl"] | N-(2-aminophenyl)-4-((1-(cyclohexylmethyl)piperidin-4-yl)oxy)benzamide dihydrochloride |
| 89 | 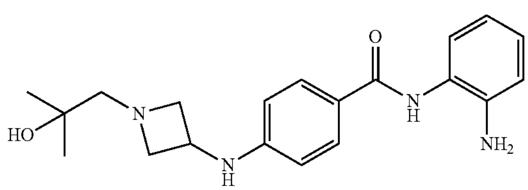 [SMILES: CC(C)(O)CN1CC(Nc2ccc(C(=O)Nc3ccccc3N)cc2)C1] | N-(2-aminophenyl)-4-((1-(2-hydroxy-2-methylpropyl)azetidin-3-yl)amino)benzamide |
| 67 | 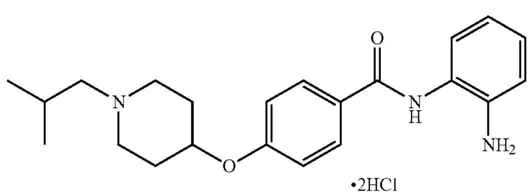 [SMILES: CC(C)CN1CCC(Oc2ccc(C(=O)Nc3ccccc3N)cc2)CC1 ; "·2HCl"] | N-(2-aminophenyl)-4-((1-isobutylpiperidin-4-yl)oxy)benzamide dihydrochloride |

| Ex No | Structure | Name |
|---|---|---|
| 75 | 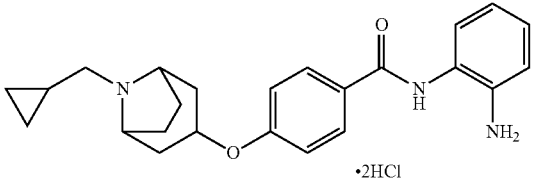 [SMILES: Nc1ccccc1NC(=O)c1ccc(OC2CC3CCC(C2)N3CC2CC2)cc1 ; "·2HCl"] •2HCl | N-(2-aminophenyl)-4-((8-(cyclopropylmethyl)-8-azabicyclo[3.2.1]octan-3-yl)oxy)benzamide dihydrochloride |
| 72 | 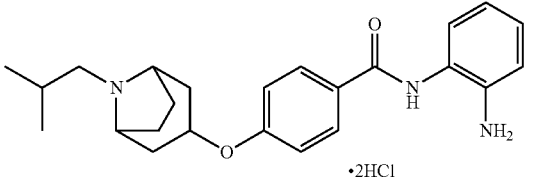 [SMILES: CC(C)CN1C2CCC1CC(Oc1ccc(C(=O)Nc3ccccc3N)cc1)C2 ; "·2HCl"] •2HCl | N-(2-aminophenyl)-4-((8-isobutyl-8-azabicyclo[3.2.1]octan-3-yl)oxy)benzamide dihydrochloride |
| 70 | 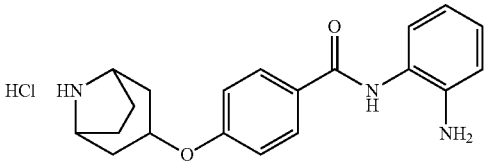 [SMILES: Cl ; Nc1ccccc1NC(=O)c1ccc(OC2CC3CCC(C2)N3)cc1] | 4-((8-azabicyclo[3.2.1]octan-3-yl)oxy)-N-(2-aminophenyl)benzamide hydrochloride |
| 71 | 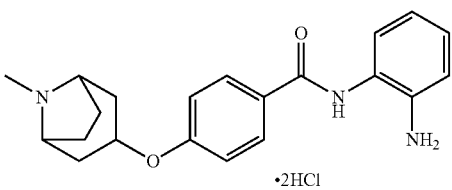 [SMILES: CN1C2CCC1CC(Oc1ccc(C(=O)Nc3ccccc3N)cc1)C2 ; "·2HCl"] •2HCl | N-(2-aminophenyl)-4-((8-methyl-8-azabicyclo[3.2.1]octan-3-yl)oxy)benzamide dihydrochloride |
| 73 | 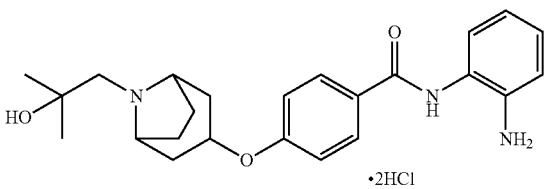 [SMILES: CC(C)(O)CN1C2CCC1CC(Oc1ccc(C(=O)Nc3ccccc3N)cc1)C2 ; "·2HCl"] •2HCl | N-(2-aminophenyl)-4-((8-(2-hydroxy-2-methylpropyl)-8-azabicyclo[3.2.1]octan-3-yl)oxy)benzamide dihydrochloride |
| 86 | 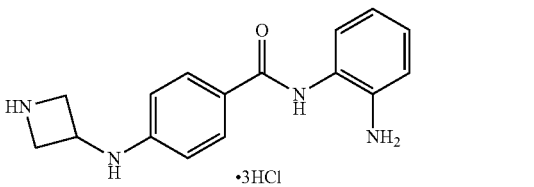 [SMILES: Nc1ccccc1NC(=O)c1ccc(NC2CNC2)cc1 ; "·3HCl"] •3HCl | N-(2-aminophenyl)-4-(azetidin-3-ylamino)benzamide trihydrochloride |
| 91 | 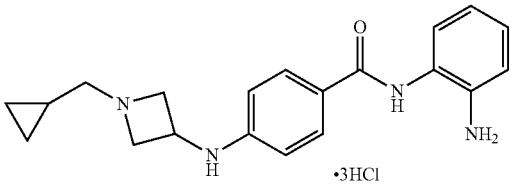 [SMILES: Nc1ccccc1NC(=O)c1ccc(NC2CN(CC3CC3)C2)cc1 ; "·3HCl"] •3HCl | N-(2-aminophenyl)-4-((1-(cyclopropylmethyl)azetidin-3-yl)amino)benzamide trihydrochloride |
| 110 | 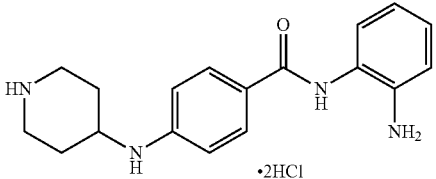 [SMILES: Nc1ccccc1NC(=O)c1ccc(NC2CCNCC2)cc1 ; "·2HCl"] •2HCl | N-(2-aminophenyl)-4-((1-methylpiperidin-4-yl)amino)benzamide dihydrochloride |

-continued

| Ex No | Structure | Name |
|---|---|---|
| 112 | •3HCl | N-(2-aminophenyl)-4-((1-isobutylpiperidin-4-yl)amino)benzamide trihydrochloride |
| 34 | •2CF₃COOH | N-(2-aminophenyl)-4-((1-methylazepan-4-yl)oxy)benzamide bis(2,2,2-trifluoroacetate) |
| 77 | •2HCl | N-(2-aminophenyl)-4-((8-(cyclohexylmethyl)-8-azabicyclo[3.2.1]octan-3-yl)oxy)benzamide dihydrochloride |
| 78 | •3CF₃COOH | N-(2-aminophenyl)-4-(azepan-4-ylamino)benzamide tris(2,2,2-trifluoroacetate) |
| 85 | 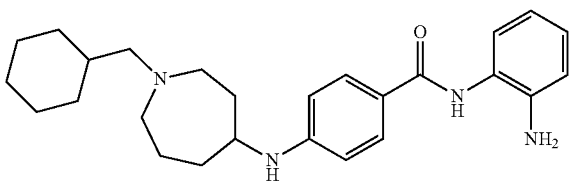 [SMILES: Nc1ccccc1NC(=O)c1ccc(NC2CCCN(CC3CCCCC3)CC2)cc1] | N-(2-aminophenyl)-4-((1-(cyclohexylmethyl)azepan-4-yl)amino)benzamide |
| 88 | •3HCl | N-(2-aminophenyl)-4-((1-isobutylazetidin-3-yl)amino)benzamide trihydrochloride |
| 93 | 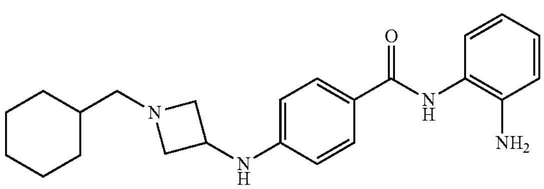 [SMILES: Nc1ccccc1NC(=O)c1ccc(NC2CN(CC3CCCCC3)C2)cc1] | N-(2-aminophenyl)-4-((1-(cyclohexylmethyl)azetidin-3-yl)amino)benzamide |
| 94 | •3HCl | (S)-N-(2-aminophenyl)-4-(pyrrolidin-3-ylamino)benzamide trihydrochloride |

-continued

| Ex No | Structure | Name |
|---|---|---|
| 111 | 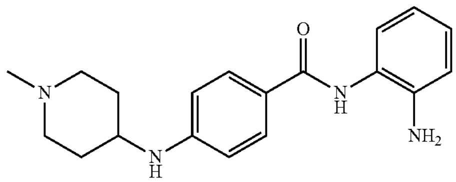 [SMILES: CN1CCC(Nc2ccc(C(=O)Nc3ccccc3N)cc2)CC1] | N-(2-aminophenyl)-4-((1-methylpiperidin-4-yl)amino)benzamide |
| 114 | 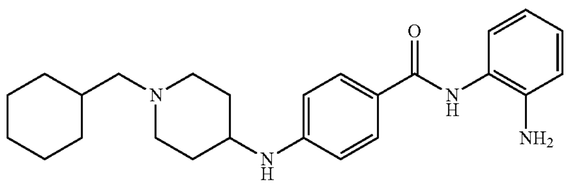 [SMILES: Nc1ccccc1NC(=O)c1ccc(NC2CCN(CC3CCCCC3)CC2)cc1] | N-(2-aminophenyl)-4-((1-(cyclohexylmethyl)piperidin-4-yl)amino)benzamide |
| 123 | 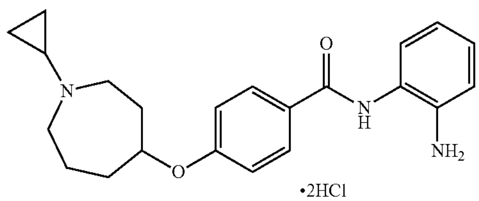 [SMILES: Nc1ccccc1NC(=O)c1ccc(OC2CCCN(C3CC3)CC2)cc1 ; "·2HCl"] | N-(2-aminophenyl)-4-((1-cyclopropylazepan-4-yl)oxy)benzamide benzamide dihydrochloride |
| 40A | 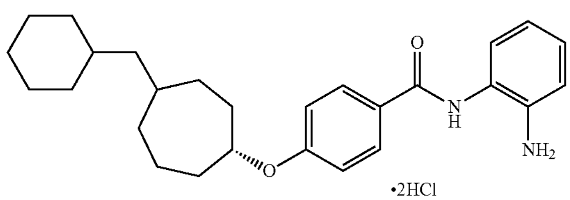 [SMILES: Nc1ccccc1NC(=O)c1ccc(O[C@@H]2CCCC(CC3CCCCC3)CC2)cc1 ; "·2HCl"] | stereochem not yet established N-(2-aminophenyl)-4-((1-(cyclohexylmethyl)azepan-4-yl)oxy)benzamide dihydrochloride |
| 40B | 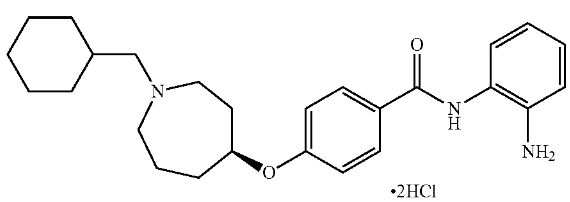 [SMILES: Nc1ccccc1NC(=O)c1ccc(O[C@H]2CCCN(CC3CCCCC3)CC2)cc1 ; "·2HCl"] | stereochem not yet established N-(2-aminophenyl)-4-((1-(cyclohexylmethyl)azepan-4-yl)oxy)benzamide dihydrochloride |
| 129 | 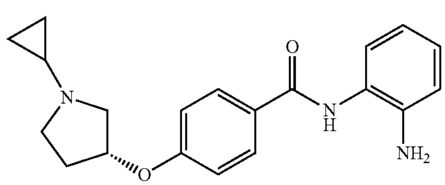 [SMILES: Nc1ccccc1NC(=O)c1ccc(O[C@@H]2CCN(C3CC3)C2)cc1] | (R)-N-(2-aminophenyl)-4-((1-cyclopropylpyrrolidin-3-yl)oxy)benzamide |
| 136 | 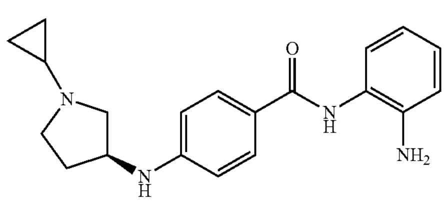 [SMILES: Nc1ccccc1NC(=O)c1ccc(N[C@H]2CCN(C3CC3)C2)cc1] | (S)-N-(2-aminophenyl)-4-((1-cyclopropylpyrrolidin-3-yl)amino)benzamide |

| Ex No | Structure | Name |
|---|---|---|
| 87 | 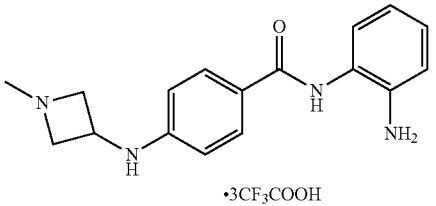 [SMILES: CN1CC(Nc2ccc(C(=O)Nc3ccccc3N)cc2)C1 ; "·3CF3COOH"] •3CF₃COOH | N-(2-aminophenyl)-4-((1-methylazetidin-3-yl)amino)benzamide tris(2,2,2-trifluoroacetate) |
| 97 | 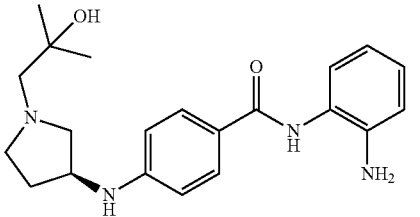 [SMILES: CC(C)(O)CN1CC[C@H](Nc2ccc(C(=O)Nc3ccccc3N)cc2)C1] | (S)-N-(2-aminophenyl)-4-((1-(2-hydroxy-2-methylpropyl)pyrrolidin-3-yl)amino)benzamide |
| 134 | 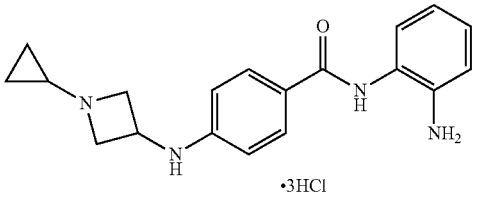 [SMILES: Nc1ccccc1NC(=O)c1ccc(NC2CN(C3CC3)C2)cc1] •3HCl | N-(2-aminophenyl)-4-((1-cyclopropylazetidin-3-yl)amino)benzamide trihydrochloride |
| 140 | 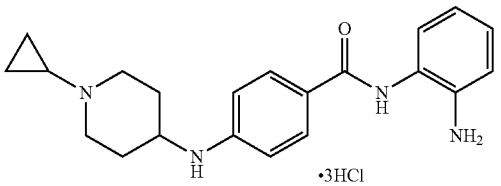 [SMILES: Nc1ccccc1NC(=O)c1ccc(NC2CCN(C3CC3)CC2)cc1 ; "·3HCl"] •3HCl | N-(2-aminophenyl)-4-((1-cyclopropylpiperidin-4-yl)amino)benzamide trihydrochloride trihydrochloride |
| 131 | 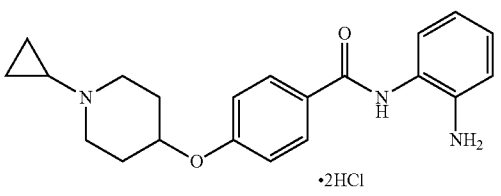 [SMILES: Nc1ccccc1NC(=O)c1ccc(OC2CCN(C3CC3)CC2)cc1 ; "·2HCl"] •2HCl | N-(2-aminophenyl)-4-((1-cyclopropylpiperidin-4-yl)oxy)benzamide dihydrochloride |
| 81 | 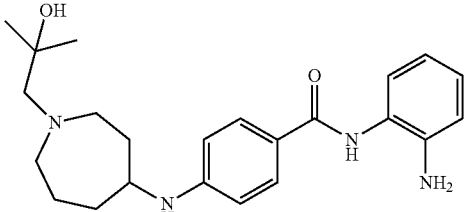 •3HCl | N-(2-aminophenyl)-4-((1-(2-hydroxy-2-methylpropyl)azepan-4-yl)amino)benzamide trihydrochloride |
| 95 | 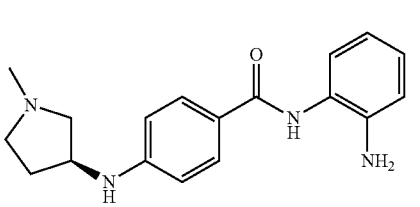 [SMILES: CN1CC[C@H](Nc2ccc(C(=O)Nc3ccccc3N)cc2)C1] | (S)-N-(2-aminophenyl)-4-((1-methylpyrrolidin-3-yl)amino)benzamide |

| Ex No | Structure | Name |
|---|---|---|
| 99 | 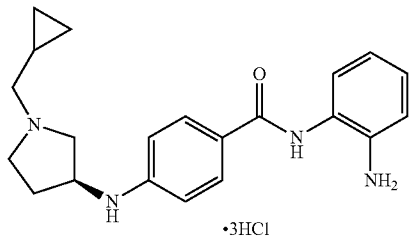 [SMILES: Nc1ccccc1NC(=O)c1ccc(N[C@H]2CCN(CC3CC3)C2)cc1 ; "·3HCl"] | (S)-N-(2-aminophenyl)-4-((1-(cyclopropylmethyl)pyrrolidin-3-yl)amino)benzamide trihydrochloride |
| 101 | 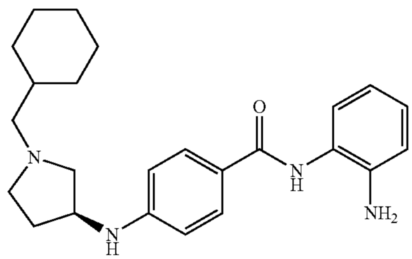 [SMILES: Nc1ccccc1NC(=O)c1ccc(N[C@H]2CCN(CC3CCCCC3)C2)cc1] | (S)-N-(2-aminophenyl)-4-((1-(cyclohexylmethyl)pyrrolidin-3-yl)amino)benzamide |
| 107 | 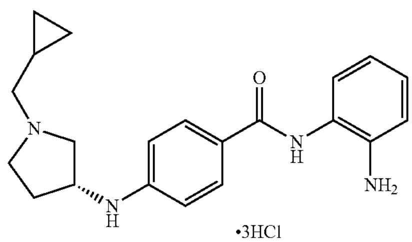 [SMILES: Nc1ccccc1NC(=O)c1ccc(N[C@@H]2CCN(CC3CC3)C2)cc1 ; "·3HCl"] | (R)-N-(2-aminophenyl)-4-((1-(cyclopropylmethyl)pyrrolidin-3-yl)amino)benzamide trihydrochloride |
| 124 | 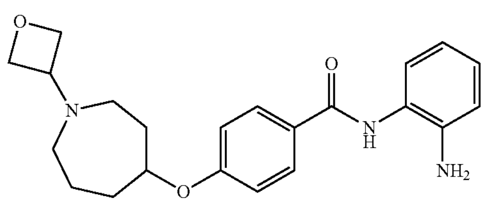 [SMILES: Nc1ccccc1NC(=O)c1ccc(OC2CCCN(C3COC3)CC2)cc1] | N-(2-aminophenyl)-4-((1-(oxetan-3-yl)azepan-4-yl)oxy)benzamide |
| 125 | 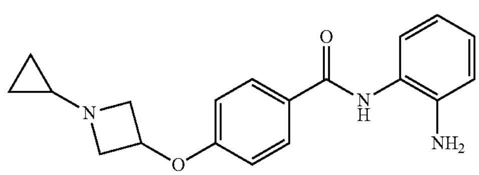 [SMILES: Nc1ccccc1NC(=O)c1ccc(OC2CN(C3CC3)C2)cc1] | N-(2-aminophenyl)-4-((1-cyclopropylazetidin-3-yl)oxy)benzamide |
| 126 | 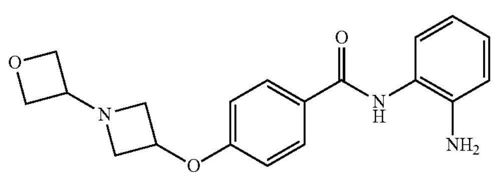 [SMILES: Nc1ccccc1NC(=O)c1ccc(OC2CN(C3COC3)C2)cc1] | N-(2-aminophenyl)-4-((1-(oxetan-3-yl)azetidin-3-yl)oxy)benzamide |
| 127 | 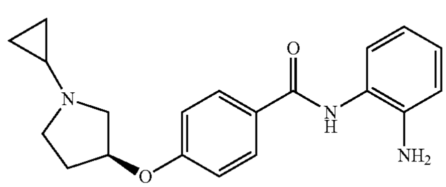 | (S)-N-(2-aminophenyl)-4-((1-cyclopropylpyrrolidin-3-yl)oxy)benzamide dihydrochloride |

-continued

| Ex No | Structure | Name |
|---|---|---|
| 128 | 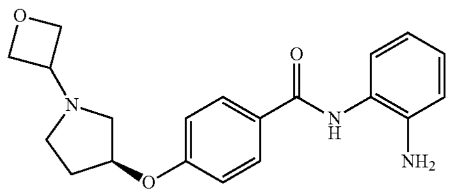 [SMILES: Nc1ccccc1NC(=O)c1ccc(O[C@H]2CCN(C3COC3)C2)cc1] | (S)-N-(2-aminophenyl)-4-((1-(oxetan-3-yl)pyrrolidin-3-yl)oxy)benzamide |
| 132 | 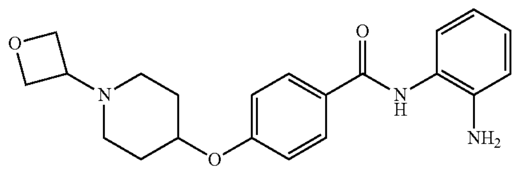 [SMILES: Nc1ccccc1NC(=O)c1ccc(OC2CCN(C3COC3)CC2)cc1] | N-(2-aminophenyl)-4-((1-(oxetan-3-yl)piperidin-4-yl)oxy)benzamide |
| 138 | 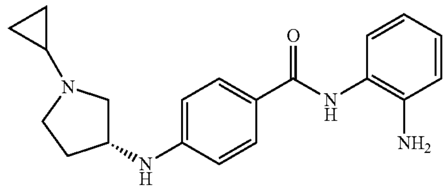 | (R)-N-(2-aminophenyl)-4-((1-cyclopropylpyrrolidin-3-yl)amino)benzamide trihydrochloride |
| 80 | 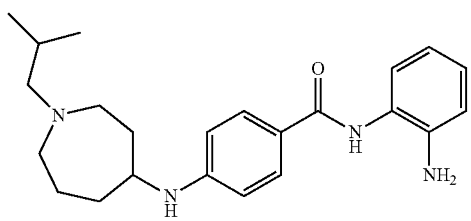 [SMILES: CC(C)CN1CCCC(Nc2ccc(C(=O)Nc3ccccc3N)cc2)CC1] | N-(2-aminophenyl)-4-((1-isobutylazepan-4-yl)amino)benzamide |
| 83 | 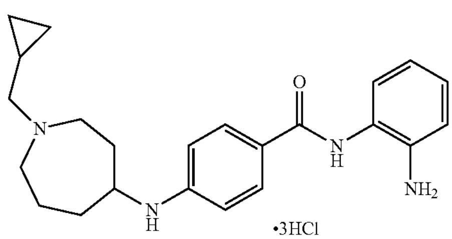 [SMILES: Nc1ccccc1NC(=O)c1ccc(NC2CCCN(CC3CC3)CC2)cc1 ; "·3HCl"] | N-(2-aminophenyl)-4-((1-(cyclopropylmethyl)azepan-4-yl)amino)benzamide trihydrochloride |
| 96 | 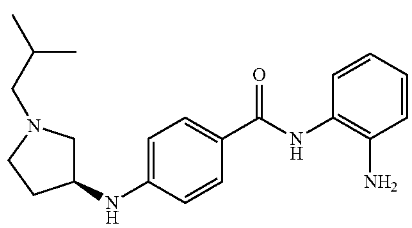 [SMILES: CC(C)CN1CC[C@H](Nc2ccc(C(=O)Nc3ccccc3N)cc2)C1] | (S)-N-(2-aminophenyl)-4-((1-isobutylpyrrolidin-3-yl)amino)benzamide |
| 105 | 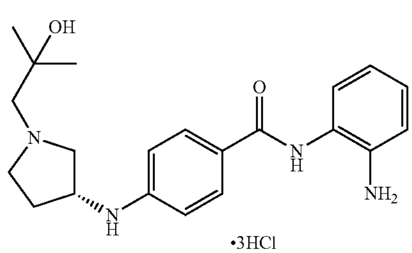 [SMILES: CC(C)(O)CN1CC[C@@H](Nc2ccc(C(=O)Nc3ccccc3N)cc2)C1] | (R)-N-(2-aminophenyl)-4-((1-(2-hydroxy-2-methylpropyl)pyrrolidin-3-yl)amino)benzamide trihydrochloride |

-continued

| Ex No | Structure | Name |
|---|---|---|
| 109 | 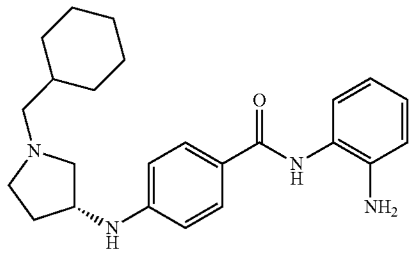 [SMILES: Nc1ccccc1NC(=O)c1ccc(N[C@@H]2CCN(CC3CCCCC3)C2)cc1] | (R)-N-(2-aminophenyl)-4-((1-(cyclohexylmethyl)pyrrolidin-3-yl)amino)benzamide |
| 130 | 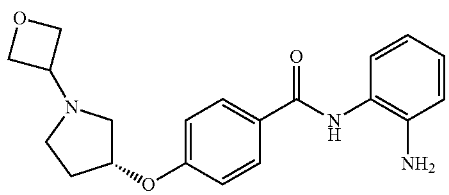 [SMILES: Nc1ccccc1NC(=O)c1ccc(O[C@@H]2CCN(C3COC3)C2)cc1] | (R)-N-(2-aminophenyl)-4-((1-(oxetan-3-yl)pyrrolidin-3-yl) oxy-benzamide |
| 141 | 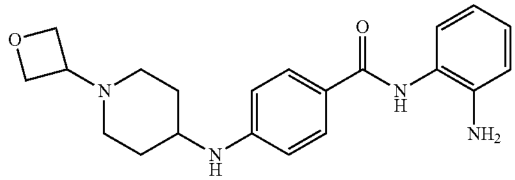 [SMILES: Nc1ccccc1NC(=O)c1ccc(NC2CCN(C3COC3)CC2)cc1] | N-(2-aminophenyl)-4-((1-(oxetan-3-yl)piperidin-4-yl) amino)benzamide |
| 170 | 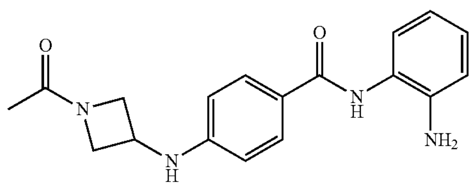 [SMILES: CC(=O)N1CC(Nc2ccc(C(=O)Nc3ccccc3N)cc2)C1] | 4-((1-acetylazetidin-3-yl) amino)-N-(2-aminophenyl)benzamide |
| 102 | 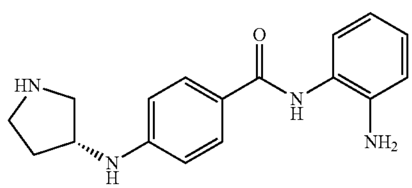 | (R)-N-(2-aminophenyl)-4-(pyrrolidin-3-ylamino) benzamide trihydrochloride |
| 103 | 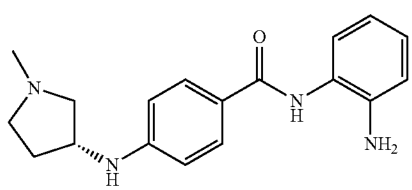 [SMILES: CN1CC[C@@H](Nc2ccc(C(=O)Nc3ccccc3N)cc2)C1] | (R)-N-(2-aminophenyl)-4-((1-methylpyrrolidin-3-yl) amino)benzamide |
| 104 | 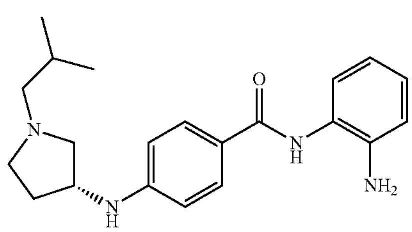 | (R)-N-(2-aminophenyl)-4-((1-isobutylpyrrolidin-3-yl)amino)benzamide trihydrochloride |

-continued

| Ex No | Structure | Name |
|---|---|---|
| 135 | 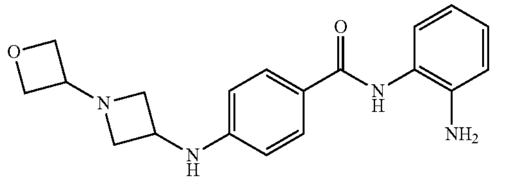 [SMILES: Nc1ccccc1NC(=O)c1ccc(NC2CN(C3COC3)C2)cc1] | N-(2-aminophenyl)-4-((1-(oxetan-3-yl)azetidin-3-yl)amino)benzamide |
| 137 | 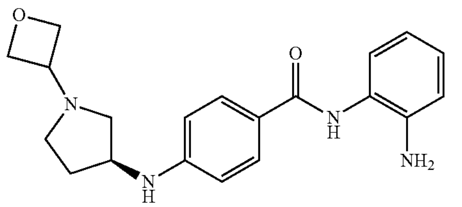 [SMILES: Nc1ccccc1NC(=O)c1ccc(N[C@H]2CCN(C3COC3)C2)cc1] | (S)-N-(2-aminophenyl)-4-((1-(oxetan-3-yl)pyrrolidin-3-yl)amino)benzamide |
| 139 | ·3CF₃COOH | (R)-N-(2-aminophenyl)-4-((1-(oxetan-3-yl)pyrrolidin-3-yl)amino)benzamide tris(2,2,2-trifluoroacetate) |
| 45 | ·2HCl | N-(2-aminophenyl)-4-((1-isobutylazetidin-3-yl)oxy)benzamide dihydrochloride |
| 53 | 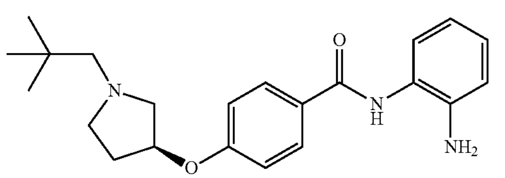 [SMILES: CC(C)(C)CN1CC[C@H](Oc2ccc(C(=O)Nc3ccccc3N)cc2)C1] | (S)-N-(2-aminophenyl)-4-((1-neopentylpyrrolidin-3-yl)oxy)benzamide |
| 61 | 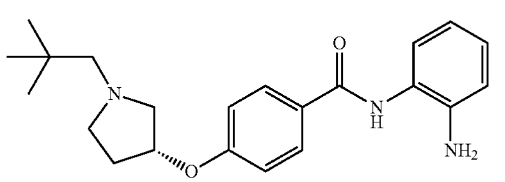 [SMILES: CC(C)(C)CN1CC[C@@H](Oc2ccc(C(=O)Nc3ccccc3N)cc2)C1] | (R)-N-(2-aminophenyl)-4-((1-neopentylpyrrolidin-3-yl)oxy)benzamide |
| 74 | ·2HCl | N-(2-aminophenyl)-4-((8-neopentyl-8-azabicyclo[3.2.1]octan-3-yl)oxy)benzamide dihydrochloride |

| Ex No | Structure | Name |
|---|---|---|
| 90 | 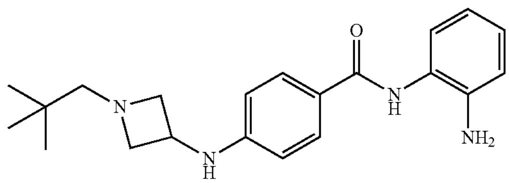 [SMILES: CC(C)(C)CN1CC(Nc2ccc(C(=O)Nc3ccccc3N)cc2)C1] | N-(2-aminophenyl)-4-((1-neopentylazetidin-3-yl)amino)benzamide |
| 98 | •3HCl | (S)-N-(2-aminophenyl)-4-((1-neopentylpyrrolidin-3-yl)amino)benzamide trihydrochloride |
| 106 | 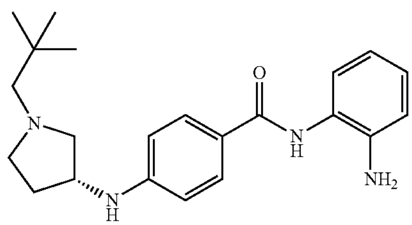 [SMILES: CC(C)(C)CN1CC[C@@H](Nc2ccc(C(=O)Nc3ccccc3N)cc2)C1] | (R)-N-(2-aminophenyl)-4-((1-neopentylpyrrolidin-3-yl)amino)benzamide |
| 68 | •2HCl | N-(2-aminophenyl)-4-((1-((1-methylcyclopropyl)methyl)piperidin-4-yl)oxy)benzamide dihydrochloride |
| 142 | •3HCl | 4-((1-(((3r,5r,7r)-adamantan-1-yl)methyl)piperidin-4-yl)amino)-N-(2-aminophenyl)benzamide trihydrochloride |
| 92 | 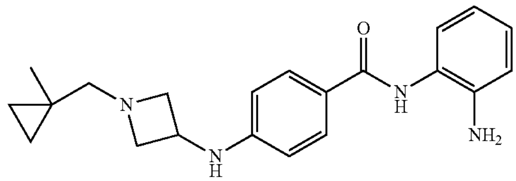 [SMILES: CC1(CN2CC(Nc3ccc(C(=O)Nc4ccccc4N)cc3)C2)CC1] | N-(2-aminophenyl)-4-((1-((1-methylcyclopropyl)methyl)azetidin-3-yl)amino)benzamide |
| 47 | •2HCl | N-(2-aminophenyl)-4-((1-((1-methylcyclopropyl)methyl)azetidin-3-yl)oxy)benzamide dihydrochloride |

| Ex No | Structure | Name |
|---|---|---|
| 76 | 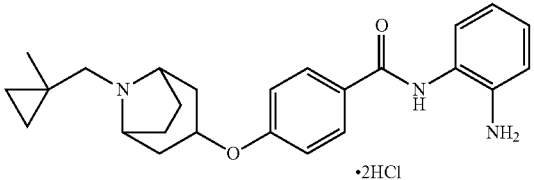 [SMILES: CC1(CN2C3CCC2CC(Oc2ccc(C(=O)Nc4ccccc4N)cc2)C3)CC1 ; "·2HCl"] •2HCl | N-(2-aminophenyl)-4-((8-((1-methylcyclopropyl)methyl)-8-azabicyclo[3.2.1]octan-3-yl)oxy)benzamide dihydrochloride |
| 133 | 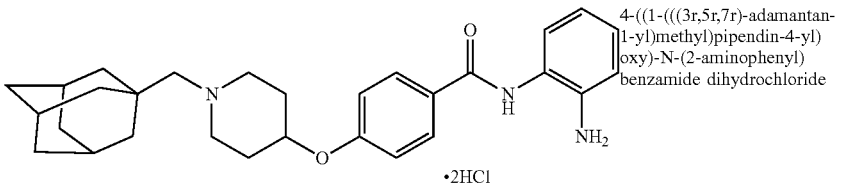 •2HCl | 4-((1-(((3r,5r,7r)-adamantan-1-yl)methyl)pipendin-4-yl)oxy)-N-(2-aminophenyl)benzamide dihydrochloride |
| 100 | 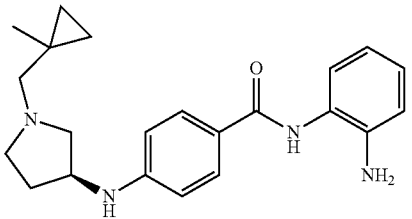 [SMILES: CC1(CN2CC[C@H](Nc3ccc(C(=O)Nc4ccccc4N)cc3)C2)CC1] | (S)-N-(2-aminophenyl)-4-((1-((1-methylcyclopropyl)methyl)pyrrolidin-3-yl)amino)benzamide |
| 113 | 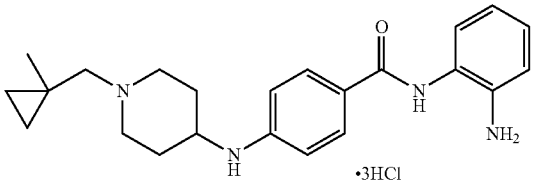 [SMILES: CC1(CN2CCC(Nc3ccc(C(=O)Nc4ccccc4N)cc3)CC2)CC1 ; "·3HCl"] •3HCl | N-(2-aminophenyl)-4-((1-((1-methylcyclopropyl)methyl)piperidin-4-yl)amino)benzamide trihydrochloride |
| 63 | 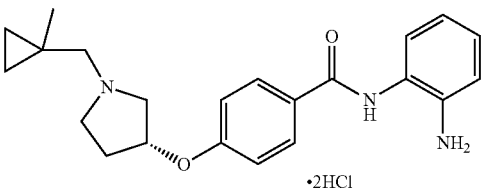 [SMILES: CC1(CN2CC[C@@H](Oc3ccc(C(=O)Nc4ccccc4N)cc3)C2)CC1 ; "·2HCl"] •2HCl | (R)-N-(2-aminophenyl)-4-((1-((1-methylcyclopropyl)methyl)pyrrolidin-3-yl)oxy)benzamide dihydrochloride |
| 37 | 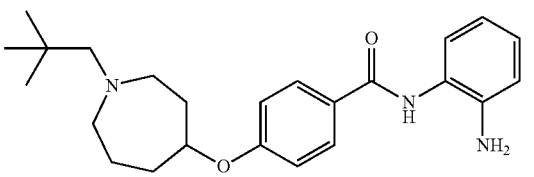 | N-(2-aminophenyl)-4-((1-neopentylazepan-4-yl)oxy)benzamide |
| 39 | 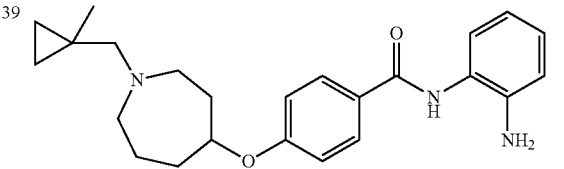 | N-(2-aminophenyl)-4-((1-((1-methylcyclopropyl)methyl)azepan-4-yl)oxy)benzamide |

| Ex No | Structure | Name |
|---|---|---|
| 55 | 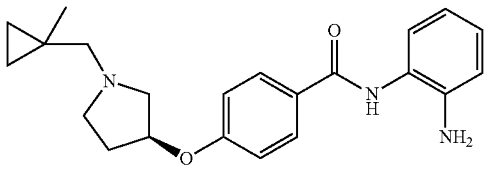 | (S)-N-(2-aminophenyl)-4-((1-((1-methylcyclopropyl)methyl)pyrrolidin-3-yl)oxy)benzamide dihydrochloride |
| 108 | 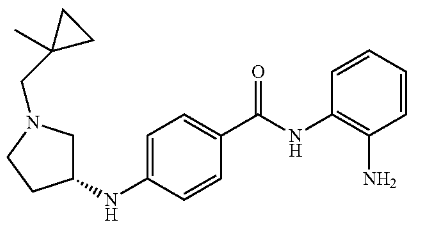 [SMILES: CC1(CN2CC[C@@H](Nc3ccc(C(=O)Nc4ccccc4N)cc3)C2)CC1] | (R)-N-(2-aminophenyl)-4-((1-((1-methylcyclopropyl)methyl)pyrrolidin-3-yl)amino)benzamide |
| 120 | 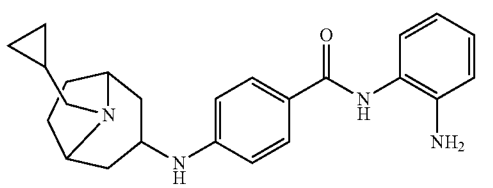 | N-(2-aminophenyl)-4-((8-(cyclopropylmethyl)-8-azabicyclo[3.2.1]octan-3-yl)amino)benzamide trihydrochloride |
| 38A | 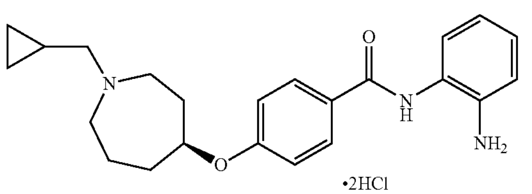 [SMILES: Nc1ccccc1NC(=O)c1ccc(O[C@H]2CCCN(CC3CC3)CC2)cc1 ; "·2HCl"] | (S)-N-(2-aminophenyl)-4-((1-(cyclopropylmethyl)azepan-4-yl)oxy)benzamide |
| 38B | 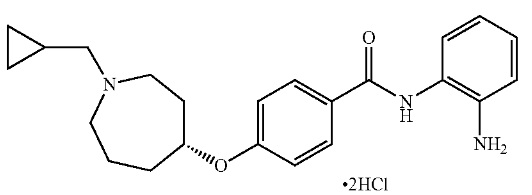 [SMILES: Nc1ccccc1NC(=O)c1ccc(O[C@@H]2CCCN(CC3CC3)CC2)cc1 ; "·2HCl"] | (R)-N-(2-aminophenyl)-4-((1-(cyclopropylmethyl)azepan-4-yl)oxy)benzamide |
| 116 | 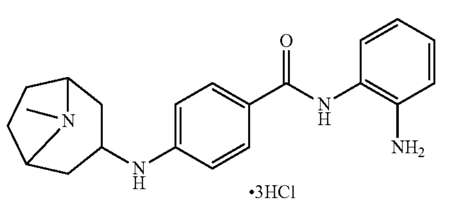 [SMILES: CN1C2CCC1CC(Nc1ccc(C(=O)Nc3ccccc3N)cc1)C2 ; "·3HCl"] | N-(2-aminophenyl)-4-((8-methyl-8-azabicyclo[3.2.1]octan-3-yl)amino)benzamide trihydrochloride |
| 117 | 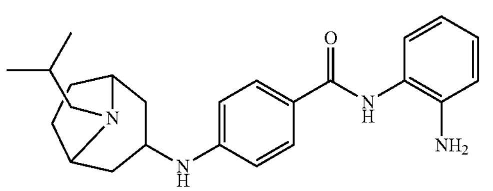 [SMILES: CC(C)CN1C2CCC1CC(Nc1ccc(C(=O)Nc3ccccc3N)cc1)C2] | N-(2-aminophenyl)-4-((8-isobutyl-8-azabicyclo[3.2.1]octan-3-yl)amino)benzamide |

| Ex No | Structure | Name |
|---|---|---|
| 118 | 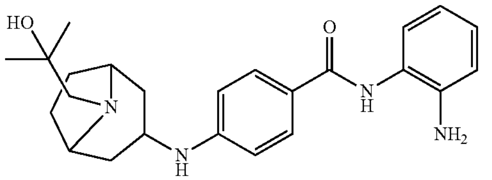 [SMILES: CC(C)(O)CN1C2CCC1CC(Nc1ccc(C(=O)Nc3ccccc3N)cc1)C2] | N-(2-aminophenyl)-4-((8-(2-hydroxy-2-methylpropyl)-8-azabicyclo[3.2.1]octan-3-yl)amino)benzamide |
| 122 | 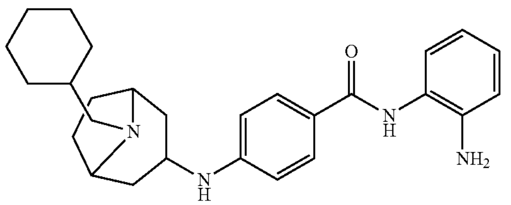 [SMILES: Nc1ccccc1NC(=O)c1ccc(NC2CC3CCC(C2)N3CC2CCCCC2)cc1] | N-(2-aminophenyl)-4-((8-(cyclohexylmethyl)-8-azabicyclo[3.2.1]octan-3-yl)amino)benzamide |
| 115 | 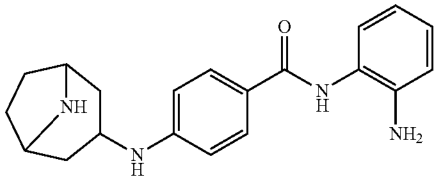 [SMILES: Nc1ccccc1NC(=O)c1ccc(NC2CC3CCC(C2)N3)cc1] | 4-((8-azabicyclo[3.2.1]octan-3-yl)amino)-N-(2-aminophenyl)benzamide |
| 119 | 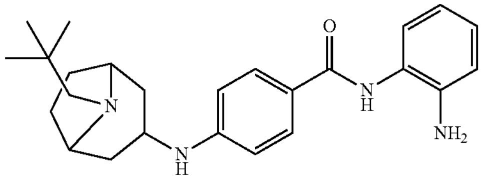 [SMILES: CC(C)(C)CN1C2CCC1CC(Nc1ccc(C(=O)Nc3ccccc3N)cc1)C2] | N-(2-aminophenyl)-4-((8-neopentyl-8-azabicyclo[3.2.1]octan-3-yl)amino)benzamide |
| 369 | 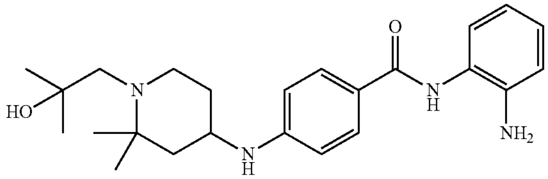 [SMILES: CC(C)(O)CN1CCC(Nc2ccc(C(=O)Nc3ccccc3N)cc2)CC1(C)C] | N-(2-aminophenyl)-4-((1-(2-hydroxy-2-methylpropyl)-2,2-dimethylpiperidin-4-yl)amino)benzamide |
| 363 | 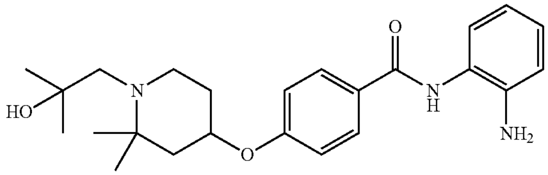 [SMILES: CC(C)(O)CN1CCC(Oc2ccc(C(=O)Nc3ccccc3N)cc2)CC1(C)C] | N-(2-aminophenyl)-4-((1-(2-hydroxy-2-methylpropyl)-2,2-dimethylpiperidin-4-yl)oxy)benzamide |
| 375 | 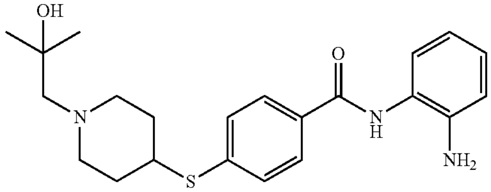 [SMILES: CC(C)(O)CN1CCC(Sc2ccc(C(=O)Nc3ccccc3N)cc2)CC1] | N-(2-aminophenyl)-4-((1-(2-hydroxy-2-methylpropyl)piperidin-4-yl)thio)benzamide |
| 362 | 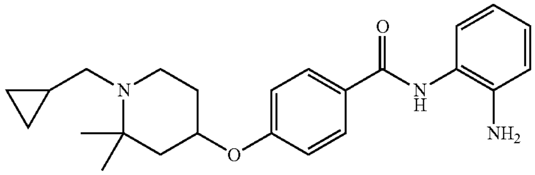 [SMILES: CC1(C)CC(Oc2ccc(C(=O)Nc3ccccc3N)cc2)CCN1CC1CC1] | N-(2-aminophenyl)-4-((1-(cyclopropylmethyl)-2,2-dimethylpiperidin-4-yl)oxy)benzamide |

| Ex No | Structure | Name |
|---|---|---|
| 368 | 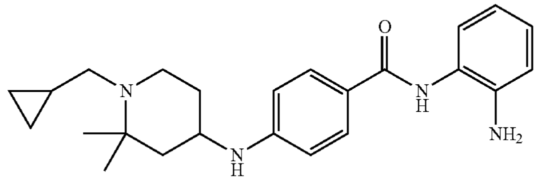 [SMILES: CC1(C)CC(Nc2ccc(C(=O)Nc3ccccc3N)cc2)CCN1CC1CC1] | N-(2-aminophenyl)-4-((1-(cyclopropylmethyl)-2,2-dimethylpiperidin-4-yl)amino)benzamide |

The compounds described herein also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8] each of which is incorporated herein by reference in their entireties.

Methods of Use

Provided herein are methods of inhibiting one or more HDAC enzymes (e.g., HDAC1 or HDAC2; e.g., HDAC3) or more than one HDAC (e.g., HDAC1 and HDAC2; e.g., HDAC1 and HDAC3; e.g., HDAC2 or HDAC3; e.g., HDAC1, HDAC2, and HDAC3) using a compound or a salt thereof as disclosed herein. In some embodiments, the methods can include contacting one or more HDAC enzymes (e.g., HDAC1 or HDAC2; e.g., HDAC3) in a sample with a compound or a salt thereof as disclosed herein. In other embodiments, the methods can include administering a compound or a salt thereof as disclosed herein to a subject (e.g., a mammal, such as a human).

A histone deacetylase (HDAC), as described herein, can be any polypeptide having features characteristic of polypeptides that catalyze the removal of the acetyl group (deacetylation) from acetylated target proteins. Features characteristic of HDAC enyzmes are known in the art (see, for example, Finnin et al., 1999, Nature, 401:188). Thus, an HDAC enzyme can be a polypeptide that represses gene transcription by deacetylating the ε-amino groups of conserved lysine residues located at the N-termini of histones, e.g., H3, H4, H2A, and H2B, which form the nucleosome. HDAC enyzmes also deacetylate other proteins such as p53, E2F, α-tubulin, and MyoD (see, for example, Annemieke et al., 2003, Biochem. J., 370:737). HDAC enzymes can also be localized to the nucleus and certain HDAC enzymes can be found in both the nucleus and also the cytoplasm.

Compounds of formula (I) described herein, e.g., compounds of formula (II) or compounds of formula (III), can interact with any HDAC enzyme. In some embodiments, the compounds of formula (I) described herein will have at least about 2-fold (e.g., at least about 5-fold, 10-fold, 15-fold, or 20-fold) greater activity to inhibit one or more class I HDAC enzymes (e.g., HDAC1, HDAC2, or HDAC3) as compared to one or more other HDAC enzymes (e.g., one or more HDAC enzymes of class IIa, IIb, or IV).

In some embodiments, a compound or a salt thereof as disclosed herein selectively inhibits HDAC3, e.g., selectively inhibits HDAC3 over HDAC1 and HDAC2 (e.g exhibiting 5-fold or greater selectivity, e.g. exhibiting 25-fold or greater selectivity). While not wishing to be bound by theory, it is believed that HDAC3-selective inhibitors can increase expression of frataxin, and can therefore be useful in the treatment of neurological conditions (e.g., neurological conditions associated with reduced frataxin expression, such as Friedreich's ataxia). It is also believed that HDAC3 inhibition plays an important role in memory consolidation (McQuown S C et al, J Neurosci 31 764 (2011)). Selective inhibitors of HDAC3 provide advantages for treatment of neurological conditions over the use of broad-spectrum HDAC inhibitors by reducing toxicities associated with inhibition of other HDAC enzymes. Such specific HDAC3 inhibitors can provide a higher therapeutic index, resulting in better tolerance by patients during chronic or long-term treatment.

In some further embodiments, compounds selectively inhibit HDAC1 and/or HDAC2 (e.g exhibiting 5-fold or greater selectivity, e.g. exhibiting 25-fold or greater selectivity). Inhibition of HDAC1 and/or 2 can be useful in treating cancer, or another disease as disclosed herein.

In some embodiments, a compound or a salt thereof as disclosed herein exhibits enhanced brain penetration. For example, brain/plasma ratios of greater than about 0.25 (e.g., greater than about 0.50, greater than about 1.0, greater than about 1.5, or greater than about 2.0) are observed when rats, mice, dogs, or monkeys are dosed with some of the compounds disclosed herein. In some embodiments, a compound or a salt thereof as disclosed herein selectively inhibits HDAC3, e.g., selectively inhibits HDAC3 over HDAC1 and HDAC2 (e.g, exhibiting 5-fold or greater selectivity, e.g. exhibiting 25-fold or greater selectivity) and exhibits enhanced brain penetration. In some embodiments, a compound described herein selectively inhibits HDAC1 and/or HDAC2, e.g., selectively inhibit HDAC1 and/or HDAC2 over HDAC3 (e.g exhibiting 5-fold or greater selectivity, e.g. exhibiting 25-fold or greater selectivity) and exhibits enhanced brain penetration.

Compounds with enhanced brain penetration are suitable for therapies targeting the brain (e.g., neurological conditions such as Friedreich's ataxia, myotonic dystrophy, spinal muscular atrophy, fragile X syndrome, Huntington's disease, spinocerebellar ataxia, Kennedy's disease, amyotrophic lateral sclerosis, spinal and bulbar muscular atrophy, and Alzheimer's disease; a memory impairment condition, frontotemportal dementia; post-traumatic stress disorder; a drug addiction).

Provided herein are methods of treating a disease or disorder mediated by HDAC in a subject (e.g., a mammal, such as a human) in need thereof, which include administering a compound or a salt thereof as disclosed herein to the subject.

Further provided herein are methods of preventing a disease or disorder mediated by HDAC in a subject (e.g., a mammal, such as a human) in need thereof. Prevention can include delaying the onset of or reducing the risk of developing, a disease, disorder, or condition or symptoms thereof.

The disclosure further provides a method of treating a cancer in patient in need thereof, comprising administering a therapeutically effective amount of an HDAC inhibitor as described herein, or salt thereof. In some embodiments, the cancer is a solid tumor, neoplasm, carcinoma, sarcoma, leukemia, or lymphoma. In some embodiments, leukemias include acute leukemias and chronic leukemias such as acute lymphocytic leukemia (ALL), acute myeloid leukemia, chronic lymphocytic leukemia (CLL), chronic myelogenous leukemia (CML) and Hairy Cell Leukemia; lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), Hodgkin's disease and non-Hodgkin's lymphomas, large-cell lymphomas, diffuse large B-cell lymphoma (DLBCL); Burkitt's lymphoma; primary central nervous system (CNS) lymphoma; multiple myeloma; childhood solid tumors such as brain tumors, neuroblastoma, retinoblastoma, Wilm's tumor, bone tumors, and soft-tissue sarcomas, common solid tumors of adults such as head and neck cancers (e.g., oral, laryngeal and esophageal), genitor-urinary cancers (e.g., prostate, bladder, renal, uterine, ovarian, testicular, rectal and colon), lung cancer, breast cancer.

In some embodiments, the cancer is (a) Cardiac: sarcoma (angiosarcoma, fibrosarcoma, rhabdomyosarcoma, liposarcoma), myxoma, rhabdomyoma, fibroma, lipoma and teratoma; (b) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; (c) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); (d) Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (e) Liver: hepatoma (hepatocellular carcinoma), cholangiocarcinoma, hepatoblastoma, angiosarcoma, hepatocellular adenoma, hemangioma; (f) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; (g) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord (neurofibroma, meningioma, glioma, sarcoma); (h) Gynecological: uterus (endometrial carcinoma), cervix (cervical carcinoma, pre-tumor cervical dysplasia), ovaries (ovarian carcinoma, serous cystadenocarcinoma, mucinous cystadenocarcinoma), unclassified carcinoma (granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma), embryonal rhabdomyosarcoma, fallopian tubes (carcinoma); (i) Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); (j) Skin: malignant melanoma, basal cell carcinoma, squamous cell carcinoma, Karposi's sarcoma, moles dysplastic nevi, lipoma, angioma, dermatofibroma, keloids, psoriasis; and (k) Adrenal glands: neuroblastoma conditions.

In another aspect, provided is a method of treating an inflammatory disorder in patient in need thereof, comprising administering a therapeutically effective amount of a compound of formula (I) (e.g., formula (II) or formula (III)) as described herein, or salt thereof. In some embodiments, the inflammatory disorder is an acute and chronic inflammatory disease, autoimmune disease, allergic disease, disease associated with oxidative stress, and diseases characterized by cellular hyperproliferation. Non-limiting examples are inflammatory conditions of a joint including rheumatoid arthritis (RA) and psoriatic arthritis; inflammatory bowel diseases such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs, ischemic injury, including cerebral ischemia (e.g., brain injury as a result of trauma, epilepsy, hemorrhage or stroke, each of which may lead to neurodegeneration); HIV, heart failure, chronic, acute or malignant liver disease, autoimmune thyroiditis; systemic lupus erythematosus, Sjorgren's syndrome, lung diseases (e.g., ARDS); acute pancreatitis; amyotrophic lateral sclerosis (ALS); Alzheimer's disease; cachexia/anorexia; asthma; atherosclerosis; chronic fatigue syndrome, fever; diabetes (e.g., insulin diabetes or juvenile onset diabetes); glomerulonephritis; graft versus host rejection (e.g., in transplantation); hemorrhagic shock; hyperalgesia: inflammatory bowel disease; multiple sclerosis; myopathies (e.g., muscle protein metabolism, esp. in sepsis); osteoarthritis; osteoporosis; Parkinson's disease; pain; pre-term labor; psoriasis; reperfusion injury; cytokine-induced toxicity (e.g., septic shock, endotoxic shock); side effects from radiation therapy, temporal mandibular joint disease, tumor metastasis; or an inflammatory condition resulting from strain, sprain, cartilage damage, trauma such as burn, orthopedic surgery, infection or other disease processes.

Allergic diseases and conditions, include but are not limited to respiratory allergic diseases such as asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies, and the like.

In another aspect, provided is a method of preventing or treating a memory-related disorder in patient in need thereof, comprising administering a therapeutically effective amount of a compound of formula (I) (e.g., formula (II) or formula (III)) or salt thereof as described herein. Compounds of formula (I) (e.g., formula (II) or formula (III)) can be used to treat patients with memory impairments associated with direct cognitive disorders such as amnesia, dementia and delirium, frontotemporal dementia; anxiety disorders such as phobias, panic disorders, psychosocial stress (e.g. as seen in disaster, catastrophe or violence victims), obsessive-compulsive disorder, generalized anxiety disorder and post-traumatic stress disorder; mood disorders such as depression and bipolar disorder; and psychotic disorders such as schizophrenia and delusional disorder. Memory impairment, a hallmark of neurodegenerative diseases such as, but not limited to, Parkinson's, Alzheimer's, Huntington's, amyotrophic lateral sclerosis (ALS), spinocerebellar ataxia, as well as aging, can also be treated by using compounds of formula (I) (e.g., formula (II) or formula (III)) or salt thereof. In addition, compounds disclosed can be used to treat drug addiction through extinction of drug-seeking behavior.

HDAC inhibitors, e.g., HDAC1 and/or HDAC 2 selective inhibitors, may also be useful to treat sickle cell disease (SCD) and β-thalassemia (bT). They may also be useful in treating mood disorders or brain disorders with altered chomatin-mediated neuroplasticity (Schoreder, et al., PLoS ONE 8(8): e71323 (2013)).

In another aspect, provided is a method of preventing or treating a hemoglobin disorder in patient in need thereof, comprising administering a therapeutically effective amount of a compound of formula (I) (e.g., formula (II) or formula (III)) as described herein, or salt thereof. Compounds of formula (I) (e.g., formula (II) or formula (III)) can be used to treat patients with sickle cell anemia or β-thalassemia. In various embodiments, the compound is a selective HDAC1 and/or HDAC 2 inhibitor and is used to prevent or treat the hemoglobin disorder (e.g., sickle cell anemia or β-thalassemia).

Further provided is a method of preventing or treating a mood disorder or brain disorders with altered chomatin-mediated neuroplasticity in patient in need thereof, comprising administering a therapeutically effective amount of a compound of formula (I) (e.g., formula (II) or formula (III)) as described herein, or salt thereof. Compounds of formula (I) (e.g., formula (II) or formula (III)) can be used to treat patients with a mood disorder.

In a further aspect, this application features methods of treating a neurological condition (e.g., Friedreich's ataxia (FRDA), myotonic dystrophy, spinal muscular atrophy, fragile X syndrome, Huntington's disease, a spinocerebellar ataxia, Kennedy's disease, amyotrophic lateral sclerosis, Niemann Pick, Pitt Hopkins, spinal and bulbar muscular atrophy, Alzheimer's disease or schizophrenia, bipolar disorder, and related diseases) that include administering a compound of formula (I) (e.g., formula (II) or formula (III)) described herein or salt thereof to a patient having a neurological condition.

In another aspect, provided herein is the use of a compound of formula (I) (e.g., formula (II) or formula (III)) described herein or salt thereof in the preparation of a medicament for the treatment or prevention of a neurological condition (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, Niemann Pick, Pitt Hopkins, spinal and bulbar muscular atrophy, or Alzheimer's disease); a memory-affecting condition or disease, a cancer; or an inflammatory disorder, or a *Plasmodium falciparum* infection (e.g., malaria).

Further provided herein method of using a compound or a salt thereof as disclosed herein to inhibit class I histone deacetylases, wherein this inhibition results in an in vitro increased frataxin mRNA expression in Friedreich's ataxia patient peripheral blood mononuclear cells (PBMCs). In other embodiments compounds disclosed herein inhibit in vitro proliferation of colorectal cancer cells in a dose-dependent fashion. In further embodiments compounds disclosed herein increase long term memory in vivo using the novel object recognition paradigm.

In a further aspect, provide herein is a kit for the treatment or prevention of a disorder selected from a neurological disorder (e.g., Friedreich's ataxia, myotonic dystrophy, spinal muscular atrophy, fragile X syndrome, Huntington's disease, a spinocerebellar ataxia, Kennedy's disease, amyotrophic lateral sclerosis, spinal and bulbar muscular atrophy, or Alzheimer's disease), a memory-affecting condition or disease, a cancer, an inflammatory disorder, or a *Plasmodium falciparum* infection (e.g., malaria) in a patient in need thereof, comprising (i) a compound of formula (I) (e.g., formula (II) or formula (III)) described herein or a salt thereof; and (ii) instructions comprising a direction to administer said compound to said patient.

In another aspect, provided are methods of treating a neurological condition (e.g., Friedreich's ataxia, myotonic dystrophy, spinal muscular atrophy, fragile X syndrome, Huntington's disease, spinocerebellar ataxias, Kennedy's disease, amyotrophic lateral sclerosis, spinal and bulbar muscular atrophy, or Alzheimer's disease) that include performing any of the above methods, formulating the candidate compound in a pharmaceutical composition, and administering the pharmaceutical composition to a patient having a neurological condition.

HDAC inhibitors have been shown to have antimalarial activity (Andrews, et al., 2000, Int. J. Parasitol., 30:761-768; Andrews, et al., Antimicrob. Agents Chemother., 52:1454-61). The present disclosure provides methods of treating a *Plasmodium falciparum* infection (e.g., malaria) in a patient in need thereof.

HDAC inhibitors may also be useful to treat infectious disease such as viral infections. For example, treatment of HIV infected cells with HDAC inhibitors and anti-retroviral drugs can eradicate virus from treated cells (Blazkova, J., et al J Infect Dis. 2012 Sep. 1; 206(5):765-9; Archin, N. M., et al Nature 2012 Jul. 25, 487(7408):482-5). The present disclosure provides methods of treating a HIV infection in need thereof.

Pharmaceutical Compositions

HDAC inhibitors as disclosed herein can be administered neat or formulated as pharmaceutical compositions. Pharmaceutical compositions include an appropriate amount of the HDAC inhibitor in combination with an appropriate carrier and optionally other useful ingredients.

Thus, provided herein are pharmaceutical compositions comprising a compound described herein and one or more pharmaceutically acceptable carriers. The pharmaceutical compositions are administered to a subject in need thereof by any route which makes the compound bioavailable. In one embodiment, the composition is a solid formulation adapted for oral administration. In another embodiment, the composition is a tablet, powder, or capsule; or the composition is a tablet. In one embodiment, the composition is a liquid formulation adapted for oral administration. In one embodiment, the composition is a liquid formulation adapted for parenteral administration. In another embodiment, the composition is a solution, suspension, or emulsion; or the composition is a solution. In another embodiment, solid form compositions can be converted, shortly before use, to liquid form compositions for either oral or parenteral administration. These particular solid form compositions are provided in unit dose form and as such are used to provide a single liquid dosage unit. These and other pharmaceutical compositions and processes for preparing the same are well known in the art. (See, for example, Remington: The Science and Practice of Pharmacy (D. B. Troy, Editor, 21st Edition, Lippincott, Williams & Wilkins, 2006).

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

The compounds and compositions described herein may be administered initially in a suitable dosage that may be adjusted as required, depending on the desired clinical response. In certain embodiments, the compounds are administered to a subject at a daily dosage of between 0.01 to about 50 mg/kg of body weight. In other embodiments, the dose is from 1 to 1000 mg/day. In certain embodiments, the daily dose is from 1 to 750 mg/day; or from 10 to 500 mg/day.

In another embodiment, the pharmaceutical composition is in unit dosage form. The composition can be subdivided into unit doses containing appropriate quantities of the active component(s). The unit dosage form can be a tablet, capsule, or powder in a vial or ampule, or it may be the appropriate number of any of these in a packaged form. The unit dosage form can be a packaged form, the package containing discrete quantities of composition such as packeted tablets, capsules, or powders in vials or ampules. The quantity of active compound(s) in a unit dose of the composition may be varied or adjusted from about 1 mg to about 100 mg, or from about 1 mg to about 50 mg, or from about 1 mg to about 25 mg, according to the particular application.

General Synthesis of Compounds of Formula (I)

Compounds of the present disclosure can be conveniently prepared in accordance with the procedures outlined in the Examples section, from commercially available starting materials, compounds known in the literature, or readily prepared intermediates, by employing conventional synthetic methods and procedures known to those skilled in the art. Conventional synthetic methods and procedures for the preparation of organic molecules and functional group transformations and manipulations can be readily obtained from the relevant scientific literature or from standard textbooks in the field. It will be appreciated that, where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Abbreviations used herein include the following:

| Abbreviation | Meaning |
| --- | --- |
| aq. | aqueous |
| Boc | tert-butoxycarbonyl |
| BSA | bis(trimethylsilyl)acetamide |
| CBz | benzyloxycarbonyl |
| conc | concentrated |
| DCM | dichloromethane |
| DEAD | diethyl azodicarboxylate |
| DIPEA | diisoproylethylamine |
| DMF | dimethylformamide |
| DMP | Dess-Martin periodinane |
| DMSO | dimethyl sulfoxide |
| eq. or equiv. | equivalent |
| g | gram |
| h | hours |
| HATU | O-(7-azabenzotriazol-1-yl)-N,N,N',N'-tetramethyluronium hexafluorophosphate |
| HCl | hydrochloric acid |
| HPLC | high performance liquid chromatography |
| IPA | isopropanol |
| kg | kilogram |
| LC-MS | liquid chromatography - mass spectrometry |
| m. | minute |
| MCPBA | meta-chloroperoxybenzoic acid |
| MeOH | methanol |
| mg | milligram |
| mHz | megahertz |
| min | minute |
| mL | milliliter |
| μL | microliter |
| μM | micromole |
| mmol | millimole |
| MS | mass spectrometry |
| MTBE | methyl tert-butyl ether |
| NMR | nuclear magnetic resonance |
| OAc | acetate |
| ppm | parts per million |
| rt or RT | room temperature |
| sat | saturated |
| TBDMS | tert-butyldimethylsilyl |
| TEA | triethylamine |
| TES | triethylsilane |
| TFAA | trifluoroacetic anhydride |
| THF | tetrahydrofuran |
| TLC | thin layer chromatography |
| UV | ultraviolet |

Compounds of formula (I) where Z=O can be prepared according to the steps described in Scheme A.

Scheme A

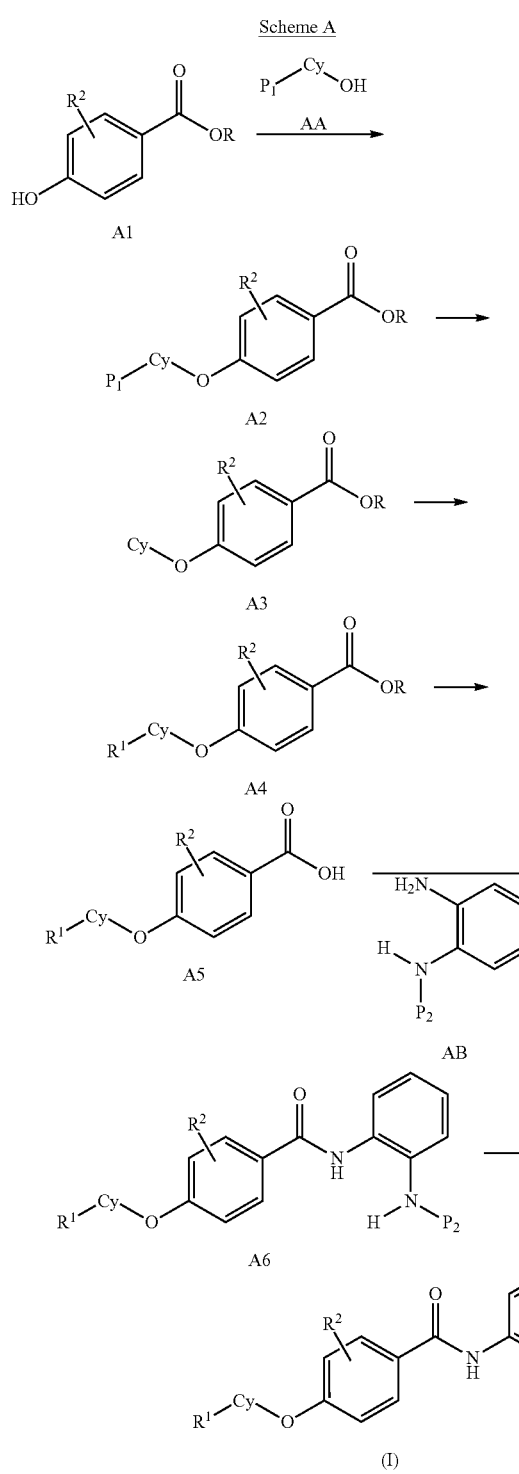

adding and removing them are well known to those skilled in the art and can be found, for example, in P. G. M. Wuts and T. W. Greene, 2006, Greene's Protective Groups in Organic Synthesis, Fourth Edition, John Wiley & Sons, Inc., Hoboken, N.J., USA. The ring nitrogen on Intermediate A3 can be derivatized by adding $R^1$ substituents to generate Intermediate A4 using such well known methods as acylation, alkylation, reductive amination, or displacement reactions. Saponification of the benzoate ester Intermediate A4 can generate the corresponding acid Intermediate A5, which can be reacted with Intermediate AB to generate Intermediate A6. Alternatively, Intermediate A4 can be reacted directly with Intermediate AB to generate Intermediate A6. Additionally, Intermediate AB can be used in its unprotected form, as the free amine, where $P_2$ is replaced by a hydrogen atom, to generate Intermediate A6 with the corresponding unprotected amino group. The coupling of Intermediate AB with the appropriate phenyl ester can be introduced at any earlier step in the synthesis. Intermediate A6 can be deprotected by well-known methods to generate compounds of formula (I).

Compounds of formula (I) where $Z=NR^3$ can be prepared according to the steps described in Scheme B.

Scheme B

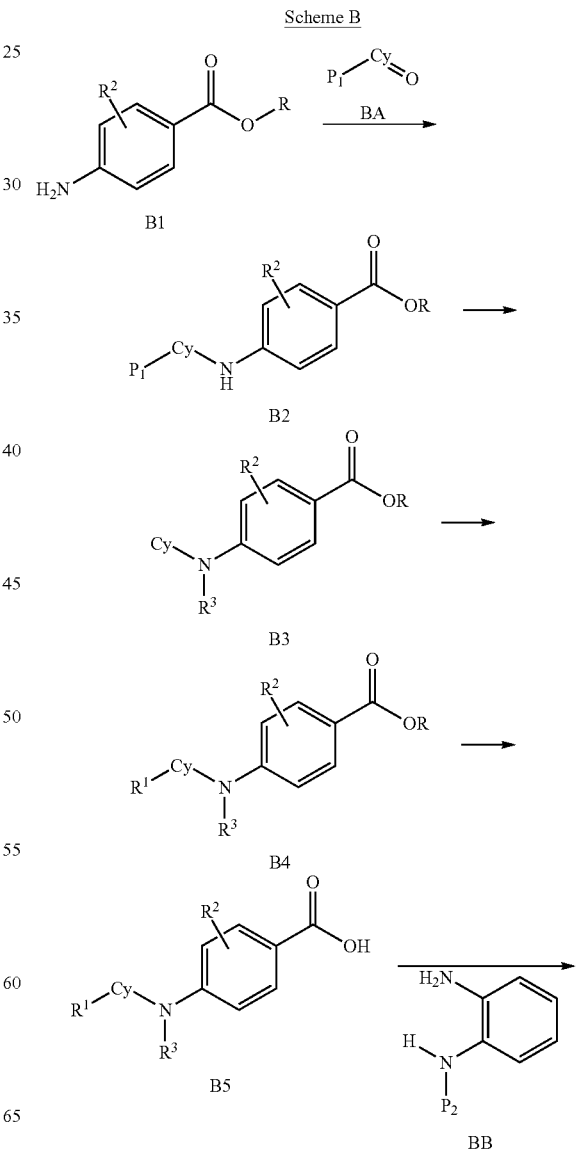

Intermediate AA ($P_1$-Cy-OH, where Cy represents ring A optionally substituted with $R^4$, and $P_1$ is a nitrogen-protecting group bonded to the ring nitrogen of ring A) can be obtained from commercial sources, or can be prepared by protecting the corresponding heterocycloalkyl alcohol (Cy-OH) with a nitrogen-protecting group by various methods. Intermediate AA can be coupled with Intermediate A1 (where R is alkyl) by known methods, such as Mitsunobu coupling, to obtain Intermediate A2. The $P_1$ protecting group on Intermediate A2 can be removed to generate Intermediate A3. Nitrogen protecting groups $P_1$ and $P_2$, and methods of

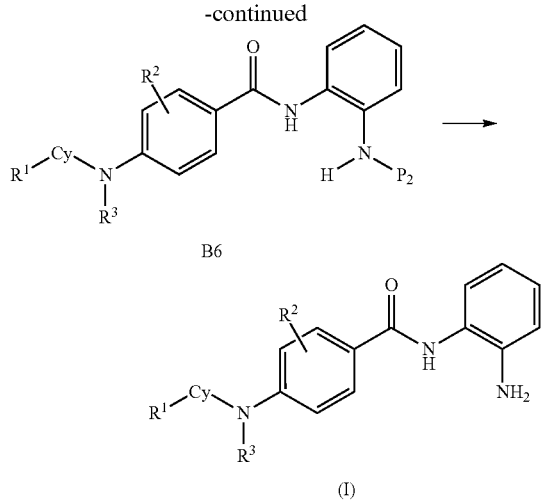

B6

(I)

Intermediate BA ($P_1$-Cy=O, where Cy represents ring A optionally substituted with $R^4$, and with a carbonyl on one of the ring carbon atoms, and $P_1$ is a nitrogen-protecting group bonded to the ring nitrogen of ring A) can be obtained from commercial sources, or can be prepared by methods known to those skilled in the art. Intermediate BA can be coupled with aromatic amine Intermediate B1 (where R is alkyl) by various known methods such as a reductive amination to generate protected Intermediate B2. The $P_1$ protecting group on Intermediate B2 can be removed to generate Intermediate B3. Nitrogen protecting groups $P_1$ and $P_2$, and methods of adding and removing them are well known to those skilled in the art and can be found, for example, in P. G. M. Wuts and T. W. Greene, 2006, Greene's Protective Groups in Organic Synthesis, Fourth Edition, John Wiley & Sons, Inc., Hoboken, N.J., USA. The ring nitrogen on Intermediate B3 can be derivatized by adding $R^1$ substituents to generate Intermediate B4 using such well known methods as acylation, alkylation, reductive amination, or displacement reactions. Intermediate B2 can be functionalized at the anilino nitrogen by $R^3$ substituents to generate Intermediate B3 (where Z=$NR^3$) by using known methods such as acylation, alkylation, reductive amination, and displacement prior to deprotection of Intermediate B2 in step 2. Saponification of the benzoate ester Intermediate B4 can generate the corresponding acid Intermediate B5, which can be reacted with Intermediate BB, to generate Intermediate B6. Alternatively, Intermediate B4 can be reacted directly with Intermediate BB to generate Intermediate B6. Additionally, Intermediate BB can be used in its unprotected form, as the free amine, where $P_2$ is replaced by a hydrogen atom, to generate Intermediate B6 with the corresponding unprotected amino group. The coupling of Intermediate BB with the appropriate phenyl ester can be introduced at any earlier step in the synthesis. Intermediate B6 can be deprotected by well-known methods to generate compounds of formula (I).

EXAMPLES

General Procedures for Compounds 1-6:
General Procedure for Boc-Deprotection:
To a stirred solution of Boc (tert-butoxycarbonyl) protected compound (1 eq) in dioxane:methanol (4:1, 5 vol), 4N HCl in dioxane (3 vol) was added and the reaction mixture was stirred at room temperature. The progress of the reaction was monitored by TLC. After completion, the reaction mixture was evaporated to dryness (if the compound precipitated, it was then filtered and further purified). The crude product was triturated with ether/pentane/MTBE or purified by prep HPLC to afford the title compound.

General Procedure for N-Alkylation:
Procedure A:
To a stirred solution of amine substrate (1 eq) and cesium carbonate/potassium carbonate (3 eq) in DMF (10 vol), corresponding alkyl halide (1.1 eq) was added. The reaction mixture was heated at 80° C. for 5 h to 30 h. The progress of the reaction was monitored by TLC. After completion, the reaction mixture was poured into ice-water and extracted with ethyl acetate. The combined organic extracts were washed with water, brine, dried over anhydrous $Na_2SO_4$, filtered and concentrated under reduced pressure to provide a crude residue which was purified by silica gel column chromatography.

Procedure B:
To a solution of amine substrate (1 eq) in 5 vol of ethanol was added TEA (3 eq) followed by 2, 2-dimethyloxirane (2.5 eq) at room temperature and the reaction mixture was heated at 90° C. for 4 h. The progress of the reaction was monitored by TLC. After completion, the reaction mixture was allowed to cool, and then concentrated to give a crude compound which was purified by Combiflash chromatography/silica gel chromatography.

General Procedure for Ester Hydrolysis:
To a stirred solution of ester (1 eq) in methanol:water (1:1), LiOH/NaOH (2 eq) in minimum amount of water was added and the reaction mixture was stirred at room temperature (for certain compounds, heating at reflux is required). The progress of the reaction was monitored by TLC. After completion, the reaction mixture was diluted with ethyl acetate and the aqueous layer was separated. The aqueous layer was acidified with 1N HCl, and the resulting solid was filtered and dried to afford the desired acid. The crude acid product was used as such for the next step without further purification.

General Procedure for Amide Coupling:
Procedure A:
To a mixture of acid compound (1 eq) and HATU (1.5 eq) in DMF, DIPEA (2.5 eq) was added, and the reaction mixture was stirred at room temperature for 10 min. The respective amine (1.2 eq) was added slowly and the reaction mixture was further stirred for 2 h up to 30 h at a desired temperature between room temperature to 80° C. The progress of the reaction was monitored by TLC. After completion, water was added and extracted with ethyl acetate. The combined organic extracts were dried over anhydrous $Na_2SO_4$ and evaporated under reduced pressure. The crude product was purified by column chromatography/preparative HPLC to afford the desired product.

Procedure B:
To a mixture of acid compound (1 eq) and HATU (1.5 eq) in acetonitrile, pyridine (10 eq) was added, and the reaction mixture was stirred at room temperature for 10 min. The respective amine (1.2 eq) was added slowly and the reaction mixture was further stirred at room temperature for 2 h and then heated at 80° C. overnight. The progress of the reaction was monitored by TLC. After completion, acetonitrile was removed under vacuum, and water was added to the residue and the resultant mixture was extracted with ethyl acetate. The combined organic extracts were dried over anhydrous $Na_2SO_4$ and evaporated under reduced pressure. The crude product was purified by column chromatography/preparative HPLC to afford the desired product.

Synthesis of N-(2-aminophenyl)-4-((1-(cyclopropylmethyl)piperidin-4-yl)oxy)benzamide (Compound 1)

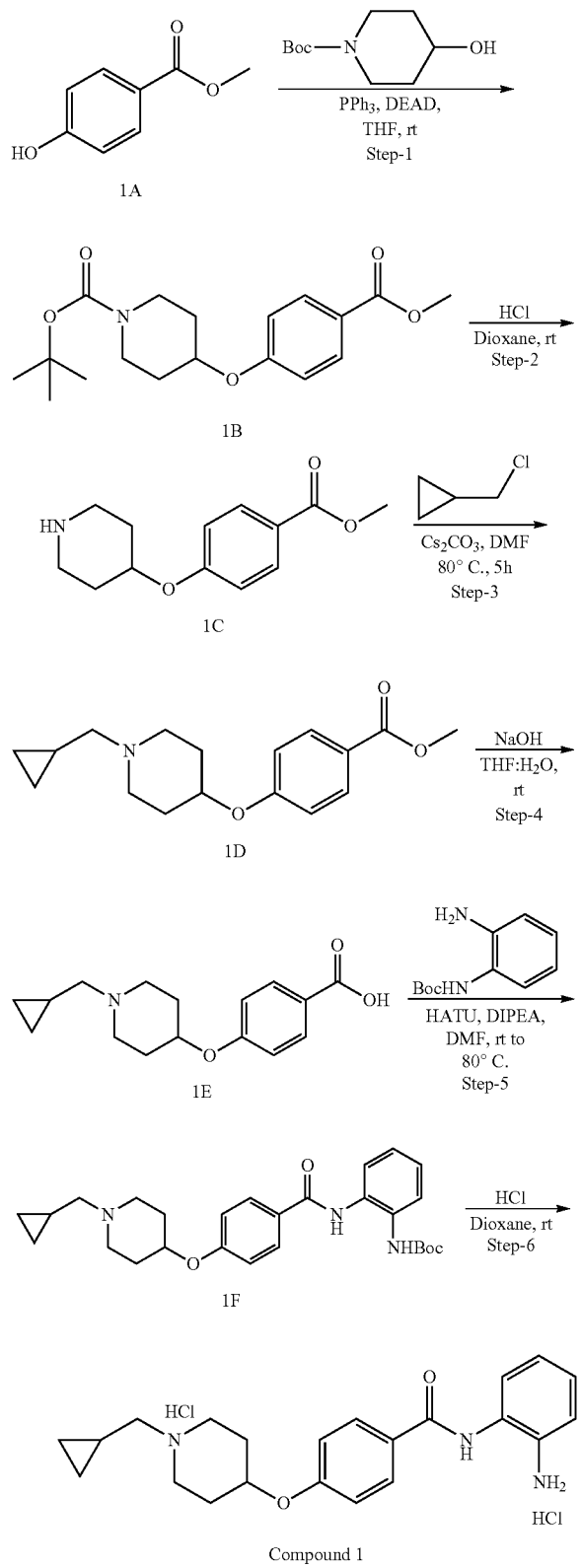

Compound 1

Step-1: Synthesis of Tert-Butyl 4-(4-(methoxycarbonyl)phenoxy)piperidine-1-carboxylate (1B)

To a solution of Compound 1A (22 g, 144 mmol, 1 eq) in 1 L of anhydrous THF was added tert-butyl 4-hydroxypiperidine-1-carboxylate (29 g, 144 mmol, 1 eq) followed by triphenyl phosphine (56 g, 213 mmol, 1.5 eq) and the reaction mixture was stirred at room temperature for 30 min. The reaction mixture was then cooled to 0° C., and DEAD (34 mL, 217 mmol, 1.5 eq) was added slowly (drop wise) for 1 h and then stirring was continued at room temperature for 16 h. The progress of the reaction was monitored by TLC. After completion, the volatiles were removed under vacuum, and 500 mL di-ethyl ether was added and the suspension was allowed to stir at 0° C. for 1-2 h. The above reaction mixture was then filtered through celite, the filtrate was concentrated and the crude compound was purified using silica gel column chromatography to afford Compound 1B. LCMS (m/z): 321.05 (M-15)+ and 236.05 (M-100)+.

Step-2: Synthesis of Methyl 4-(piperidin-4-yloxy)benzoate (1C)

The title compound was synthesized by following the general procedure described above for Boc-deprotection. $^1$H NMR (400 MHz, DMSO-$d_6$): δ 9.09 (s, 1H), 7.89 (d, J=8.8 Hz, 2H), 7.10 (d, J=8.8 Hz, 2H), 4.81-4.77 (m, 1H), 3.81 (s, 3H), 3.25-3.19 (m, 2H), 3.09-3.03 (m, 2H), 2.16-2.11 (m, 2H), 1.91-1.82 (m, 2H).

Step-3: Synthesis of Methyl 4-((1-(cyclopropylmethyl)piperidin-4-yl)oxy)benzoate (1D)

The title compound was synthesized by following the general procedure described above for N-alkylation. LCMS (m/z): 290.15 (M+1)+.

Step-4: Synthesis of 4-((1-(cyclopropylmethyl)piperidin-4-yl)oxy)benzoic Acid (1E)

The title compound was synthesized by following the general procedure described above for Ester Hydrolysis (NaOH was used as base). The crude material used as such in the next step. LCMS (m/z): 275.95 (M+1)+.

Step-5: Synthesis tert-butyl (2-(4-((1-(cyclopropylmethyl)piperidin-4-yl)oxy)benzamido) phenyl)carbamate (1F)

The title compound was synthesized by following the general Procedure B described above for Amide Coupling. LCMS (m/z): 466.35 (M+1)+.

Step-6: Synthesis of N-(2-aminophenyl)-4-((1-(cyclopropylmethyl)piperidin-4-yl)oxy)benzamide (Compound 1)

The title compound was synthesized by following the general procedure described above for Boc-Deprotection. $^1$H NMR (400 MHz, DMSO-$d_6$): δ 10.90-10.35 (m, 2H), 8.11-8.08 (m, 2H), 7.52-7.15 (m, 6H), 4.93-4.69 (m, 1H), 3.63-3.44 (m, 2H), 3.19-2.98 (m, 4H), 2.31-1.94 (m, 4H), 1.15-1.12 (m, 1H), 0.68-0.63 (m, 2H), 0.42-0.41 (m, 2H); LCMS Calculated for free base $C_{22}H_{27}N_3O_2$: 365.21; Observed (m/z): 366.15 (M+1)+.

Synthesis of N-(2-aminophenyl)-4-((1-(2-hydroxy-2-methylpropyl)piperidin-4-yl)oxy)benzamide (Compound 2)

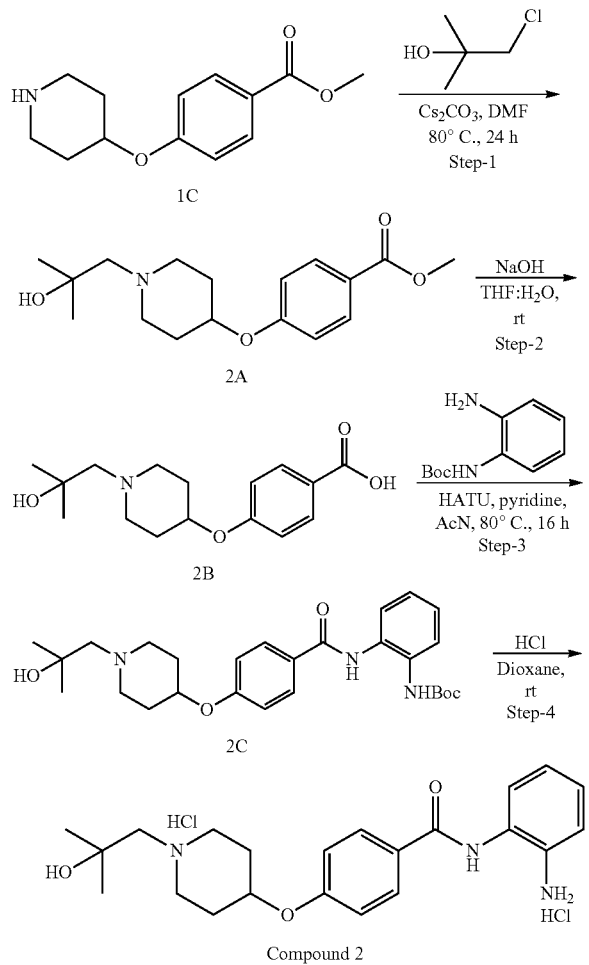

Step-1: Synthesis of Methyl 4-((1-(2-hydroxy-2-methylpropyl)piperidin-4-yl)oxy)benzoate (2A)

The title compound was synthesized by following the general Procedure A described above for N-alkylation utilizing Compound 1C. LCMS (m/z): 308.15 (M+1)$^+$.

Step-2: Synthesis of 4-((1-(2-hydroxy-2-methylpropyl)piperidin-4-yl)(methyl)amino)benzoic Acid (2B)

The title compound was synthesized by following the general procedure described above for Ester Hydrolysis (NaOH was used). The crude material used as such in the next step; LCMS (m/z): 294.10 (M+1)$^+$.

Step-3: Synthesis of Tert-Butyl (2-(4-((1-(2-hydroxy-2-methylpropyl)piperidin-4-yl)(methyl)amino) benzamido)phenyl)carbamate (2C)

The title compound was synthesized by following the general Procedure B described above for Amide Coupling. LCMS (m/z): 484.25 (M+1)$^+$.

Step-4: Synthesis of N-(2-aminophenyl)-4-((1-(2-hydroxy-2-methylpropyl) piperidin-4-yl)oxy)benzamide (Compound 2)

The title compound was synthesized by following the general described above for Boc-deprotection. $^1$H NMR (400 MHz, DMSO-d$_6$): δ 10.32 (s, 1H), 9.45 (brs, 1H), 8.11-8.09 (m, 2H), 7.51-7.13 (m, 6H), 4.88-4.74 (m, 1H), 3.68-3.47 (m, 3H), 3.29-3.15 (m, 4H), 2.36-1.99 (m, 4H), 1.28 (s, 6H); LCMS Calculated for free base C$_{22}$H$_{29}$N$_3$O$_3$: 383.22; Observed (m/z): 384.05 (M+1)$^+$.

Synthesis of N-(2-aminophenyl)-4-((1-(cyclopropylmethyl)piperidin-4-yl)amino) Benzamide (Compound 3)

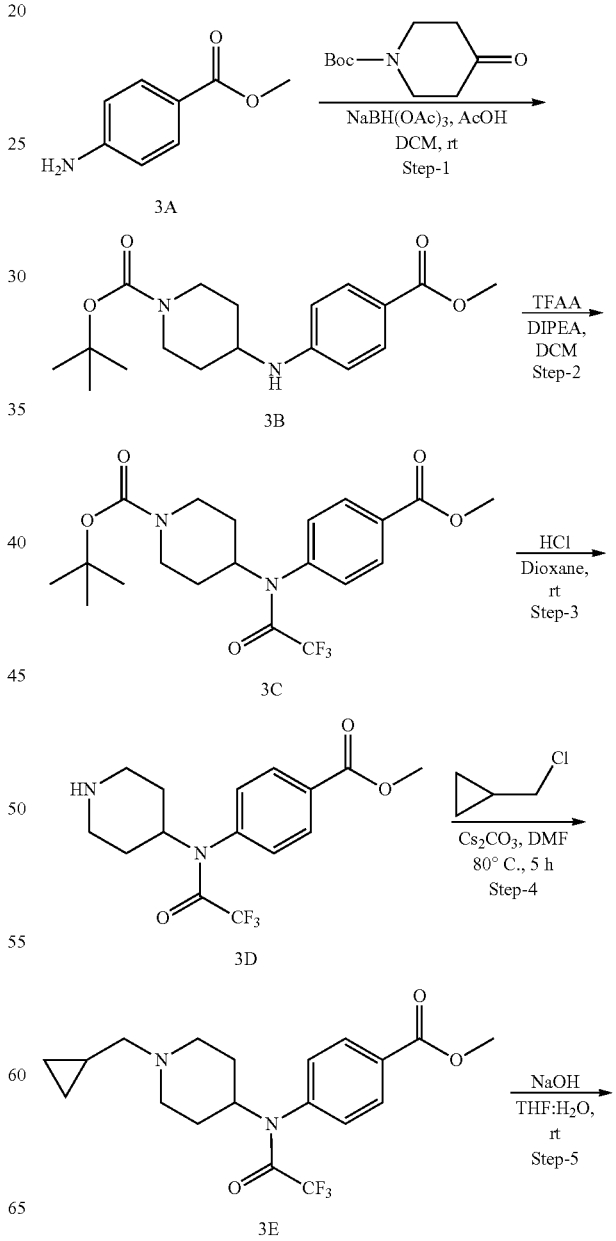

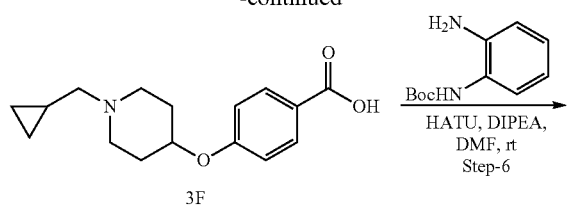

3F

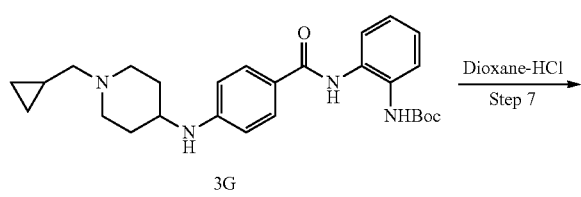

3G

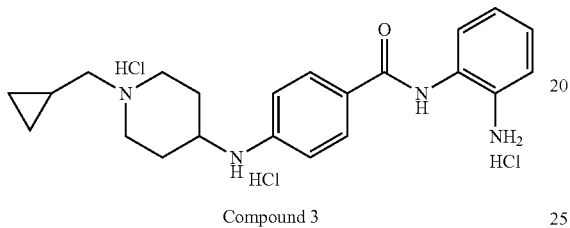

Compound 3

Step-1: Synthesis of Tert-Butyl 4-((4-(methoxycarbonyl)phenyl)amino) piperidine-1-carboxylate (3B)

To a solution of tert-butyl 4-oxo-1-piperidinecarboxylate (29.6 g, 148.8 mmol, 0.9 eq) and methyl 4-aminobenzoate (3A) (25 g, 165.3 mmol, 1 eq) in 250 mL of DCM was added acetic acid (56.67 mL, 991.8 mmol, 6 eq) at 0° C., and the reaction mixture was stirred for 30 min. To the reaction mixture was added NaBH(OAc)$_3$ (104.9 g, 495 mmol, 3 eq), and the mixture was allowed to stir at room temperature for 12 h. The progress of the reaction was monitored by TLC/LCMS. After completion, the reaction mixture was poured into aq. saturated sodium bicarbonate solution at 0° C. and extracted with DCM. The combined organic layers were washed with brine, dried over anhydrous Na$_2$SO$_4$, filtered and concentrated to give desired compound 3B which was used in the next step without further purification. LCMS (m/z): 375.10 (M+41)$^+$.

Step-2: Synthesis of Tert-Butyl 4-(2,2,2-trifluoro-N-(4-(methoxycarbonyl) phenyl)acetamido)piperidine-1-carboxylate (3C)

To a solution of compound 3B (34 g, 101.6 mmol, 1 eq) in 450 mL of DCM were added DIPEA (52.80 mL, 304.8 mmol, 3 eq) followed by TFAA (21.64 mL, 152.5 mmol, 1.5 eq) at 0° C. and the reaction mixture was allowed to stir at room temperature for 2 h. The progress of the reaction was monitored by TLC. After completion, the reaction mixture was allowed to cool; water was added and the reaction mixture was extracted with DCM. The combined organic layers were washed with brine, dried over anhydrous Na$_2$SO$_4$, filtered and concentrated to give a crude compound which was purified using flash silica gel (7% ethyl acetate in hexane) to provide compound 3C. LCMS (m/z): 330.70 (M-Boc)$^+$.

Step-3: Synthesis of Methyl 4-(2,2,2-trifluoro-N-(piperidin-4-yl)acetamido) Benzoate (3D)

The title compound was synthesized by following the general procedure described above for Boc-deprotection. The crude material used as such in the next step. LCMS (m/z): 330.90 (M+1)$^+$.

Step-4: Synthesis of Methyl 4-(N-(1-(cyclopropylmethyl)piperidin-4-yl)-2,2,2-trifluoroacetamido) Benzoate (3E)

The title compound was synthesized by following the general Procedure A described above for N-alkylation. LCMS (m/z): 385.15 (M+1)$^+$.

Step-5: Synthesis of 4-((1-(cyclopropylmethyl)piperidin-4-yl)amino)benzoic Acid (3F)

The title compound was synthesized by following the general procedure described above for Ester Hydrolysis (NaOH was used and the reaction mixture was heated at 75° C.). The crude material used as such in the next reaction. LCMS (m/z): 275.10 (M+1)$^+$.

Step-6: Synthesis of Tert-Butyl (2-(4-((1-(cyclopropylmethyl)piperidin-4-yl)amino)benzamido) phenyl) carbamate (3G)

The title compound was synthesized by following the general Procedure B described above for Amide Coupling. LCMS (m/z): 465.25 (M+1)$^+$.

Step-7: Synthesis of N-(2-aminophenyl)-4-((1-(cyclopropylmethyl)piperidin-4-yl)amino)benzamide (Compound 3)

The title compound was synthesized by following the general procedure described above for Boc-deprotection. $^1$H NMR (400 MHz, DMSO-d$_6$): δ 10.46 (brs, 1H), 10.19 (s, 1H), 7.91 (d, J=7.2 Hz, 2H), 7.55-7.29 (m, 4H), 6.77-6.69 (m, 2H), 3.59-2.95 (m, 7H), 2.14-2.11 (m, 2H), 1.86-1.79 (m, 2H), 1.12-1.08 (m, 1H), 0.65-0.63 (m, 2H), 0.40-0.39 (m, 2H); LCMS Calculated for free base C$_{22}$H$_{28}$N$_4$O: 364.23; Observed (m/z): 365.25 (M+1)$^+$.

Synthesis of N-(2-aminophenyl)-4-((1-(2-hydroxy-2-methylpropyl)piperidin-4-yl)amino)benzamide (Compound 4)

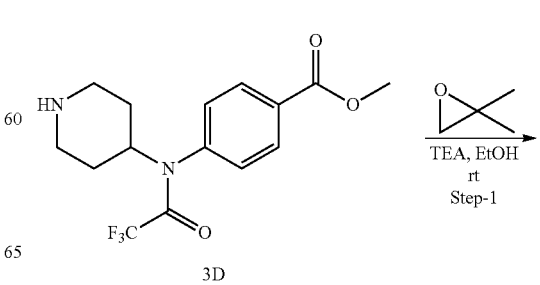

3D

-continued

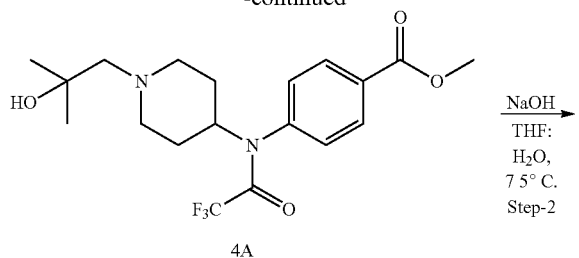
4A

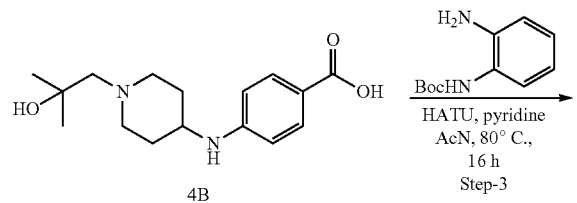
4B

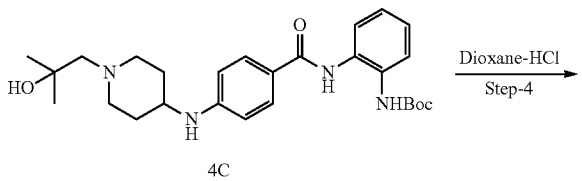
4C

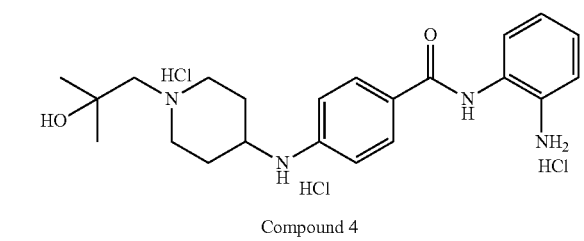
Compound 4

Step-1: Synthesis of Methyl 4-(2,2,2-trifluoro-N-(1-(2-hydroxy-2-methylpropyl)piperidin-4-yl)acet-amido)benzoate (4A)

To a solution of Compound 3D (5.9 g, 13.6 mmol, 1 eq) in 25 mL of ethanol was added TEA (5.7 mL, 40.8 mmol, 3 eq) followed by 2,2-dimethyloxirane (3.06 mL, 34 mmol, 2.5 eq) at room temperature and the reaction mixture was allowed to heat at 90° C. for 4 h. The progress of the reaction was monitored by TLC. After completion, the reaction mixture was allowed to cool. The reaction mixture was then concentrated to give crude compound which was purified using Combiflash chromatography to provide Compound 4A. LCMS (m/z): 403.15 (M+1)$^+$.

Step-2: Synthesis of 4-((1-(2-hydroxy-2-methylpropyl)piperidin-4-yl)amino) Benzoic Acid (4B)

The title compound was synthesized by following the general procedure described above for Ester Hydrolysis (NaOH was used). The reaction mixture was heated at 75° C. for 12 h. The crude compound was used as such in the next step. LCMS (m/z): 293.15 (M+1)$^+$.

Step-3: Synthesis of Tert-Butyl (2-(4-((1-(2-hydroxy-2-methylpropyl)piperidin-4-yl)(methyl)amino)benzamido)phenyl)carbamate (4C)

The title compound was synthesized by following the general Procedure B described above for Amide Coupling. LCMS (m/z): 483.30 (M+1)$^+$.

Step 4: Synthesis of N-(2-aminophenyl)-4-((1-(2-hydroxy-2-methylpropyl) piperidin-4-yl)amino) Benzamide (Compound 4)

The title compound was synthesized by following the general procedure described above for Boc-deprotection. $^1$H NMR (400 MHz, DMSO-d$_6$): δ 10.07 (s, 1H), 9.2 (brs, 1H), 7.89 (d, J=6.8 Hz, 2H), 7.47-7.29 (m, 4H), 6.75-6.69 (m, 2H), 3.75-3.10 (m, 8H), 2.10-1.61 (m, 4H), 1.28 (s, 6H); LCMS Calculated for free base C$_{22}$H$_{30}$N$_4$O$_2$: 382.24; Observed (m/z): 383.20 (M+1)$^+$.

Synthesis of N-(2-aminophenyl)-4-((1-(cyclopropyl-methyl)piperidin-4-yl)(methyl) amino)benzamide (Compound 5)

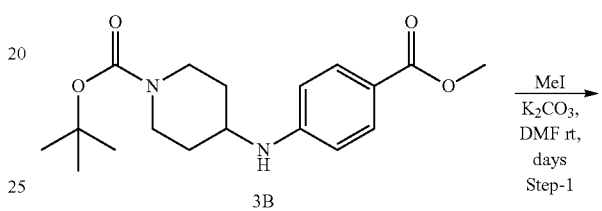
3B

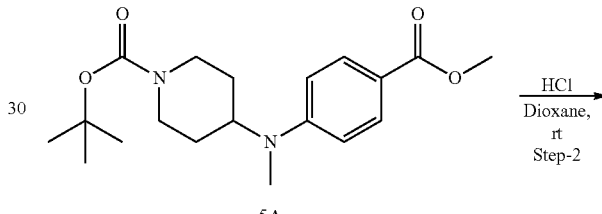
5A

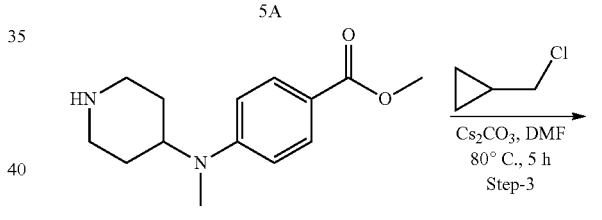
5B

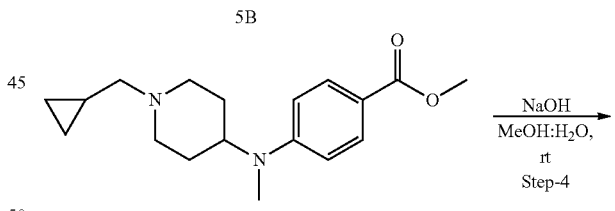
5C

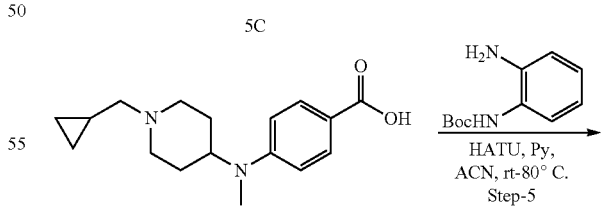
5D

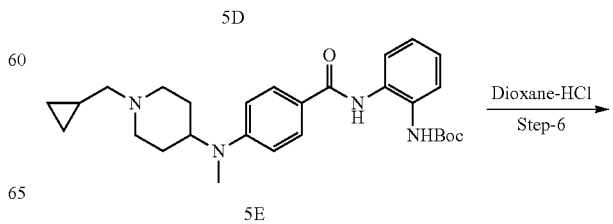
5E

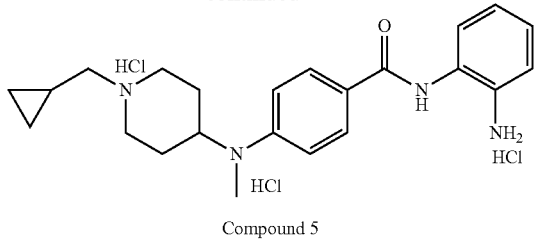

Compound 5

Step-1: Synthesis of Tert-Butyl 4-((4-(methoxycarbonyl)phenyl)(methyl)amino)piperidine-1-carboxylate (5A)

The title compound was synthesized by following the general Procedure A described above for N-alkylation utilizing Compound 3B. LCMS (m/z): 349.30 (M+1)$^+$.

Step-2: Synthesis of Methyl 4-(methyl(piperidin-4-yl)amino)benzoate (5B)

The title compound was synthesized by following the general procedure described above for Boc-deprotection. The reaction was monitored by TLC and the crude material was isolated and used in the next step without further purification.

Step-3: Synthesis of Methyl 4-((1-(cyclopropylmethyl)piperidin-4-yl)(methyl) amino)benzoate (5C)

The title compound was synthesized by following the general Procedure A described above for N-alkylation. LCMS (m/z): 303.34 (M+1)$^+$.

Step-4: Synthesis of 4-((1-(cyclopropylmethyl)piperidin-4-yl)(methyl) amino)benzoic Acid (5D)

The title compound was synthesized by following the general procedure described above for Ester Hydrolysis (NaOH was used). The crude material was isolated and used in the next step without further purification. LCMS (m/z): 289.20 (M+1)$^+$.

Step-5: Synthesis of Tert-Butyl (2-(4-((1-(cyclopropylmethyl)piperidin-4-yl)(methyl)amino) benzamido)phenyl)carbamate (5E)

The title compound was synthesized by following the general Procedure B described above for Amide Coupling. LCMS (m/z): 377.15 (M-Boc)$^+$.

Step-6: Synthesis of N-(2-aminophenyl)-4-((1-(cyclopropylmethyl)piperidin-4-yl)(methyl)amino) Benzamide (Compound 5)

The title compound was synthesized by following the general procedure described above for Boc-deprotection. The final compound was purified using prep-HPLC. $^1$H NMR (400 MHz, DMSO-d$_6$): δ 9.37 (s, 1H), 8.23 (m, 1H), 7.84 (d, J=8.4 Hz, 2H), 7.13 (d, J=7.6 Hz, 1H), 6.96-6.76 (m, 4H), 6.59 (d, J=7.6 Hz, 1H), 3.82-3.77 (m, 1H), 3.17 (d, J=9.6 Hz, 1H), 2.95-2.94 (m, 1H), 2.81 (s, 3H), 2.38-2.33 (m, 4H), 1.87-1.64 (m, 4H), 0.90-0.88 (m, 1H), 0.51-0.49 (m, 2H), 0.15-0.14 (m, 2H); LCMS Calculated for free base C$_{23}$H$_{30}$N$_4$O: 378.24; Observed (m/z): 379.21 (M+1)$^+$.

Synthesis of N-(2-aminophenyl)-4-((1-(2-hydroxy-2-methylpropyl)piperidin-4-yl)(methyl)amino) Benzamide (Compound 6)

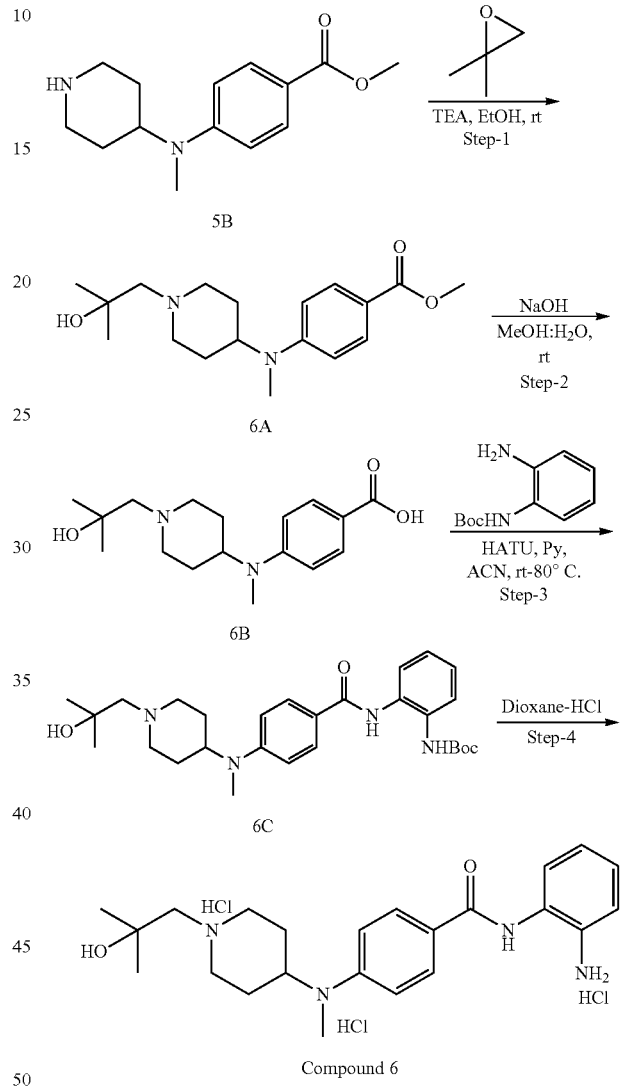

Compound 6

Step-1: Synthesis of Methyl 4-((1-(2-hydroxy-2-methylpropyl)piperidin-4-yl)(methyl)amino)benzoate (6A)

The title compound was synthesized by following the general Procedure B described above for N-alkylation utilizing Compound 5B. LCMS (m/z): 320.95 (M+1)$^+$.

Step-2: Synthesis of 4-((1-(2-hydroxy-2-methylpropyl)piperidin-4-yl)(methyl)amino)benzoic Acid (6B)

The title compound was synthesized by following the general procedure described above for Ester Hydrolysis (NaOH was used). The crude compound was used as such in the next step. LCMS (m/z): 307.33 (M+1)$^+$.

Step-3: Synthesis of Tert-Butyl (2-(4-((1-(2-hydroxy-2-methylpropyl)piperidin-4-yl)(methyl)amino) benzamido)phenyl)carbamate (6C)

The title compound was synthesized by following the general Procedure B described above for Amide Coupling. LCMS (m/z): 497.40 (M+1)⁺.

Synthesis of N-(2-aminophenyl)-4-((1-(2-hydroxy-2-methylpropyl)piperidin-4-yl)(methyl)amino) Benzamide (Compound 6)

The title compound was synthesized by following the general procedure described above for Boc-deprotection. $^1$H NMR (400 MHz, DMSO-$d_6$): δ 10.18 (s, 1H), 9.37-9.28 (m, 1H), 7.99 (d, J=9.2 Hz, 2H), 7.51 (d, J=7.6 Hz, 1H), 7.40-7.26 (m, 3H), 6.98-6.91 (m, 2H), 4.23-4.18 (m, 2H), 3.69-3.66 (m, 2H), 3.47-3.22 (m, 3H), 2.84 (3, 3H), 2.44-2.14 (m, 3H), 1.77-1.70 (m, 2H), 1.29 (s, 6H); LCMS Calculated for free base $C_{23}H_{32}N_4O_2$: 396.25; Observed (m/z): 397.25 (M+1)⁺.

Synthesis of Compounds 33-77 and 123-133

Synthesis of Compounds 33-77 and 123-133 are generally described in the following Scheme C:

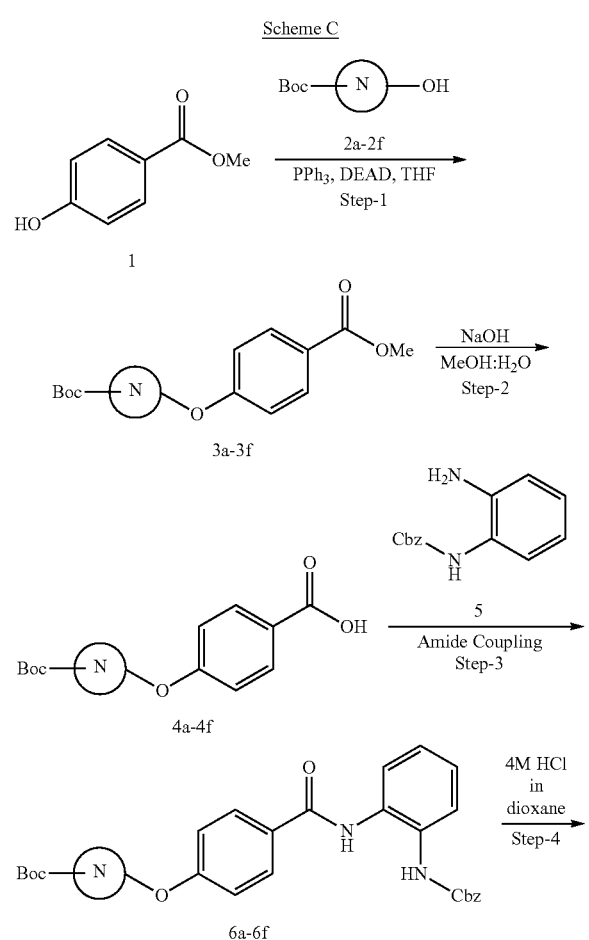
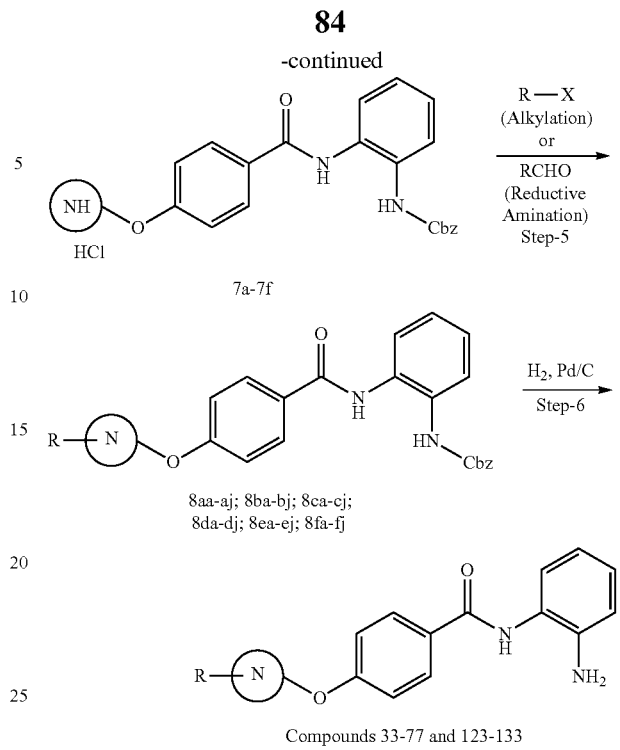
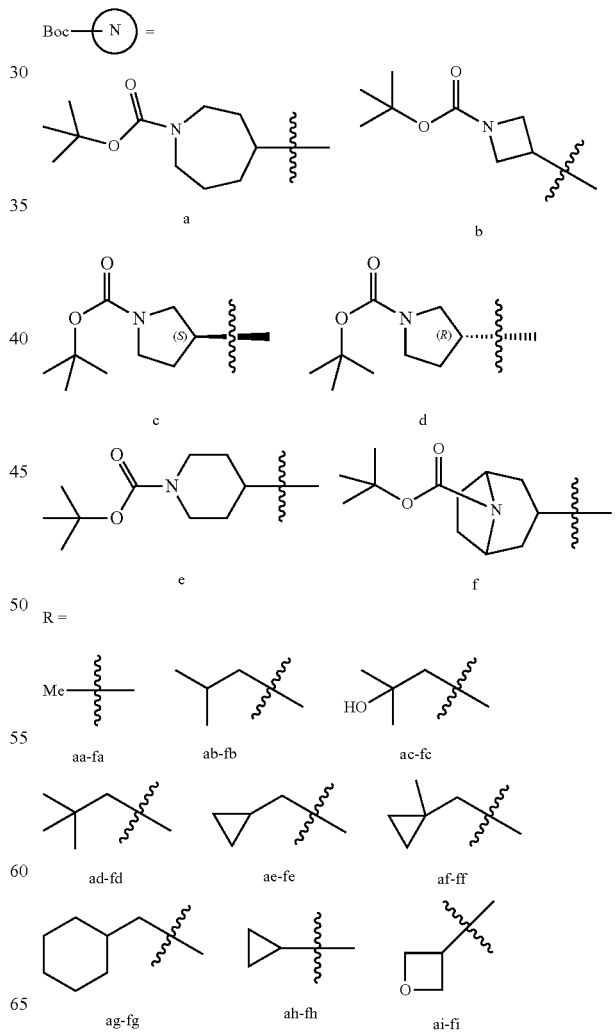

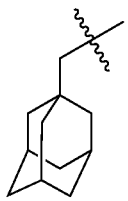

aj-fj

General Procedure for Mitsunobu Reaction:

To a solution of the ester (1 eq) in anhydrous THF was added the corresponding Boc-protected alcohol (1 eq), followed by triphenyl phosphine (1.5 eq). The reaction mixture was allowed to stir at room temperature for 30 min. The reaction mixture was cooled to 0° C., and DEAD (1.5 eq) was added slowly (drop wise) for 1 h and stirring was continued at room temperature for an additional 16 h. The progress of the reaction was monitored by TLC. After completion of the reaction, the volatiles were removed under vacuum, di-ethyl ether was added and the suspension was allowed to stir at 0° C. for 1-2 h. The reaction mixture was then filtered through a pad of celite and the filtrate was concentrated. The crude compound was purified using silica gel column chromatography to afford the desired compound.

General Procedure for Ester Hydrolysis:

To stirred solution of the ester in methanol:water (1:1) was added NaOH (1.5 eq) at room temperature and the reaction mixture was heated at 90° C. for 5 h. The progress of the reaction was monitored by TLC. After completion of the reaction, the reaction mixture was concentrated and the resulting residue was washed with diethyl ether. The residue was diluted with water and acidified using 1N HCl at 0° C. until pH of 7, the solid obtained was filtered, washed with water and dried under vacuum to provide the desired compound.

General Procedure for Amide Coupling:

Procedure A:

To a stirred solution of the acid (1 eq) and the corresponding amino compound (1.1 eq) in ACN, was added pyridine (5 eq) and HATU (1.5 eq) at room temperature. After stirring the reaction mixture at 80° C. for overnight, the reaction progress was monitored by TLC and LCMS. After completion of the reaction, the reaction mixture was concentrated and resulting residue was partitioned between water and ethyl acetate. The organic layer was separated, washed with water and 1N HCl to remove traces of excess amine dried over Na$_2$SO$_4$ and concentrated. The crude product was purified by silica gel column chromatography to provide the desired compound.

Procedure B:

To a stirred solution of the acid (1 eq) and the corresponding amino compound (1.1 eq) in DMF were added DIPEA (2 eq) and HATU (1.5 eq) at room temperature. The reaction mixture was stirred at ambient temperature for 12 h. The reaction progress was monitored by TLC and LCMS. After completion, the reaction mixture was concentrated and resulting residue was partitioned between water and ethyl acetate. The organic layer was separated, washed with water and 1% HCl, dried over Na$_2$SO$_4$ and concentrated. The crude was purified by silica gel column chromatography to provide the desired compound.

General Procedure for Boc-Deprotection:

To a stirred solution of Boc-protected compound (1 eq) in 1,4-dioxane was added 4M HCl in dioxane at room temperature. After completion of reaction, the reaction mixture was concentrated and the resulting residue was triturated with n-pentane and dried under vacuum to provide the desired compound.

General Procedure for Reductive Amination:

Procedure A:

To a stirred solution of the amino compound (1 eq) and the corresponding aldehyde (1.2 eq) in DCM was added acetic acid (6 eq) at room temperature followed by sodium triacetoxyborohydride (STAB) (3 eq). The reaction mixture was stirred at room temperature for 12 h. After completion of reaction, the reaction mixture was partitioned between DCM and water. The organic layers were separated, washed with water and brine, dried over Na$_2$SO$_4$ and evaporated to get crude product which was purified by silica gel column chromatography to provide the desired compound.

Procedure B:

To a stirred solution of the amino compound (1 eq) and corresponding aldehyde (1.2 eq) in DCE was added titanium tetra-isopropoxide (Ti(OiPr)$_4$) at room temperature. After 5 min. STAB (3 eq) was added and the mixture was heated at 60° C. for 12 h. The progress of the reaction was monitored by TLC and LCMS. After completion of reaction, the reaction mixture was diluted with DCM and the resulting mixture was filtered over a pad of celite. The filtrate was concentrated and the resulting residue was purified by silica gel column chromatography to provide the desired compound.

General Procedure for N-Alkylation:

Procedure A:

To a stirred solution of the amino compound (1 eq) and cesium carbonate/potassium carbonate (3 eq) in DMF (10 vol), corresponding alkyl halide (1.1 eq) was added. The reaction mixture was heated at 80° C. for 5 h to 30 h. The progress of reaction was monitored by TLC. After completion, the reaction mixture was poured into ice-water and extracted with ethyl acetate. The combined organic extracts were washed with water, brine, dried over anhydrous Na$_2$SO$_4$, filtered and concentrated under reduced pressure to provide a crude residue which was purified by silica gel column chromatography.

Procedure B:

To a solution of the amino compound (1 eq) in 5 volumes of ethanol was added TEA (3 eq) followed by 2,2-dimethyloxirane (2.5 eq) at room temperature and the reaction mixture was heated at 90° C. for 4 h. The progress of reaction was monitored by TLC. After completion, the reaction mixture was allowed to cool to ambient temperature and concentrated to provide a crude compound which was purified by Combiflash chromatography/flash column chromatography.

General Procedure for Cbz-Deprotection:

To a stirred solution of the benzyl compound (1 eq) in methanol, 10% Pd/C (10% w/w of substrate) was added and reaction mixture was stirred under hydrogen atmosphere (balloon pressure) at room temperature for 3 h. The progress of the reaction was monitored by TLC. After completion, the reaction mixture was filtered through a pad of celite and the filtrate was evaporated under reduced pressure to afford the title compound.

Step 1: Synthesis of Compounds 3a-3f

The title compounds were synthesized by following the general procedure described above for the Mitsunobu Reaction.

Step 2: Synthesis of Compound 4a-4f

The title compounds were synthesized by following the general procedure described above for the Ester Hydrolysis.

Step 3: Synthesis of Compounds 6a-6f

The title compounds were synthesized by following the general procedure described above for the Amide Coupling.

Step 4: Synthesis of Compound 7a-7f

The title compounds were synthesized by following the general procedure described above for the Boc Deprotection.

Step 5: Synthesis of Compounds 8aa-aj, 8ba-bj, 8ca-cj, 8da-dj, 8ea-ej, and 8fa-fj The title compounds were synthesized by following the general procedure described above for N-alkylation or Reductive Amination.

| No | Core Structure | R |
|---|---|---|
| 8aa | [azepane-N(R) linked via 4-O to phenyl-C(=O)NH-phenyl-NH-Cbz] | Me |
| 8ab | | isobutyl |
| 8ac | | 2-hydroxy-2-methylpropyl |
| 8ad | | neopentyl |
| 8ae | | cyclopropylmethyl |
| 8af | | (1-methylcyclopropyl)methyl |
| 8ag | | cyclohexylmethyl |
| 8ah | | cyclopropyl |
| 8ai | | oxetan-3-yl |
| 8ba | [azetidine-N(R) linked via 3-O to phenyl-C(=O)NH-phenyl-NH-Cbz] | Me |
| 8bb | | isobutyl |

-continued
| No | Core Structure | R |
|---|---|---|
| 8bc | | 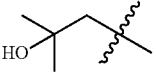 |
| 8bd | |  |
| 8be | | 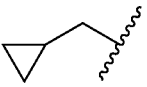 |
| 8bf | | 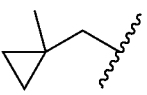 [SMILES: *CC1(C)CC1] |
| 8bg | | 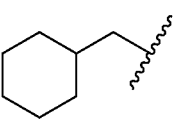 [SMILES: *CC1CCCCC1] |
| 8bh | |  |
| 8bi | | 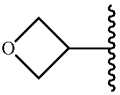 |
| 8ca | 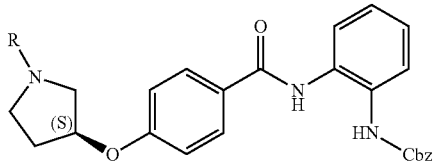 | Me |
| 8cb | | 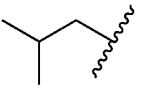 [SMILES: *CC(C)C] |
| 8cc | | 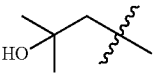 |
| 8cd | |  |
| 8ce | | 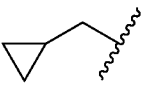 [SMILES: *CC1CC1] |
| 8cf | | 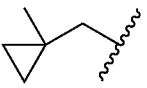 |
| 8cg | | 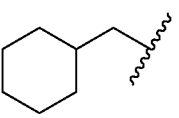 [SMILES: *CC1CCCCC1] |

-continued
| No | Core Structure | R |
|---|---|---|
| 8ch | |  |
| 8ci | | 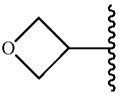 |
| 8da | 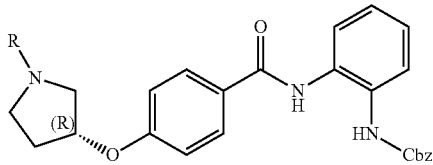 | Me |
| 8db | | 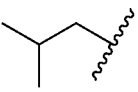 |
| 8dc | | 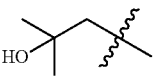 [SMILES: *CC(C)(C)O] |
| 8dd | | 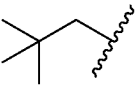 |
| 8de | | 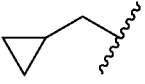 [SMILES: *CC1CC1] |
| 8df | | 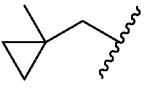 [SMILES: *CC1(C)CC1] |
| 8dg | | 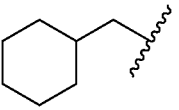 |
| 8dh | |  |
| 8di | | 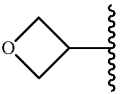 |
| 8ea | 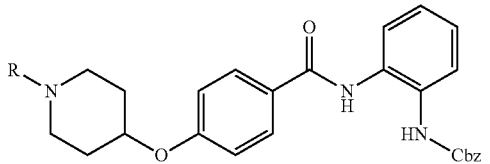 | Me |
| 8eb | | 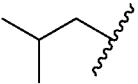 [SMILES: *CC(C)C] |

-continued
| No | Core Structure | R |
|---|---|---|
| 8ef | | 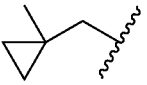 [SMILES: *CC1(C)CC1] |
| 8eg | | 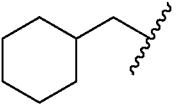 [SMILES: *CC1CCCCC1] |
| 8eh | |  |
| 8ei | | 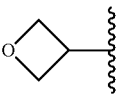 |
| 8ej | | 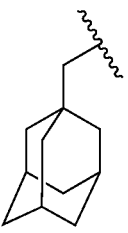 [SMILES: *CC12CC3CC(CC(C3)C1)C2] |
| 8fa | 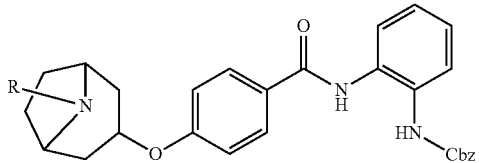 | Me |
| 8fb | | 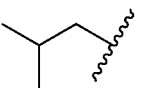 [SMILES: *CC(C)C] |
| 8fc | | 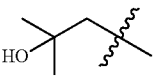 |
| 8fd | | 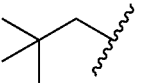 [SMILES: *CC(C)(C)C] |
| 8fe | | 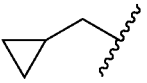 [SMILES: *CC1CC1] |
| 8ff | | 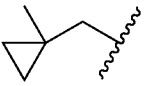 [SMILES: *CC1(C)CC1] |
| 8fg | | 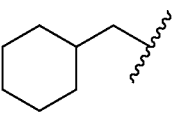 [SMILES: *CC1CCCCC1] |

Step-6: Synthesis of Compounds 33-77 and 123-133

The titled compounds were synthesized by following the general procedure described above for Cbz Deprotection.

Synthesis of N-(2-aminophenyl)-4-(azepan-4-yloxy)benzamide Hydrochloride (Compound 33)

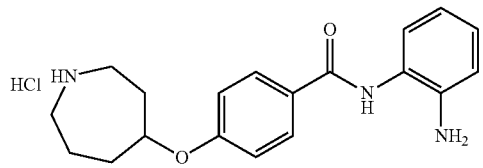
Compound-33

The title compound was synthesized by following the general procedure described above for Cbz Deprotection using Compound 7a. $^1$H NMR (400 MHz, DMSO-d6) δ 10.28 (s, 1H), 9.16-9.09 (m, 2H), 8.08 (d, J=8.4 Hz, 2H), 7.52-7.45 (m, 1H), 7.37-7.20 (m, 3H), 7.09 (d, J=8.6 Hz, 2H), 4.86-4.83 (m, 1H), 3.26-3.07 (m, 4H), 2.29-2.18 (m, 1H), 2.10-2.04 (m, 2H), 1.93-1.86 (m, 2H), 1.81-1.75 (m, 1H); LCMS Calculated for $C_{19}H_{23}N_3O_2$: 325.18; Observed: 326.20 (M+1)$^+$.

Synthesis of N-(2-aminophenyl)-4-((1-methylazepan-4-yl)oxy)benzamide bis(2,2,2-trifluoroacetate) (Compound 34)

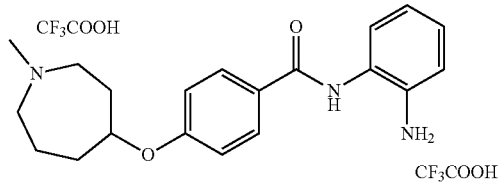
Compound-34

The title compound was synthesized by following the general procedure described above for Cbz Deprotection using Compound 8aa. $^1$H NMR (400 MHz, DMSO-d6) δ 9.68-9.65 (m, 1H), 8.01-7.89 (m, 2H), 7.19-7.15 (m, 1H), 7.08-7.02 (m, 4H), 6.92-6.74 (m, 2H), 4.88-4.84 (m, 2H), 3.47-3.35 (m, 3H), 3.17-3.13 (m, 2H), 2.84 (s, 3H), 2.20-2.15 (m, 2H), 2.04-1.85 (m, 4H); LCMS Calculated for $C_{20}H_{25}N_3O_2$: 339.19; Observed: 340.14 (M+1)$^+$.

Synthesis of N-(2-aminophenyl)-4-((1-isobutylazepan-4-yl)oxy)benzamide Dihydrochloride (Compound 35)

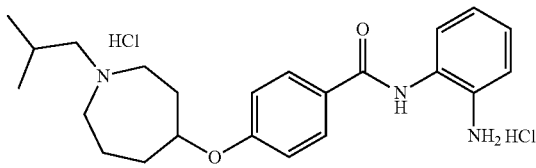
Compound-35

The title compound was synthesized by following the general procedure described above for Cbz Deprotection using Compound 8ab. $^1$H NMR (400 MHz, DMSO-d6) δ 10.10 (s, 1H), 9.55 (s, 1H), 8.03 (d, J=8.2 Hz, 2H), 7.37 (d, J=7.7 Hz, 1H), 7.20-7.18 (m, 2H), 7.11-7.15 (m, 3H), 4.89-4.78 (m, 1H), 3.56-3.53 (m, 1H), 3.50-3.26 (m, 2H), 3.14-3.10 (m, 2H), 2.99-2.95 (m, 2H), 2.27-2.16 (m, 1H), 2.21-1.86 (m, 4H), 1.83-1.80 (m, 1H), 0.97 (d, J=6.0 Hz, 6H); LCMS Calculated for $C_{23}H_{31}N_3O_2$: 381.24; Observed: 382.30 (M+1)$^+$.

Synthesis of N-(2-aminophenyl)-4-((1-(2-hydroxy-2-methylpropyl)azepan-4-yl)oxy)benzamide Dihydrochloride (Compound 36)

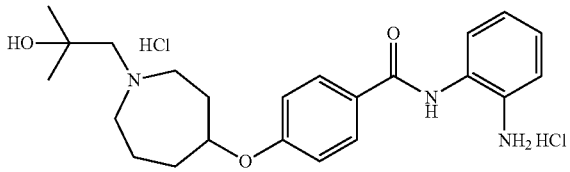
Compound-36

The title compound was synthesized by following the general procedure described above for Cbz Deprotection using Compound 8ac. $^1$H NMR (400 MHz, DMSO-d6) δ 10.09 (s, 1H), 9.69 (s, 1H), 9.31 (d, J=17.3 Hz, 1H), 8.05 (d, J=8.4 Hz, 2H), 7.39 (d, J=7.8 Hz, 1H), 7.20 (d, J=4.7 Hz, 2H), 7.12-7.07 (m, 3H), 4.86-4.83 (m, 1H), 3.69-3.32 (m, 3H), 3.19-3.11 (m, 2H), 3.09-3.04 (m, 2H), 2.28-2.22 (m, 1H), 2.20-2.07 (m, 2H), 2.07-1.93 (m, 1H), 1.96-1.76 (m, 2H), 1.29-1.15 (m, 6H); LCMS Calculated for $C_{23}H_{31}N_3O_3$: 397.24; Observed: 398.30 (M+1)$^+$.

Synthesis of N-(2-aminophenyl)-4-((1-neopentylazepan-4-yl)oxy)benzamide (Compound 37)

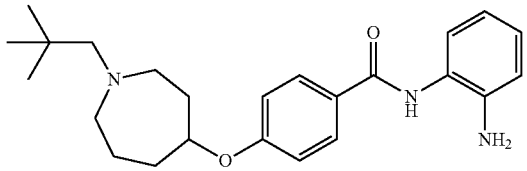
Compound-37

The title compound was synthesized by following the general procedure described above for Cbz Deprotection using Compound 8ad. $^1$H NMR (400 MHz, DMSO-d6) δ 9.49 (s, 1H), 7.93 (d, J=8.4 Hz, 2H), 7.15 (d, J=7.6 Hz, 1H), 7.00-6.93 (m, 3H), 6.77 (d, J=7.6 Hz, 1H), 6.59 (t, J=7.6 Hz, 1H), 4.85 (s, 2H), 4.69-4.66 (m, 1H), 2.84-2.66 (m, 4H), 2.25 (s, 2H), 2.09-1.98 (m, 2H), 1.97-1.73 (m, 3H), 1.60-1.57 (m, 1H), 0.85 (s, 9H); LCMS Calculated for $C_{24}H_{33}N_3O_2$: 395.26; Observed: 396.30 (M+1)$^+$.

Synthesis of N-(2-aminophenyl)-4-((1-(cyclopropyl-methyl)azepan-4-yl)oxy)benzamide Dihydrochloride (Compound 38)

Synthesis of N-(2-aminophenyl)-4-((1-(cyclohexyl-methyl)azepan-4-yl)oxy)benzamide Dihydrochloride (Compound 40)

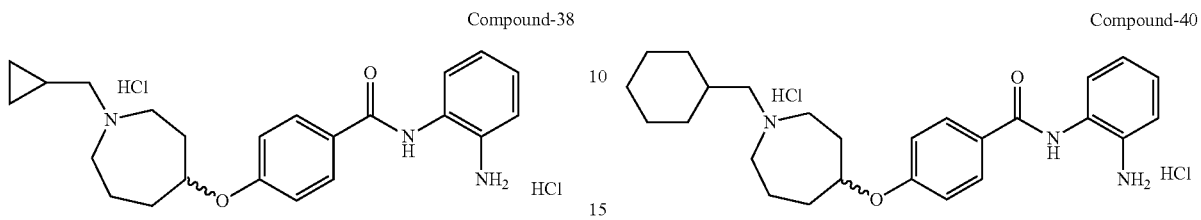

Compound-38

Compound-40

The title compound was synthesized by following the general procedure described above for Cbz Deprotection using Compound 8ae. $^1$H NMR (400 MHz, DMSO-d6) δ 10.09-9.99 (m, 2H), 8.02 (d, J=8.3 Hz, 2H), 7.34 (d, J=7.8 Hz, 1H), 7.18-7.03 (m, 5H), 4.92-4.80 (m, 1H), 3.57-3.55 (m, 1H), 3.43-3.39 (m, 1H), 3.18-3.16 (m, 2H), 3.05-3.03 (m, 2H), 2.29-2.10 (m, 3H), 2.06-1.82 (m, 3H), 1.14-1.12 (m, 1H), 0.65-0.63 (m, 2H), 0.42-0.39 (m, 2H); LCMS Calculated for $C_{23}H_{29}N_3O_2$: 379.23; Observed: 380.30 $(M+1)^+$.

The individual enantiomers of Compound 38 were separated by Chiral Prep HPLC using Chiral amylose SA, 250 mm*4.6 mm*5 um column to provide enantiomer Compounds 38-A and 38-B, with retention times of 10.57 and 12.07, respectively.

The title compound was synthesized by following the general procedure described above for Cbz Deprotection using Compound 8ag. $^1$H NMR (400 MHz, DMSO-d6) δ 10.12 (s, 1H), 9.69 (s, 1H), 8.04 (d, J=8.4 Hz, 2H), 7.39 (d, J=7.9 Hz, 1H), 7.24-7.05 (m, 5H), 4.90-4.79 (m, 1H), 3.47-3.33 (m, 2H), 3.20-3.04 (m, 2H), 2.99-2.94 (m, 2H), 2.33-2.27 (m, 1H), 2.16-2.14 (m, 1H), 1.99-1.92 (m, 1H), 1.82-1.79 (m, 4H), 1.71-1.61 (m, 4H), 1.26-1.11 (m, 4H), 1.00-0.94 (m, 2H); LCMS Calculated for $C_{26}H_{35}N_3O_2$: 421.27; Observed: 422.35 $(M+1)^+$.

The individual enantiomers of Compound 40 were separated by Chiral Prep-HPLC using CHIRALART CELLULOSE SC, 250 mm×4.6 mm, 5 μm column and delivered as Compound 40-A and 40-B, with retention times of 12.23 and 15.20, respectively.

Synthesis of N-(2-aminophenyl)-4-((1-((1-methcy-clopropylcyclopropyl)methyl)azepan-4-yl)oxy)benz-amide (Compound 39)

Synthesis of N-(2-aminophenyl)-4-((1-cyclopropy-lazepan-4-yl)oxy)benzamide Benzamide Dihydro-chloride (Compound 123)

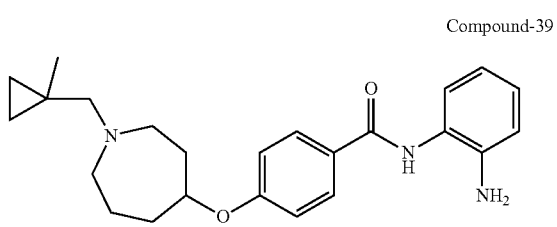 [SMILES: CC1(CN2CCCC(Oc3ccc(C(=O)Nc4ccccc4N)cc3)CC2)CC1]

Compound-39

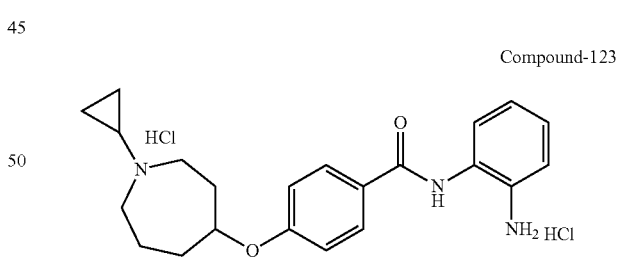

Compound-123

The title compound was synthesized by following the general procedure described above for Cbz Deprotection using Compound 8af. $^1$H NMR (400 MHz, DMSO-d6) δ 9.49 (s, 1H), 7.94 (d, J=8.4 Hz, 2H), 7.15 (d, J=7.8 Hz, 1H), 7.03-6.91 (m, 3H), 6.77 (d, J=8.0 Hz, 1H), 6.64-6.55 (m, 1H), 4.84 (s, 2H), 4.71-4.69 (m, 1H), 2.67-2.63 (m, 4H), 2.33-2.28 (m, 2H), 2.08-1.79 (m, 5H), 1.60-1.55 (m, 1H), 1.05 (s, 3H), 0.28-0.26 (m, 4H); LCMS Calculated for $C_{24}H_{31}N_3O_2$: 393.24; Observed: 393.85 $(M+1)^+$.

The title compound was synthesized by following the general procedure described above for Cbz Deprotection using Compound 8ah. $^1$H NMR (400 MHz, DMSO-d6) δ 10.80 (bs, 1H), 10.27 (s, 1H), 8.08 (d, J=8.4 Hz, 2H), 7.76-7.70 (m, 1H), 7.52-7.45 (m, 1H), 7.42-7.19 (m, 2H), 7.11-7.08 (m, 2H), 4.94-4.82 (m, 1H), 3.53-3.48 (m, 2H), 3.32-3.28 (m, 2H), 3.00-2.95 (m, 1H), 2.20-2.16 (m, 1H), 2.10-1.79 (m, 4H), 1.18-1.15 (m, 2H), 0.95-0.75 (m, 2H); LCMS Calculated for $C_{22}H_{27}N_3O_2$: 365.21; Observed: 366.00 $(M+1)^+$.

Synthesis of N-(2-aminophenyl)-4-((1-(oxetan-3-yl)azepan-4-yl)oxy)benzamide (Compound 124)

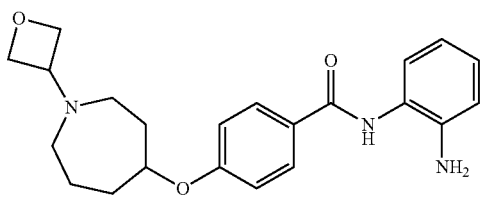

Compound-124

The title compound was synthesized by following the general procedure described above for Cbz Deprotection using Compound 8ai. $^1$H NMR (400 MHz, DMSO-d6) δ 9.51 (s, 1H), 7.93 (d, J=8.8 Hz, 2H), 7.14 (dd, J=8.0 Hz, 1H), 7.03-6.91 (m, 3H), 6.77 (d, J=8.0 Hz, 1H), 6.59 (t, J=7.6 Hz, 1H), 4.85 (s, 2H), 4.73-4.70 (m, 1H), 4.53 (t, J=6.5 Hz, 2H), 4.40-4.35 (m, 2H), 3.63 (p, J=6.5 Hz, 1H), 2.46-2.36 (m, 4H), 2.11-2.00 (m, 2H), 1.84-1.76 (m, 3H), 1.64-1.58 (m, 1H); LCMS Calculated for $C_{22}H_{27}N_3O_3$: 381.21; Observed: 382.25 (M+1)$^+$.

Synthesis of N-(2-aminophenyl)-4-(azetidin-3-yloxy)benzamide Hydrochloride (Compound 41)

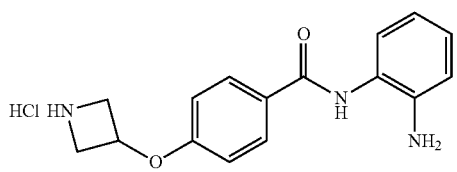

Compound-41

The title compound was synthesized by following the general procedure described above for Cbz Deprotection using Compound 7b. $^1$H NMR (400 MHz, DMSO-d6) δ 9.60 (s, 1H), 9.15-9.17 (m, 2H), 7.98 (d, J=8.4 Hz, 2H), 7.12 (d, J=7.8 Hz, 1H), 6.98-6.93 (m, 3H), 6.77 (d, J=7.9 Hz, 1H), 6.58 (t, J=7.7 Hz, 1H), 5.16-5.13 (m, 1H), 4.87 (s, 2H), 4.48-4.43 (m, 2H), 4.00-3.97 (m, 2H). LCMS Calculated for $C_{16}H_{17}N_3O_2$: 283.13; Observed: 283.85 (M+1)$^+$.

Synthesis of N-(2-aminophenyl)-4-((1-methylazetidin-3-yl)oxy)benzamide Compound 42)

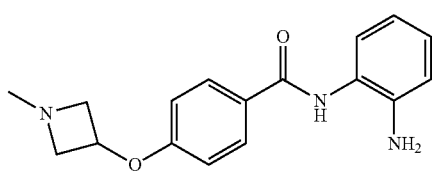

Compound-42

The title compound was synthesized by following the general procedure described above for Cbz Deprotection using Compound 8ba. $^1$H NMR (400 MHz, DMSO-d6) δ 9.51 (s, 1H), 7.93 (t, J=6.9 Hz, 2H), 7.18-7.10 (m, 1H), 7.06 (d, J=8.2 Hz, 1H), 7.00-6.88 (m, 2H), 6.77 (d, J=7.9 Hz, 1H), 6.59 (t, J=7.7 Hz, 1H), 4.92-4.81 (m, 2H), 4.63-4.60 (m, 1H), 3.86-3.77 (m, 1H), 3.13-3.04 (m, 2H), 2.87-2.68 (m, 1H), 2.21 (s, 3H); LCMS Calculated for $C_{17}H_{19}N_3O_2$: 297.15; Observed: 298.15 (M+1)$^+$.

Synthesis of N-(2-aminophenyl)-4-((1-isobutylazetidin-3-yl)oxy)benzamide Dihydrochloride (Compound 43)

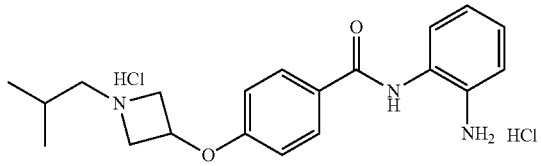

Compound-43

The title compound was synthesized by following the general procedure described above for Cbz Deprotection using Compound 8bb. $^1$H NMR (400 MHz, DMSO-d6) δ 10.80 (bs, 1H), 10.32 (s, 1H), 8.14-8.09 (m, 2H), 7.47 (d, J=7.0 Hz, 1H), 7.35-7.19 (m, 3H), 7.03-6.98 (m, 2H), 5.25-5.09 (m, 1H), 4.76-4.73 (m, 1H), 4.51-4.48 (m, 1H), 4.36-4.27 (m, 1H), 4.18-4.16 (m, 2H), 3.19-3.09 (m, 2H), 1.93-1.91 (m, 1H), 0.94 (d, J=6.5 Hz, 6H); LCMS Calculated for $C_{20}H_{25}N_3O_2$: 339.19; Observed: 340.25 (M+1)$^+$.

Synthesis of N-(2-aminophenyl)-4-((1-(2-hydroxy-2-methylpropyl)azetidin-3-yl)oxy)benzamide Dihydrochloride (Compound 44)

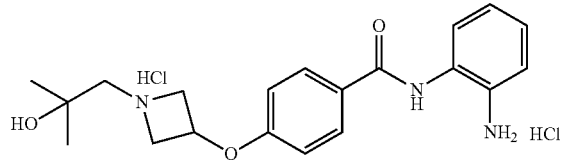

Compound-44

The title compound was synthesized by following the general procedure described above for Cbz Deprotection using Compound 8bc. $^1$H NMR (400 MHz, DMSO-d6) δ 10.35-10.25 (m, 1H), 10.13 (s, 1H), 8.08-8.06 (m, 2H), 7.39 (d, J=7.9 Hz, 1H), 7.18 (d, J=4.6 Hz, 2H), 7.06-6.98 (m, 3H), 5.10 (p, J=6.2 Hz, 1H), 4.84-4.79 (m, 2H), 4.63-4.61 (m, 1H), 4.41-4.32 (m, 1H), 4.28-4.23 (m, 2H), 1.19 (s, 6H); LCMS Calculated for $C_{20}H_{25}N_3O_3$: 355.19; Observed: 355.90 (M+1)$^+$.

Synthesis of N-(2-aminophenyl)-4-((1-isobutylazetidin-3-yl)oxy)benzamide Dihydrochloride (Compound 45)

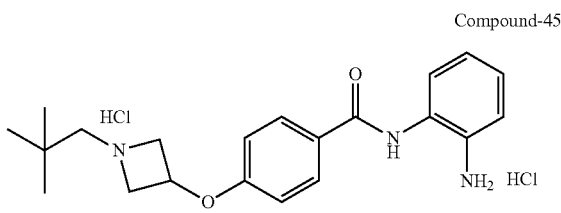 [SMILES: CC(C)(C)CN1CC(Oc2ccc(C(=O)Nc3ccccc3N)cc2)C1 ; Cl ; Cl]

The title compound was synthesized by following the general procedure described above for Cbz Deprotection using Compound 8bd. $^1$H NMR (400 MHz, DMSO-d6) δ 10.61 (s, 1H), 10.40 (s, 1H), 8.15-8.10 (m, 2H), 7.52-7.49 (m, 1H), 7.41-7.24 (m, 3H), 7.02-6.98 (m, 2H), 4.86-4.84 (m, 1H), 4.59-4.42 (m, 2H), 4.24-4.18 (m, 2H), 3.21 (s, 3H), 0.99 (s, 9H); LCMS Calculated for $C_{21}H_{27}N_3O_2$: 353.21; Observed: 353.90 (M+1)$^+$.

Synthesis of N-(2-aminophenyl)-4-((1-(cyclopropylmethyl)azetidin-3-yl)oxy)benzamide Dihydrochloride (Compound 46)

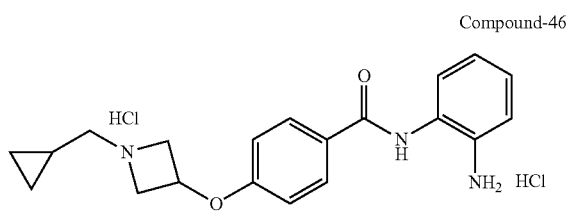 [SMILES: Nc1ccccc1NC(=O)c1ccc(OC2CN(CC3CC3)C2)cc1 ; Cl ; Cl]

The title compound was synthesized by following the general procedure described above for Cbz Deprotection using Compound 8be. $^1$H NMR (400 MHz, DMSO-d6) δ 10.89-10.82 (m, 1H), 10.20 (s, 1H), 8.08 (t, J=8.4 Hz, 2H), 7.41 (d, J=7.7 Hz, 1H), 7.28-7.13 (m, 3H), 7.02 (t, J=8.9 Hz, 2H), 5.22-5.09 (m, 1H), 4.70-4.68 (m, 1H), 4.53-4.50 (m, 1H), 4.27-4.09 (m, 2H), 3.14-3.12 (m, 2H), 1.02-1.00 (m, 1H), 0.55 (t, J=8.1 Hz, 2H), 0.39-0.37 (m, 2H); LCMS Calculated for $C_{20}H_{23}N_3O_2$: 337.18; Observed: 338.20 (M+1)$^+$.

Synthesis of N-(2-aminophenyl)-4-((1-((1-methcyclopropylcyclopropyl)methyl)azetidin-3-yl)oxy)benzamide Dihydrochloride (Compound 47)

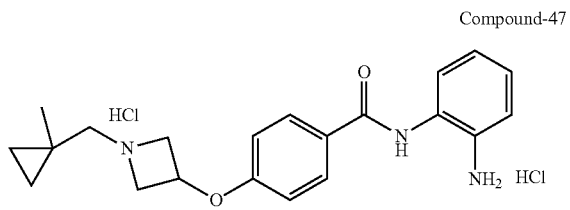 [SMILES: CC1(CN2CC(Oc3ccc(C(=O)Nc4ccccc4N)cc3)C2)CC1 ; Cl ; Cl]

The title compound was synthesized by following the general procedure described above for Cbz Deprotection using Compound 8bf. $^1$H NMR (400 MHz, DMSO-d6) δ 10.83 (s, 1H), 10.38 (s, 1H), 8.16-8.11 (m, 2H), 7.51-7.49 (m, 1H), 7.44-7.36 (m, 1H), 7.30-7.27 (m, 2H), 7.04-7.00 (m, 2H), 5.14-5.10 (m, 1H), 4.75-4.72 (m, 1H), 4.58-4.55 (m, 1H), 4.35-4.33 (m, 1H), 4.20-4.17 (m, 1H), 3.20 (s, 3H), 1.14-1.10 (m, 3H), 0.62-0.60 (m, 2H), 0.43-0.33 (m, 2H); LCMS Calculated for $C_{21}H_{25}N_3O_2$: 351.19; Observed: 351.92 (M+1)$^+$.

Synthesis of N-(2-aminophenyl)-4-((1-(cyclohexylmethyl)azetidin-3-yl)oxy)benzamide Dihydrochloride (Compound 48)

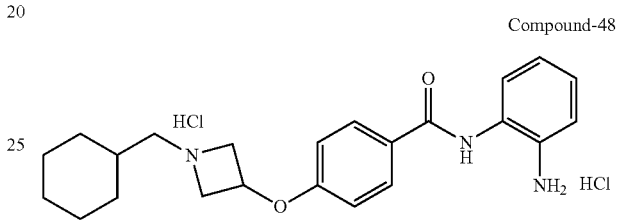

The title compound was synthesized by following the general procedure described above for Cbz Deprotection using Compound 8bg. $^1$H NMR (400 MHz, DMSO-d6) δ 10.66-10.60 (m, 1H), 10.27 (s, 1H), 8.10 (t, J=8.2 Hz, 2H), 7.45 (d, J=7.6 Hz, 1H), 7.32-7.15 (m, 3H), 7.01 (t, J=9.1 Hz, 2H), 5.25-5.23 (m, 1H), 5.09 (p, J=6.4 Hz, 1H), 4.75-4.73 (m, 1H), 4.50-447 (m, 1H), 4.32-4.30 (m, 1H), 4.16-4.14 (m, 1H), 3.14 (t, J=5.6 Hz, 2H), 1.77-1.56 (m, 6H), 1.27-1.05 (m, 2H), 0.95 (q, J=12.4 Hz, 2H); LCMS Calculated for $C_{23}H_{29}N_3O_2$: 379.23; Observed: 380.30 (M+1)$^+$.

Synthesis of N-(2-aminophenyl)-4-((1-cyclopropylazetidin-3-yl)oxy)benzamide (Compound 125)

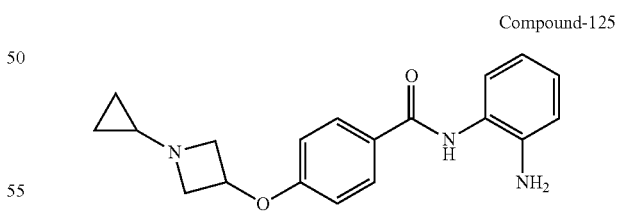

The title compound was synthesized by following the general procedure described above for Cbz Deprotection using Compound 8bh. $^1$H NMR (400 MHz, DMSO-d6) δ 9.51 (s, 1H), 7.92 (d, J=8.4 Hz, 2H), 7.12 (d, J=8.0 Hz, 1H), 6.96-6.90 (m, 3H), 6.75 (d, J=7.6 Hz, 1H), 6.57 (t, J=7.2 Hz, 1H), 4.84 (s, 3H), 3.74 (t, J=7.2 Hz, 2H), 3.14 (t, J=6.8 Hz, 2H), 1.93-1.91 (m, 1H), 0.35-0.34 (m, 2H), 0.24-0.22 (m, 2H); LCMS Calculated for $C_{19}H_{21}N_3O_2$: 323.16; Observed: 323.90 (M+1)$^+$.

Synthesis of N-(2-aminophenyl)-4-((1-(oxetan-3-yl)azetidin-3-yl)oxy)benzamide (Compound 126)

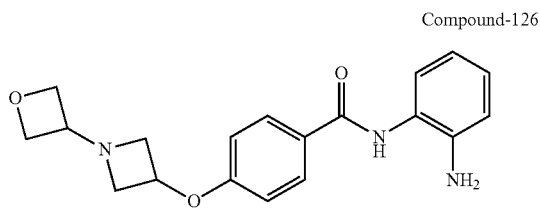 [SMILES: Nc1ccccc1NC(=O)c1ccc(OC2CN(C3COC3)C2)cc1]
Compound-126

The title compound was synthesized by following the general procedure described above for Cbz Deprotection using Compound 8bi. $^1$H NMR (400 MHz, DMSO-d6) δ 9.55 (s, 1H), 7.96 (d, J=8.8 Hz, 2H), 7.14 (d, J=7.6 Hz, 1H), 6.98-6.93 (m, 3H), 6.77 (d, J=8.0 Hz, 1H), 6.59 (t, J=7.6 Hz, 1H), 4.99-4.95 (m, 1H), 4.60 (t, J=6.8 Hz, 2H), 4.39 (t, J=6.0 Hz, 2H), 3.90-3.87 (m, 2H), 3.32-3.27 (m, 3H); LCMS Calculated for $C_{19}H_{21}N_3O_3$: 339.16; Observed: 340.15 (M+1)$^+$.

Synthesis of (S)—N-(2-aminophenyl)-4-(pyrrolidin-3-yloxy)benzamide Hydrochloride (Compound 49)

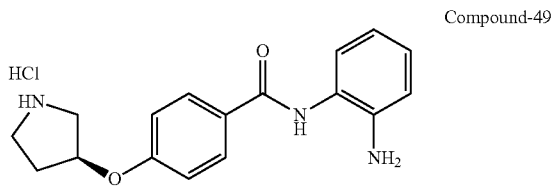 [SMILES: Nc1ccccc1NC(=O)c1ccc(O[C@H]2CCNC2)cc1 ; Cl]
Compound-49

The title compound was synthesized by following the general procedure described above for Cbz Deprotection using Compound 7c. $^1$H NMR (400 MHz. DMSO-d6) δ9.69 (s, 2H), 9.60-9.49 (m, 1H), 8.01 (d, J=8.3 Hz, 2H), 7.19 (d, J=7.8 Hz, 1H), 7.08 (d, J=8.3 Hz, 2H), 6.99 (t, J=7.6 Hz, 1H), 6.84 (d, J=1.9 Hz, 1H), 6.66 (t, J=7.6 Hz, 1H), 5.26 (s, 1H), 3.53-3.50 (m, 1H), 3.35-3.25 (m, 4H), 2.26-2.16 (m, 2H); LCMS Calculated for $C_{17}H_{19}N_3O_2$: 297.15; Observed: 298.00 (M+1)$^+$.

Synthesis of (S)—N-(2-aminophenyl)-4-(pyrrolidin-3-yloxy)benzamide Dihydrochloride (Compound 50)

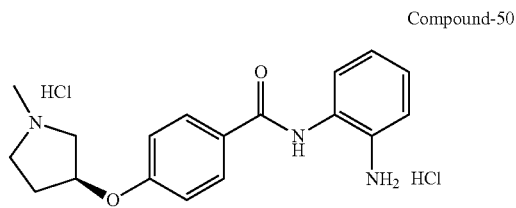 [SMILES: CN1CC[C@H](Oc2ccc(C(=O)Nc3ccccc3N)cc2)C1 ; Cl ; Cl]
Compound-50

The title compound was synthesized by following the general procedure described above for Cbz Deprotection using Compound 8ca. $^1$H NMR (400 MHz, DMSO-d6) δ 10.90 (s, 1H), 10.36 (s, 1H), 8.13 (d, J=8.4 Hz, 2H), 7.52-7.50 (m, 1H), 7.37-7.33 (m, 1H), 7.29-7.26 (m, 2H), 7.13-7.09 (m, 2H), 5.31-5.25 (m, 1H), 4.07-3.99 (m, 1H), 3.74-3.65 (m, 2H), 3.25-3.21 (m, 2H), 2.88-2.85 (m, 3H), 2.40-2.36 (m, 1H), 2.10-2.00 (m, 1H); LCMS Calculated for $C_{18}H_{21}N_3O_2$: 311.16; Observed: 311.90 (M+1)$^+$.

Synthesis of (S)—N-(2-aminophenyl)-4-((1-isobutylpyrrolidin-3-yl)oxy)benzamide Dihydrochloride (Compound 51)

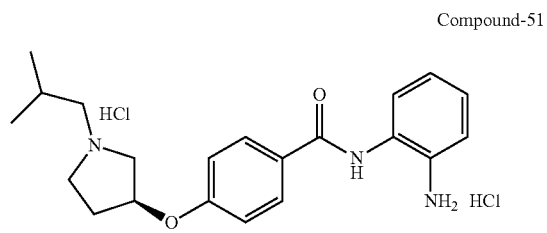 [SMILES: CC(C)CN1CC[C@H](Oc2ccc(C(=O)Nc3ccccc3N)cc2)C1 ; Cl ; Cl]
Compound-51

The title compound was synthesized by following the general procedure described above for Cbz Deprotection using Compound 8cb. $^1$H NMR (400 MHz, DMSO-d6) δ 10.73 (s, 1H), 10.22 (s, 1H), 8.10 (d, J=8.2 Hz, 2H), 7.45 (d, J=7.6 Hz, 1H), 7.31-7.06 (m, 5H), 5.27 (s, 1H), 3.73-3.70 (m, 1H), 3.29-3.24 (m, 3H), 3.09-3.07 (m, 2H), 2.40-2.32 (m, 1H), 2.25-1.98 (m, 2H), 1.04-0.99 (m, 6H); LCMS Calculated for $C_{21}H_{27}N_3O_2$: 353.21; Observed: 354.25 (M+1)$^+$.

Synthesis of (S)—N-(2-aminophenyl)-4-((1-(2-hydroxy-2-methylpropyl)pyrrolidin-3-yl)oxy)benzamide Dihydrochloride (Compound 52)

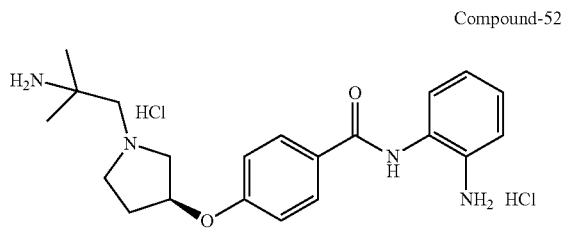 [SMILES: CC(C)(N)CN1CC[C@H](Oc2ccc(C(=O)Nc3ccccc3N)cc2)C1 ; Cl ; Cl]
Compound-52

The title compound was synthesized by following the general procedure described above for Cbz Deprotection using Compound 8cc. $^1$H NMR (400 MHz, DMSO-d6) δ 10.34 (s, 1H), 10.23 (s, 1H), 8.12 (d, J=8.5 Hz, 2H), 7.51-7.49 (m, 1H), 7.40-7.31 (m, 1H), 7.32-7.23 (m, 2H), 7.11 (t, J=8.8 Hz, 2H), 5.33-5.21 (m, 1H), 4.15-4.11 (m, 1H), 3.79-3.67 (m, 2H), 3.57-3.16 (m, 4H), 2.43-2.33 (m, 1H), 2.22-2.12 (m, 1H), 1.29-1.17 (m, 6H); LCMS Calculated for $C_{21}H_{27}N_3O_3$: 369.21; Observed: 370.15 (M+1)$^+$.

Synthesis of (S)—N-(2-aminophenyl)-4-((1-neopentylpyrrolidin-3-yl)oxy)benzamide (Compound 53)

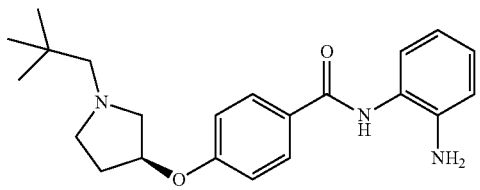

Compound-53

The title compound was synthesized by following the general procedure described above for Cbz Deprotection using Compound 8cd. $^1$H NMR (400 MHz, DMSO-d6) δ 10.30-10.20 (m, 1H), 9.57 (s, 1H), 7.97 (s, 2H), 7.14 (d, J=7.6 Hz, 1H), 6.98-6.94 (m, 2H), 6.77 (d, J=7.6 Hz, 1H), 6.59 (t, J=7.2 Hz, 1H), 5.25-5.23 (m, 1H), 4.87 (s, 2H), 3.82-2.68 (m, 5H), 2.34-2.26 (m, 2H), 1.85-1.80 (m, 1H), 1.07-0.88 (m, 9H); LCMS Calculated for $C_{22}H_{29}N_3O_2$: 367.23; Observed: 368.00 (M+1)$^+$.

Synthesis of (S)—N-(2-aminophenyl)-4-((1-(cyclopropylmethyl)pyrrolidin-3-yl)oxy)benzamide Dihydrochloride (Compound 54)

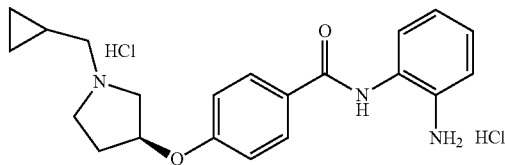

Compound-54

The title compound was synthesized by following the general procedure described above for Cbz Deprotection using Compound 8ce. $^1$H NMR (400 MHz, DMSO-d6) δ 11.04-10.66 (m, 1H), 10.25 (s, 1H), 8.12-8.08 (m, 2H), 7.45 (d, J=7.4 Hz, 1H), 7.28-7.19 (m, 3H), 7.12 (d, J=8.4 Hz, 2H), 5.30-5.26 (m, 1H), 4.07-4.03 (m, 1H), 3.74-3.71 (m, 1H), 3.39-3.06 (m, 4H), 2.41-2.32 (m, 1H), 2.26-2.04 (m, 1H), 1.14-1.12 (m, 1H), 0.67-0.55 (m, 2H), 0.42-0.40 (m, 2H); LCMS Calculated for $C_{21}H_{25}N_3O_2$: 351.19; Observed: 352.20 (M+1)$^+$.

Synthesis of (S)—N-(2-aminophenyl)-4-((1-((1-methylcyclopropyl)methyl) pyrrolidin-3-yl)oxy)benzamide Dihydrochloride (Compound 55)

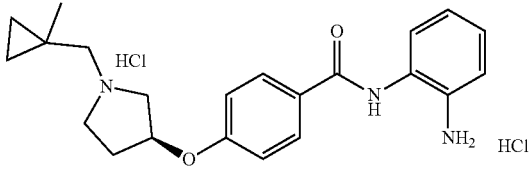

Compound-55

The title compound was synthesized by following the general procedure described above for Cbz Deprotection using Compound 8cf. $^1$H NMR (400 MHz, DMSO-d6) δ 10.89 (s, 1H), 10.35 (s, 1H), 8.14-8.11 (m, 2H), 7.51-7.49 (m, 1H), 7.40-7.33 (m, 1H), 7.31-7.20 (m, 2H), 7.11 (d, J=8.4 Hz, 2H), 5.26-5.23 (m, 1H), 4.13-4.09 (m, 1H), 3.73-3.60 (m, 3H), 3.27-3.12 (m, 4H), 2.21-2.16 (m, 1H), 1.22 (s, 3H), 0.66-0.58 (m, 2H), 0.45-0.43 (m, 2H); LCMS Calculated for $C_{22}H_{27}N_3O_2$: 365.21; Observed: 365.85 (M+1)$^+$.

Synthesis of (S)—N-(2-aminophenyl)-4-((1-(cyclohexylmethyl)pyrrolidin-3-yl)oxy)benzamide Dihydrochloride (Compound 56)

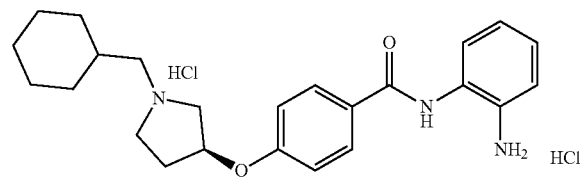

Compound-56

The title compound was synthesized by following the general procedure described above for Cbz Deprotection using Compound 8cg. $^1$H NMR (400 MHz, DMSO-d6) δ 10.70 (s, 1H), 10.31 (s, 1H), 8.11 (d, J=8.4 Hz, 2H), 7.52-7.45 (m, 1H), 7.31-7.20 (m, 3H), 7.11 (t, J=7.9 Hz, 2H), 5.78-5.45 (m, 1H), 4.10-4.06 (m, 1H), 3.78-3.66 (m, 2H), 3.56-3.53 (m, 1H), 3.31-3.14 (m, 2H), 3.12-2.98 (m, 2H), 2.22-2.12 (m, 1H), 1.91-1.58 (m, 6H), 1.35-1.03 (m, 3H), 0.98-0.94 (m, 2H); LCMS Calculated for $C_{24}H_{31}N_3O_2$: 393.24; Observed: 394.35 (M+1)$^+$.

Synthesis of (S)—N-(2-aminophenyl)-4-((1-cyclopropylpyrrolidin-3-yl)oxy)benzamide Dihydrochloride (Compound 127)

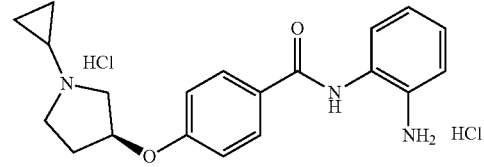

Compound-127

The title compound was synthesized by following the general procedure described above for Cbz Deprotection using Compound 8ch. $^1$H NMR (400 MHz, DMSO-d6) δ 11.61-11.15 (m, 1H), 10.26 (s, 1H), 8.10 (d, J=8.8 Hz, 2H), 7.47-7.44 (m, 1H), 7.33-7.07 (m, 5H), 5.34-5.23 (m, 1H), 3.60-3.52 (m, 2H), 3.48-3.38 (m, 2H), 2.99-2.97 (m, 1H), 2.30-2.23 (m, 2H), 1.10-1.04 (m, 2H), 0.81-0.79 (m, 2H); LCMS Calculated for $C_{20}H_{23}N_3O_2$: 337.18; Observed: 337.95 (M+1)$^+$.

Synthesis of (S)—N-(2-aminophenyl)-4-((1-(oxetan-3-yl)pyrrolidin-3-yl)oxy)benzamide (Compound 128)

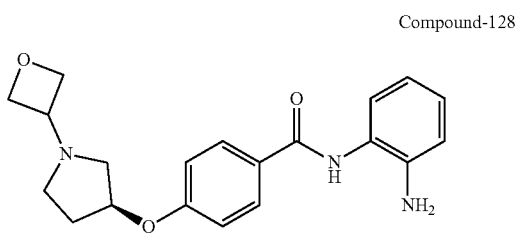 [SMILES: Nc1ccccc1NC(=O)c1ccc(O[C@H]2CCN(C3COC3)C2)cc1]
Compound-128

The title compound was synthesized by following the general procedure described above for Cbz Deprotection using Compound 8ci. $^1$H NMR (400 MHz, DMSO-d6) δ 9.53 (s, 1H), 7.95 (d, J=8.4 Hz, 2H), 7.14 (d, J=7.6 Hz, 1H), 7.04-6.91 (m, 2H), 6.77 (d, J=6.8 Hz, 1H), 6.61-6.57 (m, 1H), 5.06-5.03 (m, 1H), 4.92-4.87 (m, 2H), 4.59 (t, J=6.8 Hz, 2H), 4.49 (q, J=6.7 Hz, 2H), 3.72-3.68 (m, 1H), 3.07-2.54 (m, 3H), 2.67-2.33 (m, 1H), 1.91-1.85 (m, 1H); LCMS Calculated for $C_{20}H_{23}N_3O_3$: 353.17; Observed: 354.00 (M+1)$^+$.

Synthesis of (R)—N-(2-aminophenyl)-4-(pyrrolidin-3-yloxy)benzamide Hydrochloride (Compound 57)

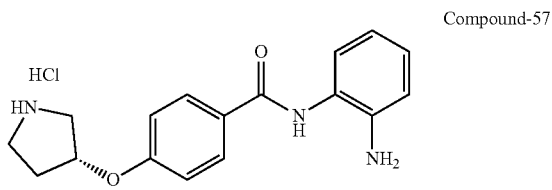 [SMILES: Nc1ccccc1NC(=O)c1ccc(O[C@@H]2CCNC2)cc1 ; Cl]
Compound-57

The title compound was synthesized by following the general procedure described above for Cbz Deprotection using Compound 7d. $^1$H NMR (400 MHz, DMSO-d6) δ 9.60 (s, 1H), 9.45 (s, 2H), 8.00 (d, J=8.4 Hz, 2H), 7.14 (d, J=7.2 Hz, 1H), 7.07 (d, J=8.0 Hz, 2H), 6.96 (t, J=7.6 Hz, 1H), 6.78 (d, J=7.9 Hz, 1H), 6.59 (t, J=7.5 Hz, 1H), 5.27-5.24 (m, 1H), 4.90-4.85 (m, 2H), 3.53-3.48 (m, 1H), 3.37-3.21 (m, 3H), 2.32-2.08 (m, 2H); LCMS Calculated for $C_{17}H_{19}N_3O_2$: 297.15; Observed: 298.15 (M+1)$^+$.

Synthesis of (R)—N-(2-aminophenyl)-4-((1-methylpyrrolidin-3-yl)oxy)benzamide (Compound 58)

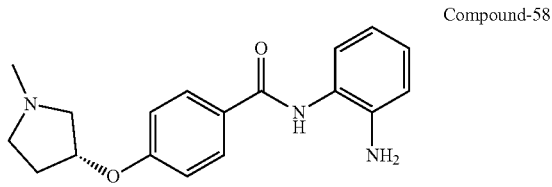 [SMILES: CN1CC[C@@H](Oc2ccc(C(=O)Nc3ccccc3N)cc2)C1]
Compound-58

The title compound was synthesized by following the general procedure described above for Cbz Deprotection using Compound 8da. $^1$H NMR (400 MHz, DMSO-d6) δ 9.51 (s, 1H), 7.94 (d, J=8.8 Hz, 2H), 7.14 (d, J=8.0 Hz, 1H), 6.99-6.93 (m, 3H), 6.77 (d, J=7.6 Hz, 1H), 6.59 (t, J=7.2 Hz, 1H), 5.00-4.92 (m, 1H), 4.86 (s, 2H), 2.82-2.78 (m, 1H), 2.72-2.62 (m, 2H), 2.43-2.25 (m, 2H), 2.27 (s, 3H), 1.79-1.75 (m, 1H); LCMS Calculated for $C_{18}H_{21}N_3O_2$: 311.16; Observed: 312.15 (M+1)$^+$.

Synthesis of (R)—N-(2-aminophenyl)-4-((1-isobutylpyrrolidin-3-yl)oxy)benzamide Dihydrochloride (Compound 59)

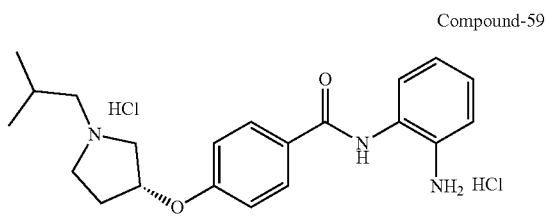 [SMILES: CC(C)CN1CC[C@@H](Oc2ccc(C(=O)Nc3ccccc3N)cc2)C1 ; Cl ; Cl]
Compound-59

The title compound was synthesized by following the general procedure described above for Cbz Deprotection using Compound 8db. $^1$H NMR (400 MHz, DMSO-d6) δ 10.85 (s, 1H), 10.37 (s, 1H), 8.13 (d, J=8.0 Hz, 2H), 7.53-7.51 (m, 1H), 7.39-7.37 (m, 1H), 7.29-7.26 (m, 2H), 7.13-7.11 (m, 2H), 5.28-5.25 (m, 1H), 4.07-4.03 (m, 1H), 3.72-3.69 (m, 2H), 3.62-3.52 (m, 1H), 3.31-3.14 (m, 1H), 3.09-3.05 (m, 2H), 2.40-2.32 (m, 1H), 2.21-2.04 (m, 1H), 0.99 (d, J=5.2 Hz, 6H); LCMS Calculated for $C_{21}H_{27}N_3O_2$: 353.21; Observed: 354.25 (M+1)$^+$.

Synthesis of (R)—N-(2-aminophenyl)-4-((1-(2-hydroxy-2-methylpropyl)pyrrolidin-3-yl)oxy)benzamide Dihydrochloride (Compound 60)

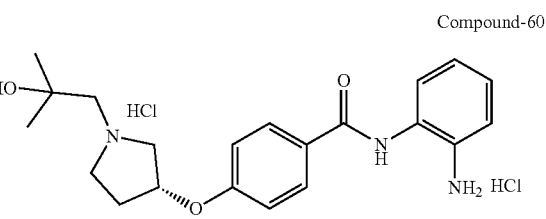
Compound-60

The title compound was synthesized by following the general procedure described above for Cbz Deprotection using Compound 8dc. $^1$H NMR (400 MHz, DMSO-d6) δ 10.23 (bs, 1H), 10.08 (s, 1H), 8.08 (d, J=7.6 Hz, 1H), 7.37 (d, J=7.2 Hz, 1H), 7.15-7.10 (m, 5H), 7.05-7.01 (m, 1H), 5.26-5.23 (m, 1H), 4.14-4.11 (m, 1H), 3.80-3.69 (m, 2H), 3.47-3.23 (m, 4H), 2.45-2.34 (m, 1H), 2.24-2.09 (m, 1H), 1.25 (d, J=5.8 Hz, 6H); LCMS Calculated for $C_{21}H_{27}N_3O_3$: 369.21; Observed: 370.25 (M+1)$^+$.

Synthesis of (R)—N-(2-aminophenyl)-4-((1-neopentylpyrrolidin-3-yl)oxy)benzamide (Compound 61)

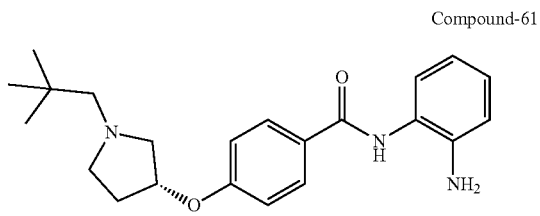 [SMILES: CC(C)(C)CN1CC[C@@H](Oc2ccc(C(=O)Nc3ccccc3N)cc2)C1]
Compound-61

The title compound was synthesized by following the general procedure described above for Cbz Deprotection using Compound 8dd. $^1$H NMR (400 MHz, DMSO-d6) δ 9.52 (s, 1H), 7.93 (d, J=8.8 Hz, 2H), 7.14 (d, J=7.2 Hz, 1H), 7.03-6.91 (m, 3H), 6.77 (d, J=7.2 Hz, 1H), 6.59 (t, J=7.2 Hz, 1H), 4.96-4.94 (m, 1H), 4.86 (s, 2H), 3.08-3.03 (m, 1H), 2.86-2.68 (m, 2H), 2.61-2.59 (m, 1H), 2.34-2.20 (m, 3H), 1.86-1.73 (m, 1H), 0.88 (s, 9H); LCMS Calculated for $C_{22}H_{29}N_3O_2$: 367.23; Observed: 368.00 (M+1)$^+$.

Synthesis of (R)—N-(2-aminophenyl)-4-((1-(cyclopropylmethyl)pyrrolidin-3-yl)oxy)benzamide Dihydrochloride (Compound 62)

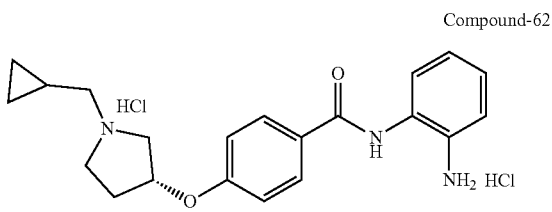 [SMILES: Nc1ccccc1NC(=O)c1ccc(O[C@@H]2CCN(CC3CC3)C2)cc1 ; Cl ; Cl]
Compound-62

The title compound was synthesized by following the general procedure described above for Cbz Deprotection using Compound 8de. $^1$H NMR (400 MHz, DMSO-d6) δ 11.28-10.86 (m, 1H), 10.09 (s, 1H), 8.08 (d, J=8.1 Hz, 2H), 7.39 (d, J=7.2 Hz, 1H), 7.17-7.15 (m, 2H), 7.10 (d, J=8.4 Hz, 2H), 7.07-7.00 (m, 1H), 5.29-5.27 (m, 1H), 4.05-4.01 (m, 1H), 3.70-3.66 (m, 2H), 3.56-3.50 (m, 2H), 3.33-3.00 (m, 2H), 2.67-2.63 (m, 1H), 2.22-2.10 (m, 1H), 1.16-1.09 (m, 1H), 0.63-0.58 (m, 2H), 0.44-0.39 (m, 2H); LCMS Calculated for $C_{21}H_{25}N_3O_2$: 351.19; Observed: 352.19 (M+1)$^+$.

Synthesis of (R)—N-(2-aminophenyl)-4-((1-((1-methylcyclopropyl)methyl) pyrrolidin-3-yl)oxy)benzamide Dihydrochloride (Compound 63)

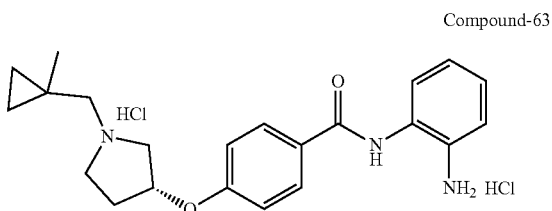
Compound-63

The title compound was synthesized by following the general procedure described above for Cbz Deprotection using Compound 8df. $^1$H NMR (400 MHz, DMSO-d6) δ 10.87 (s, 1H), 10.28 (s, 1H), 8.13-8.09 (m, 2H), 7.51-7.42 (m, 1H), 7.34-7.06 (m, 5H), 5.26-5.24 (m, 1H), 4.13-4.09 (m, 1H), 3.73-3.58 (m, 3H), 3.30-3.12 (m, 3H), 2.33-2.16 (m, 1H), 1.20 (s, 3H), 0.69-0.52 (m, 2H), 0.50-0.38 (m, 2H); LCMS Calculated for $C_{22}H_{27}N_3O_2$: 365.21; Observed: 366.34 (M+1)$^+$.

Synthesis of (R)—N-(2-aminophenyl)-4-((1-(cyclohexylmethyl)pyrrolidin-3-yl)oxy)benzamide Dihydrochloride (Compound 64)

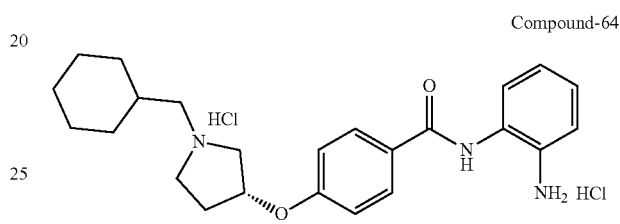
Compound-64

The title compound was synthesized by following the general procedure described above for Cbz Deprotection using Compound 8dg. $^1$H NMR (400 MHz, DMSO-d6) δ 10.87 (s, 1H), 10.34 (s, 1H), 9.19 (s, 1H), 8.13 (d, J=8.2 Hz, 2H), 7.52-7.50 (m, 1H), 7.37-7.34 (m, 1H), 7.30-7.23 (m, 2H), 7.12-7.08 (m, 2H), 5.27-5.25 (m, 1H), 4.10-4.07 (m, 1H), 3.72-3.70 (m, 2H), 3.58-3.56 (m, 1H), 3.30-3.24 (m, 1H), 3.08-3.06 (m, 2H), 2.21-2.13 (m, 1H), 1.92-1.58 (m, 6H), 1.25-1.11 (m, 3H), 0.97-0.95 (m, 2H); LCMS Calculated for $C_{24}H_{31}N_3O_2$: 393.24; Observed: 394.35 (M+1)$^+$.

Synthesis of (R)—N-(2-aminophenyl)-4-((1-cyclopropylpyrrolidin-3-yl)oxy)benzamide (Compound 129)

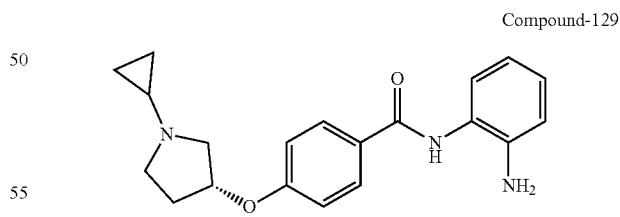
Compound-129

The title compound was synthesized by following the general procedure described above for Cbz Deprotection using Compound 8dh. $^1$H NMR (400 MHz, DMSO-d6) δ 9.51 (s, 1H), 7.93 (d, J=8.4 Hz, 2H), 7.14 (d, J=8.0 Hz, 1H), 7.10-6.91 (m, 3H), 6.77 (d, J=8.0 Hz, 1H), 6.63-6.54 (m, 1H), 4.96-4.93 (m, 1H), 4.86 (s, 2H), 3.05-3.01 (m, 1H), 2.88-2.72 (m, 2H), 2.64-2.54 (m, 1H), 2.33-2.28 (m, 1H), 1.82-1.62 (m, 2H), 0.46-0.26 (m, 4H); LCMS Calculated for $C_{20}H_{23}N_3O_2$: 337.18; Observed: 338.05 (M+1)$^+$.

Synthesis of (R)—N-(2-aminophenyl)-4-((1-(oxetan-3-yl)pyrrolidin-3-yl)oxy)benzamide (Compound 130)

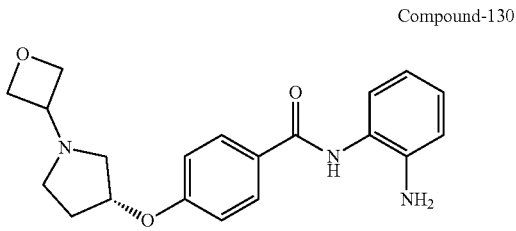 [SMILES: Nc1ccccc1NC(=O)c1ccc(O[C@@H]2CCN(C3COC3)C2)cc1]

Compound-130

The title compound was synthesized by following the general procedure described above for Cbz Deprotection using Compound 8di. $^1$H NMR (400 MHz, DMSO-d6) δ 9.51 (s, 1H), 7.98-7.90 (m, 2H), 7.15 (d, J=8.0 Hz, 1H), 7.03-6.91 (m, 3H), 6.77 (d, J=8.0 Hz, 1H), 6.59 (t, J=7.6 Hz, 1H), 5.02-4.98 (m, 1H), 4.85 (s, 2H), 4.57 (t, J=6.5 Hz, 2H), 4.49-4.43 (m, 2H), 3.63 (p, J=6.2 Hz, 1H), 2.90-2.86 (m, 1H), 2.76-2.60 (m, 2H), 2.49-2.26 (m, 2H), 1.84-1.80 (m, 1H); LCMS Calculated for $C_{20}H_{23}N_3O_3$: 353.17; Observed: 354.00 (M+1)$^+$.

Synthesis of N-(2-aminophenyl)-4-(piperidin-4-yloxy)benzamide Hydrochloride (Compound 65)

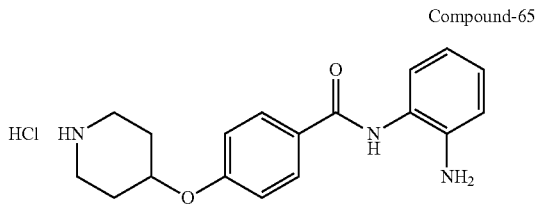 [SMILES: Cl ; Nc1ccccc1NC(=O)c1ccc(OC2CCNCC2)cc1]

Compound-65

The title compound was synthesized by following the general procedure described above for Cbz Deprotection using Compound 7e. $^1$H NMR (400 MHz, DMSO-d6) δ 9.58 (s, 1H), 8.99 (s, 2H), 7.98 (d, J=8.4 Hz, 2H), 7.15-7.09 (m, 3H), 6.96-6.94 (m, 1H), 6.78 (d, J=7.6 Hz, 1H), 6.61-6.57 (m, 1H), 4.80-4.76 (m, 2H), 3.29-3.21 (m, 2H), 3.11-3.05 (m, 2H), 2.16-2.12 (m, 2H), 1.91-1.82 (m, 2H); LCMS Calculated for $C_{18}H_{21}N_3O_2$: 311.16; Observed: 311.95 (M+1)$^+$.

Synthesis of N-(2-aminophenyl)-4-((1-methylpiperidin-4-yl)oxy)benzamide Dihydrochloride (Compound 66)

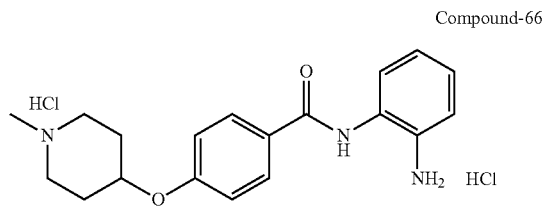 [SMILES: CN1CCC(Oc2ccc(C(=O)Nc3ccccc3N)cc2)CC1 ; Cl ; Cl]

Compound-66

The title compound was synthesized by following the general procedure described above for Cbz Deprotection using Compound 8ea. $^1$H NMR (400 MHz, DMSO-d6) δ 10.68 (s, 1H), 9.63 (s, 1H), 8.01-7.99 (m, 2H), 7.20-7.07 (m, 3H), 7.00-6.95 (m, 1H), 6.82 (d, J=7.9 Hz, 1H), 6.64 (t, J=7.7 Hz, 1H), 4.88 (s, 1H), 3.50-3.46 (m, 1H), 3.31-3.27 (m, 1H), 3.13-3.10 (m, 2H), 2.80-2.69 (m, 3H), 2.21-2.02 (m, 3H), 1.96-1.92 (m, 1H); LCMS Calculated for $C_{19}H_{23}N_3O_2$: 325.18; Observed: 325.90 (M+1)$^+$.

Synthesis of N-(2-aminophenyl)-4-((1-isobutylpiperidin-4-yl)oxy)benzamide Dihydrochloride (Compound 67)

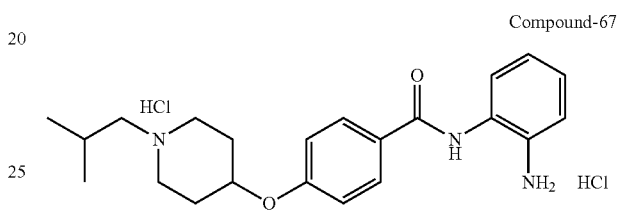

Compound-67

The title compound was synthesized by following the general procedure described above for Cbz Deprotection using Compound 8eb. $^1$H NMR (400 MHz, DMSO-d6) δ 10.14 (s, 1H), 9.96 (s, 1H), 8.09-8.05 (m, 2H), 7.42 (d, J=7.2 Hz, 1H), 7.24-7.10 (m, 5H), 4.95-4.80 (m, 1H), 3.57-3.54 (m, 1H), 3.39-3.35 (m, 1H), 3.19-2.88 (m, 4H), 2.37-2.20 (m, 2H), 2.19-1.99 (m, 3H), 1.01-0.99 (m, 6H); LCMS Calculated for $C_{22}H_{29}N_3O_2$: 367.23; Observed: 368.23 (M+1)$^+$.

Synthesis of N-(2-aminophenyl)-4-((1-((1-methylcyclopropyl)methyl)piperidin-4-yl)oxy)benzamide Dihydrochloride (Compound 68)

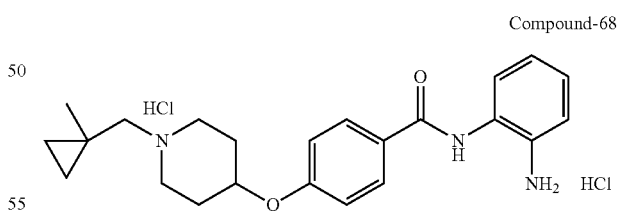

Compound-68

The title compound was synthesized by following the general procedure described above for Cbz Deprotection using Compound 8ef. $^1$H NMR (400 MHz, DMSO-d6) δ 10.37-10.36 (m, 2H), 8.14-8.10 (m, 2H), 7.54 (d, J=7.6 Hz, 1H), 7.42 (d, J=7.2 Hz, 1H), 7.30-7.26 (m, 2H), 7.18-7.12 (m, 2H), 4.92-4.90 (m, 1H), 3.63-3.54 (m, 1H), 3.43-3.32 (m, 1H), 3.20-2.98 (m, 4H), 2.40-1.99 (m, 4H), 1.22 (s, 3H), 0.63-0.62 (m, 2H), 0.48-0.46 (m, 2H); LCMS Calculated for $C_{23}H_{29}N_3O_2$: 379.23; Observed: 380.32 (M+1)$^+$.

Synthesis of N-(2-aminophenyl)-4-((1-(cyclohexylmethyl)piperidin-4-yl)oxy)benzamide Dihydrochloride (Compound 69)

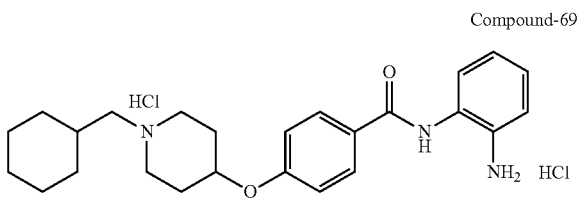 [SMILES: Nc1ccccc1NC(=O)c1ccc(OC2CCN(CC3CCCCC3)CC2)cc1 ; Cl ; Cl]

Compound-69

The title compound was synthesized by following the general procedure described above for Cbz Deprotection using Compound 8eg. $^1$H NMR (400 MHz, DMSO-d6) δ 10.33 (s, 1H), 10.17 (s, 1H), 8.14-8.07 (m, 2H), 7.55-7.48 (m, 1H), 7.40-7.36 (m, 1H), 7.30-7.27 (m, 2H), 7.18-7.12 (m, 2H), 4.91-4.69 (m, 1H), 3.56-3.53 (m, 1H), 3.39-3.35 (m, 1H), 3.12-3.05 (m, 2H), 2.96-2.90 (m, 2H), 2.38-2.19 (m, 2H), 2.11-2.01 (m, 2H), 1.86-1.82 (m, 3H), 1.70-1.60 (m, 3H), 1.35-1.33 (m, 2H), 1.15-1.12 (m, 1H), 0.98-0.95 (m, 2H); LCMS Calculated for $C_{25}H_{33}N_3O_2$: 407.26; Observed: 408.24 (M+1)$^+$.

Synthesis of N-(2-aminophenyl)-4-((1-cyclopropylpiperidin-4-yl)oxy)benzamide Dihydrochloride (Compound 131)

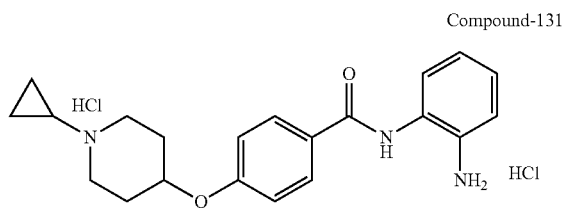 [SMILES: Nc1ccccc1NC(=O)c1ccc(OC2CCN(C3CC3)CC2)cc1 ; Cl ; Cl]

Compound-131

The title compound was synthesized by following the general procedure described above for Cbz Deprotection using Compound 8eh. $^1$H NMR (400 MHz, DMSO-d6) δ 10.35 (s, 1H), 8.15-8.08 (m, 2H), 7.53-7.50 (m, 1H), 7.43-7.36 (m, 1H), 7.33-7.23 (m, 2H), 7.22-7.10 (m, 2H), 4.91 (s, 1H), 3.59-3.51 (m, 1H), 3.37-3.27 (m, 3H), 2.44-2.31 (m, 1H), 2.29-2.20 (m, 2H), 2.11-1.97 (m, 2H), 1.18-1.15 (m, 2H), 0.83-0.76 (m, 2H); LCMS Calculated for $C_{21}H_{25}N_3O_2$: 351.19; Observed: 352.25 (M+1)$^+$.

Synthesis of N-(2-aminophenyl)-4-((1-(oxetan-3-yl)piperidin-4-yl)oxy)benzamide (Compound 132)

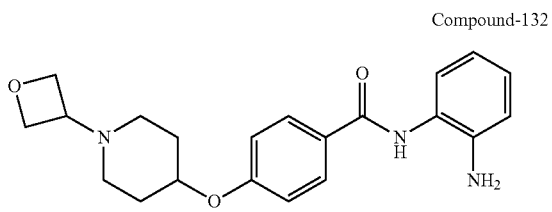 [SMILES: Nc1ccccc1NC(=O)c1ccc(OC2CCN(C3COC3)CC2)cc1]

Compound-132

The title compound was synthesized by following the general procedure described above for Cbz Deprotection using Compound 8ei. $^1$H NMR (400 MHz, DMSO-d6) δ 9.52 (s, 1H), 7.94 (d, J=8.8 Hz, 2H), 7.14 (d, J=8.0 Hz, 1H), 7.05 (d, J=8.8 Hz, 2H), 6.96 (t, J=8.0 Hz, 1H), 6.77 (d, J=7.6 Hz, 1H), 6.59 (t, J=7.2 Hz, 1H), 4.88-4.86 (m, 2H), 4.56-4.52 (m, 3H), 4.43 (t, J=5.6 Hz, 2H), 3.44-3.42 (m, 1H), 2.58-2.50 (m, 2H), 2.13-2.14 (m, 2H), 2.04-1.88 (m, 2H), 1.70-1.65 (m, 2H); LCMS Calculated for $C_{21}H_{25}N_3O_3$: 367.19; Observed: 368 (M+1)$^+$.

Synthesis of 4-((1-(((3r,5r,7r)-adamantan-1-yl)methyl)piperidin-4-yl)oxy)-N-(2-aminophenyl)benzamide Dihydrochloride (Compound 133)

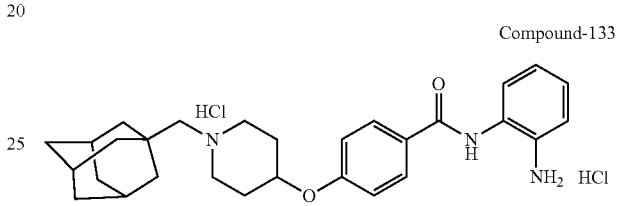

Compound-133

The title compound was synthesized by following the general procedure described above for Cbz Deprotection using Compound 8ej. $^1$H NMR (400 MHz, DMSO-d6) δ 10.28 (s, 1H), 9.71 (s, 1H), 8.10 (d, J=8.4 Hz, 2H), 7.53-7.46 (m, 1H), 7.34 (d, J=6.7 Hz, 1H), 7.30-7.06 (m, 4H), 4.90-4.82 (m, 1H), 4 3.64-3.47 (m, 1H), 3.46-3.33 (m, 1H), 3.28-3.10 (m, 1H), 2.91-2.88 (m, 2H), 2.33-2.16 (m, 3H), 1.98-1.96 (m, 5H), 1.76-1.63 (m, 14H); LCMS Calculated for $C_{29}H_{37}N_3O_2$: 459.29; Observed: 459.95 (M+1)$^+$.

Synthesis of 4-((8-azabicyclo[3.2.1]octan-3-yl)oxy)-N-(2-aminophenyl)benzamide Hydrochloride (Compound 70)

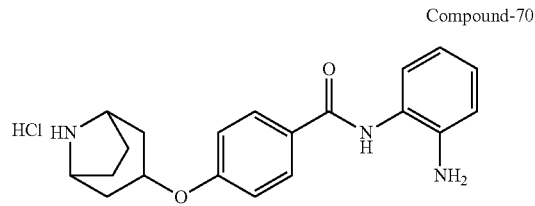 [SMILES: Cl ; Nc1ccccc1NC(=O)c1ccc(OC2CC3CCC(C2)N3)cc1]

Compound-70

The title compound was synthesized by following the general procedure described above for Cbz Deprotection using Compound 7f. $^1$H NMR (400 MHz, DMSO-d6) δ 9.57 (s, 1H), 8.92 (s, 2H), 7.95 (d, J=8.4 Hz, 2H), 7.15-7.11 (m, 3H), 6.97 (t, J=7.6 Hz, 1H), 6.78 (d, J=7.9 Hz, 1H), 6.60 (t, J=7.5 Hz, 1H), 4.94-4.81 (m, 3H), 4.14-4.02 (m, 2H), 2.27-2.23 (m, 2H), 2.11-2.09 (m, 1H), 1.99-1.96 (m, 2H), 1.91-1.83 (m, 2H); LCMS Calculated for $C_{20}H_{23}N_3O_2$: 337.18; Observed: 338.14 (M+1)$^+$.

Synthesis of N-(2-aminophenyl)-4-((8-methyl-8-azabicyclo[3.2.1]octan-3-yl)oxy)benzamide Dihydrochloride (Compound 71)

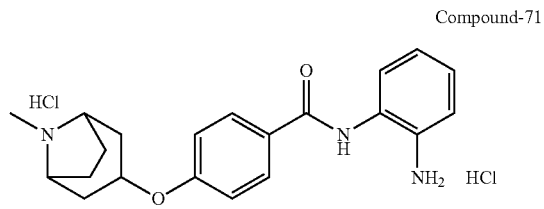 [SMILES: CN1C2CCC1CC(Oc1ccc(C(=O)Nc3ccccc3N)cc1)C2 ; Cl ; Cl]

Compound-71

The title compound was synthesized by following the general procedure described above for Cbz Deprotection using Compound 8fa. $^1$H NMR (400 MHz, DMSO-d6) δ 10.89 (s, 1H), 10.34 (s, 1H), 8.09 (d, J=8.2 Hz, 2H), 7.55-7.48 (m, 1H), 7.40-7.36 (m, 1H), 7.32-7.24 (m, 2H), 7.16 (d, J=8.2 Hz, 2H), 4.95-4.90 (m, 1H), 3.95-3.92 (m, 2H), 2.66 (s, 3H), 2.34-2.12 (m, 8H); LCMS Calculated for $C_{21}H_{25}N_3O_2$: 351.19; Observed: 352.25 (M+1)$^+$.

Synthesis of N-(2-aminophenyl)-4-((8-isobutyl-8-azabicyclo[3.2.1]octan-3-yl)oxy)benzamide Dihydrochloride (Compound 72)

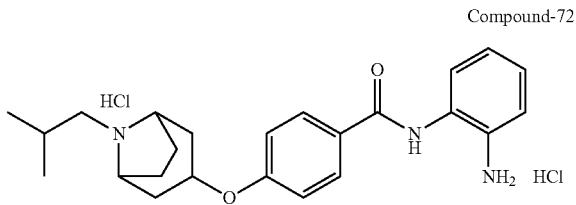 [SMILES: CC(C)CN1C2CCC1CC(Oc1ccc(C(=O)Nc3ccccc3N)cc1)C2 ; Cl ; Cl]

Compound-72

The title compound was synthesized by following the general procedure described above for Cbz Deprotection using Compound 8fb. $^1$H NMR (400 MHz, DMSO-d6) δ 10.41 (s, 1H), 9.97-9.89 (m, 1H), 8.11 (d, J=8.4 Hz, 2H), 7.55 (d, J=7.6 Hz, 1H), 7.43 (d, J=7.4 Hz, 1H), 7.33-7.27 (m, 2H), 7.17 (d, J=8.4 Hz, 2H), 4.94-4.92 (m, 1H), 4.04 (s, 2H), 2.80 (t, J=6.4 Hz, 2H), 2.39-2.30 (m, 4H), 2.18-2.10 (m, 5H), 1.00 (d, J=6.5 Hz, 6H); LCMS Calculated for $C_{24}H_{31}N_3O_2$: 393.24; Observed: 392.20 (M+1)$^+$.

Synthesis of N-(2-aminophenyl)-4-((8-(2-hydroxy-2-methylpropyl)-8-azabicyclo[3.2.1]octan-3-yl)oxy)benzamide Dihydrochloride (Compound 73)

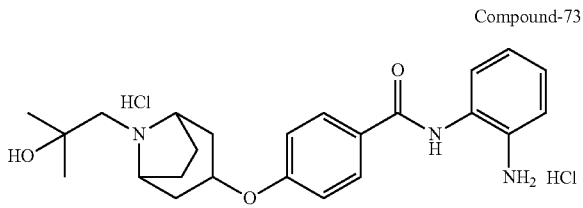 [SMILES: CC(C)(O)CN1C2CCC1CC(Oc1ccc(C(=O)Nc3ccccc3N)cc1)C2 ; Cl ; Cl]

Compound-73

The title compound was synthesized by following the general procedure described above for Cbz Deprotection using Compound 8fc. $^1$H NMR (400 MHz, DMSO-d6) δ 10.34 (s, 1H), 9.46 (s, 1H), 8.09 (d, J=8.4 Hz, 2H), 7.56-7.48 (m, 1H), 7.42-7.34 (m, 1H), 7.31-7.23 (m, 2H), 7.16 (d, J=8.2 Hz, 2H), 4.95-4.92 (m, 1H), 4.19 (s, 2H), 3.00 (d, J=4.8 Hz, 2H), 2.44 (t, J=12.0 Hz, 2H), 2.33-2.05 (m, 6H), 1.29 (s, 6H); LCMS Calculated for $C_{24}H_{31}N_3O_3$: 409.24; Observed: 409.90 (M+1)$^+$.

Synthesis of N-(2-aminophenyl)-4-((8-neopentyl-8-azabicyclo[3.2.1]octan-3-yl)oxy)benzamide Dihydrochloride (Compound 74)

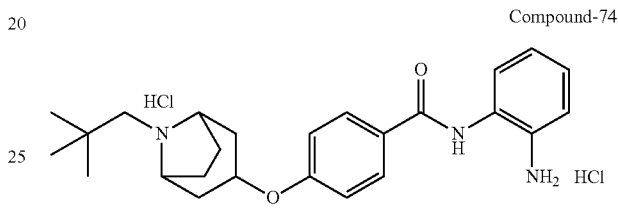

Compound-74

The title compound was synthesized by following the general procedure described above for Cbz Deprotection using Compound 8fd. $^1$H NMR (400 MHz, DMSO-d6) δ 10.38 (s, 1H), 8.60 (s, 1H), 8.12 (d, J=8.4 Hz, 2H), 7.58-7.51 (m, 1H), 7.42 (d, J=7.1 Hz, 1H), 7.29-7.27 (m, 2H), 7.16 (d, J=8.8 Hz, 2H), 4.96-4.92 (m, 1H), 4.05 (s, 2H), 2.89-2.87 (m, 2H), 2.31-2.13 (m, 8H), 1.11 (s, 9H); LCMS Calculated for $C_{25}H_{33}N_3O_2$: 407.26; Observed: 407.95 (M+1)$^+$.

Synthesis of N-(2-aminophenyl)-4-((8-(cyclopropylmethyl)-8-azabicyclo[3.2.1]octan-3-yl)oxy)benzamide Dihydrochloride (Compound 75)

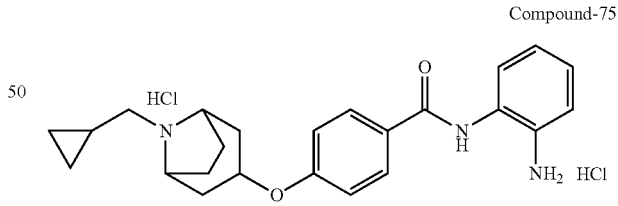

Compound-75

The title compound was synthesized by following the general procedure described above for Cbz Deprotection using Compound 8fe. $^1$H NMR (400 MHz, DMSO-d6) δ 10.74 (s, 1H), 10.38 (s, 1H), 8.09 (d, J=7.6 Hz, 1H), 7.53 (d, J=6.8 Hz, 1H), 7.41-7.38 (m, 1H), 7.31-7.28 (m, 2H), 7.17 (d, J=8.4 Hz, 2H), 4.96-4.92 (m, 1H), 4.16-4.13 (m, 2H), 2.89-2.85 (m, 2H), 2.30-2.23 (m, 4H), 2.19-2.13 (m, 4H), 1.25-1.20 (m, 1H), 0.64-0.61 (m, 2H), 0.46-0.39 (m, 2H); LCMS Calculated for $C_{24}H_{29}N_3O_2$: 391.23; Observed: 392.20 (M+1)$^+$.

Synthesis of N-(2-aminophenyl)-4-((8-((1-methylcyclopropyl)methyl)-8-azabicyclo[3.2.1]octan-3-yl)oxy)benzamide Dihydrochloride (Compound 76)

Compound-76

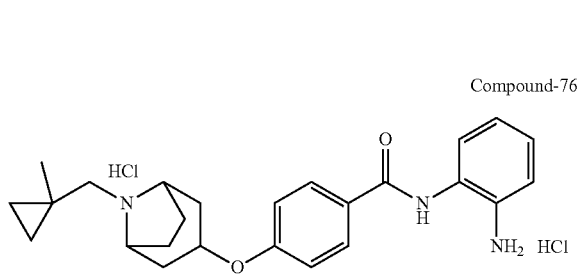 [SMILES: CC1(CN2C3CCC2CC(Oc2ccc(C(=O)Nc4ccccc4N)cc2)C3)CC1 ; Cl ; Cl]

The title compound was synthesized by following the general procedure described above for Cbz Deprotection using Compound 8ff. $^1$H NMR (400 MHz, DMSO-d6) δ 10.30 (s, 1H), 9.71 (s, 1H), 8.09 (d, J=8.4 Hz, 2H), 7.53-7.46 (m, 1H), 7.37-7.22 (m, 3H), 7.21-7.13 (m, 2H), 5.06-4.91 (m, 1H), 4.12 (s, 2H), 2.91 (d, J=6.0 Hz, 2H), 2.41-2.11 (m, 8H), 1.22 (s, 3H), 0.69-0.57 (m, 2H), 0.46-0.44 (m, 2H); LCMS Calculated for $C_{25}H_{31}N_3O_2$: 405.24; Observed: 406.36 (M+1)$^+$.

Synthesis of N-(2-aminophenyl)-4-((8-(cyclohexylmethyl)-8-azabicyclo[3.2.1]octan-3-yl)oxy)benzamide Dihydrochloride (Compound 77)

Compound-77

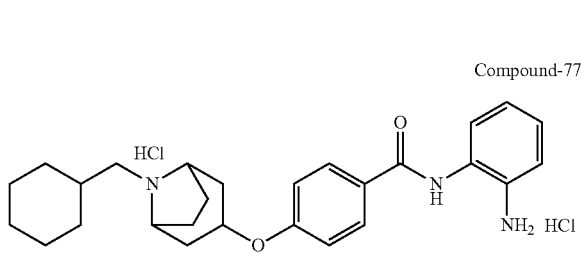 [SMILES: Nc1ccccc1NC(=O)c1ccc(OC2CC3CCC(C2)N3CC2CCCCC2)cc1 ; Cl ; Cl]

The title compound was synthesized by following the general procedure described above for Cbz Deprotection using Compound 8fg. $^1$H NMR (400 MHz, DMSO-d6) δ 10.29 (s, 1H), 9.94 (s, 1H), 8.07 (d, J=8.1 Hz, 2H), 7.50-7.47 (m, 1H), 7.37-7.30 (m, 1H), 7.27-7.20 (m, 2H), 7.14 (d, J=8.0 Hz, 2H), 4.94-4.90 (m, 1H), 4.02-4.00 (m, 2H), 2.79-2.75 (m, 2H), 2.27-2.11 (m, 8H), 1.85-1.76 (m, 3H), 1.69-1.59 (m, 3H), 1.31-1.08 (m, 3H), 1.02-0.96 (m, 2H); LCMS Calculated for $C_{27}H_{35}N_3O_2$: 433.27; Observed: 434.45 (M+1)$^+$.

Synthesis of Compounds 78, 81, 85, 87-93, 110-120, 122, 134, 135, 140-142 and 170

Synthesis of Compounds 78, 81, 85, 87-93, 110-120, 122, 134, 135, 140-142 and 170 are generally described in the following Scheme D:

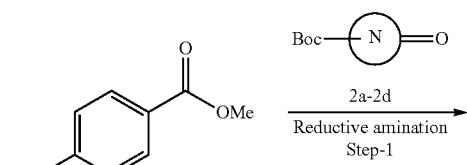

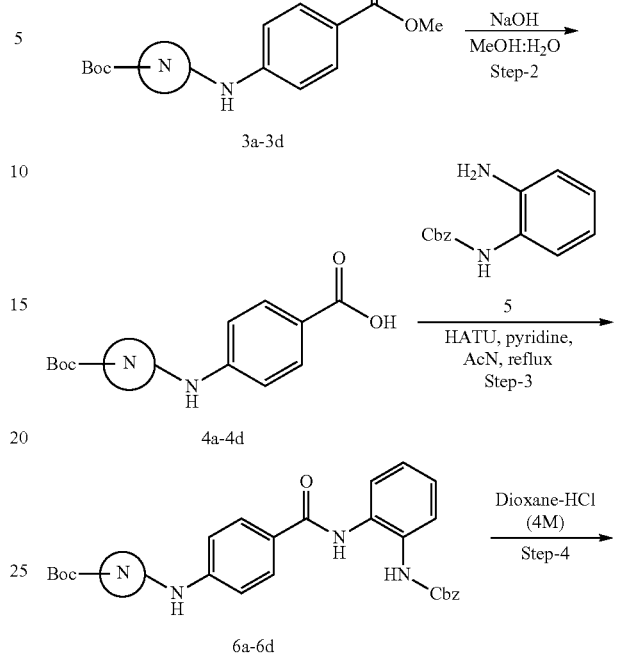

-continued

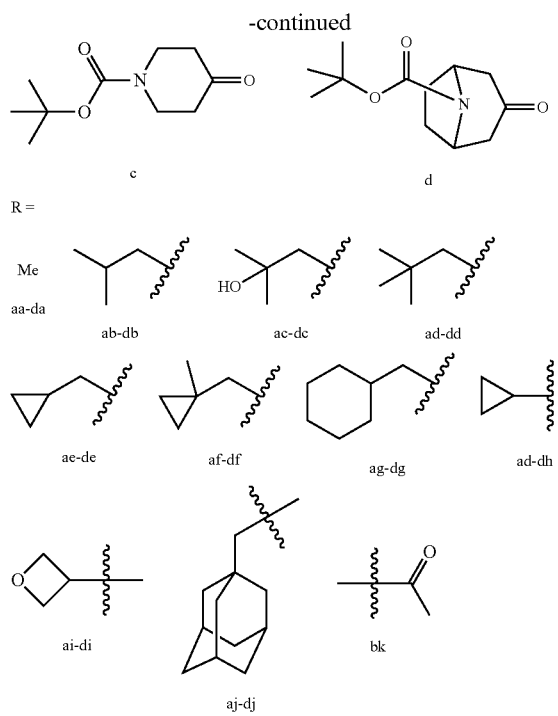

General Procedure for Reductive Amination:

Procedure A:

To a stirred solution of the amino compound (1 eq) and the corresponding aldehyde (1.2 eq) in DCM was added acetic acid (6 eq) and sodium triacetoxyborohydride (STAB) (3 eq) at room temperature. After stirring the reaction mixture at ambient temperature overnight, the reaction progress was monitored by TLC and LCMS. After completion of reaction, the reaction mixture was partitioned between DCM and water. The organic layers were separated, washed with water and brine, dried over $Na_2SO_4$ and evaporated to get the crude product which was purified by silica gel column chromatography to afford the desired compound.

Procedure B:

To a stirred solution of the amino compound (1 eq) and the corresponding aldehyde (1.2 eq) in DCE/DCM was added titanium tetra-isopropoxide (Ti(O-i-Pr)$_4$) (1.5 eq), AcOH (1.5 eq) at room temperature. After 5 min, STAB (1.5 eq) was added and the mixture was heated at 60° C. for 12 h. The reaction progress was monitored by TLC and LCMS. After completion of reaction, the reaction mixture was diluted with DCM and the resulting mixture was filtered over a pad of celite. The filtrate was concentrated and the resulting residue was purified by silica gel column chromatography to provide the desired compound.

General Procedure for Ester Hydrolysis:

To stirred solution of the ester compound in methanol: water (1:1) was added NaOH (1.5 eq) at room temperature. The above mixture was heated to 90° C. for 5 h. The progress of the reaction was monitored by TLC. After completion of reaction, the reaction mixture was concentrated and the resulting residue was washed with diethyl ether followed by treatment with water. The aqueous layer was neutralized to pH=7 using 1N HCl at 0° C. The solid obtained was filtered, washed with water and dried under vacuum to provide the desired compound.

General Procedure for Amide Coupling:

To a stirred solution of the acid compound (1 eq) and the corresponding amino compound (1.1 eq) in ACN was added pyridine (5eq) and HATU (1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over $Na_2SO_4$ and concentrated. The crude residue was purified by silica gel column chromatography to provide the desired compound.

General Procedure for Boc-Deprotection:

To a stirred solution of the Boc compound (1 eq) in 1,4-dioxane was added 4M HCl in dioxane at room temperature. After completion of reaction, the reaction mixture was concentrated and the resulting residue was triturated with n-pentane and dried under vacuum to give desired compound.

General Procedure for N-Alkylation:

Procedure A:

To a stirred solution of the amino compound (1 eq) and cesium carbonate/potassium carbonate (3 eq) in DMF/ACN (10 vol), corresponding alkyl halide (1.1 eq) was added. The reaction mixture was heated at 80° C. for 5 h to 30 h. The progress of reaction was monitored by TLC. After completion, the reaction mixture was poured into ice-water and extracted with ethyl acetate. The combined organic extracts were washed with water, brine, dried over anhydrous $Na_2SO_4$, filtered and concentrated under reduced pressure to provide a crude residue which was purified by silica gel column chromatography.

Procedure B:

To a solution of the amino compound (1 eq) in 5 vol of ethanol was added TEA (3 eq) followed by 2, 2-dimethyloxirane (2.5 eq) at room temperature and the reaction mixture was heated at 90° C. for 4 h. The progress of reaction was monitored by TLC. After completion, the reaction mixture was allowed to cool, concentrated to give a crude compound which was purified by Combiflash chromatography/silica gel column chromatography.

General Procedure for Cbz Deprotection:

To a stirred solution of the Cbz compound (1 eq) in methanol/4M HCl in MeOH, 10% Pd/C (10% w/w of substrate) was added and the reaction mixture was stirred under hydrogen atmosphere (balloon pressure) at room temperature for 3 h. The progress of the reaction was monitored by TLC. After completion, the reaction mixture was filtered through a pad of celite, the filtrate was evaporated under reduced pressure and the resulting residue was triturated with diethyl ether and n-pentane and then dried under vacuum to afford the title compound. Some of the final compounds were purified by Prep-HPLC.

Step 1: Synthesis of Compounds 3a-3d

The title compounds were synthesized by following the general procedure described in Scheme D for the Reductive Amination reaction using Compound 1 and Compounds 2a-2d.

Step 2: Synthesis of Compounds 4a-4d

The title compounds were synthesized by following the general procedure described in Scheme D for the Ester Hydrolysis of respective esters 3a-3d.

Step 3: Synthesis of Compounds 6a-6d

The title Compounds 6a to 6d were synthesized by following the general procedure described in Scheme D for the Amide Coupling using Compounds 4a-4d and Compound 5.

Step 4: Synthesis of Compounds 7a-7d

The title Compounds 7a-7d were synthesized by following the general procedure described in Scheme D for the Boc deprotection from Compounds 6a-6d.

Step 5: Synthesis of Compounds 8aa-8da, 8ab-db, 8ac-dc, 8ad-dd, 8ae-de, 8af-df, 8ag-dg, 8ah-dh, 8ai-di, and 8aj-dj The title compounds were synthesized by following the general procedure described in Scheme D for N-alkylation or Reductive Amination.

| No | Structure | R |
|---|---|---|
| 8ac | | HO-C(Me)₂-CH₂- |
| 8ag | R-N-azepane-NH-C₆H₄-C(O)NH-C₆H₄-NHCbz | cyclohexyl-CH₂- |
| 8ba | R-N-azetidine-NH-C₆H₄-C(O)NH-C₆H₄-NHCbz | Me |
| 8bb | | isobutyl |
| 8bc | | HO-C(Me)₂-CH₂- |
| 8bd | | neopentyl |
| 8be | | cyclopropyl-CH₂- |
| 8bf | | (1-methylcyclopropyl)-CH₂- |
| 8bg | | cyclohexyl-CH₂- |
| 8bh | | cyclopropyl |

-continued
| No | Structure | R |
|---|---|---|
| 8bi | | 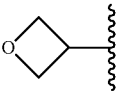 |
| 8bk | | —COCH3 |
| 8ca | 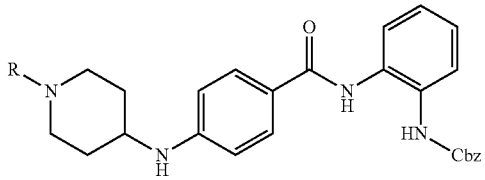 | Me |
| 8cb | | 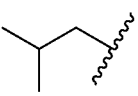 |
| 8cf | | 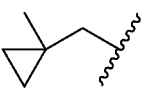 [SMILES: *CC1(C)CC1] |
| 8cg | | 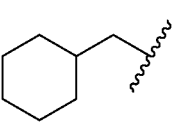 [SMILES: *CC1CCCCC1] |
| 8ch | |  |
| 8ci | | 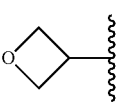 |
| 8cj | | 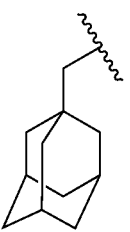 [SMILES: *CC12CC3CC(CC(C3)C1)C2] |
| 8da | 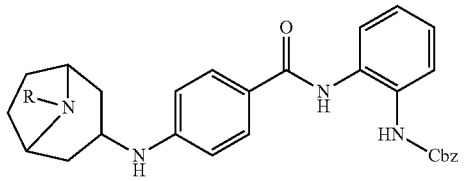 | Me |
| 8db | | 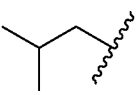 |
| 8dc | | 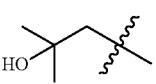 |

-continued

| No | Structure R |
|---|---|
| 8dd | ![structure] |
| 8de | ![structure] |
| 8dg | ![structure] |

Step-6: Synthesis of Compounds 78, 81, 85, 87-93, 110-120, 122, 134, 135, 140-142 and 170

The titled compounds has been synthesized by following the general procedure described in Scheme D for Cbz-Deprotection.

Synthesis of N-(2-aminophenyl)-4-(azepan-4-ylamino)benzamide tris(2,2,2-trifluoroacetate) (Compound 78)

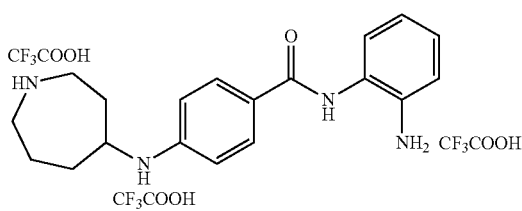

Compound-78

The title compound was synthesized from Compound 7a by following the general procedure described in Scheme D for Cbz Deprotection. $^1$H NMR (400 MHz, DMSO-d6) δ 9.59 (s, 1H), 8.62 (s, 2H), 7.80 (d, J=8.4 Hz, 2H), 7.24 (d, J=7.8 Hz, 1H), 7.11-7.06 (m, 1H), 7.00 (d, J=7.7 Hz, 1H), 6.89 (t, J=7.5 Hz, 1H), 6.63 (d, J=8.4 Hz, 2H), 3.74-3.65 (m, 2H), 3.29-3.03 (m, 3H), 2.06-2.01 (m, 2H), 1.96-1.68 (m, 3H), 1.64-1.50 (m, 1H); LCMS Calculated for $C_{19}H_{24}N_4O$: 324.20; Observed: 324.90 (M+1)$^+$.

Synthesis of N-(2-aminophenyl)-4-((1-(2-hydroxy-2-methylpropyl)azepan-4-yl)amino)benzamide Tri-hydrochloride (Compound 81)

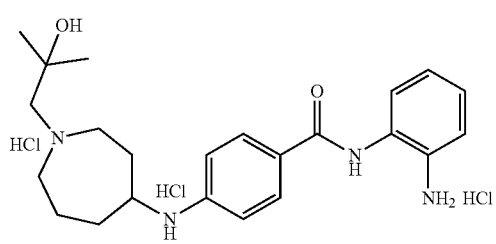

Compound-81

The title compound was synthesized from Compound 8ac by following the general procedure described in Scheme D for Cbz Deprotection. $^1$H NMR (400 MHz, DMSO-d6) δ 10.16 (s, 1H), 9.49 (bs, 1H), 7.94-7.90 (m, 2H), 7.54 (d, J=8.0 Hz, 1H), 7.50-7.24 (m, 3H), 6.67 (dd, J=13.6, 8.5 Hz, 2H), 3.47-3.43 (m, 1H), 3.63-3.39 (m, 3H), 3.33-3.03 (m, 4H), 2.07-1.96 (m, 5H), 1.58-1.55 (m, 1H), 1.26 (s, 6H); LCMS Calculated for $C_{23}H_{32}N_4O_2$: 396.25; Observed: 397.00 (M+1)$^+$.

Synthesis of N-(2-aminophenyl)-4-((1-(cyclohexylmethyl)azepan-4-yl)amino)benzamide (Compound 85)

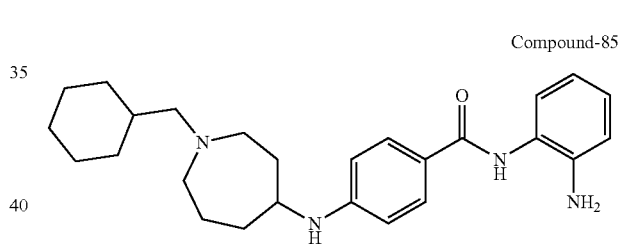

Compound-85

The title compound was synthesized by from Compound 8ag following the general procedure described in Scheme D for Cbz Deprotection. $^1$H NMR (400 MHz, DMSO-d6) δ 9.27 (s, 1H), 7.76 (d, J=8.4 Hz, 2H), 7.13 (d, J=8.0 Hz, 1H), 6.93 (t, J=7.5 Hz, 1H), 6.76 (d, J=8.0 Hz, 1H), 6.61-6.57 (m, 3H), 6.20-6.15 (m, 1H), 4.80 (s, 2H), 3.62-3.58 (m, 1H), 2.96-2.93 (m, 2H), 2.33-1.91 (m, 4H), 1.77-1.62 (m, 11H), 1.22-0.93 (m, 6H); LCMS Calculated for $C_{26}H_{36}N_4O$: 420.29; Observed: 420.95 (M+1)$^+$.

Synthesis of N-(2-aminophenyl)-4-((1-methylazetidin-3-yl)amino)benzamide tris(2,2,2-trifluoroacetate) (Compound 87)

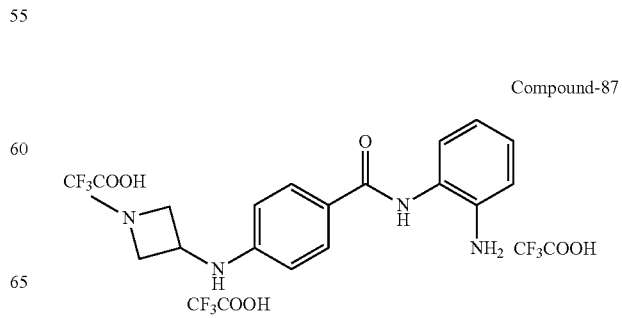

Compound-87

The title compound was synthesized from Compound 8ba by following the general procedure described in Scheme D for Cbz Deprotection. $^1$H NMR (400 MHz, DMSO-d6) δ 9.98-9.86 (m, 1H), 9.54 (s, 1H), 7.84 (d, J=8.4 Hz, 2H), 7.27-7.16 (m, 1H), 7.07-6.82 (m, 3H), 6.76 (t, J=7.6 Hz, 1H), 6.64-6.54 (m, 2H), 4.68-4.52 (m, 2H), 4.42-4.31 (m, 1H), 4.23-4.20 (m, 1H), 4.17-4.09 (m, 1H), 2.93-2.88 (m, 3H); LCMS Calculated for $C_{17}H_{20}N_4O$: 296.16; Observed: 296.90 (M+1)$^+$.

Synthesis of N-(2-aminophenyl)-4-((1-isobutylazetidin-3-yl)amino)benzamide Trihydrochloride (Compound 88)

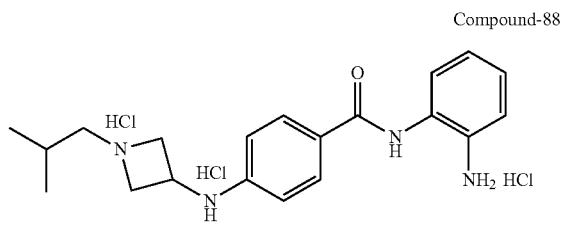 [SMILES: CC(C)CN1CC(Nc2ccc(C(=O)Nc3ccccc3N)cc2)C1 ; Cl ; Cl ; Cl]

Compound-88

The title compound was synthesized from Compound 8bb by following the general procedure described in Scheme D for Cbz Deprotection. $^1$H NMR (400 MHz, DMSO-d6) δ 10.63 (bs, 1H), 10.15 (s, 1H), 7.97-7.94 (m, 2H), 7.51-7.49 (m, 1H), 7.38-7.36 (m, 1H), 7.28-7.24 (m, 2H), 6.65-6.62 (m, 1H), 4.59-4.52 (m, 2H), 4.41-4.31 (m, 2H), 4.15-4.09 (m, 1H), 3.92-3.89 (m, 2H), 3.17-3.07 (m, 2H), 1.95-1.88 (m, 1H), 0.96-0.93 (m, 6H); LCMS Calculated for $C_{20}H_{26}N_4O$: 338.21; Observed: 338.85 (M+1)$^+$.

Synthesis of N-(2-aminophenyl)-4-((1-(2-hydroxy-2-methylpropyl)azetidin-3-yl)amino)benzamide (Compound 89)

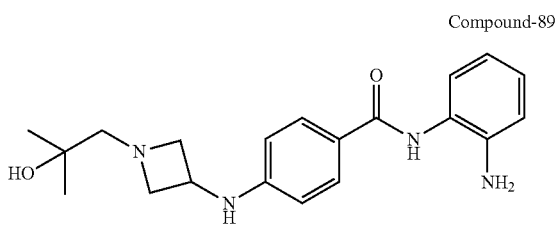 [SMILES: CC(C)(O)CN1CC(Nc2ccc(C(=O)Nc3ccccc3N)cc2)C1]

Compound-89

The title compound was synthesized from Compound 8bc by following the general procedure described in Scheme D for Cbz Deprotection. $^1$H NMR (400 MHz, DMSO-d6) δ 9.27 (s, 1H), 7.76 (d, J=8.8 Hz, 2H), 7.14 (d, J=8.0 Hz, 1H), 6.93 (t, J=7.2 Hz, 1H), 6.76 (d, J=7.6 Hz, 1H), 6.67-6.50 (m, 4H), 4.81 (s, 2H), 4.07-3.96 (m, 2H), 3.75 (t, J=6.8 Hz, 2H), 2.92 (t, J=6.8 Hz, 2H), 2.35 (s, 2H), 1.05 (s, 6H); LCMS Calculated for $C_{20}H_{26}N_4O_2$: 354.21; Observed: 354.90 (M+1)$^+$.

Synthesis of N-(2-aminophenyl)-4-((1-neopentylazetidin-3-yl)amino)benzamide (Compound 90)

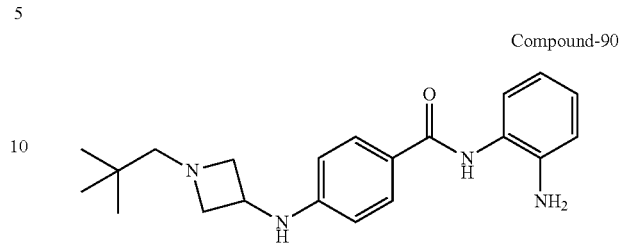

Compound-90

The title compound was synthesized from Compound 8bd by following the general procedure described in Scheme D for Cbz Deprotection. $^1$H NMR (400 MHz, DMSO-d6) δ 9.29 (s, 1H), 7.76 (d, J=8.0 Hz, 2H), 7.13 (d, J=8.0 Hz, 1H), 6.93 (t, J=7.6 Hz, 1H), 6.76 (d, J=8.0 Hz, 1H), 6.66 (d, J=6.4 Hz, 1H), 6.63-6.51 (m, 3H), 4.82 (s, 2H), 4.06-4.02 (m, 1H), 3.75-3.73 (m, 2H), 2.91-2.89 (m, 2H), 2.21 (s, 2H), 0.84 (s, 9H); LCMS Calculated for $C_{21}H_{28}N_4O$: 352.23; Observed: 353.25 (M+1)$^+$.

Synthesis of N-(2-aminophenyl)-4-((1-(cyclopropylmethyl)azetidin-3-yl)amino)benzamide Trihydrochloride (Compound 91)

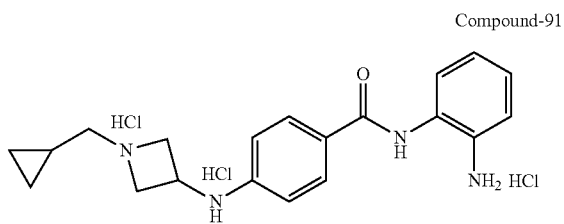 [SMILES: Nc1ccccc1NC(=O)c1ccc(NC2CN(CC3CC3)C2)cc1 ; Cl ; Cl ; Cl]

Compound-91

The title compound was synthesized from Compound 8be by following the general procedure described in Scheme D for Cbz Deprotection. $^1$H NMR (400 MHz, DMSO-d6) δ 10.92 (s, 1H), 10.24 (s, 1H), 8.00-7.95 (m, 2H), 7.56-7.53 (m, 1H), 7.45-7.43 (m, 1H), 7.39-7.34 (m, 1H), 7.32-7.27 (m, 1H), 6.67-6.62 (m, 2H), 4.60-4.49 (m, 2H), 4.47-4.24 (m, 2H), 4.10-4.04 (m, 1H), 3.96-3.93 (m, 1H), 3.14-3.05 (m, 2H), 1.02-1.00 (m, 1H), 0.62-0.50 (m, 2H), 0.41-0.37 (m, 2H); LCMS Calculated for $C_{20}H_{24}N_4O$: 336.20; Observed: 336.95 (M+1)$^+$.

Synthesis of N-(2-aminophenyl)-4-((1-((1-methcyclopropylcyclopropyl)methyl)azetidin-3-yl)amino)benzamide (Compound 92)

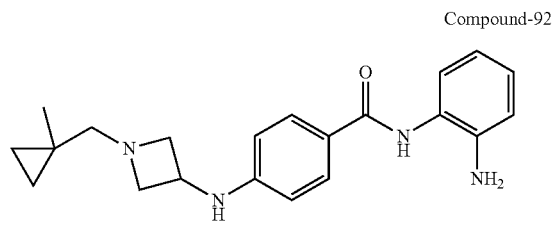 [SMILES: CC1(CN2CC(Nc3ccc(C(=O)Nc4ccccc4N)cc3)C2)CC1]

Compound-92

The title compound was synthesized from Compound 8bf by following the general procedure described in Scheme D for Cbz Deprotection. $^1$H NMR (400 MHz, DMSO-d6) δ 9.28 (s, 1H), 7.76 (d, J=8.8 Hz, 2H), 7.13 (d, J=7.6 Hz, 1H), 6.93 (t, J=7.6 Hz, 1H), 6.76 (d, J=8.0 Hz, 1H), 6.68-6.51 (m, 3H), 4.81 (s, 2H), 4.05-4.03 (m, 1H), 3.70-3.65 (m, 2H), 2.82-2.78 (m, 2H), 2.26-2.24 (m, 2H), 1.02 (s, 3H), 0.28-0.19 (m, 4H); LCMS Calculated for $C_{21}H_{26}N_4O$: 350.21; Observed: 351.25 (M+1)$^+$.

Synthesis of N-(2-aminophenyl)-4-((1-(cyclohexyl-methyl)azetidin-3-yl)amino)benzamide (Compound-93)

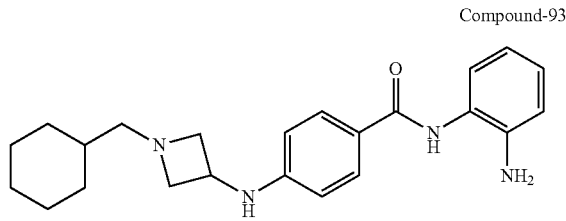 [SMILES: Nc1ccccc1NC(=O)c1ccc(NC2CN(CC3CCCCC3)C2)cc1]
Compound-93

The title compound was synthesized from Compound 8bg by following the general procedure described in Scheme D for Cbz Deprotection. $^1$H NMR (400 MHz, DMSO-d6) δ 9.25 (m, 1H), 7.78-7.70 (m, 2H), 7.19-7.08 (m, 1H), 6.93-6.90 (m, 1H), 6.78-6.71 (m, 1H), 6.66-6.49 (m, 3H), 4.79 (s, 2H), 4.00-3.97 (m, 1H), 3.64-3.60 (m, 2H), 2.79-2.75 (m, 2H), 2.26-2.23 (m, 2H), 1.69-1.60 (m, 5H), 1.22-1.08 (m, 4H), 0.88-0.82 (m, 2H); LCMS Calculated for $C_{23}H_{30}N_4O$: 378.24; Observed: 378.90 (M+1)$^+$.

Synthesis of N-(2-aminophenyl)-4-((1-cyclopropy-lazetidin-3-yl)amino)benzamide Trihydrochloride (Compound 134)

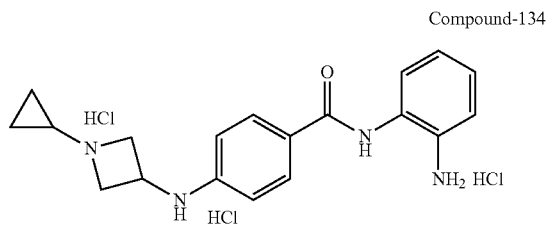 [SMILES: Nc1ccccc1NC(=O)c1ccc(NC2CN(C3CC3)C2)cc1 ; Cl ; Cl ; Cl]
Compound-134

The title compound was synthesized from Compound 8bh by following the general procedure described in Scheme D for Cbz Deprotection. $^1$H NMR (400 MHz, DMSO-d6) δ 11.43 (s, 1H), 10.18 (s, 1H), 9.31 (s, 2H), 7.95 (d, J=8.0 Hz, 2H), 7.52 (d, J=7.4 Hz, 1H), 7.44-7.21 (m, 2H), 6.66-6.63 (m, 2H), 4.59-3.92 (m, 6H), 3.10-3.05 (m, 1H), 0.94-0.78 (m, 4H); LCMS Calculated for $C_{19}H_{22}N_4O$: 322.18; Observed: 323.00 (M+1)$^+$.

Synthesis of N-(2-aminophenyl)-4-((1-(oxetan-3-yl)azetidin-3-yl)amino)benzamide (Compound 135)

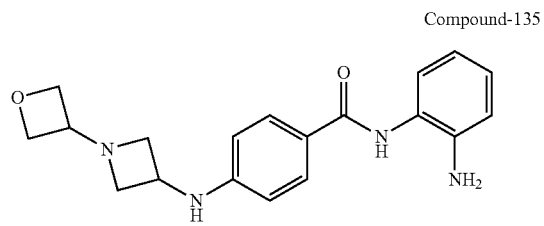 [SMILES: Nc1ccccc1NC(=O)c1ccc(NC2CN(C3COC3)C2)cc1]
Compound-135

The title compound was synthesized from Compound 8bi by following the general procedure described in Scheme D for Cbz Deprotection. $^1$H NMR (400 MHz, DMSO-d6) δ 9.31 (s, 1H), 7.76 (d, J=8.8 Hz, 2H), 7.15-7.12 (m, 1H), 6.98-6.80 (m, 1H), 6.77-6.71 (m, 2H), 6.65-6.55 (m, 3H), 4.81 (s, 2H), 4.61-4.44 (m, 2H), 4.39 (t, J=5.8 Hz, 2H), 4.22-4.11 (m, 1H), 3.87-3.72 (m, 1H), 3.68 (t, J=7.2 Hz, 2H), 2.98 (t, J=6.8 Hz, 2H); LCMS Calculated for $C_{19}H_{22}N_4O_2$: 338.17; Observed: 339 (M+1)$^+$.

Synthesis of 4-((1-acetylazetidin-3-yl)amino)-N-(2-aminophenyl)benzamide (Compound 170)

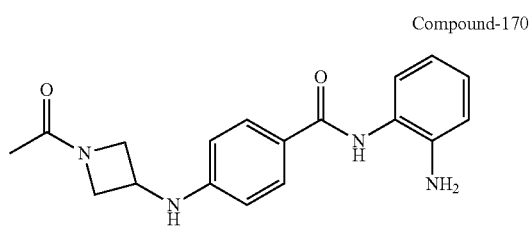 [SMILES: CC(=O)N1CC(Nc2ccc(C(=O)Nc3ccccc3N)cc2)C1]
Compound-170

The title compound was synthesized from Compound 8bk by following the general procedure described in Scheme D for Cbz Deprotection. $^1$H NMR (400 MHz, DMSO-d6) δ 9.33 (s, 1H), 7.81-7.75 (m, 2H), 7.15-7.12 (m, 1H), 6.98-6.83 (m, 2H), 6.77-6.75 (m, 1H), 6.63-6.55 (m, 3H), 4.82 (s, 2H), 4.55-4.48 (m, 1H), 4.35-4.23 (m, 2H), 3.89-3.86 (m, 1H), 3.74-3.64 (m, 1H), 1.77 (s, 3H); LCMS Calculated for $C_{18}H_{20}N_4O_2$: 324.16; Observed: 325.05 (M+1)$^+$.

Synthesis of N-(2-aminophenyl)-4-((1-methylpiperi-din-4-yl)amino)benzamide Dihydrochloride (Compound 110)

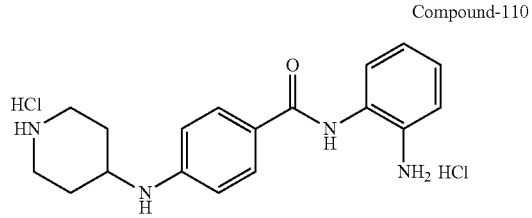 [SMILES: Cl ; Nc1ccccc1NC(=O)c1ccc(NC2CCNCC2)cc1 ; Cl]
Compound-110

The title compound was synthesized from Compound 7c by following the general procedure described in Scheme D for Cbz Deprotection. $^1$H NMR (400 MHz, DMSO-d6) δ 10.09 (s, 1H), 9.02-8.98 (m, 2H), 7.92 (d, J=8.4 Hz, 2H), 7.55-7.48 (m, 1H), 7.39 (d, J=6.7 Hz, 1H), 7.34-7.21 (m, 2H), 6.70 (d, J=8.4 Hz, 2H), 3.66-3.63 (m, 1H), 3.31-3.27 (m, 2H), 3.07-2.93 (m, 2H), 2.11-2.00 (m, 2H), 1.72-1.57 (m, 2H); LCMS Calculated for $C_{18}H_{22}N_4O$: 310.18; Observed: 311.11 (M+1)$^+$.

Synthesis of N-(2-aminophenyl)-4-((1-methylpiperidin-4-yl)amino)benzamide (Compound 111)

Compound-111

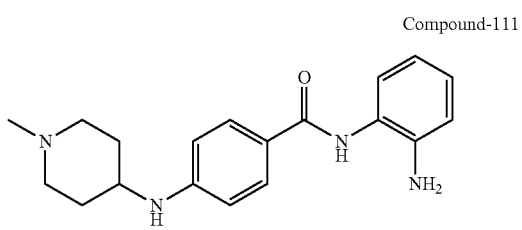 [SMILES: CN1CCC(Nc2ccc(C(=O)Nc3ccccc3N)cc2)CC1]

The title compound was synthesized from Compound 8ca by following the general procedure described in Scheme D for Cbz Deprotection. $^1$H NMR (400 MHz, DMSO-d6) δ 9.27 (s, 1H), 7.75 (d, J=8.8 Hz, 2H), 7.13 (d, J=7.6 Hz, 1H), 6.93 (t, J=7.6 Hz, 1H), 6.76 (d, J=7.8 Hz, 1H), 6.64-6.54 (m, 3H), 6.15-6.08 (m, 1H), 4.81 (s, 2H), 3.33-3.29 (m, 1H), 2.86-2.83 (m, 2H), 2.27-2.21 (m, 5H), 1.93-1.85 (m, 2H), 1.77-1.58 (m, 2H); LCMS Calculated for $C_{19}H_{24}N_4O$: 324.20; Observed: 324.90 (M+1)$^+$.

Synthesis of N-(2-aminophenyl)-4-((1-isobutylpiperidin-4-yl)amino)benzamide Trihydrochloride (Compound 112)

Compound-112

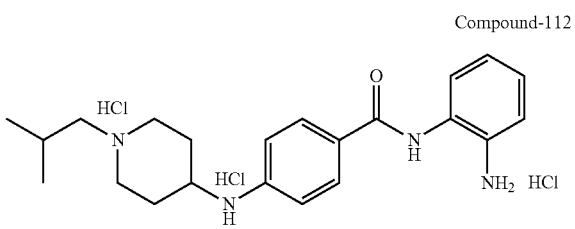 [SMILES: CC(C)CN1CCC(Nc2ccc(C(=O)Nc3ccccc3N)cc2)CC1 ; Cl ; Cl ; Cl]

The title compound was synthesized from Compound 8cb by following the general procedure described in Scheme D for Cbz Deprotection. $^1$H NMR (400 MHz, DMSO-d6) δ 10.27 (s, 2H), 7.98 (d, J=8.2 Hz, 2H), 7.59 (dd, J=27.4, 7.9 Hz, 2H), 7.43 (t, J=7.9 Hz, 1H), 7.31 (t, J=7.7 Hz, 1H), 6.80 (d, J=8.4 Hz, 1H), 6.72 (d, J=8.3 Hz, 1H), 3.85-3.83 (m, 1H), 3.59-3.49 (m, 2H), 3.31-3.28 (m, 1H), 3.05-2.83 (m, 4H), 2.22-1.90 (m, 5H), 1.00 (d, J=6.4 Hz, 6H); LCMS Calculated for $C_{22}H_{30}N_4O$: 366.24; Observed: 367.30 (M+1)$^+$.

Synthesis of N-(2-aminophenyl)-4-((1-((1-methylcyclopropyl)methyl)piperidin-4-yl)amino)benzamide Trihydrochloride (Compound 113)

Compound-113

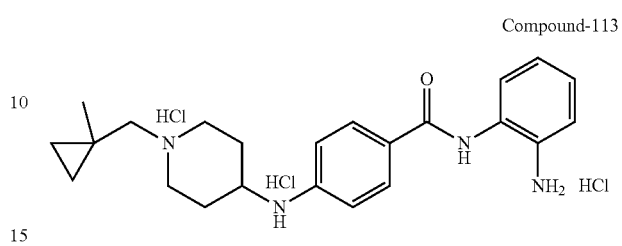

The title compound was synthesized from Compound 8cf by following the general procedure described in Scheme D for Cbz Deprotection. $^1$H NMR (400 MHz, DMSO-d6) δ 10.19-10.13 (m, 2H), 7.94 (d, J=8.4 Hz, 2H), 7.55 (d, J=8.0 Hz, 1H), 7.49-7.21 (m, 3H), 6.77-6.68 (m, 2H), 3.58-3.32 (m, 3H), 3.05-2.98 (m, 4H), 2.20-2.07 (m, 2H), 1.96-1.87 (m, 2H), 1.21 (s, 3H), 0.48-0.35 (m, 4H); LCMS Calculated for $C_{23}H_{30}N_4O$: 378.24; Observed: 378.80 (M+1)$^+$.

Synthesis of N-(2-aminophenyl)-4-((1-(cyclohexylmethyl)piperidin-4-yl)amino)benzamide (Compound 114 Compound-114

Compound-114

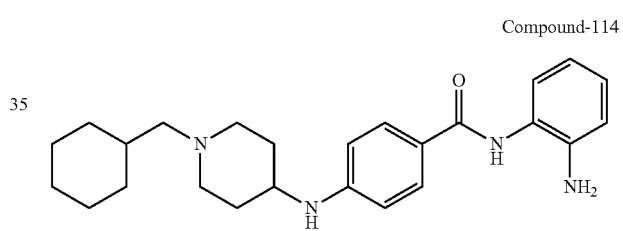

The title compound was synthesized from Compound 8cg by following the general procedure described in Scheme D for Cbz Deprotection. $^1$H NMR (400 MHz, DMSO-d6) δ 9.27 (s, 1H), 7.75 (d, J=8.8 Hz, 2H), 7.13 (d, J=7.6 Hz, 1H), 6.93 (t, J=7.6 Hz, 1H), 6.76 (d, J=7.8 Hz, 1H), 6.64-6.54 (m, 3H), 6.15-6.08 (m, 1H), 4.81 (s, 2H), 3.33-3.29 (m, 1H), 2.86-2.83 (m, 2H), 2.07-1.88 (m, 6H), 1.74-1.64 (m, 4H), 1.45-1.38 (m, 3H), 1.23-1.08 (m, 4H), 0.84-0.81 (m, 2H); LCMS Calculated for $C_{25}H_{34}N_4O$: 406.27; Observed: 407.45 (M+1)$^+$.

Synthesis of N-(2-aminophenyl)-4-((1-cyclopropylpiperidin-4-yl)amino)benzamide Trihydrochloride Trihydrochloride (Compound 140)

Compound-140

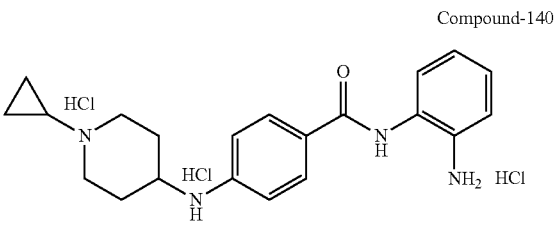 [SMILES: Nc1ccccc1NC(=O)c1ccc(NC2CCN(C3CC3)CC2)cc1 ; Cl ; Cl ; Cl]

The title compound was synthesized from Compound 8ch by following the general procedure described in Scheme D for Cbz Deprotection. $^1$H NMR (400 MHz, DMSO-d6) δ 10.80-10.64 (m, 1H), 10.19 (s, 1H), 7.94 (d, J=5.2 Hz, 2H), 7.60-7.30 (m, 4H), 6.81-6.69 (m, 2H), 3.67-3.48 (m, 3H), 3.47-3.14 (m, 3H), 2.75-2.73 (m, 1H), 2.11-2.08 (m, 2H), 1.90-1.84 (m, 2H), 1.18-1.15 (m, 2H), 0.80-0.75 (m, 2H); LCMS Calculated for $C_{21}H_{26}N_4O$: 350.21; Observed: 351.00 (M+1)$^+$.

Synthesis of N-(2-aminophenyl)-4-((1-(oxetan-3-yl)piperidin-4-yl)amino)benzamide (Compound 141)

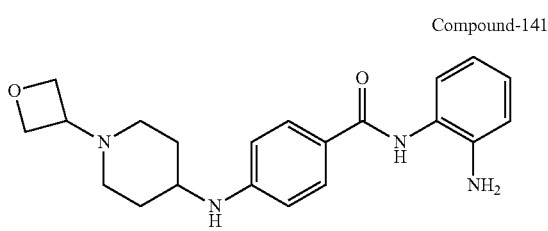 [SMILES: Nc1ccccc1NC(=O)c1ccc(NC2CCN(C3COC3)CC2)cc1]

Compound-141

The title compound was synthesized from Compound 8ci by following the general procedure described in Scheme D for Cbz Deprotection. $^1$H NMR (400 MHz, DMSO-d6) δ 9.26 (s, 1H), 7.78-7.71 (m, 2H), 7.11 (d, J=7.6 Hz, 1H), 6.97-6.91 (m, 1H), 6.76-6.73 (m, 1H), 6.60-6.56 (m, 3H), 6.15-6.13 (m, 1H), 4.80 (s, 1H), 4.51 (t, J=6.4 Hz, 2H), 4.40 (t, J=6.0 Hz, 2H), 4.13-4.09 (m, 1H), 3.40-3.37 (m, 2H), 2.66-2.63 (m, 2H), 1.92-1.88 (m, 4H), 1.44-1.35 (m, 2H); LCMS Calculated for $C_{21}H_{26}N_4O_2$: 366.21; Observed: 366.95 (M+1)$^+$.

Synthesis of 4-((1-(((3r,5r,7r)-adamantan-1-yl)methyl)piperidin-4-yl)amino)-N-(2-aminophenyl)benzamide Trihydrochloride (Compound 142)

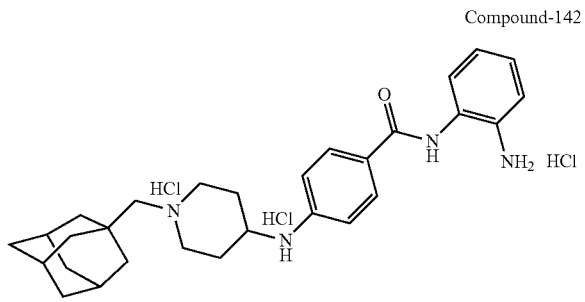 [SMILES: Nc1ccccc1NC(=O)c1ccc(NC2CCN(CC34CC5CC(CC(C5)C3)C4)CC2)cc1 ; Cl ; Cl ; Cl]

Compound-142

The title compound was synthesized from Compound 8cj by following the general procedure described in Scheme D for Cbz Deprotection. $^1$H NMR (400 MHz, DMSO-d6) δ 10.06 (s, 1H), 9.39 (s, 1H), 7.91 (d, J=8.4 Hz, 2H), 7.50 (d, J=8.0 Hz, 1H), 7.41-7.32 (m, 1H), 7.34-7.21 (m, 2H), 6.76-6.69 (m, 2H), 3.64-3.48 (m, 2H), 3.41-3.30 (m, 1H), 3.24-3.11 (m, 1H), 2.95-2.83 (m, 2H), 2.19-2.16 (m, 1H), 1.99-1.95 (m, 5H) 1.72-1.67 (m, 14H); LCMS Calculated for $C_{29}H_{38}N_4O$: 458.30; Observed: 458.85 (M+1)$^+$.

Synthesis of 4-((8-azabicyclo[3.2.1]octan-3-yl)amino)-N-(2-aminophenyl)benzamide (Compound 115)

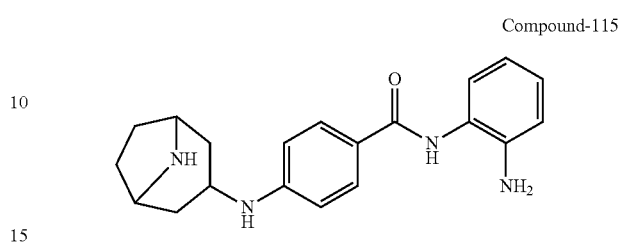

Compound-115

The title compound was synthesized from Compound 7d by following the general procedure described in Scheme D for Cbz Deprotection. $^1$H NMR (400 MHz, DMSO-d6) δ 9.30 (s, 1H), 8.41 (s, 1H), 7.78 (d, J=8.8 Hz, 2H), 7.13 (d, J=7.2 Hz, 1H), 6.93 (t, J=7.6 Hz, 1H), 6.76 (d, J=7.2 Hz, 1H), 6.62-6.57 (m, 3H), 6.22-6.21 (m, 1H), 4.90-4.80 (m, 2H), 3.76-3.62 (m, 3H), 2.22-2.16 (m, 4H), 1.87-1.81 (m, 4H); LCMS Calculated for $C_{20}H_{24}N_4O$: 336.20; Observed: 337.15 (M+1)$^+$.

Synthesis of N-(2-aminophenyl)-4-((8-methyl-8-azabicyclo[3.2.1]octan-3-yl)amino)benzamide Trihydrochloride (Compound 116)

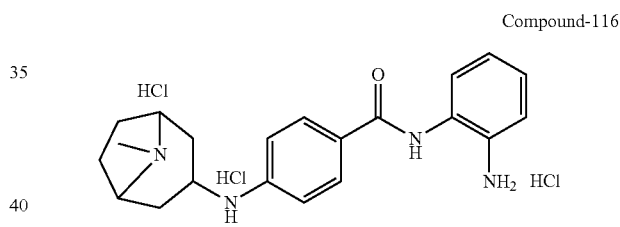

Compound-116

The title compound was synthesized from Compound 8da by following the general procedure described in Scheme D for Cbz Deprotection. $^1$H NMR (400 MHz, DMSO-d6) δ 10.20 (s, 1H), 10.05 (s, 1H), 7.91 (d, J=8.4 Hz, 2H), 7.49-7.42 (m, 1H), 7.37-7.21 (m, 3H), 6.72-6.61 (m, 2H), 6.51-6.49 (m, 1H), 3.85-3.83 (m, 2H), 3.70-3.56 (m, 1H), 2.66-2.64 (m, 3H), 2.35-2.31 (m, 3H), 2.25-2.13 (m, 2H), 2.04-2.02 (m, 2H); LCMS Calculated for $C_{21}H_{26}N_4O$: 350.21; Observed: 350.90 (M+1)$^+$.

Synthesis of N-(2-aminophenyl)-4-((8-isobutyl-8-azabicyclo[3.2.1]octan-3-yl)amino)benzamide (Compound 117)

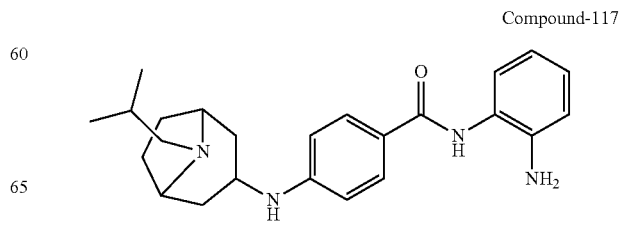

Compound-117

The title compound was synthesized from Compound 8db by following the general procedure described in Scheme D for Cbz Deprotection. $^1$H NMR (400 MHz, DMSO-d6) δ 9.45 (s, 1H), 9.32 (s, 1H), 7.80 (d, J=8.4 Hz, 2H), 7.12 (d, J=7.6 Hz, 1H), 6.92 (t, J=7.6 Hz, 1H), 6.75 (d, J=7.6 Hz, 1H), 6.66-6.53 (m, 3H), 6.40 (s, 1H), 4.81 (s, 2H), 3.92-3.90 (m, 2H), 3.63-3.57 (m, 1H), 2.77-2.74 (m, 2H), 2.62-2.59 (m, 2H), 2.31-2.29 (m, 2H), 2.20-2.05 (m, 3H), 1.99-1.97 (m, 2H), 0.98 (d, J=5.2 Hz, 6H); LCMS Calculated for $C_{24}H_{32}N_4O$: 392.26; Observed: 393.25 (M+1)$^+$.

Synthesis of N-(2-aminophenyl)-4-((8-(2-hydroxy-2-methylpropyl)-8-azabicyclo[3.2.1]octan-3-yl)amino)benzamide (Compound 118)

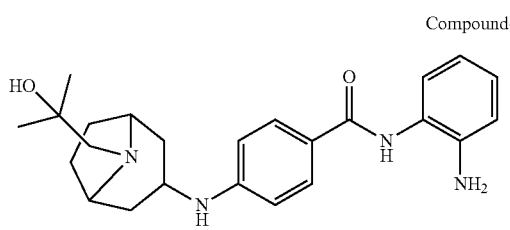

Compound-118

The title compound was synthesized from Compound 8de by following the general procedure described in Scheme D for Cbz Deprotection. $^1$H NMR (400 MHz, DMSO-d6) δ 9.34 (s, 1H), 7.81 (d, J=6.8 Hz, 2H), 7.12 (d, J=6.8 Hz, 1H), 6.96-6.94 (m, 1H), 6.78-6.76 (m, 1H), 6.64-6.59 (m, 3H), 6.41-6.39 (m, 1H), 5.35-5.32 (m, 1H), 4.85-4.83 (m, 2H), 4.06-4.04 (m, 2H), 3.59-3.57 (m, 1H), 2.99-2.96 (m, 2H), 2.74-2.66 (m, 2H), 2.33-2.28 (m, 2H), 2.20-2.18 (m, 1H), 2.01-1.97 (m, 1H), 1.28 (s, 6H); LCMS Calculated for $C_{24}H_{32}N_4O_2$: 408.25; Observed: 409.20 (M+1)$^+$.

Synthesis of N-(2-aminophenyl)-4-((8-neopentyl-8-azabicyclo[3.2.1]octan-3-yl)amino)benzamide (Compound 119)

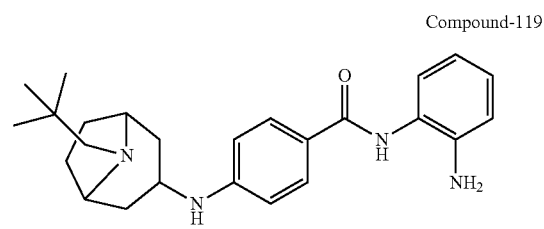 [SMILES: CC(C)(C)CN1C2CCC1CC(Nc1ccc(C(=O)Nc3ccccc3N)cc1)C2]

Compound-119

The title compound was synthesized from Compound 8dd by following the general procedure described in Scheme D for Cbz Deprotection. $^1$H NMR (400 MHz, DMSO-d6) δ 9.22 (s, 1H), 7.73 (d, J=8.8 Hz, 2H), 7.12 (d, J=8.0 Hz, 1H), 6.91 (t, J=8.0 Hz, 1H), 6.74 (d, J=8.0 Hz, 1H), 6.58-6.54 (m, 3H), 5.99-5.97 (m, 1H), 3.52-3.49 (m, 1H), 3.01-2.99 (m, 2H), 2.11-2.08 (m, 2H), 1.95-1.89 (m, 4H), 1.77-1.75 (m, 2H), 1.68-1.64 (m, 2H), 0.83 (s, 9H); LCMS Calculated for $C_{25}H_{34}N_4O$: 406.27; Observed: 407.25 (M+1)$^+$.

Synthesis of N-(2-aminophenyl)-4-((8-(cyclopropylmethyl)-8-azabicyclo[3.2.1]octan-3-yl)amino)benzamide Trihydrochloride (Compound 120)

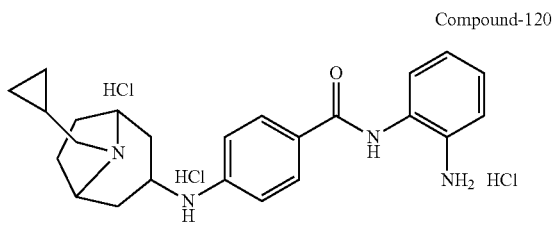 [SMILES: Nc1ccccc1NC(=O)c1ccc(NC2CC3CCC(C2)N3CC2CC2)cc1 ; Cl ; Cl ; Cl]

Compound-120

The title compound was synthesized from Compound 8de by following the general procedure described in Scheme D for Cbz Deprotection. $^1$H NMR (400 MHz, DMSO-d6) δ 10.66 (s, 1H), 10.25 (s, 1H), 7.97 (d, J=8.4 Hz, 2H), 7.60 (d, J=7.6 Hz, 1H), 7.53 (d, J=7.8 Hz, 1H), 7.42 (t, J=7.8 Hz, 1H), 7.31 (t, J=7.6 Hz, 1H), 6.69 (d, J=8.4 Hz, 2H), 4.03 (s, 2H), 3.67-3.65 (m, 1H), 2.89-2.80 (m, 2H), 2.69-2.66 (m, 2H), 2.35-2.33 (m, 2H), 2.13-2.00 (m, 4H), 1.23-1.21 (m, 1H), 0.61-0.43 (m, 4H); LCMS Calculated for $C_{24}H_{30}N_4O$: 390.24; Observed: 391.24 (M+1)$^+$.

Synthesis of N-(2-aminophenyl)-4-((8-(cyclohexylmethyl)-8-azabicyclo[3.2.1]octan-3-yl)amino)benzamide (Compound 122)

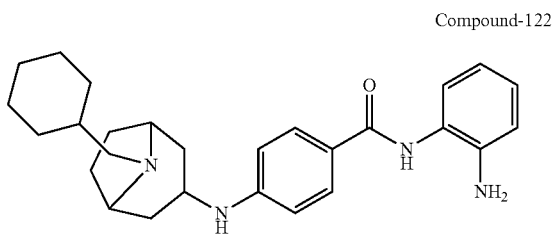 [SMILES: Nc1ccccc1NC(=O)c1ccc(NC2CC3CCC(C2)N3CC2CCCCC2)cc1]

Compound-122

The title compound was synthesized from Compound 8dg by following the general procedure described in Scheme D for Cbz Deprotection. $^1$H NMR (400 MHz, DMSO-d6) δ 9.26 (s, 1H), 7.75 (d, J=8.4 Hz, 2H), 7.13 (d, J=8.0 Hz, 1H), 6.93 (t, J=8.0 Hz, 1H), 6.76 (d, J=7.6 Hz, 1H), 6.60-6.54 (m, 3H), 6.03 (d, J=4.4 Hz, 1H), 4.81-4.79 (m, 2H), 3.53-3.51 (m, 1H), 3.08-3.06 (m, 2H), 2.12-2.04 (m, 4H), 1.92-1.77 (m, 6H), 1.68-1.60 (m, 4H), 1.34-1.11 (m, 5H), 0.89-0.80 (m, 2H); LCMS Calculated for $C_{27}H_{36}N_4O$: 432.29; Observed: 433.30 (M+1)$^+$.

Synthesis of N-(2-aminophenyl)-4-((1-isobutylazepan-4-yl)amino)benzamide and N-(2-aminophenyl)-4-((1-(cyclopropylmethyl)azepan-4-yl)amino)benzamide Trihydrochloride (Compounds 80 and 83)

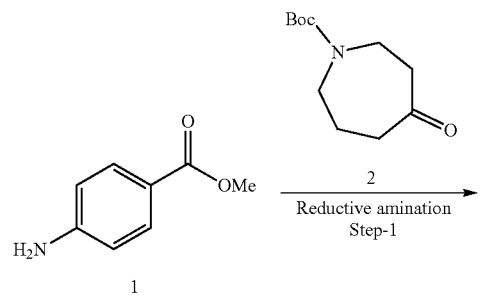

-continued

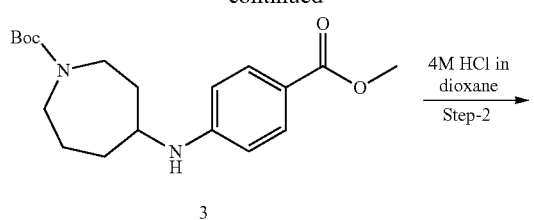
3

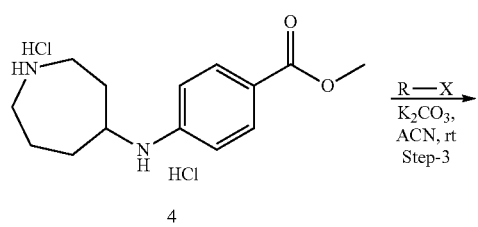
4

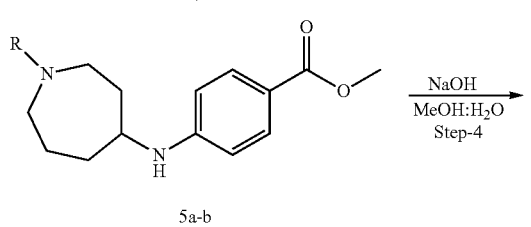
5a-b

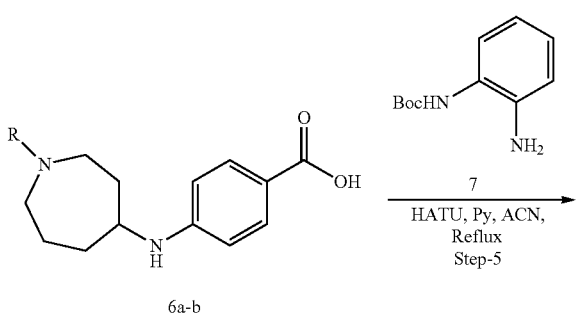
6a-b

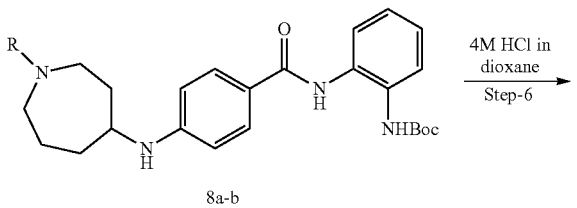
8a-b

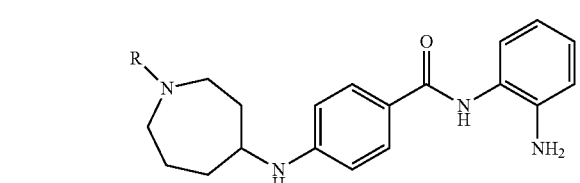

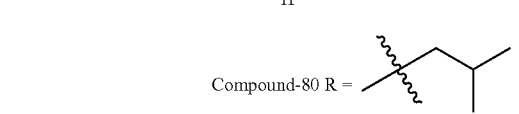

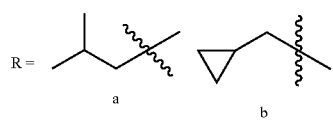

Step-1: Synthesis of Compound 3

The titled compound 3 has been synthesized by following the general procedure described in Scheme D for Reductive Amination (Procedure-B) using Compounds 1 and 2.

Step-2: Synthesis of Compound 4

The titled Compound 4 has been synthesized by following the general procedure described in Scheme D for Boc-Deprotection from Compound 3.

Step-3: Synthesis of Compounds 5a and 5b

The titled Compounds 5a and 5b has been synthesized by following general procedure described in Scheme D for N-alkylation (Procedure-A) using Compound 4 and the respective halides.

Step-4: Synthesis of Compounds 6a and 6b

The titled Compounds 6a and 6b has been synthesized by following general procedure described in Scheme D for Ester Hydrolysis of Compounds 5a-5b.

Step-5: Synthesis of Compounds 8a and 8b

The titled Compounds 8a and 8b has been synthesized by following the general procedure described in Scheme D for Amide Coupling by treating Compounds 6a-b with Compound 7.

Step-6: Synthesis of Compounds 80 and 83

Synthesis of N-(2-aminophenyl)-4-((1-isobutylazepan-4-yl)amino)benzamide (Compound 80)

The title compound was synthesized using Compound 8a by following the general procedure described in Scheme D for Boc-Deprotection. $^1$H NMR (400 MHz, DMSO-d6) δ 9.26 (s, 1H), 7.74 (d, J=8.8 Hz, 2H), 7.13 (d, J=7.6 Hz, 1H), 6.98-6.88 (m, 1H), 6.76 (d, J=7.6 Hz, 1H), 6.63-6.51 (m, 3H), 6.15 (d, J=7.6 Hz, 1H), 4.81 (s, 2H), 3.58-3.55 (m, 1H), 2.67-2.56 (m, 5H), 2.18-2.15 m, 2H), 1.94-1.82 (m, 2H), 1.76-1.53 (m, 4H), 0.87 (d, J=6.4 Hz, 6H); LCMS Calculated for $C_{23}H_{32}N_4O$: 380.26; Observed: 380.90 (M+1)$^+$.

Synthesis of N-(2-aminophenyl)-4-((1-(cyclopropylmethyl)azepan-4-yl)amino)benzamide Trihydrochloride (Compound 83)

The title compound was synthesized using Compound 8b by following the general procedure described in Scheme D for Boc-Deprotection. $^1$H NMR (400 MHz, DMSO-d6) δ 10.48 (s, 1H), 10.16 (s, 1H), 7.96-7.88 (m, 2H), 7.53 (d, J=8.0 Hz, 1H), 7.48-7.19 (m, 3H), 6.69-6.65 (m, 2H), 4.06-4.00 (m, 2H), 3.80-3.17 (m, 3H), 3.08-2.90 (m, 2H), 2.19-1.82 (m, 5H), 1.73-1.49 (m, 1H), 1.23-1.14 (m, 1H), 0.65-0.62 (m, 2H), 0.42-0.40 (m, 2H); LCMS Calculated for $C_{23}H_{30}N_4O$: 378.24; Observed: 379.26 (M+1)$^+$.

Synthesis of N-(2-aminophenyl)-4-(azetidin-3-ylamino)benzamide Trihydrochloride (Compound 86)

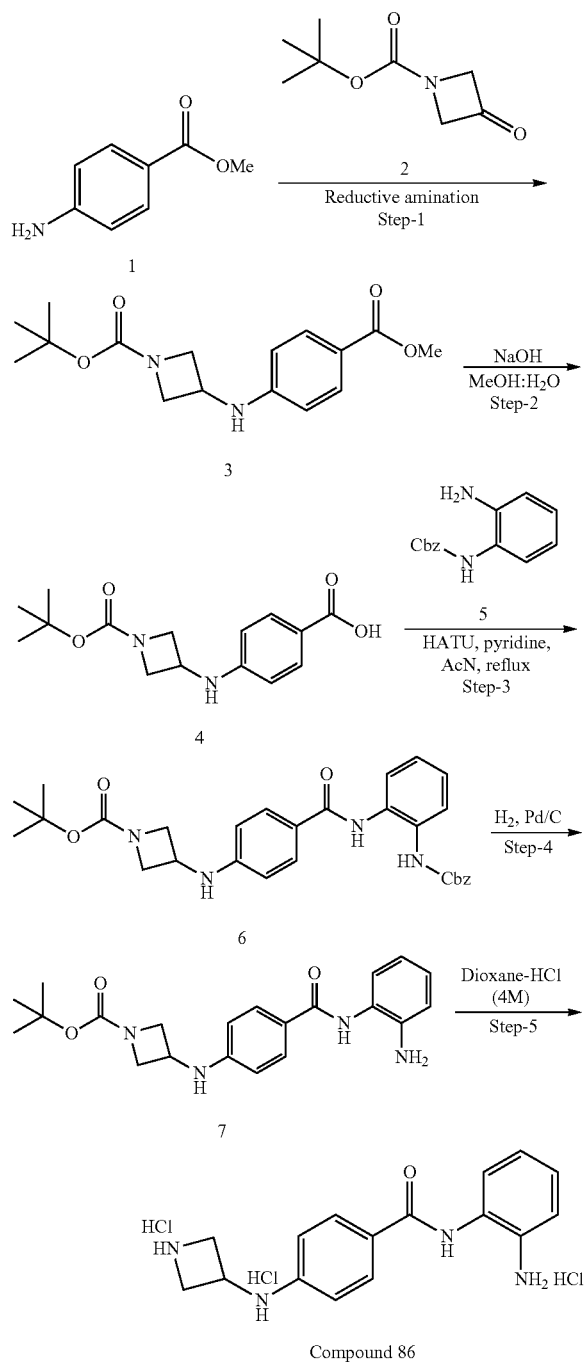

Step-1: Synthesis of Tert-Butyl 3-((4-(methoxycarbonyl)phenyl)amino)azetidine-1-carboxylate (3)

The titled Compound 3 has been synthesized using Compounds 1 and 2 by following the general procedure described in Scheme D for Reductive Amination (Procedure-A).

Step-2: Synthesis of 4-((1-(tert-butoxycarbonyl)azetidin-3-yl)amino)benzoic Acid (4)

The titled Compound 4 has been synthesized from Compound 3 by following general procedure described in Scheme D for Ester Hydrolysis.

Step-3: Synthesis of Tert-Butyl 3-((4-((2-(((benzyloxy)carbonyl)amino) phenyl)carbamoyl)phenyl)amino)azetidine-1-carboxylate (6)

The titled Compound 6 has been synthesized by following the general procedure described in Scheme D for Amide Coupling using Compounds 4 and 5.

Step-4: Synthesis of Tert-Butyl 3-((4-((2-aminophenyl)carbamoyl)phenyl) amino)azetidine-1-carboxylate (7)

The titled Compound 7 has been synthesized by following the general procedure described in Scheme D for Cbz Deprotection using Compound 6.

Step-5: Synthesis of N-(2-aminophenyl)-4-(azetidin-3-ylamino)benzamide Trihydrochloride (Compound 86)

The title Compound 86 was synthesized from Compound 7 by following the general procedure described in Scheme D for Boc-Deprotection. $^1$H NMR (400 MHz, DMSO-d6) δ 10.10 (s, 1H), 9.19 (s, 2H), 7.94 (d, J=8.4 Hz, 2H), 7.52-7.44 (m, 1H), 7.38-7.21 (m, 3H), 6.62 (d, J=8.4 Hz, 2H), 4.47-4.42 (m, 1H), 4.30-4.28 (m, 2H), 3.86-3.82 (m, 2H); LCMS Calculated for C16H18N4O: 282.15; Observed: 282.90 $(M+1)^+$.

Synthesis of Compounds 95-101, 103-109 and 136-139

Synthesis of these compounds is described in the following Scheme E:

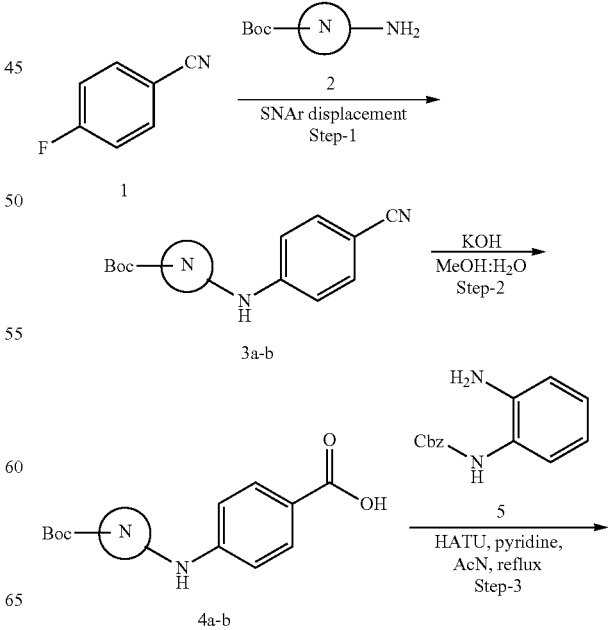

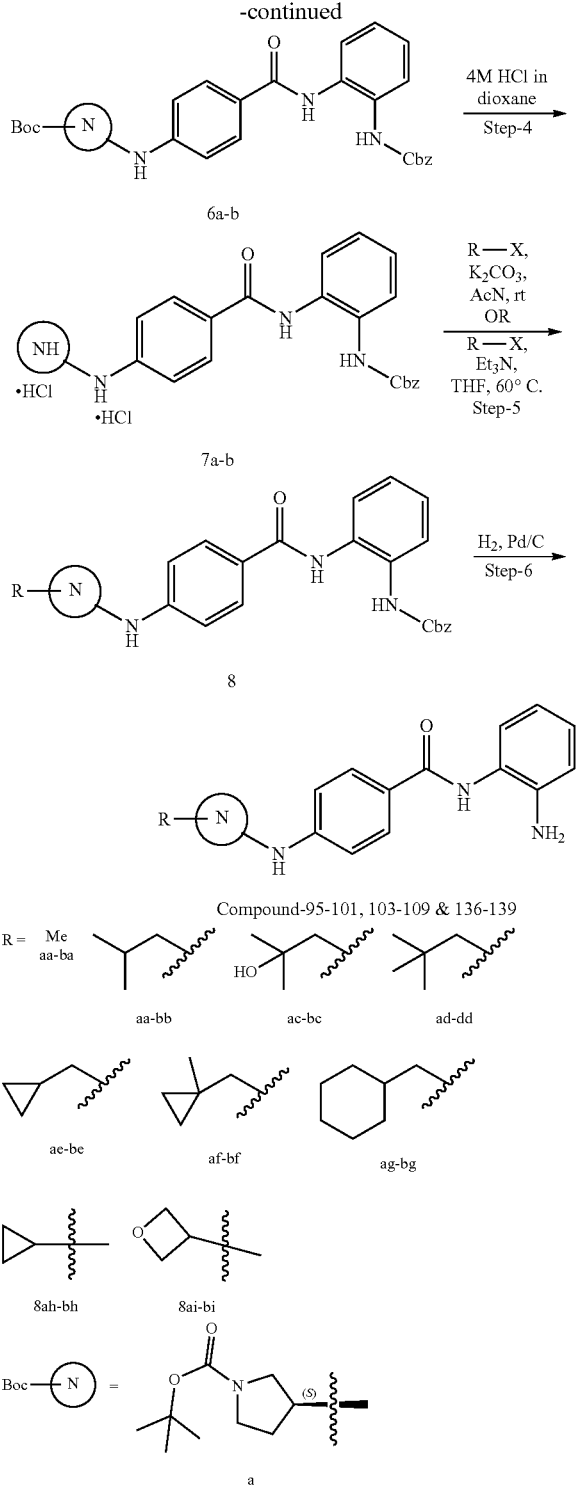

General Procedure for SNAr Displacement:
To a stirred suspension of the cyano compound (1 eq) and the corresponding amino compound (1 eq) in DMSO:H₂O (9:1) was added sodium bicarbonate (2 eq) at room temperature. After stirring the reaction mixture at 90° C. for 72 h, the reaction progress was monitored by TLC and LCMS. After completion, the reaction mixture was concentrated and resulting residue was partitioned between water and ethyl acetate. The organic layers were separated, washed with water, dried over $Na_2SO_4$ and concentrated. The crude residue was purified by silica gel column chromatography to provide the desired compound.

General Procedure for Cyano Hydrolysis:
To a stirred solution of the cyano compound (1 eq) in methanol (10 v) was added 50% KOH (aq) at room temperature. After stirring the reaction mixture at 65° C. for 5 days, the reaction progress was monitored by TLC and LCMS. The reaction mixture was concentered and resulting residue was dissolved in minimum water and the resulting mixture was neutralized with 6N HCl (pH=7). The solid obtained was filtered, washed with water and dried under vacuum to provide the desired compound.

Step 1: Synthesis of Compounds 3a and 3b

The title Compounds 3a-3b were synthesized from Compound 1 and respective Compounds 2a and 2b by following the general procedure described above for the SNAr Displacement.

Step 2: Synthesis of Compound 4

The title Compounds 4a and 4b were synthesized from Compound 3a and 3b by following the general procedure described above for the Cyano Hydrolysis.

Step 3: Synthesis of Compounds 6a and 6b

The title Compounds 6a and 6b were synthesized by treating acid 4a and 4b with Compound 5 by following the general procedure described in Scheme D for the Amide Coupling.

Step 4: Synthesis of Compounds 7a and 7b

The title Compounds 7a and 7b were synthesized from Compound 6a and 6b by following the general procedure described in Scheme D for the Boc-Deprotection.

Step 5: Synthesis of Compounds 8aa-8ai and 8ba-8bi

The title compounds were synthesized by following the general procedure described in Scheme D for the N-alkylation or Reductive Amination of Compounds 7a and 7b and the corresponding alkyl halide or aldehyde.

| No | Structure | R |
|---|---|---|
| 8aa | 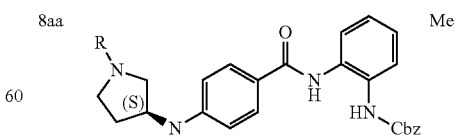 | Me |
| 8ab | |  |

Step-6: Cbz Deprotection

The titled compounds has been synthesized by following the general procedure described in Scheme D for Cbz Deprotection.

Synthesis of (S)—N-(2-aminophenyl)-4-((1-methyl-pyrrolidin-3-yl)amino)benzamide (Compound 95)

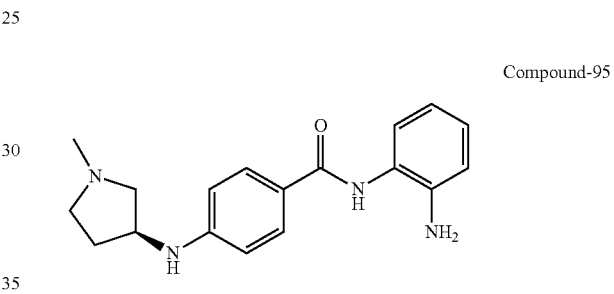

Compound-95

The title compound was synthesized from Compound 8aa by following the general procedure described in Scheme D for Cbz Deprotection. $^1$H NMR (400 MHz, DMSO-d6) δ 9.34 (s, 1H), 7.81 (d, J=8.4 Hz, 2H), 7.14 (d, J=7.6 Hz, 1H), 6.96-6.88 (m, 1H), 6.77 (d, J=8.0 Hz, 1H), 6.67-6.53 (m, 3H), 4.82 (s, 2H), 4.20-4.18 (m, 1H), 3.35-3.32 (m, 1H), 3.08-3.00 (m, 2H), 2.71 (s, 3H), 2.67-2.60 (m, 1H), 2.43-2.33 (m, 1H), 1.93-1.80 (m, 1H); LCMS Calculated for $C_{18}H_{22}N_4O$: 310.18; Observed: 311.10 (M+1)$^+$.

Synthesis of (S)—N-(2-aminophenyl)-4-((1-isobu-tylpyrrolidin-3-yl)amino)benzamide (Compound 96)

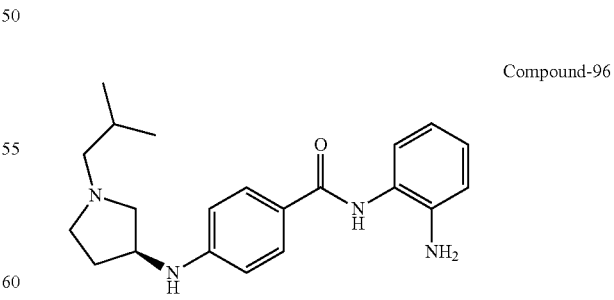

Compound-96

The title compound was synthesized from Compound 8ab by following the general procedure described in Scheme D for Cbz Deprotection. $^1$H NMR (400 MHz, DMSO-d6) δ 9.58-9.55 (m, 2H), 7.83 (d, J=8.4 Hz, 2H), 7.27-7.21 (m, 1H), 7.11-7.03 (m, 2H), 6.99-6.93 (m, 1H), 6.82 (t, J=7.6 Hz, 1H), 6.67 (d, J=8.0 Hz, 2H), 4.31-4.20 (m, 2H), 3.74-3.67 (m, 1H), 3.50-3.17 (m, 2H), 3.08-3.04 (m, 2H), 2.33-2.30 (m, 1H), 2.00-1.98 (m, 2H), 0.96 (d, J=6.0 Hz, 6H); LCMS Calculated for $C_{21}H_{28}N_4O$: 352.23; Observed: 352.90 $(M+1)^+$.

Synthesis of (S)—N-(2-aminophenyl)-4-((1-(2-hydroxy-2-methylpropyl)pyrrolidin-3-yl)amino)benzamide (Compound 97)

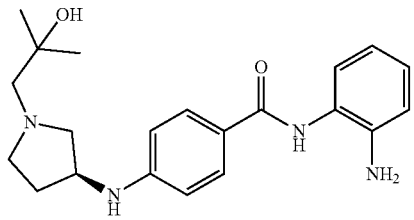

Compound-97

The title compound was synthesized from Compound 8ac by following the general procedure described in Scheme D for Cbz Deprotection. $^1$H NMR (400 MHz, DMSO-d6) δ 9.78 (s, 1H), 9.62-9.60 (m, 1H), 7.87 (d, J=8.4 Hz, 2H), 7.35-7.26 (m, 1H), 7.16-7.11 (m, 2H), 7.03-7.00 (m, 1H), 6.69-6.65 (m, 2H), 5.56-5.20 (m, 2H), 4.35-4.05 (m, 2H), 3.79-3.36 (m, 3H), 3.30-3.21 (m, 2H), 3.10-3.07 (m, 1H), 2.33-2.30 (m, 1H), 1.97-1.93 (m, 1H), 1.24 (s, 6H); LCMS Calculated for $C_{21}H_{28}N_4O_2$: 368.22; Observed: 368.90 $(M+1)^+$.

Synthesis of (S)—N-(2-aminophenyl)-4-((1-neopentylpyrrolidin-3-yl)amino)benzamide Trihydrochloride (Compound 98)

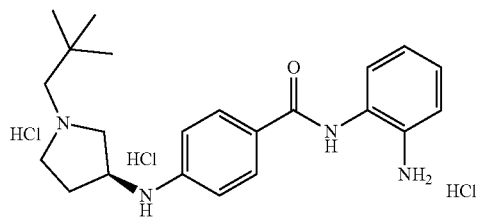

Compound-98

The title compound was synthesized from Compound 8ad by following the general procedure described in Scheme D for Cbz Deprotection. $^1$H NMR (400 MHz, DMSO-d6) δ 10.29-10.20 (m, 2H), 7.95 (d, J=7.2 Hz, 2H), 7.54 (d, J=7.6 Hz, 1H), 7.44 (d, J=7.6 Hz, 1H), 7.36 (t, J=8.0 Hz, 1H), 7.33-7.28 (m, 1H), 6.72-6.67 (m, 2H), 4.40-4.27 (m, 2H), 4.11-4.05 (m, 1H), 3.84-3.71 (m, 1H), 3.56-3.52 (m, 1H), 3.39-3.32 (m, 1H), 3.26-3.17 (m, 2H), 3.05-3.00 (m, 1H), 2.40-2.32 (m, 1H), 2.00-1.98 (m, 1H), 1.29 (s, 9H); LCMS Calculated for $C_{22}H_{30}N_4O$: 366.24; Observed: 367.00 $(M+1)^+$.

Synthesis of (S)—N-(2-aminophenyl)-4-((1-(cyclopropylmethyl)pyrrolidin-3-yl)amino)benzamide Trihydrochloride (Compound 99)

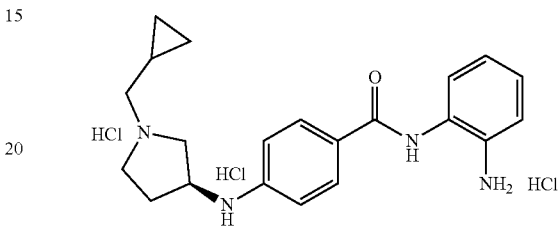

Compound-99

The title compound was synthesized from Compound 8ae by following the general procedure described in Scheme D for Cbz Deprotection. $^1$H NMR (400 MHz, DMSO-d6) δ 11.10 (s, 1H), 10.24 (s, 1H), 7.99-7.96 (m, 2H), 7.57 (d, J=8.4 Hz, 1H), 7.48 (d, J=7.8 Hz, 1H), 7.40 (t, J=7.6 Hz, 1H), 7.32-7.28 (m, 1H), 6.71-6.69 (m, 2H), 4.36-4.25 (m, 1H), 3.97-3.91 (m, 1H), 3.71-3.61 (m, 1H), 3.44-3.42 (m, 1H), 3.18-3.00 (m, 3H), 2.38-2.23 (m, 1H), 2.00-1.91 (m, 1H), 0.64-0.53 (m, 2H), 0.42-0.40 (m, 2H); LCMS Calculated for $C_{21}H_{26}N_4O$: 350.21; Observed: 350.90 $(M+1)^+$.

Synthesis of (S)—N-(2-aminophenyl)-4-((1-((1-methylcyclopropyl) methyl)pyrrolidin-3-yl)amino) benzamide (Compound 100)

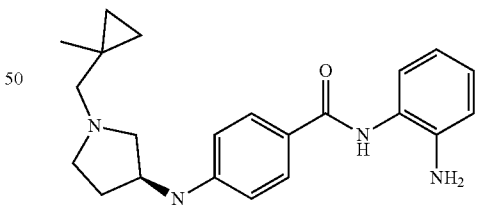

Compound-100

The title compound was synthesized from Compound 8af by following the general procedure described in Scheme D for Cbz Deprotection. $^1$H NMR (400 MHz, DMSO-d6) δ 9.27 (s, 1H), 7.76 (d, J=8.4 Hz, 2H), 7.13 (d, J=8.0 Hz, 1H), 6.93 (t, J=7.6 Hz, 1H), 6.76 (d, J=8.0 Hz, 1H), 6.64-6.54 (m, 3H), 6.37 (d, J=6.4 Hz, 1H), 4.81 (s, 2H), 3.96-3.94 (m, 1H), 2.81-2.61 (m, 2H), 2.41-2.13 (m, 5H), 1.62-1.59 (m, 1H), 1.05 (s, 3H), 0.26-0.24 (m, 4H); LCMS Calculated for $C_{22}H_{28}N_4O$: 364.23; Observed: 364.95 $(M+1)^+$.

Synthesis of (S)—N-(2-aminophenyl)-4-((1-(cyclohexylmethyl)pyrrolidin-3-yl)amino)benzamide (Compound 101)

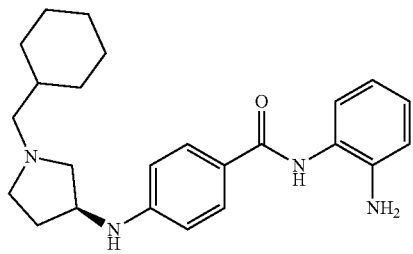

Compound-101

The title compound was synthesized from Compound 8ag by following the general procedure described in Scheme D for Cbz Deprotection. $^1$H NMR (400 MHz, DMSO-d6) δ 9.27 (s, 1H), 7.76 (d, J=8.4 Hz, 2H), 7.12 (d, J=7.6 Hz, 1H), 6.92 (t, J=7.2 Hz, 1H), 6.75 (d, J=8.0 Hz, 1H), 6.61-6.57 (m, 3H), 6.37-6.35 (m, 1H), 4.80 (s, 2H), 3.95-3.93 (m, 1H), 2.77-2.74 (m, 1H), 2.67-2.62 (m, 1H), 2.40-2.38 (m, 1H), 2.23-2.26 (m, 2H), 1.81-1.71 (m, 2H), 1.69-1.56 (m, 4H), 1.43-1.40 (m, 1H), 1.27-1.04 (m, 4H), 0.86-0.82 (m, 3H); LCMS Calculated for $C_{24}H_{32}N_4O$: 392.26; Observed: 393.00 (M+1)$^+$.

Synthesis of (S)—N-(2-aminophenyl)-4-((1-cyclopropylpyrrolidin-3-yl)amino)benzamide (Compound 136)

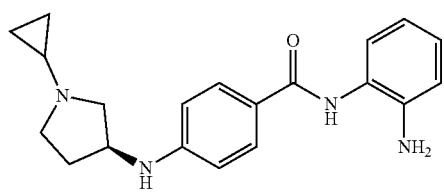

Compound-136

The title compound was synthesized from Compound 8ah by following the general procedure described in Scheme D for Cbz Deprotection. $^1$H NMR (400 MHz, DMSO-d6) δ 9.26 (s, 1H), 7.75 (d, J=8.8 Hz, 2H), 7.14 (d, J=8.0 Hz, 1H), 6.93 (t, J=7.2 Hz, 1H), 6.76 (d, J=7.6 Hz, 1H), 6.59-6.54 (m, 3H), 6.34 (d, J=6.8 Hz, 1H), 4.81 (s, 2H), 3.96-3.87 (m, 1H), 2.99-2.94 (m, 2H), 2.76-2.74 (m, 1H), 2.65-2.57 (m, 1H), 2.23-2.16 (m, 1H), 1.70-1.51 (m, 2H), 0.46-0.24 (m, 4H); LCMS Calculated for $C_{20}H_{24}N_4O$: 336.20; Observed: 337.00 (M+1)$^+$.

Synthesis of (S)—N-(2-aminophenyl)-4-((1-(oxetan-3-yl)pyrrolidin-3-yl)amino)benzamide (Compound 137)

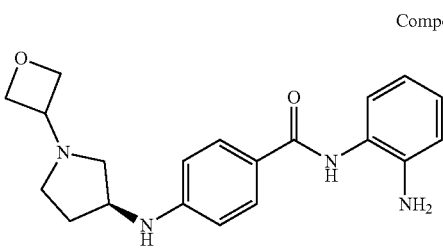

Compound-137

The title compound was synthesized from Compound 8ai by following the general procedure described in Scheme D for Cbz Deprotection. $^1$H NMR (400 MHz, DMSO-d6) δ 9.28 (s, 1H), 7.76 (d, J=8.4 Hz, 2H), 7.13 (d, J=8.8 Hz, 1H), 6.93 (t, J=7.6 Hz, 1H), 6.76 (d, J=8.0 Hz, 1H), 6.63-6.54 (m, 3H), 6.42 (d, J=6.8 Hz, 1H), 4.82 (s, 2H), 4.59-4.54 (m, 2H), 4.48-4.42 (m, 2H), 3.99-3.97 (m, 1H), 3.60-3.56 (m, 1H), 2.83-2.71 (m, 1H), 2.65-2.62 (m, 1H), 2.47-2.33 (m, 2H), 2.27-2.22 (m, 1H), 1.65-1.61 (m, 1H); LCMS Calculated for $C_{20}H_{24}N_4O_2$: 352.19; Observed: 352.85 (M+1)$^+$.

Synthesis of (R)—N-(2-aminophenyl)-4-((1-methylpyrrolidin-3-yl)amino)benzamide (Compound 103)

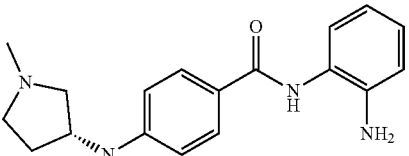

Compound-103

The title compound was synthesized from Compound 8ba by following the general procedure described in Scheme D for Cbz Deprotection. $^1$H NMR (400 MHz, DMSO-d6) δ 9.34 (s, 1H), 7.80 (d, J=8.4 Hz, 2H), 7.13 (d, J=8.0 Hz, 1H), 6.93 (t, J=7.2 Hz, 1H), 6.76 (d, J=7.6 Hz, 1H), 6.64-6.57 (m, 3H), 4.81 (s, 2H), 4.21-4.18 (m, 1H), 3.46-3.36 (m, 2H), 3.12-3.03 (m, 2H), 2.73 (s, 3H), 2.44-2.32 (m, 1H), 1.90-1.86 (m, 1H); LCMS Calculated for $C_{18}H_{22}N_4O$: 310.18; Observed: 310.85 (M+1)$^+$.

Synthesis of (R)—N-(2-aminophenyl)-4-((1-isobutylpyrrolidin-3-yl)amino)benzamide Trihydrochloride (Compound 104)

Compound-104

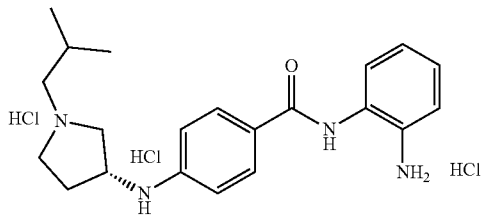

The title compound was synthesized from Compound 8bb by following the general procedure described in Scheme D for Cbz Deprotection. $^1$H NMR (400 MHz, DMSO-d6) δ 10.70-10.58 (m, 1H), 9.98 (s, 1H), 7.93 (d, J=8.8 Hz, 2H), 7.44 (d, J=7.2 Hz, 1H), 7.30-7.10 (m, 3H), 7.01-6.79 (m, 1H), 6.69 (d, J=8.8 Hz, 2H), 4.37-4.26 (m, 2H), 3.78-3.61 (m, 1H), 3.46-3.43 (m, 1H), 3.20-2.90 (m, 4H), 2.37-2.33 (m, 1H), 2.10-1.88 (m, 2H), 1.00 (d, J=6.4 Hz, 6H); LCMS Calculated for $C_{21}H_{28}N_4O$: 352.23; Observed: 353.29 (M+1)$^+$.

Synthesis of (R)—N-(2-aminophenyl)-4-((1-neopentylpyrrolidin-3-yl)amino)benzamide (Compound 106)

Compound-106

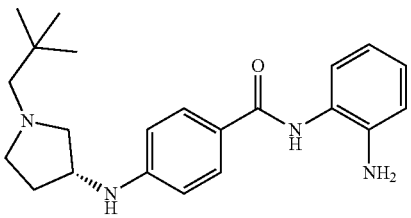

The title compound was synthesized from Compound 8bd by following the general procedure described in Scheme D for Cbz Deprotection. $^1$H NMR (400 MHz, DMSO-d6) δ 9.27 (s, 1H), 7.76 (d, J=8.0 Hz, 2H), 7.14 (d, J=7.2 Hz, 1H), 6.98-6.89 (m, 1H), 6.76 (d, J=8.0 Hz, 1H), 6.64-6.54 (m, 3H), 6.36-6.34 (m, 1H), 4.81 (s, 2H), 3.96-3.93 (m, 1H), 2.96-2.62 (m, 3H), 2.26-2.20 (m, 4H), 1.62-1.58 (m, 1H), 0.88 (s, 9H); LCMS Calculated for $C_{22}H_{30}N_4O$: 366.24; Observed: 366.95 (M+1)$^+$.

Synthesis of (R)—N-(2-aminophenyl)-4-((1-(2-hydroxy-2-methylpropyl)pyrrolidin-3-yl)amino)benzamide Trihydrochloride (Compound 105)

Compound-105

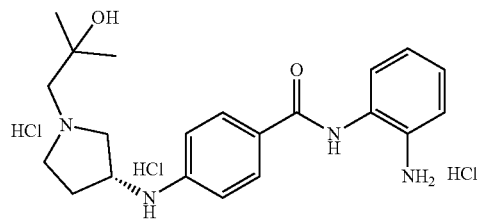

The title compound was synthesized from Compound 8bc by following the general procedure described in Scheme D for Cbz Deprotection. $^1$H NMR (400 MHz, DMSO-d6) δ 10.29-10.17 (m, 2H), 7.99 (d, J=8.4 Hz, 2H), 7.60 (d, J=8.0 Hz, 1H), 7.53 (d, J=7.6 Hz, 1H), 7.42 (t, J=7.2 Hz, 1H), 7.31 (t, J=7.6 Hz, 1H), 6.70 (dd, J=8.7, 3.3 Hz, 1H), 4.38-4.26 (m, 2H), 4.06-4.02 (m, 1H), 3.85-3.65 (m, 1H), 3.58-3.55 (m, 1H), 3.46-3.03 (m, 3H), 2.35-2.30 (m, 1H), 2.00-1.94 (m, 1H), 1.26 (s, 6H); LCMS Calculated for $C_{21}H_{28}N_4O_2$: 368.22; Observed: 369 (M+1)$^+$.

Synthesis of (R)—N-(2-aminophenyl)-4-((1-(cyclopropylmethyl)pyrrolidin-3-yl)amino)benzamide Trihydrochloride (Compound 107)

Compound-107

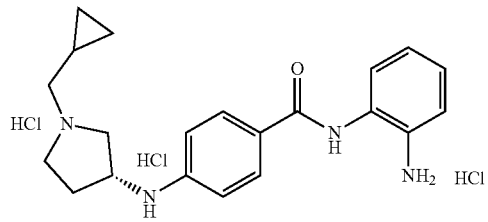

The title compound was synthesized from Compound 8be by following the general procedure described in Scheme D for Cbz Deprotection. $^1$H NMR (400 MHz, DMSO-d6) δ 11.09-11.02 (m, 1H), 10.24 (s, 1H), 8.00-7.92 (m, 2H), 7.60-7.46 (m, 2H), 7.40-7.30 (m, 2H), 6.72-6.65 (m, 2H), 4.35-4.24 (m, 1H), 3 3.63-3.55 (m, 1H), 3.44-3.40 (m, 1H), 3.18-2.93 (m, 4H), 2.32-2.30 (m, 1H), 1.95-1.90 (m, 1H), 1.14-1.11 (m, 1H), 0.60-0.56 (m, 2H), 0.44-0.37 (m, 2H); LCMS Calculated for $C_{21}H_{26}N_4O$: 350.21; Observed: 351.00 (M+1)$^+$.

Synthesis of (R)—N-(2-aminophenyl)-4-((1-((1-methylcyclopropyl)methyl) pyrrolidin-3-yl)amino)benzamide (Compound 108)

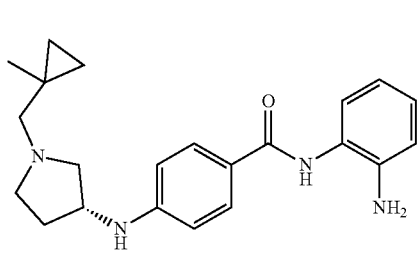

Compound-108

The title compound was synthesized from Compound 8bf by following the general procedure described in Scheme D for Cbz Deprotection. $^1$H NMR (400 MHz, DMSO-d6) δ 9.23 (s, 1H), 7.73 (d, J=8.4 Hz, 2H), 7.11 (d, J=8.0 Hz, 1H), 6.90 (t, J=7.6, 1H), 6.73 (d, J=8.0 Hz, 1H), 6.61-6.51 (m, 3H), 6.32 (d, J=6.6 Hz, 1H), 4.77 (s, 2H), 3.93-3.91 (m, 1H), 2.79-2.59 (m, 2H), 2.29-2.15 (m, 2H), 2.29-2.12 (m, 3H), 1.60-1.58 (m, 1H), 1.03 (s, 3H), 0.25-0.23 (m, 4H); LCMS Calculated for $C_{22}H_{28}N_4O$: 364.23; Observed: 364.85 $(M+1)^+$.

Synthesis of (R)—N-(2-aminophenyl)-4-((1-(cyclohexylmethyl)pyrrolidin-3-yl)amino)benzamide (Compound 109)

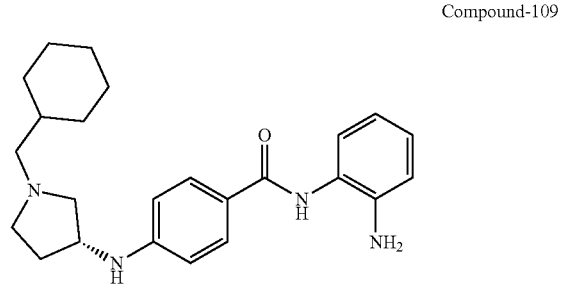 [SMILES: Nc1ccccc1NC(=O)c1ccc(N[C@@H]2CCN(CC3CCCCC3)C2)cc1]

Compound-109

The title compound was synthesized from Compound 8bg by following the general procedure described in Scheme D for Cbz Deprotection. $^1$H NMR (400 MHz, DMSO-d6) δ 9.27 (s, 1H), 7.75 (d, J=8.8 Hz, 2H), 7.13 (d, J=7.6 Hz, 1H), 6.93 (t, J=6.8 Hz, 1H), 6.76 (d, J=7.2 Hz, 1H), 6.60-6.56 (m, 3H), 6.35 (d, J=6.4 Hz, 1H), 4.85 (s, 2H), 3.95-3.92 (m, 1H), 2.78-2.75 (m, 1H), 2.60-2.56 (m, 1H), 2.42-2.36 (m, 2H), 2.25-2.20 (m, 2H), 1.76-1.60 (m, 6H), 1.45-1.40 (m, 1H), 1.23-1.08 (m, 3H), 0.85-0.82 (m, 2H); LCMS Calculated for $C_{24}H_{32}N_4O$: 392.26; Observed: 392.90 $(M+1)^+$.

Synthesis of (R)—N-(2-aminophenyl)-4-((1-cyclopropylpyrrolidin-3-yl)amino)benzamide Trihydrochloride (Compound 138)

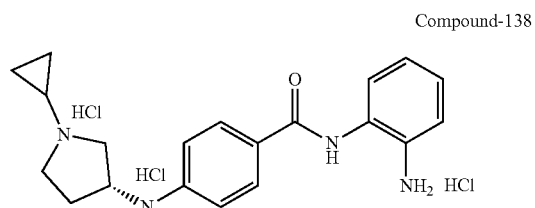

Compound-138

The title compound was synthesized from Compound 8bh by following the general procedure described in Scheme D for Cbz Deprotection. $^1$H NMR (400 MHz, DMSO-d6) δ 11.47-11.32 (m, 1H), 10.26 (s, 1H), 7.97 (d, J=8.8 Hz, 2H), 7.58 (d, J=8.0 Hz, 1H), 7.50 (d, J=7.6 Hz, 1H), 7.40 (t, J=7.6 Hz, 1H), 7.31 (t, J=7.6 Hz, 1H), 6.71-6.67 (m, 2H), 4.40-4.21 (m, 1H), 3.66-3.59 (m, 2H), 3.43-3.37 (m, 1H), 3.30-3.27 (m, 1H), 3.00-2.93 (m, 1H), 2.30-2.25 (m, 1H), 2.03-1.88 (m, 1H), 1.09-1.06 (m, 2H), 0.80-0.77 (m, 2H); LCMS Calculated for $C_{20}H_{24}N_4O$: 336.20; Observed: 336.95 $(M+1)^+$.

Synthesis of (R)—N-(2-aminophenyl)-4-((1-(oxetan-3-yl)pyrrolidin-3-yl)amino)benzamide tris(2,2,2-trifluoroacetate) (Compound 139)

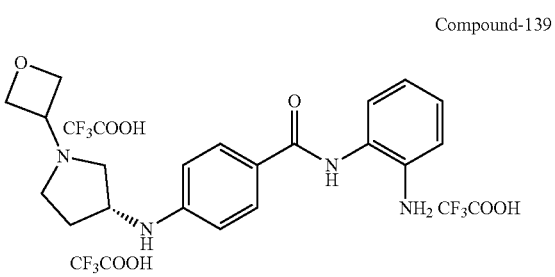

Compound-139

The title compound was synthesized from Compound 8bi by following the general procedure described in Scheme D for Cbz Deprotection. $^1$H NMR (400 MHz, DMSO-d6) δ 9.60 (s, 1H), 7.84 (d, J=8.0 Hz, 2H), 7.22 (d, J=8.0 Hz, 1H), 7.07 (t, J=7.6 Hz, 1H), 6.96 (d, J=8.0 Hz, 1H), 6.83 (t, J=7.2 Hz, 1H), 6.67 (d, J=8.0 Hz, 2H), 4.78 (t, J=7.2 Hz, 2H), 4.66-4.64 (m, 2H), 4.57-4.53 (m, 2H), 4.29-4.27 (m, 1H), 3.75-3.15 (m, 4H), 2.02-1.98 (m, 1H); LCMS Calculated for $C_{20}H_{24}N_4O_2$: 352.19; Observed: 353 $(M+1)^+$.

Synthesis of (S)—N-(2-aminophenyl)-4-(pyrrolidin-3-ylamino)benzamide Trihydrochloride and (R)—N-(2-aminophenyl)-4-(pyrrolidin-3-ylamino)benzamide Trihydrochloride (Compounds 94 and 102)

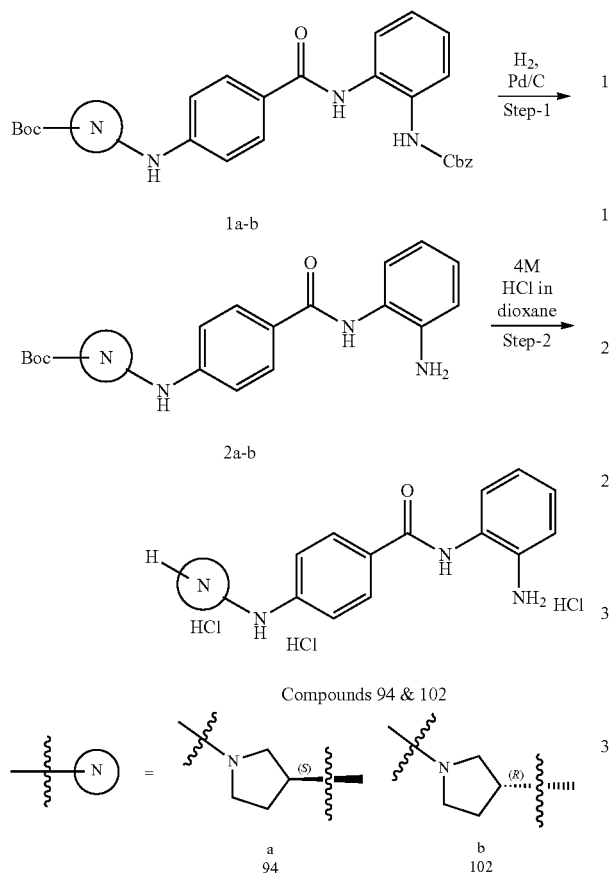

Step-1: Synthesis of Compounds 2a and 2b

The titled Compounds 2a-b has been synthesized from Compounds 1a-b by following the general procedure described in Scheme D for Cbz Deprotection.

Step-2: Synthesis of (S)—N-(2-aminophenyl)-4-(pyrrolidin-3-ylamino)benzamide Trihydrochloride (Compound 94)

The title compound was synthesized from Compound 2a by following the general procedure described in Scheme D for Boc-Deprotection. $^1$H NMR (400 MHz, DMSO-d6) δ 10.09 (s, 1H), 9.30 (s, 2H), 7.93 (d, J=8.4 Hz, 2H), 7.51-7.42 (m, 1H), 7.38-7.21 (m, 3H), 6.70-6.67 (m, 3H), 4.21-4.19 (m, 1H), 3.49-3.41 (m, 1H), 3.39-3.24 (m, 2H), 3.07-3.00 (m, 1H), 2.33-2.20 (m, 1H), 1.94-1.86 (m, 1H); LCMS Calculated for $C_{17}H_{20}N_4O$: 296.16; Observed: 296.95 $(M+1)^+$.

Synthesis of (R)—N-(2-aminophenyl)-4-(pyrrolidin-3-ylamino)benzamide Trihydrochloride (Compound 102)

The title compound was synthesized from Compound 1b by following the general procedures described in Scheme D for Cbz Deprotection and then Boc deprotection by stirring in 4M HCl in 1,4-dioxane. $^1$H NMR (400 MHz, DMSO-d6) δ 10.03 (s, 1H), 9.26 (s, 2H), 7.92 (d, J=8.4 Hz, 2H), 7.48-7.41 (m, 1H), 7.33-7.17 (m, 3H), 6.69 (d, J=8.8 Hz, 2H), 4.21-4.19 (m, 1H), 3.52-3.19 (m, 3H), 3.12-3.01 (m, 1H), 2.29-2.20 (m, 1H), 1.91-1.90 (m, 1H); LCMS Calculated for $C_{17}H_{20}N_4O$: 296.16; Observed: 297 $(M+1)^+$.

Synthesis of N-(2-aminophenyl)-4-((1-neopentylpiperidin-4-yl)amino)benzamide Trihydrochloride (Compound 30)

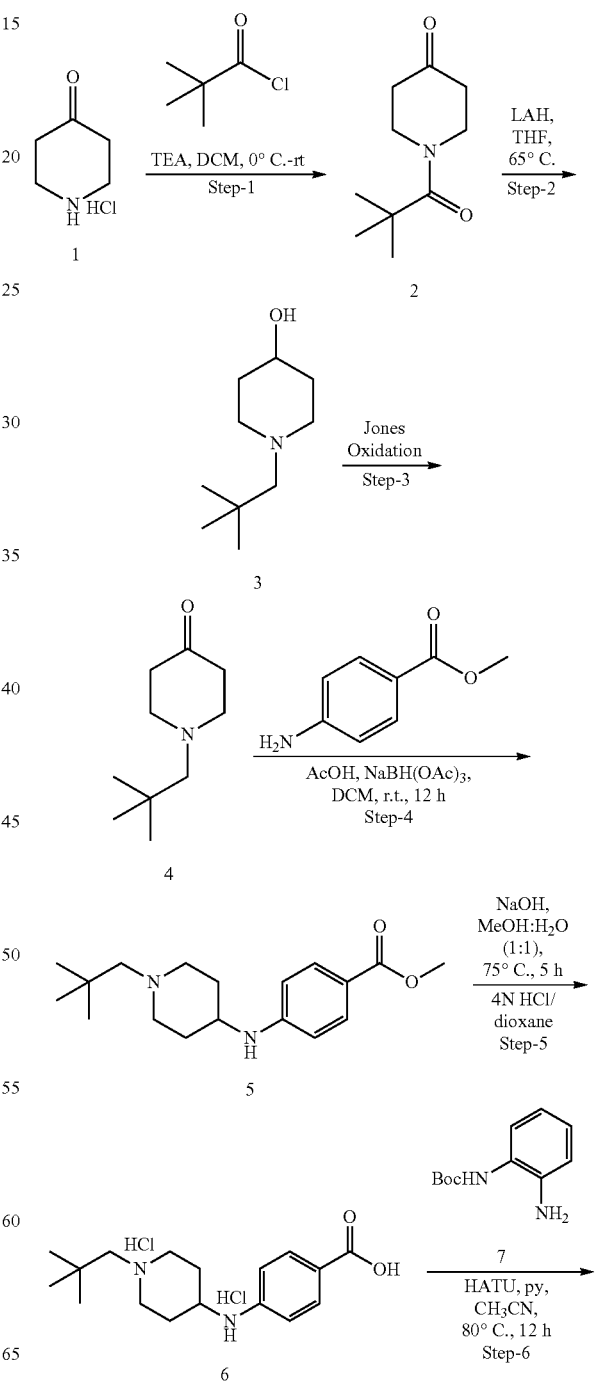

-continued

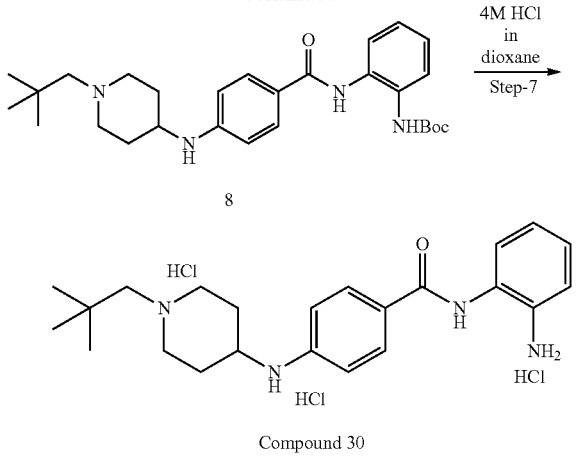

Compound 30

Step-1: Synthesis of 1-pivaloylpiperidin-4-one (2)

To a stirred solution of Compound 1 (25 g, 1 eq) in DCM (200 mL) at 0° C., TEA (64 mL, 2.5 eq) and pivaloyl chloride (27 mL, 1.2 eq) was added and stirred at room temperature for 12 h. The progress of the reaction was monitored by TLC. After completion, the reaction mixture was diluted with water and extracted with ethyl acetate. The combined organic extracts were washed with water; dried over anhydrous sodium sulfate and evaporated under reduced pressure to afford the crude title Compound 2.

Step-2: Synthesis of 1-neopentylpiperidin-4-ol (3)

To a stirred solution of Compound 2 (10 g, 1 eq) in dry THF (200 mL) at 0° C., LAH (6.2 g, 3 eq) was added slowly. The resulting reaction mixture was stirred at 65° C. for 12 h. The progress of the reaction was monitored by TLC. After completion, the reaction mixture was cooled to 0° C., the reaction mixture was diluted with sat. $Na_2SO_4$ solution and ethyl acetate. The precipitated solid was collected by filtration and the filtrate was concentrated under reduced pressure to afford the title Compound 3.

Step-3: Synthesis of 1-neopentylpiperidin-4-one (4)

To a stirred solution of Compound 3 (3 g, 1 eq) in acetone (20 mL), Jone's reagent (6 mL) was added and stirred at room temperature for 4 h. The progress of the reaction was monitored by TLC. After completion, the reaction mixture was diluted with sat. $NaHCO_3$ solution and extracted with ethyl acetate. The combined organic extracts were washed with water; dried over anhydrous sodium sulfate and evaporated under reduced pressure. The crude product was purified by column chromatography to afford the title Compound 4.

Step-4: Synthesis of Methyl 4-((1-neopentylpiperidin-4-yl)amino)benzoate (5)

To a stirred solution of Compound 4 (2.2 g, 1 eq) and methyl 4-aminobenzoate (1.96 g, 1 eq) in DCM (20 mL), AcOH (5 mL, 6 eq) was added and stirred at room temperature for 30 min. To this solution, $NaBH(OAc)_3$ (8.2 g, 3 eq) was added. The resulting reaction mixture was stirred at room temperature for 12 h. The progress of the reaction was monitored by TLC. After completion, the reaction mixture was diluted with water and extracted with DCM. The combined organic extracts were washed with water, dried over anhydrous sodium sulfate and evaporated under reduced pressure. The crude product was purified by column chromatography to afford the title Compound 5.

Step-5: Synthesis of 4-((1-neopentylpiperidin-4-yl)amino)benzoic Acid Dihydrochloride (6)

To a stirred solution of Compound 5 (1.2 g, 1 eq) in methanol:water (1:1, 10 mL) mixture, NaOH (0.31 g, 2 eq) was added and stirred at 80° C. for 6 h. The progress of the reaction was monitored by TLC. After completion, the reaction mixture was concentrated under reduced pressure. To this crude compound in 1,4-dioxane, 4M HCl in dioxane was added and stirred at rt for 10 min. The reaction mixture was concentrated and solid obtained was dissolved in 20% MeOH/DCM; filtered and dried under reduced pressure to afford the title Compound 6.

Step-6: Synthesis of Tert-Butyl (2-(4-((1-neopentylpiperidin-4-yl)amino) benzamido)phenyl)carbamate (8)

To a stirred solution of Compound 6 (0.9 g, 1 eq) and tert-butyl (2-aminophenyl)carbamate 7 (0.6 g, 1.2 eq) in ACN (20 mL), pyridine (1.9 mL, 10 eq) and HATU (1.4 g, 1.5 eq) was added. The resulting reaction mixture was stirred at 80° C. for 12 h. The reaction progress was monitored by TLC. After completion, the reaction mixture was diluted with water and extracted with ethyl acetate. The combined organic extracts were washed with water; dried over anhydrous sodium sulfate and evaporated under reduced pressure. The crude product was purified by column chromatography to afford the title Compound 8.

Step-7: Synthesis of N-(2-aminophenyl)-4-((1-neopentylpiperidin-4-yl)amino)benzamide Trihydrochloride (Compound 30)

To a stirred solution of Compound 8 (0.3 g, 1 eq) in 1,4-dioxane (3 mL), 4M HCl in dioxane (5 mL) was added and stirred at rt for 2 h. After completion of reaction, the reaction mixture was concentrated and the resulting residue was triturated with n-pentane; diethyl ether and dried under vacuum to give desired Compound 30. $^1$H NMR (400 MHz, DMSO-d6) δ 10.17 (s, 1H), 9.52-9.38 (m, 1H), 7.93 (d, J=8.0 Hz, 2H), 7.54 (d, J=8.4 Hz, 1H), 7.44 (d, J=7.6 Hz, 1H), 7.38 (t, J=7.2 Hz, 1H), 7.31-7.28 (m, 1H), 6.77-6.69 (m, 2H), 3.75-3.53 (m, 3H), 3.39-3.15 (m, 3H), 3.05-2.98 (m, 2H), 2.19-2.15 (m, 1H), 2.06-2.04 (m, 2H), 1.81-1.75 (m, 1H), 1.10 (s, 9H); LCMS Calculated for $C_{23}H_{32}N_4O$: 380.26; Observed: 381.15 $(M+1)^+$.

Synthesis of N-(2-aminophenyl)-4-((cyclopropylmethyl)(1-(2-hydroxy-2-methylpropyl)piperidin-4-yl)amino)benzamide Trihydrochloride (Compound 29)

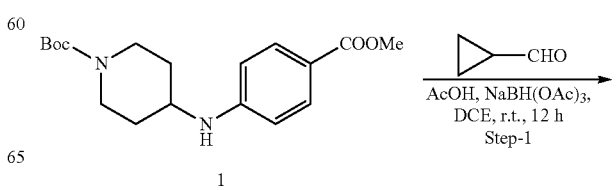

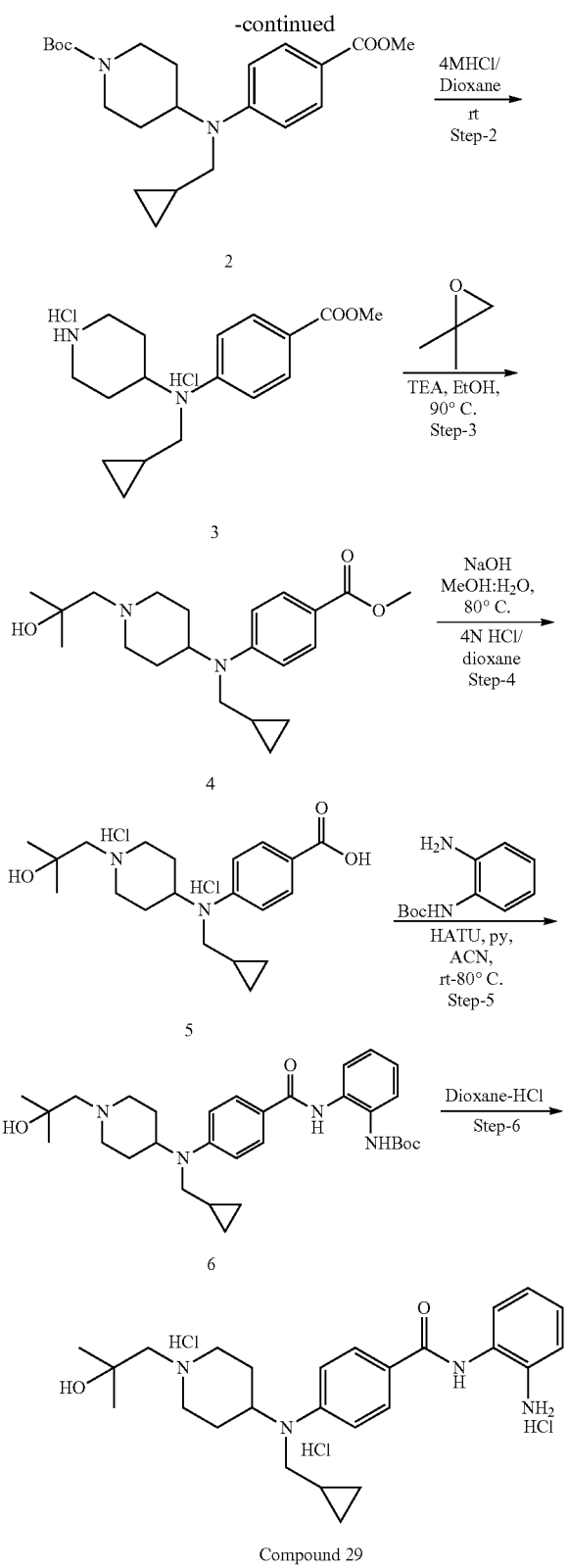

AcOH (2.4 mL, 6 eq) was added and stirred at rt for 30 min. To this solution, NaBH(OAc)$_3$ (1.27 g, 3 eq) was added. The resulting reaction mixture was stirred at rt for 12 h. The progress of the reaction was monitored by TLC. After completion, the reaction mixture was diluted with water and extracted with DCM. The combined organic extracts were washed with water; dried over anhydrous sodium sulfate and evaporated under reduced pressure. The crude product was purified by column chromatography to afford the title Compound 2.

Step-2: Synthesis of Methyl 4-((cyclopropylmethyl)(piperidin-4-yl)amino)benzoate Dihydrochloride (3)

To a stirred solution of Compound 2 (0.72 g, 1 eq) in 1,4-dioxane (5 mL), 4M HCl in dioxane (10 mL) was added and stirred at room temperature for 2 h. After completion of reaction, the reaction mixture was concentrated and the resulting residue was triturated with n-pentane; diethyl ether and dried under vacuum to provide the desired Compound 3.

Step-3: Synthesis of Methyl 4-((cyclopropylmethyl)(1-(2-hydroxy-2-methylpropyl)piperidin-4-yl)amino)benzoate (4)

To a stirred solution of Compound 3 (0.52 g, 1 eq) in EtOH (8 mL), TEA (0.66 mL, 3 eq) and 2,2-dimethyloxirane (0.36 mL, 2.5 eq) was added and stirred at 90° C. for 6 h. The progress of the reaction was monitored by TLC. After completion, the reaction mixture was diluted with water and extracted with ethyl acetate. The combined organic extracts were washed with water; dried over anhydrous sodium sulfate and evaporated under reduced pressure to afford the title Compound 4.

Step-4: Synthesis of 4-((cyclopropylmethyl)(1-(2-hydroxy-2-methylpropyl) piperidin-4-yl)amino)benzoic Acid Dihydrochloride (5)

To a stirred solution of Compound 4 (0.6 g, 1 eq) in methanol:water (1:1, 10 mL) mixture, NaOH (0.133 g, 2 eq) was added and stirred at 80° C. for 6 h. The progress of the reaction was monitored by TLC. After completion, the reaction mixture was concentrated under reduced pressure. To this crude compound in 1,4-dioxane, 4M HCl in dioxane was added and stirred at rt for 10 min. the reaction mixture was concentrated and solid obtained was dissolved in 20% MeOH/DCM; filtered and dried under reduced pressure to afford the title Compound 5.

Step-6: Synthesis of Tert-Butyl (2-(4-((cyclopropylmethyl)(1-(2-hydroxy-2-methylpropyl)piperidin-4-yl)amino)benzamido)phenyl)carbamate (6)

To a stirred solution of Compound 5 (0.59 g, 1 eq) and tert-butyl (2-aminophenyl)carbamate (0.351 g, 1.2 eq) in ACN (20 mL), pyridine (1.12 mL, 10 eq) and HATU (0.798 g, 1.5 eq) was added. The resulting reaction mixture was stirred at 80° C. for 12 h. The reaction progress was monitored by TLC. After completion, the reaction mixture was diluted with water and extracted with ethyl acetate. The combined organic extracts were washed with water; dried over anhydrous sodium sulfate and evaporated under reduced pressure. The crude product was purified by column chromatography to afford the title Compound 6.

Step-1: Synthesis of Tert-Butyl 4-((cyclopropylmethyl)(4-(methoxycarbonyl)phenyl)amino)piperidine-1-carboxylate (2)

To a stirred solution of Compound 1 (2 g, 1 eq) and cyclopropanecarbaldehyde (0.6 g, 1.5 eq) in DCE (20 mL),

Step-7: Synthesis of N-(2-aminophenyl)-4-((cyclopropylmethyl)(1-(2-hydroxy-2-methylpropyl)piperidin-4-yl)amino)benzamide Trihydrochloride (Compound 29)

To a stirred solution of Compound 6 (0.4 g, 1 eq) in 1,4-dioxane (7 mL), 4M HCl in dioxane (3 mL) was added and stirred at rt for 2 h. After completion of reaction, the reaction mixture was concentrated and the resulting residue was triturated with n-pentane; diethyl ether and dried under vacuum to give desired Compound 29. $^1$H NMR (400 MHz, DMSO-d6) δ 10.32 (s, 1H), 9.45-9.43 (m, 1H), 8.05 (d, J=8.4 Hz, 2H), 7.60 (d, J=7.2 Hz, 1H), 7.50 (d, J=8.0 Hz, 1H), 7.42 (t, J=7.2 Hz, 1H), 7.34-7.28 (m, 1H), 7.00-6.98 (m, 2H), 4.20-4.16 (m, 1H), 3.69-3.66 (m, 2H), 3.29-3.23 (m, 4H), 3.10-3.08 (m, 2H), 2.45-2.32 (m, 2H), 1.84-1.81 (m, 2H), 1.21 (s, 6H), 0.99-0.97 (m, 1H), 0.54-0.51 (m, 2H), 0.36-0.34 (m, 2H); LCMS Calculated for $C_{26}H_{36}N_4O_2$: 436.28; Observed: 437.32 (M+1)$^+$.

Synthesis of N-(2-aminophenyl)-4-((cyclopropylmethyl)(1-(cyclopropylmethyl)piperidin-4-yl)amino)benzamide Trihydrochloride (Compound 28)

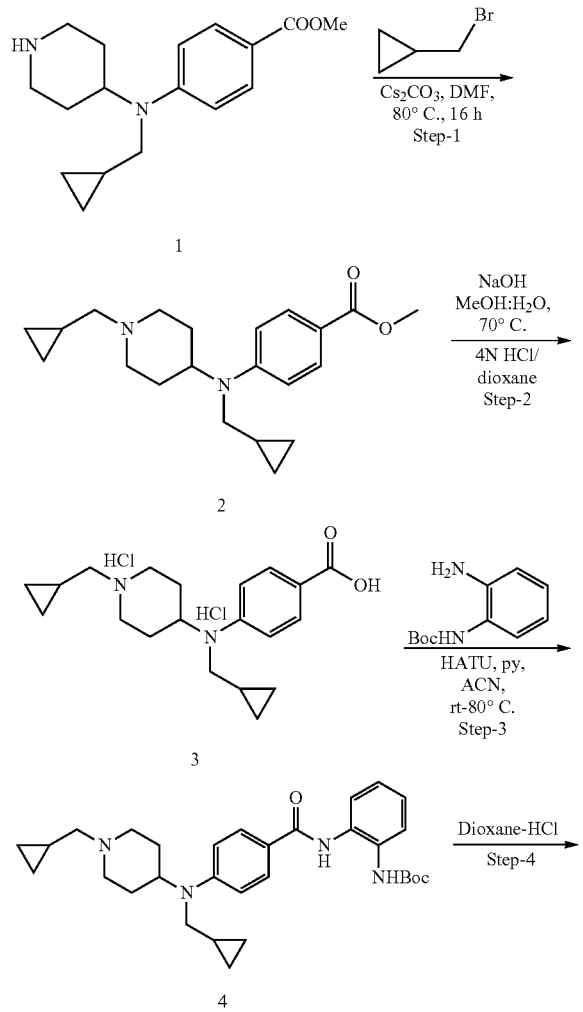

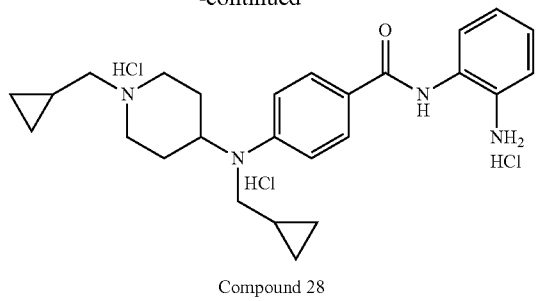

Compound 28

Step-1: Synthesis of Methyl 4-((cyclopropylmethyl)(1-(cyclopropylmethyl)piperidin-4-yl)amino)benzoate (2)

To a stirred solution of Compound 1 (0.7 g, 1 eq) in DMF (10 mL), $CS_2CO_3$ (2.09 g, 3 eq) and (bromomethyl)cyclopropane (0.31 mL, 1.5 eq) was added and stirred at 80° C. for 12 h. The progress of the reaction was monitored by TLC. After completion, the reaction mixture was diluted with water and extracted with ethyl acetate. The combined organic extracts were washed with water; dried over anhydrous sodium sulfate and evaporated under reduced pressure. The crude product was purified by column chromatography to afford the title Compound 2.

Step-2: Synthesis of 4-((cyclopropylmethyl)(1-(cyclopropylmethyl)piperidin-4-yl)amino)benzoic Acid Dihydrochloride (3)

To a stirred solution of Compound 2 (0.6 g, 1 eq) in methanol:water (1:1, 10 mL) mixture, NaOH (0.14 g, 2 eq) was added and stirred at 80° C. for 5 h. The progress of the reaction was monitored by TLC. After completion, the reaction mixture was concentrated under reduced pressure. To this crude compound in 1,4-dioxane, 4M HCl in 1,4-dioxane was added and stirred at rt for 10 min. The reaction mixture was concentrated and solid obtained was dissolved in 20% MeOH/DCM; filtered, and the filtrate was concentrated and dried under reduced pressure to afford the title Compound 3.

Step-3: Synthesis of Tert-Butyl (2-(4-((cyclopropylmethyl)(1-(cyclopropylmethyl) piperidin-4-yl)amino)benzamido)phenyl)carbamate (4)

To a stirred solution of Compound 3 (0.6 g, 1 eq) and tert-butyl (2-aminophenyl)carbamate (0.404 g, 1.2 eq) in ACN (20 mL), pyridine (1.3 mL, 10 eq) and HATU (0.923 g, 1.5 eq) were added. The resulting reaction mixture was stirred at 80° C. for 12 h. The reaction progress was monitored by TLC. After completion, the reaction mixture was diluted with water and extracted with ethyl acetate. The combined organic extracts were washed with water; dried over anhydrous sodium sulfate and evaporated under reduced pressure. The crude product was purified by column chromatography to afford the title Compound 4.

Step-4: Synthesis of N-(2-aminophenyl)-4-((cyclopropylmethyl)(1-(cyclopropylmethyl)piperidin-4-yl)amino)benzamide Trihydrochloride (Compound 28)

To a stirred solution of Compound 4 (0.18 g, 1 eq) in 1,4-dioxane (2 mL), 4M HCl in dioxane (3 mL) was added and stirred at rt for 2 h. After completion of reaction, the reaction mixture was concentrated and the resulting residue was triturated with n-pentane; diethyl ether and dried under vacuum to give desired Compound 28. $^1$H NMR (400 MHz, DMSO-d6) δ 10.57 (s, 1H), 10.27-10.25 (m, 1H), 8.02 (d, J=8.8 Hz, 2H), 7.55 (d, J=8.0 Hz, 1H), 7.44 (d, J=7.6 Hz, 1H), 7.40-7.36 (m, 1H), 7.33-7.28 (m, 1H), 7.00-6.98 (m, 2H), 4.17-4.14 (m, 1H), 3.62-3.58 (m, 2H), 3.23-3.15 (m, 4H), 2.95-2.66 (m, 2H), 2.33-2.21 (m, 2H), 1.92-1.89 (m, 2H), 1.14-0.98 (m, 2H), 0.66-0.54 (m, 2H), 0.54-0.51 (m, 2H), 0.43-0.35 (m, 4H); LCMS Calculated for $C_{26}H_{34}N_4O$: 418.27; Observed: 210.20 (M/2+1)$^+$.

Synthesis of N-(2-aminophenyl)-4-((1-(cyclopropylmethyl)piperidin-4-yl)(ethyl)amino)benzamide Trihydrochloride and N-(2-aminophenyl)-4-(ethyl(1-(2-hydroxy-2-methylpropyl)piperidin-4-yl)amino)benzamide Trihydrochloride (Compounds 26 and 27)

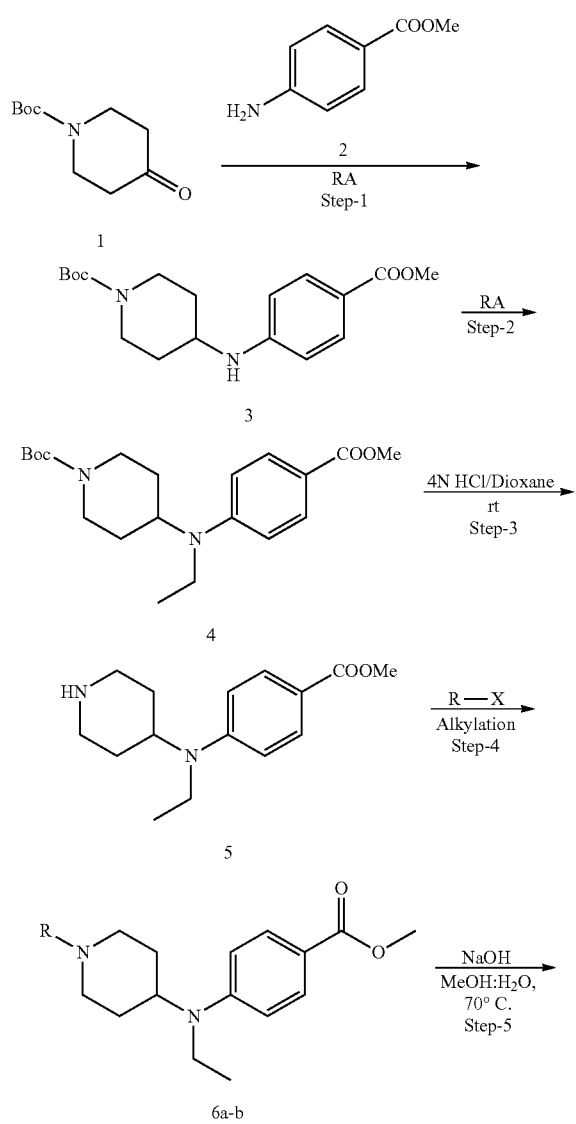

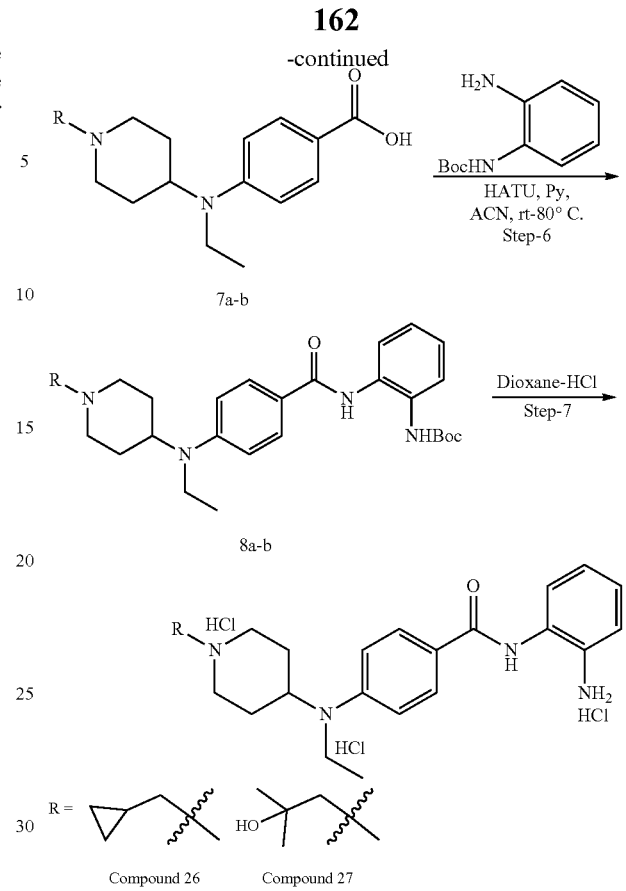

Step-1: Synthesis of Tert-Butyl 4-((4-(methoxycarbonyl)phenyl)amino) piperidine-1-carboxylate (3)

The titled compound has been synthesized by following the general procedure described in Scheme D for Reductive Amination (Procedure-A).

Step-2: Synthesis of Tert-Butyl 4-(ethyl(4-(methoxycarbonyl)phenyl) amino)piperidine-1-carboxylate (4)

The titled compounds has been synthesized by following general procedure described in Scheme D for Reductive Amination (Procedure-A).

Step-3: Synthesis of Methyl 4-(ethyl(piperidin-4-yl)amino)benzoate Hydrochloride (5)

The titled compound has been synthesized by following the general procedure described in Scheme D for Boc-Deprotection.

Step-4: Synthesis of Compound 6a-6b

The titled compounds has been synthesized by following general procedure described in Scheme D for N-alkylation.

Step-5: Synthesis of Compound 7a-7b

The titled compounds has been synthesized by following general procedure described in Scheme D for Ester Hydrolysis.

Step-6: Synthesis of Compounds 8a and 8b

The titled compounds has been synthesized by following the general procedure described in Scheme D for Amide Coupling.

Step-7: Boc Deprotection: Synthesis of N-(2-aminophenyl)-4-((1-(cyclopropylmethyl)piperidin-4-yl)(ethyl)amino)benzamide Trihydrochloride (Compound 26)

The title compound was synthesized by following the general procedure described in Scheme D for Boc-Deprotection. $^1$H NMR (400 MHz, DMSO-d6) δ 10.80 (s, 1H), 10.36 (s, 1H), 8.08-8.06 (m, 2H), 7.61 (d, J=8.0 Hz, 1H), 7.54 (d, J=7.6 Hz, 1H), 7.43 (t, J=8.0 Hz, 1H), 7.31 (t, J=7.6 Hz, 1H), 6.99-6.95 (m, 2H), 4.21-4.15 (m, 1H), 3.59-3.55 (m, 2H), 3.40-3.35 (m, 2H), 3.15-3.12 (m, 2H), 2.93-2.90 (m, 2H), 2.30-2.26 (m, 2H), 1.91-1.88 (m, 2H), 1.14-1.10 (m, 4H), 0.63-0.61 (m, 2H), 0.41-0.39 (m, 2H); LCMS Calculated for $C_{24}H_{32}N_4O$: 392.26; Observed: 393.25 $(M+1)^+$.

Synthesis of N-(2-aminophenyl)-4-(ethyl(1-(2-hydroxy-2-methylpropyl)piperidin-4-yl)amino)benzamide Trihydrochloride (Compound 27)

The title compound was synthesized by following the general procedure described in Scheme D for Boc-Deprotection. $^1$H NMR (400 MHz, DMSO-d6) δ 10.31 (s, 1H), 9.52-9.50 (m, 1H), 8.04 (d, J=8.8 Hz, 2H), 7.60 (d, J=8.4 Hz, 1H), 7.51 (d, J=7.6 Hz, 1H), 7.42 (t, J=7.6 Hz, 1H), 7.34-7.29 (m, 1H), 6.94-6.92 (m, 2H), 4.21-4.15 (m, 1H), 3.70-3.56 (m, 2H), 3.40-3.23 (m, 4H), 3.10-3.08 (m, 2H), 2.45-2.38 (m, 2H), 1.85-1.82 (m, 2H), 1.29 (s, 6H), 1.15 (t, J=6.8 Hz, 3H); LCMS Calculated for $C_{24}H_{34}N_4O_2$: 410.27; Observed: 411.29 $(M+1)^+$.

Synthesis of N-(2-aminophenyl)-4-((1-(2-hydroxy-2-methylpropyl)-2,2-dimethylpiperidin-4-yl)amino)benzamide (Compound 369)

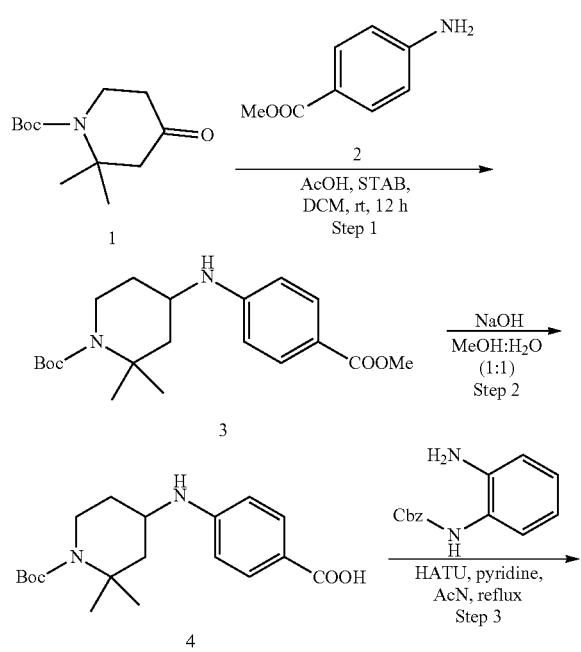

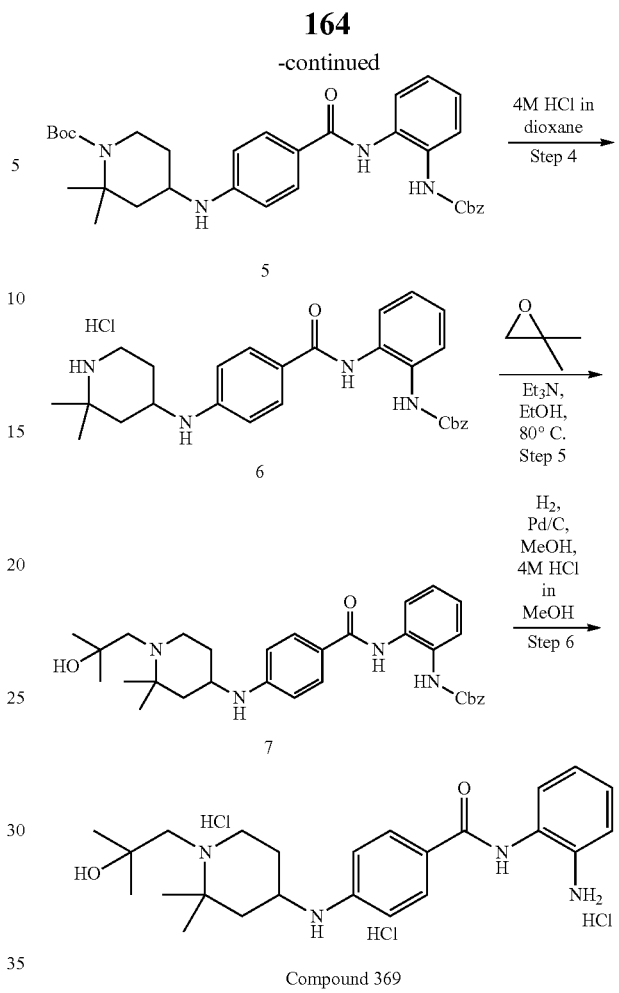

Compound 369

Step-1: Tert-Butyl 4-((4-(methoxycarbonyl)phenyl)amino)-2,2-dimethylpiperidine-1-carboxylate (3)

To a stirred solution of Compound 2 (0.8 g, 1 eq) and Compound 1 (1.5 g, 1 eq) in DCM was added acetic acid (2.4 mL, 6 eq) and sodium triacetoxyborohydride (STAB) (4.2 g, 3 eq) at room temperature. After stirring the reaction mixture at ambient temperature overnight, the reaction progress was monitored by TLC and LCMS. After completion of reaction, the reaction mixture was partitioned between DCM and water. The organic layers were separated, washed with water and brine, dried over $Na_2SO_4$ and evaporated to get the crude product which was purified by silica gel column chromatography to afford the desired compound.

Step-2: 4-((1-(tert-butoxycarbonyl)-2,2-dimethylpiperidin-4-yl)amino)benzoic Acid (4)

To stirred solution of Compound 3 (0.4 g, 1 eq) in methanol:water (1:1, 8 mL) was added NaOH (0.066 g, 1.5 eq) at room temperature. The mixture was heated to 70° C. for 4 h. The progress of the reaction was monitored by TLC. After completion of reaction, the reaction mixture was concentrated and the resulting residue was washed with diethyl ether followed by treatment with water. The aqueous layer was neutralized to pH=7 using 1N HCl at 0° C. The solid obtained was filtered, washed with water and dried under vacuum to provide the desired compound.

Step-3: Tert-Butyl 4-((4-((2-(((benzyloxy)carbonyl) amino)phenyl)carbamoyl)phenyl)amino)-2,2-dimethylpiperidine-1-carboxylate (5)

To a stirred solution of Compound 4 (0.3 g, 1 eq) and benzyl (2-aminophenyl)carbamate (0.23 g, 1.1 eq) in ACN (10 mL) was added pyridine (0.4 mL, 5 eq) and HATU (0.491 g, 1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over $Na_2SO_4$ and concentrated. The crude residue was purified by silica gel column chromatography to provide the desired compound.

Step-4: Benzyl (2-(4-((2,2-dimethylpiperidin-4-yl) amino)benzamido)phenyl)carbamate Hydrochloride (6)

To a stirred solution of Compound 5 (0.4 g, 1 eq) in 1,4-dioxane (2 mL) was added 4M HCl in dioxane (2 mL) at room temperature. After completion of reaction, the reaction mixture was concentrated and the resulting residue was triturated with n-pentane and dried under vacuum to give desired compound.

Step-5: Benzyl (2-(4-((1-(2-hydroxy-2-methylpropyl)-2,2-dimethylpiperidin-4-yl)amino)benzamido) phenyl)carbamate (7)

To a solution of Compound 6 (0.15 g, 1 eq) in ethanol (40 mL) was added TEA (0.12 mL, 3 eq) followed by 2,2-dimethyloxirane (0.029 g, 1.5 eq) at room temperature and the reaction mixture was heated at 90° C. for 4 h. The progress of reaction was monitored by TLC. After completion, the reaction mixture was allowed to cool and concentrated to give a crude compound. The crude compound was purified by silica gel column chromatography to provide the desired compound.

Step-6: N-(2-aminophenyl)-4-((1-(2-hydroxy-2-methylpropyl)-2,2-dimethylpiperidin-4-yl)amino) benzamide (Compound 369)

To a stirred solution of Compound 7 (0.07 g, 1 eq) in methanol, 4M HCl in MeOH (3 mL), 10% Pd/C (10% w/w of substrate, 50 mg) was added and the reaction mixture was stirred under hydrogen atmosphere (balloon pressure) at room temperature for 1 h. The progress of the reaction was monitored by TLC. After completion, the reaction mixture was filtered through a pad of celite, the filtrate was evaporated under reduced pressure and the resulting residue was triturated with diethyl ether and n-pentane and then dried under vacuum to afford the title compound as a trihydrochloride salt. $^1$H NMR (400 MHz, DMSO-d6) δ 10.15 (s, 1H), 8.80 (s, 1H), 7.91 (d, J=8.4 Hz, 2H), 7.53 (d, J=7.9 Hz, 1H), 7.46-7.23 (m, 3H), 6.71 (d, J=8.5 Hz, 2H), 3.82-3.62 (m, 3H), 3.44-3.28 (m, 3H), 2.69-2.66 (m, 1H), 2.16-1.90 (m, 3H), 1.48-1.26 (m, 12H); LCMS Calculated for $C_{24}H_{34}N_4O_2$: 410.27; Observed: 411.20 (M+1)$^+$.

Synthesis of N-(2-aminophenyl)-4-((1-(2-hydroxy-2-methylpropyl)-2,2-dimethylpiperidin-4-yl)oxy) benzamide (Compound 363)

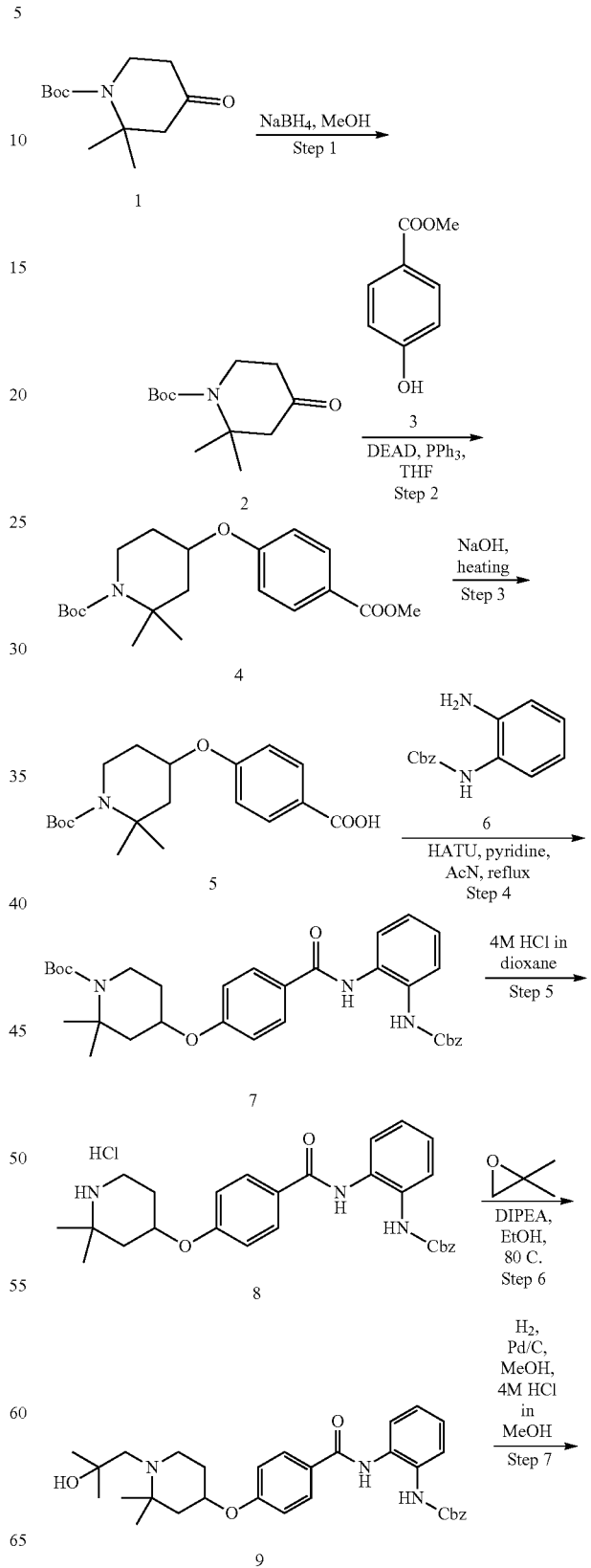

-continued

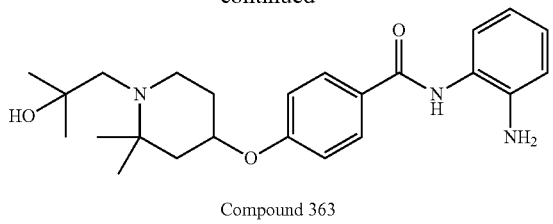

Compound 363

Step-1: Tert-Butyl 4-hydroxy-2,2-dimethylpiperidine-1-carboxylate (2)

To a stirred solution of Compound 1 (1.5 g, 1 eq) in MeOH (15 mL) at 0° C., NaBH$_4$ (0.244 g, 1 eq) was added and stirred for 30 min. the reaction progress was monitored by TLC. After completion, the reaction mixture was quenched with water and concentrated under reduced pressure. The residue was partitioned between water and ethyl acetate. The organic layers were separated, washed with water, dried over Na$_2$SO$_4$ and concentrated. The crude residue was purified by silica gel column chromatography to provide the desired compound.

Step-2: Tert-Butyl 4-(4-(methoxycarbonyl)phenoxy)-2,2-dimethylpiperidine-1-carboxylate (4)

To a solution of Compound 2 (1.5 g, 1 eq) in anhydrous THF was added Compound 3 (1.2 g, 1.2 eq) followed by triphenyl phosphine (2.57 g, 1.5 eq) and the reaction mixture was allowed to stir at room temperature for 30 min. The reaction mixture was cooled to 0° C., DEAD (1.7 g, 1.5 eq) was added slowly (dropwise) for 1 h and stirring was continued at room temperature for further 16 h. The progress of reaction was monitored by TLC. After completion of reaction, the volatiles were removed under vacuum, di-ethyl ether was added and the suspension was allowed to stir at 0° C. for 1-2 h. The above reaction mixture was then filtered through a pad of celite and the filtrate was concentrated. The crude compound was purified using silica gel column chromatography to afford the desired compound.

Step-3: 4-((1-(tert-butoxycarbonyl)-2,2-dimethylpiperidin-4-yl)oxy)benzoic Acid (5)

To stirred solution of Compound 4 (0.8 g, 1 eq) in methanol:water (1:1) was added NaOH (0.132 g, 1.5 eq) at room temperature. The above mixture was heated to 90° C. for 5 h. The progress of the reaction was monitored by TLC. After completion of reaction, the reaction mixture was concentrated and the resulting residue was washed with diethyl ether followed by treatment with water. The aqueous layer was neutralized to pH=7 using 1N HCl at 0° C. The solid obtained was filtered, washed with water and dried under vacuum to provide the desired compound.

Step-4: Tert-Butyl 4-(4-((2-(((benzyloxy)carbonyl)amino)phenyl)carbamoyl)phenoxy)-2,2-dimethylpiperidine-1-carboxylate (7)

To a stirred solution of Compound 5 (0.65 g, 1 eq) and Compound 6 (0.497 g, 1.1 eq) in ACN (10 mL) was added pyridine (0.736 g, 5 eq) and HATU (1.07 g, 1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over Na$_2$SO$_4$ and concentrated. The crude residue was purified by silica gel column chromatography to provide the desired compound.

Step-5: Benzyl (2-(4-((2,2-dimethylpiperidin-4-yl)oxy)benzamido)phenyl)carbamate Hydrochloride (8)

To a stirred solution of Compound 7 (0.9 g, 1 eq) in 1,4-dioxane (5 mL) was added 4M HCl in dioxane (2 mL) at room temperature. After completion of reaction, the reaction mixture was concentrated and the resulting residue was triturated with n-pentane and dried under vacuum to give desired compound.

Step-6: Benzyl (2-(4-((1-(2-hydroxy-2-methylpropyl)-2,2-dimethylpiperidin-4-yl)oxy)benzamido)phenyl)carbamate (9)

To a solution of Compound 8 (0.15 g, 1 eq) in ethanol (40 mL) was added DIPEA (0.122 g, 3 eq) followed by 2,2-dimethyloxirane (0.034 g, 1.5 eq) at room temperature and the reaction mixture was heated at 90° C. for 4 h. The progress of reaction was monitored by TLC. After completion, the reaction mixture was allowed to cool and concentrated to provide a crude compound. The crude compound was purified by silica gel column chromatography to provide the desired compound.

Step-7: N-(2-aminophenyl)-4-((1-(2-hydroxy-2-methylpropyl)-2,2-dimethylpiperidin-4-yl)oxy)benzamide (Compound 363)

To a stirred solution of Compound 9 (0.05 g, 1 eq) in methanol, 4M HCl in MeOH (2 mL), 10% Pd/C (10% w/w of substrate, 10 mg) was added and the reaction mixture was stirred under hydrogen atmosphere (balloon pressure) at room temperature for 1 h. The progress of the reaction was monitored by TLC. After completion, the reaction mixture was filtered through a pad of celite, the filtrate was evaporated under reduced pressure and the resulting residue was triturated with diethyl ether and n-pentane and then dried under vacuum to afford the title compound. 1H NMR (400 MHz, DMSO-d6) δ 9.51 (s, 1H), 7.93 (d, J=8.4 Hz, 2H), 7.14 (d, J=7.9 Hz, 1H), 7.06-6.88 (m, 3H), 6.77 (d, J=7.9 Hz, 1H), 6.59 (t, J=7.8 Hz, 1H), 4.86 (s, 2H), 4.62-4.60 (m, 1H), 3.97 (s, 1H), 3.05-3.03 (m, 1H), 2.62-2.55 (m, 1H), 2.45 (m, 1H), 1.99-1.95 (m, 2H), 1.87-1.79 (m, 1H), 1.60-1.42 (m, 2H), 1.11-1.02 (m, 12H); HPLC purity: 95.99%; LCMS Calculated for C$_{24}$H$_{33}$N$_3$O$_3$: 411.25; Observed: 412.20 (M+1)$^+$.

Synthesis of N-(2-aminophenyl)-4-((1-(2-hydroxy-2-methylpropyl)piperidin-4-yl)thio)benzamide (Compound 375)

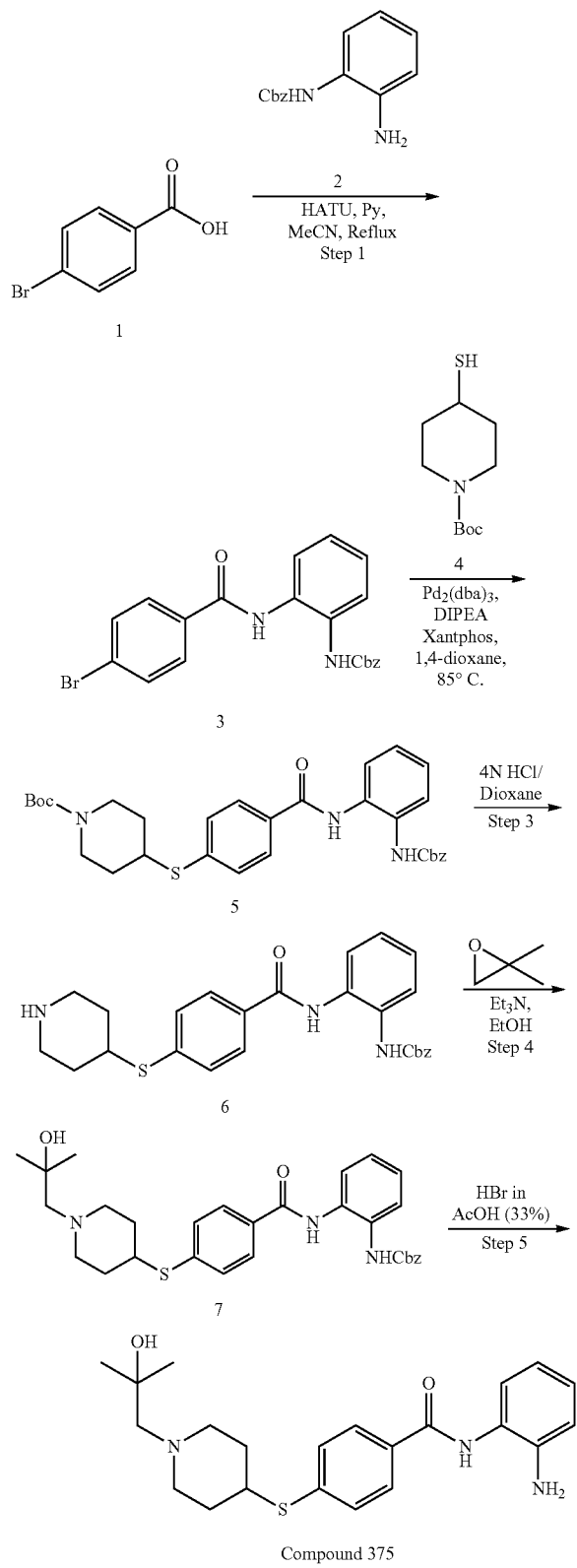

Step-1: Synthesis of Benzyl (2-(4-bromobenzamido)phenyl)carbamate (3)

To a stirred solution of Compound 1 (2 g, 1 eq) and Compound 2 (2.9 g, 1.1 eq) in ACN (25 mL) were added pyridine (3.93 g, 5 eq) and HATU (5.67 g, 1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over $Na_2SO_4$ and concentrated. The crude residue was purified by silica gel column chromatography to provide the desired compound.

Step-2: Synthesis of Tert-Butyl 4-((4-((2-(((benzyloxy)carbonyl)amino)phenyl)carbamoyl)phenyl)thio)piperidine-1-carboxylate (5)

A mixture of Compound 3 (1 g, 1 eq), Compound 4 (0.509 g, 1 eq) and DIPEA (0.603 g, 2 eq) in 1,4-dioxane were taken and purged with argon for 10 min, followed by the addition of xantphos (0.067 g, 0.05 eq) and purged with argon for additional 5 min. $Pd_2(dba)_3$ (0.107 g, 0.05 eq) was added and stirred at 85° C. for overnight. The progress of the reaction was monitored by TLC. After completion of the reaction, the reaction mixture was filtered through celite and evaporated to dryness. The residue was taken in ethyl acetate, washed with water, brine, dried over anhydrous sodium sulfate and evaporated under reduced pressure. The crude product was purified by column chromatography/preparative HPLC to afford the desired product.

Step-3: Synthesis of Benzyl (2-(4-(piperidin-4-ylthio)benzamido)phenyl)carbamate (6)

To a stirred solution of Compound 5 (0.7 g, 1 eq) in 1,4-dioxane (5 mL) was added 4M HCl in dioxane (5 mL) at room temperature. After completion of reaction, the reaction mixture was concentrated and the resulting residue was triturated with n-pentane and dried under vacuum to provide the desired compound.

Step-4: Synthesis of Benzyl (2-(4-((1-(2-hydroxy-2-methylpropyl)piperidin-4-yl)thio)benzamido)phenyl)carbamate (7)

To a solution of Compound 6 (0.6 g, 1 eq) in ethanol (10 mL) was added TEA (0.393 g, 3 eq) followed by 2,2-dimethyloxirane (0.328 g, 3.5 eq) at room temperature and the reaction mixture was heated at 90° C. for 4 h. The progress of reaction was monitored by TLC. After completion, the reaction mixture was allowed to cool and concentrated in vacuo to provide the crude compound which was purified by silica gel column chromatography to provide the desired compound.

Step-5: Synthesis of N-(2-aminophenyl)-4-((1-(2-hydroxy-2-methylpropyl)piperidin-4-yl)thio)benzamide (Compound 375)

A mixture of Compound 7 (0.1 g, 1 eq) and 33% HBr in AcOH (1 mL) was heated at 60° C. for 2 h. The progress of reaction was monitored by TLC. After completion, the reaction mixture was poured in ice cold water; basified with aq. NaOH and extracted with 10% MeOH/DCM. The combined organic extracts were collected; washed with water, brine, dried over anhydrous sodium sulfate and evaporated under reduced pressure. The crude product was purified by column chromatography to afford the desired product. $^1$H NMR (400 MHz, DMSO-d6) δ 9.65 (s, 1H), 7.94 (d, J=8.0 Hz, 2H), 7.48 (d, J=8.0 Hz, 2H), 7.14 (d, J=7.8 Hz, 1H), 6.97 (t, J=7.6 Hz, 1H), 6.81-6.74 (m, 1H), 6.59 (t, J=7.5 Hz, 1H), 4.92-4.87 (brs, 2H), 2.80-3.20 (m, 4H), 1.90-2.10 (m, 2H), 1.60-1.80 (m, 2H), 1.20 (s, 6H), 4H merged in solvent peak; HPLC purity: 95.21%; LCMS Calculated for $C_{22}H_{29}N_3O_2S$: 399.20; Observed: 400 (M+1)$^+$.

Synthesis of N-(2-aminophenyl)-4-((1-(cyclopropylmethyl)-2,2-dimethylpiperidin-4-yl)oxy)benzamide (Compound 362)

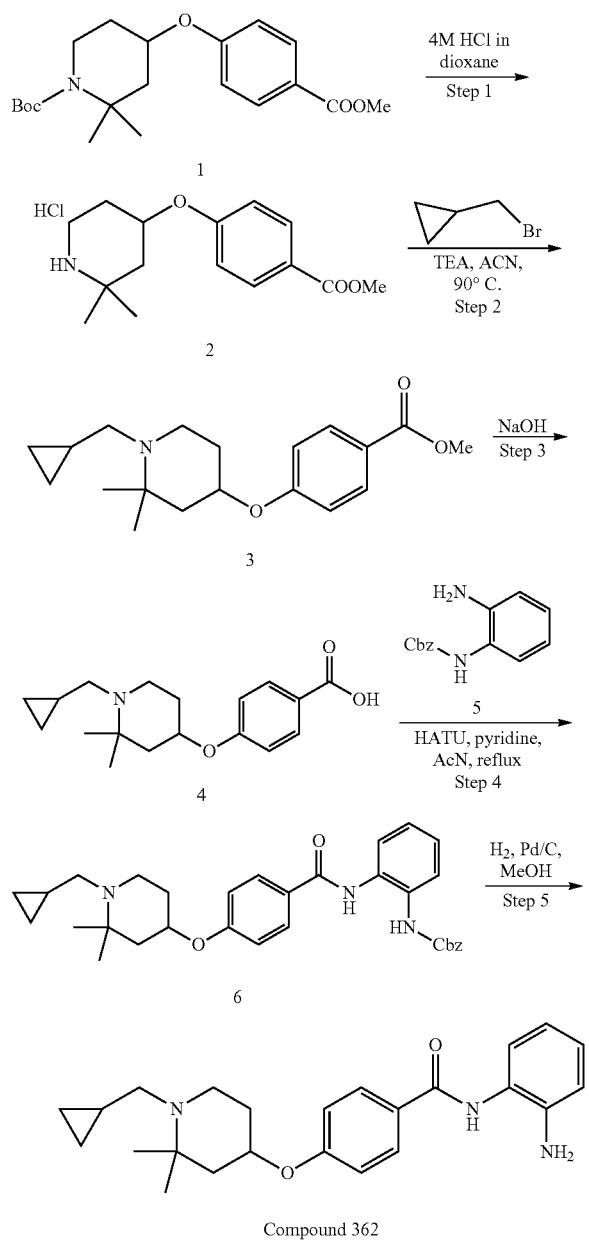

Step-1: Synthesis of Methyl 4-((2,2-dimethylpiperidin-4-yl)oxy)benzoate Hydrochloride (2)

To a stirred solution of Compound 1 (0.2 g, 1 eq) in 1,4-dioxane (1 mL) was added 4M HCl in dioxane (2 mL) at room temperature. After completion of reaction, the reaction mixture was concentrated and the resulting residue was triturated with n-pentane and dried under vacuum to provide the desired Compound 2.

Step-2: Synthesis of Methyl 4-((1-(cyclopropylmethyl)-2,2-dimethylpiperidin-4-yl)oxy)benzoate (3)

To a stirred solution of Compound 2 (0.12 g, 1 eq) in ACN (4 mL), TEA (0.276 g, 6 eq) and (bromomethyl)cyclopropane (0.185 g, 3 eq) was added and the reaction mixture was stirred at 90° C. for 24 h. The reaction progress was monitored by TLC. After completion, the reaction mixture was concentrated to dryness under reduced pressure. The crude residue was purified by silica gel column chromatography to provide the desired Compound 3.

Step-3: Synthesis of 4-((1-(cyclopropylmethyl)-2,2-dimethylpiperidin-4-yl)oxy)benzoic Acid (4)

To stirred solution of Compound 3 (0.1 g, 1eq) in methanol:water (1:1) was added NaOH (0.019 g, 1.5 eq) at room temperature. The above mixture was heated to 90° C. for 5 h. The progress of the reaction was monitored by TLC. After completion of reaction, the reaction mixture was concentrated and the resulting residue was washed with ethyl acetate followed by treatment with water. The aqueous layer was neutralized to pH=7 using 1N HCl at 0° C. The solid obtained was washed with 10% MeOH/DCM, filtered and dried under vacuum to provide the desired Compound 4.

Step-4: Synthesis of Benzyl (2-(4-((1-(cyclopropylmethyl)-2,2-dimethylpiperidin-4-yl)oxy)benzamido)phenyl)carbamate (6)

To a stirred solution of Compound 4 (0.07 g, 1 eq) and Compound 5 (0.067 g, 1.1 eq) in ACN was added pyridine (0.109 g, 5eq) and HATU (0.132 g, 1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over $Na_2SO_4$ and concentrated. The crude residue was purified by silica gel column chromatography to provide the desired Compound 6.

Step-5: Synthesis of N-(2-aminophenyl)-4-((1-(cyclopropylmethyl)-2,2-dimethylpiperidin-4-yl)oxy)benzamide (Compound 362)

To a stirred solution of Compound 6 (0.08 g, 1 eq) in methanol, 4M HCl in MeOH (3 mL), 10% Pd/C (10% w/w of substrate, 20 mg) was added and the reaction mixture was stirred under hydrogen atmosphere (balloon pressure) at room temperature for 3 h. The progress of the reaction was monitored by TLC. After completion, the reaction mixture was filtered through a pad of celite, the filtrate was evaporated under reduced pressure and the resulting residue was purified by Prep-HPLC to afford the title compound. $^1$H NMR (400 MHz, DMSO-d6) δ 9.51 (s, 1H), 7.93 (d, J=8.4

1.5 Hz, 2H), 7.14 (d, J=7.2 Hz, 1H), 7.02 (d, J=8.8 Hz, 2H), 6.98-6.91 (m, 1H), 6.78-6.76 (m, 1H), 6.60-6.57 (m, 1H), 4.86 (s, 2H), 4.61-4.58 (m, 1H), 3.02-3.00 (m, 1H), 2.49-2.41 (m, 2H), 2.06-2.04 (m, 1H), 1.93-1.77 (m, 2H), 1.60-1.41 (m, 2H), 1.08 (s, 3H), 0.99 (s, 3H), 0.79-0.77 (m, 1H), 0.54-0.33 (m, 2H), 0.15-0.03 (m, 2H); HPLC purity: 99.05%; LCMS Calculated for $C_{24}H_{31}N_3O_2$: 393.24; Observed: 394.25 $(M+1)^+$.

Synthesis of (R)—N-(2-aminophenyl)-4-((1-(cyclohexylmethyl)azepan-4-yl)amino)benzamide and (S)—N-(2-aminophenyl)-4-((1-(cyclohexylmethyl)azepan-4-yl)amino)benzamide (Compounds 85A and 85B)

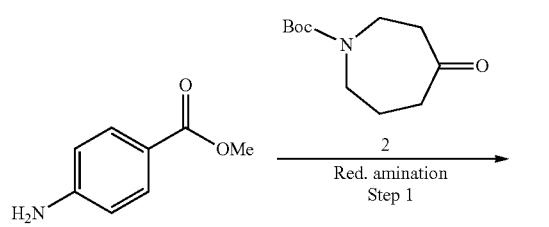

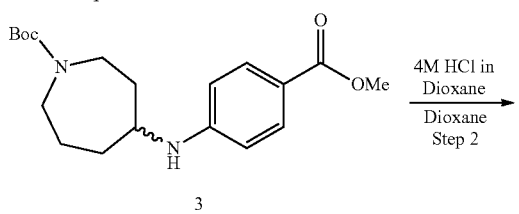

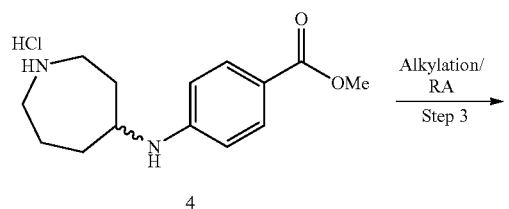

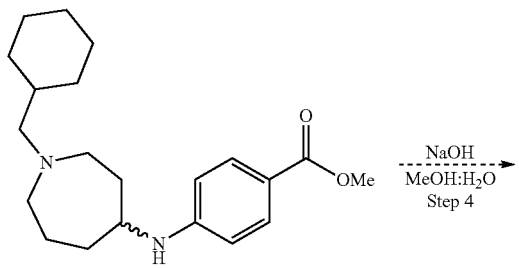

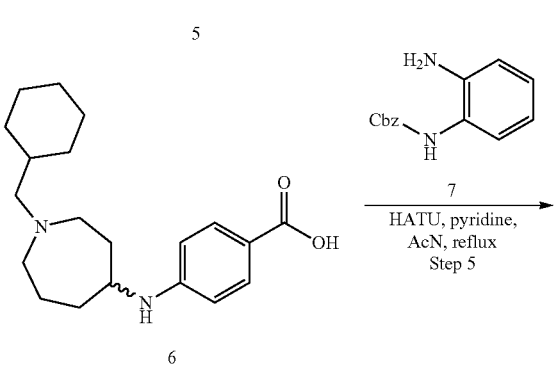

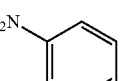

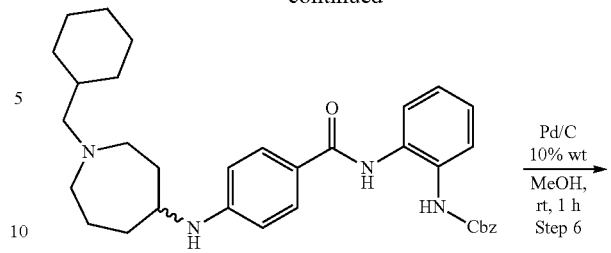

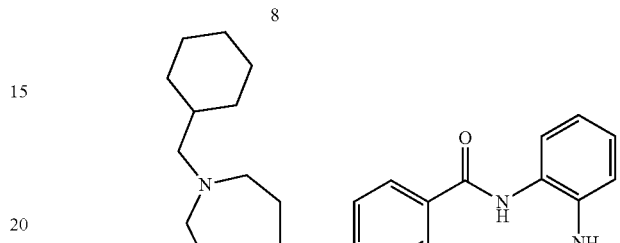

Compound 85A
Compound 85B

Step-1: Synthesis of Tert-Butyl 4-((4-(methoxycarbonyl)phenyl)amino)azepane-1-carboxylate (3)

To a stirred solution of Compound 1 (1 eq) and Compound 2 (1.2 eq) in DCE/DCM was added titanium tetraisopropoxide (Ti(O-i-Pr)$_4$) (1.5 eq), AcOH (1.5 eq) at room temperature. After 5 min, STAB (1.5 eq) was added and the mixture was heated at 60° C. for 12 h. The reaction progress was monitored by TLC and LCMS. After completion of reaction the reaction mixture was diluted with DCM and the resulting mixture was filtered over a pad of celite. The filtrate was concentrated and the resulting residue was purified by silica gel column chromatography to provide the desired compound.

Step-2: Synthesis of Methyl 4-(azepan-4-ylamino)benzoate Hydrochloride (4)

To a stirred solution of Compound 3 (1 eq) in 1,4-dioxane was added 4M HCl in dioxane at room temperature. After completion of reaction, the reaction mixture was concentrated and the resulting residue was triturated with n-pentane and dried under vacuum to give desired compound.

Step-3: Synthesis of Methyl 4-((1-(cyclohexylmethyl)azepan-4-yl)amino)benzoate (5)

To a stirred solution of amine compound (1 eq) and aldehyde (1.2 eq) in DCM was added acetic acid (6 eq) and sodium triacetoxyborohydride (STAB) (3 eq) at room temperature. After stirring the reaction mixture at ambient temperature overnight, the reaction progress was monitored by TLC and LCMS. After completion of reaction, the reaction mixture was partitioned between DCM and water. The organic layers were separated, washed with water and brine, dried over Na$_2$SO$_4$ and evaporated to get the crude product which was purified by silica gel column chromatography to afford the desired compound.

Step-4: Synthesis of 4-((1-(cyclohexylmethyl)aze-pan-4-yl)amino)benzoic Acid (6)

To stirred solution of Compound in methanol:water (1:1) was added NaOH (1.5 eq) at room temperature. The above mixture was heated to 90° C. for 5 h. The progress of the reaction was monitored by TLC. After completion of reaction, the reaction mixture was concentrated and the resulting residue was washed with diethyl ether followed by treatment with water. The aqueous layer was neutralized to pH=7 using 1N HCl at 0° C. The solid obtained was filtered, washed with water and dried under vacuum to provide the desired compound.

Step-5: Synthesis of Benzyl (2-(4-((1-(cyclohexyl-methyl)azepan-4-yl)amino)benzamido)phenyl)car-bamate (7)

To a stirred solution of Compound (1 eq) and Compound 7 (1.1 eq) in ACN was added pyridine (5eq) and HATU (1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over Na$_2$SO$_4$ and concentrated. The crude residue was purified by silica gel column chromatography to provide the desired compound.

Step-6: Synthesis of (R)—N-(2-aminophenyl)-4-((1-(cyclohexylmethyl)azepan-4-yl)amino)benzamide and (S)—N-(2-aminophenyl)-4-((1-(cyclohexylm-ethyl)azepan-4-yl)amino)benzamide (Compounds 85A and 85B)

To a stirred solution of Compound 8 (260 mg, 1 eq) in methanol/4M HCl in MeOH (2 mL), 10% Pd/C (10% w/w of substrate, 100 mg) was added and the reaction mixture was stirred under hydrogen atmosphere (balloon pressure) at room temperature for 1 h. The progress of the reaction was monitored by TLC. After completion, the reaction mixture was filtered through a pad of celite, the filtrate was evaporated under reduced pressure and the resulting residue was triturated with diethyl ether and n-pentane and then dried under vacuum to afford the title compound. The individual enantiomers of were separated by Chiral Prep-HPLC using CHIRALART CELLULOSE SC, 250 mm×4.6 mm, 5 m column and delivered as Compounds 85A and 85B as free base, their stereochemistry is yet to be confirmed and their RTs were as 4.77 and 5.71 respectively. Compound 85A: $^1$H NMR (400 MHz, DMSO-d6) δ 9.24 (s, 1H), 7.74 (d, J=8.4 Hz, 2H), 7.14 (d, J=8.0 Hz, 1H), 6.93 (t, J=7.2 Hz, 1H), 6.76 (d, J=8.0 Hz, 1H), 6.60-6.57 (m, 3H), 6.11 (d, J=7.6 Hz, 1H), 4.80 (s, 2H), 3.58-3.56 (m, 1H), 2.68-2.52 (m, 4H), 2.23-2.21 (m, 2H), 1.97-1.81 (m, 2H), 1.76-1.58 (m, 9H), 1.46-1.36 (m, 1H), 1.28-1.06 (m, 3H), 0.90-0.77 (m, 2H); Chiral HPLC purity: 97.53%; LCMS Calculated for C$_{26}$H$_{36}$N$_4$O: 420.29; Observed: 421.25 (M+1)$^+$. Compound 85B. $^1$H NMR (400 MHz, DMSO-d6) δ 9.24 (s, 1H), 7.74 (d, J=8.0 Hz, 2H), 7.14 (d, J=8.0 Hz, 1H), 6.93 (t, J=7.2 Hz, 1H), 6.76 (d, J=7.2 Hz, 1H), 6.60-6.51 (m, 3H), 6.12 (d, J=8.0 Hz, 1H), 4.80 (s, 2H), 3.63-3.44 (m, 1H), 2.68-2.50 (m, 3H), 2.23 (d, J=7.0 Hz, 2H), 1.99-1.81 (m, 2H), 1.81-1.51 (m, 9H), 1.42-1.40 (m, 1H), 1.23-1.15 (m, 3H), 0.88-0.79 (m, 2H);

Chiral HPLC purity: 96.26%; LCMS Calculated for C$_{26}$H$_{36}$N$_4$O: 420.29; Observed: 421.25 (M+1)$^+$.

Synthesis of N-(2-aminophenyl)-4-((1-(cyclopropyl-methyl)-2,2-dimethylpiperidin-4-yl)amino)benz-amide (Compound 368)

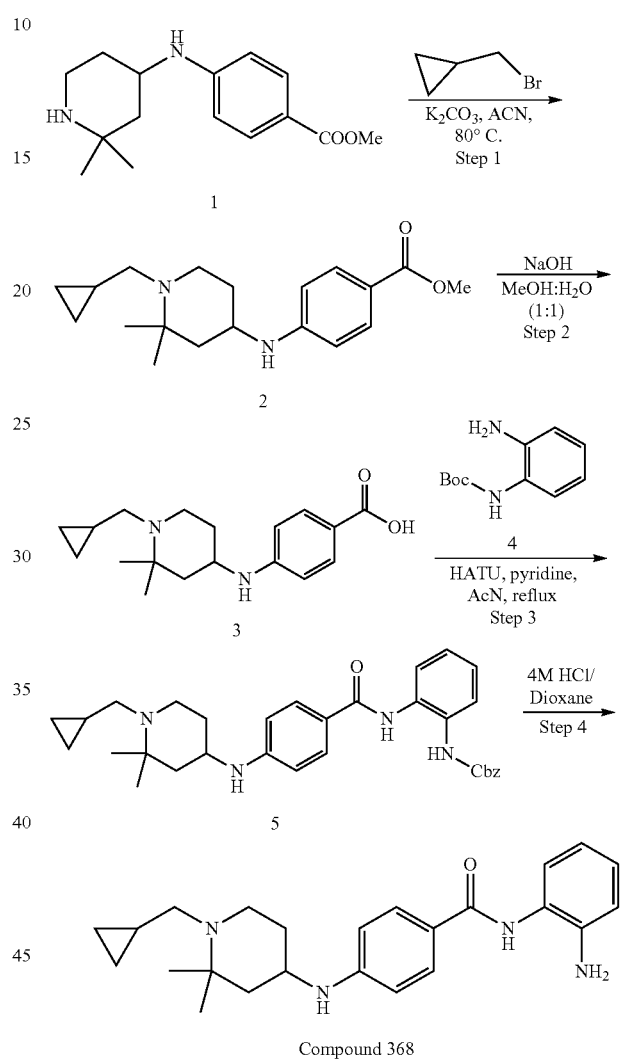

Compound 368

Step-1: Synthesis of Methyl 4-((1-(cyclopropylm-ethyl)-2,2-dimethylpiperidin-4-yl)amino)benzoate (2)

To a stirred solution of Compound 1 (1 eq) and potassium carbonate (3 eq), Et$_3$N (2 eq) in ACN (10 vol), the corresponding alkyl halide (1.2 eq) was added. The reaction mixture was heated at 80° C. for 5 h to 30 h. The progress of reaction was monitored by TLC. After completion, the reaction mixture was poured into ice-water and extracted with ethyl acetate. The combined organic extracts were washed with water, brine, dried over anhydrous Na$_2$SO$_4$, filtered and concentrated under reduced pressure to provide a crude residue which was purified by silica gel column chromatography to afford Compound 2.

Step-2: Synthesis of 4-((1-(cyclopropylmethyl)-2,2-dimethylpiperidin-4-yl)amino)benzoic Acid (3)

To stirred solution of Compound 2 (1 eq) in methanol: water (1:1) was added NaOH (1.5 eq) at room temperature. The above mixture was heated to 90° C. for 5 h. The progress of the reaction was monitored by TLC. After completion of reaction, the reaction mixture was concentrated and the resulting residue was washed with diethyl ether followed by treatment with water. The aqueous layer was neutralized to pH=7 using 1N HCl at 0° C. The solid obtained was filtered, washed with water and dried under vacuum to provide the desired Compound 3.

Step-3: Synthesis of Tert-Butyl (2-(4-((1-(cyclopropylmethyl)-2,2-dimethylpiperidin-4-yl)amino)benzamido)phenyl)carbamate (5)

To a stirred solution of Compound 3 (1 eq) and Compound 4 (1.1 eq) in ACN was added pyridine (5eq) and HATU (1.5 eq) at room temperature. After stirring the reaction mixture at 80° C. for overnight, the reaction progress was monitored by TLC and LCMS. After completion, the reaction mixture was concentrated and resulting residue was partitioned between water and ethyl acetate. The organic layers were separated, washed with water and 1% HCl to remove traces of pyridine, dried over $Na_2SO_4$ and concentrated. The crude residue was purified by silica gel column chromatography to provide the desired Compound 5.

Step-4: Synthesis of N-(2-aminophenyl)-4-((1-(cyclopropylmethyl)-2,2-dimethylpiperidin-4-yl)amino)benzamide (Compound 368)

To a stirred solution of Compound 5 (1 eq) in 1,4-dioxane was added 4M HCl in dioxane at room temperature. After completion of reaction, the reaction mixture was concentrated and the resulting residue was partitioned between sat. aq. $NaHCO_3$ and ethyl acetate. The organic layer was separated, dried over sodium sulphate and concentrated to get the crude product which was purified by prep-HPLC. $^1$H NMR (400 MHz, DMSO-d6) δ 9.25 (s, 1H), 7.74 (d, J=8.4 Hz, 2H), 7.14 (d, J=7.8 Hz, 1H), 6.93 (t, J=7.6 Hz, 1H), 6.76 (d, J=7.2 Hz, 1H), 6.61-6.58 (m, 3H), 6.02 (d, J=7.2 Hz, 1H), 4.80 (s, 2H), 3.48-3.46 (m, 1H), 3.10-3.01 (m, 1H), 2.70-2.68 (m, 1H), 2.39-2.31 (m, 1H), 1.96-1.93 (m, 1H), 1.82-1.77 (m, 1H), 1.75-1.65 (m, 1H), 1.33-1.23 (m, 2H), 1.07 (s, 3H), 0.98 (s, 3H), 0.80-0.79 (m, 1H), 0.50-0.38 (m, 2H), 0.16-0.03 (m, 2H); HPLC purity: 98.95%; LCMS Calculated for $C_{24}H_{32}N_4O$: 392.26; Observed: 393.20 $(M+1)^+$.

HDAC Enzyme Inhibition

The HDAC activity inhibition assay is performed as follows to determine the ability of a test compound to inhibit HDAC enzymatic activity. Serial dilutions of HDAC inhibitors are prepared in HDAC assay buffer (25 mM Tris/HCl, pH 8.0, 137 mM NaCl, 2.7 mM KCl, 1 mM $MgCl_2$, pH 8) in 96-well assay plates (Fisher scientific, #07-200-309) and pre-incubated for 2 hours at room temperature in the presence of 125 µg/ml BSA and purified HDAC1 (BPS Bioscience, San Diego, Calif., #50051), HDAC2 (BPS Bioscience, #50053), or HDAC3/NcoR2 (BPS Bioscience, #50003) at concentrations of 1.25, 1.32, and 0.167 µg/mL, respectively. Following pre-incubation, Fluor-de-Lys™ substrate (Enzo Life Sciences, Plymouth Meeting, Pa., BML-KI104-0050) is added to a final concentration of 10 µM and plates are further incubated for 30 minutes at room temperature. The enzymatic reaction is stopped by addition of Trichostatin A (Sigma-Aldrich, St Louis, Mo., #T8552, final concentration: 100 nM) and trypsin (MP Biomedicals, Solon, Ohio, #02101179) are added to reach a final concentration of 100 µg/mL. After a 15 minute incubation at room temperature, fluorescence is recorded using a Spectramax M2 fluorometer (Molecular Devices, Sunnyvale, Calif.) with excitation at 365 nm and emission at 460 nm. $IC_{50}$ values are calculated by using a sigmoidal dose-response (variable slope) equation in GraphPad Prism® 5 for Windows (GraphPad Software, La Jolla, Calif.).

Acid Stability Determination

A 100M solution of test compound is prepared by dilution of a 10 mM DMSO stock solution in a 0.01 M solution of HCl in deionized water. Immediately after mixing, an aliquot (100 µL) is sampled and analyzed by HPLC/UV. The area under the compound peak is determined and used as the time zero reference point. The remainder of the acid sample is incubated at 50° C. and samples were taken after 2, 4, and 24 or 30 hours of incubation. These are analyzed by the same HPLC/UV method and the area of the peak corresponding to the test compound is measured. Percent remaining at a given time point is then calculated as the ratio of the area under the peak after incubation to that at time zero times 100. In those embodiments where a 30 hour time point is recorded, the percent remaining at 24 hours is obtained by interpolation of the percent remaining versus time curve assuming a unimolecular process, i.e. a monoexponential decay.

Brain Penetration Studies

Test compounds are prepared at either 0.5 mg/ml or 5 mg/ml in 30% hydroxypropyl-β-cyclodextrin, 100 mM sodium acetate pH 5.5, 5% DMSO. Rats or C57/BL6/J mice are dosed s.c. at 5 mg/kg or 50 mg/kg, or i.v. at 5 mg/kg. Animals are euthanized at pre-dose, 5, 15, 30 min, 1, 2 and 4 hours post-dose and plasma and brain obtained. Three animals per dose per time points are used. The levels of compound in the plasma and brain are determined by standard LC/MS/MS methods. Brain/plasma ratio (BPR) is calculated as the ratio of the $C_{max}$(brain)/$C_{max}$(plasma).

In-Cell Deacetylase Inhibition Assay (DAC Assay)

GM 15850 (lymphoblastoid cells line) cells are seeded in 96-well plates at an appropriate density (100,000 cells/well) in 90 µL RPMI1640 medium containing 10% v/v fetal bovine serum (FBS), 1% v/v penicillin/streptomycin, and 1% v/v L-glutamine. Compound dilutions are made in 100% DMSO followed by parallel dilution in media with 2% DMSO. 10 µl of the compound dilutions are added to the cells to achieve the desired concentrations. The final concentration of DMSO in each well is 0.2%. The cells are incubated for 4 h at 37° C. with 5% $CO_2$. After incubation, the cells are centrifuged down and the supernatant removed. The cell pellets are washed with 100 µL phosphate-buffered saline (PBS) and then lysed with 45 µL lysis buffer (HDAC assay buffer at pH 8.0 (25 mM Tris/HCl, 137 mM NaCl, 2.7 mM KCl, 1 mM $MgCl_2)^+$1% v/v Igepal CA-630). To initiate the reaction, the HDAC substrate KI-104 (Enzo Life Sciences, Farmingdale, N.Y.) is added to a final concentration of 50 µM. The reaction is stopped after 30 min incubation by addition of 50 µL developer (6 mg/mL trypsin in HDAC assay buffer). The reaction is allowed to develop for 30 min at room temperature and the fluorescence signal is detected using a fluorometer (Spectramax M2, Molecular Devices, Sunnyvale, Calif.) with excitation and emission wavelengths of 360 nm and 470 nm respectively. The data are fitted to a sigmoidal dose response equation with variable slope in GraphPad Prism 5.0 (GraphPad Software, La Jolla, Calif.) to determine $IC_{50}$. Bottom and top of the curve are fixed to the average fluorescence response of control wells with no cells and cells but no compound respectively.

Cell Proliferation Assay

HCT 116 cells (5000 cells/well) in 80 µL McCoy's 5A medium containing 10% v/v FBS, 1% v/v penicillin/streptomycin and 1% v/v L-glutamine are incubated in 96-well plates with compounds at various concentrations for 72 h at 37° C. in a 5% $CO_2$ atmosphere. The compound dilutions are made in 100% DMSO followed by parallel dilutions in media. The final concentration of DMSO in each well is 0.05%. After 72 h, 20 µL of Cell titer 96 aqueous one solution (Promega Corporation, Madison, Wis.) are added to the cells and the plate is incubated at 37° C. for another 4 h. The absorbance at 490 nm is then recorded on a 96-well plate reader (Spectramax M2, Molecular Devices, Sunnyvale, Calif.). Data analysis is performed in Microsoft Excel (Microsoft Corp, Redmond, Wash.). ((O.D. sample−average O.D. positive control)/(average O.D. negative control−average O.D. positive control))*100, where O.D. is the measured absorbance, O.D. positive control is the absorbance from cells incubated with trichostatin A at 5 µM and O.D. negative control is the absorbance measured from cells incubated without any compound, is plotted against compound concentration and an $IC_{50}$ is determined by graphical interpolation of the concentration required for 50% inhibition of cell growth.

Effect of HDAC Inhibitors on Frataxin (FXN) mRNA Expression

Method: mRNA quantification of compound-treated iPSC derived neuronal cells Neuronal stem cells were cultured in Neurobasal A medium (Life technologies #10888022) supplemented with N2, B27 (Life technologies #17502-048 and #17504-044), L-glutamine (Life technologies #25030081), supplemented with 20 ng/ml EGF (R&D Systems #236-EG) and 20 ng/ml bFGF (BioPioneer #HRP-0011). Neuronal differentiation was initiated by removing growth factors and culturing cells in Neurobasal A with N2 and B27. Cells were allowed to differentiate for 16 days. HDAC inhibitory compound was then added and incubate for 24 h. RNA isolation was performed using the RNeasy Plus mini kit (QIAgen #74134) using a QIAcube instrument per manufacturer's instructions. qRT-PCR was performed using qScript One-Step SYBR Green qRT-PCR Kit (Quanta Biosciences 170-8893BR) with the following conditions: 20 minutes at 50° C., 5 minutes at 95° C., and then 40 cycles of 20 seconds at 95° C., 20 seconds at 55° C., 30 seconds at 72° C. The primer sequences to detect expression of FXN were: 5'-CAGAGGAAACGCTGGACTCT-3' and 5'-AGCCAGATTTGCTTGTTTGG-3'.

The data for the following compounds, for FXN mRNA fold induction at a compound concentration of 0.625 µM are shown in Table 1, where A<1, 1<B<2, 2<C<3, 3<D<5, E>5.

TABLE 1

| Compound | FXN mRNA fold induction |
|---|---|
| 1 | B |
| 2 | B |
| 3 | B |
| 4 | B |
| 5 | C |
| 6 | C |
| 26 | C |
| 27 | C |
| 29 | B |
| 28 | C |

TABLE 1-continued

| Compound | FXN mRNA fold induction |
|---|---|
| 35 | C |
| 38 | C |
| 40 | D |
| 41 | B |
| 44 | B |
| 46 | B |
| 48 | C |
| 49 | C |
| 51 | B |
| 52 | B |
| 54 | B |
| 33 | C |
| 36 | B |
| 43 | B |
| 64 | C |
| 62 | B |
| 58 | C |
| 59 | B |
| 60 | B |
| 56 | C |
| 57 | C |
| 42 | B |
| 50 | C |
| 65 | C |
| 66 | B |
| 69 | B |
| 89 | B |
| 67 | B |
| 75 | B |
| 72 | B |
| 70 | B |
| 71 | B |
| 73 | B |
| 86 | C |
| 91 | B |
| 110 | C |
| 112 | B |
| 34 | B |
| 77 | B |
| 78 | C |
| 85 | C |
| 88 | B |
| 93 | C |
| 94 | B |
| 111 | B |
| 114 | B |
| 123 | B |
| 40A | B |
| 40B | C |
| 129 | B |
| 136 | B |
| 87 | C |
| 97 | B |
| 134 | B |
| 140 | C |
| 131 | B |
| 81 | B |
| 95 | B |
| 99 | C |
| 101 | C |
| 107 | C |
| 124 | B |
| 125 | B |
| 126 | B |
| 127 | B |
| 128 | B |
| 132 | B |
| 138 | C |
| 80 | C |
| 83 | C |
| 96 | B |
| 105 | C |
| 109 | C |
| 130 | B |
| 141 | B |
| 170 | B |

TABLE 1-continued

| Compound | FXN mRNA fold induction |
|---|---|
| 102 | C |
| 103 | B |
| 104 | C |
| 135 | B |
| 137 | B |
| 139 | B |
| 45 | B |
| 53 | B |
| 61 | B |
| 74 | B |
| 90 | C |
| 98 | C |
| 106 | C |
| 68 | B |
| 142 | C |
| 92 | C |
| 47 | B |
| 76 | C |
| 133 | C |
| 100 | B |
| 113 | C |
| 63 | C |
| 37 | C |
| 39 | D |
| 55 | C |
| 108 | C |
| 120 | B |
| 38A | A |
| 38B | B |
| 116 | C |
| 117 | C |
| 118 | C |
| 122 | C |
| 115 | B |
| 119 | C |
| 369 | B |
| 363 | C |
| 375 | B |
| 85A | C |
| 85B | C |

Protocol for Compound Stability in Hepatocytes

To assess the stability and metabolism of RGFP compounds in hepatocytes. This assay was designed to evaluate the metabolism of RGFP compounds, following their incubation with human, monkey, dog and rat hepatocytes by monitoring either parent drug disappearance or metabolite appearance using HPLC.

Equipment: Applied Biosystem Triple Quadrupole LC/MS/MS; Ice bucker, timer; 96 well plates; Falcon, Cat #353072; 96 well plates shaker; Various pipettes: 10 µL, 20 µL, 200 µL, and 1000 µL; Test tubes: Catalog #VWR 47729-572, 13×100 mm Procedure: Turn on the water-bath heater to 37° C. Take out the KHB buffer and make sure it is at room temp before use. Prepare 2.5 mM concentration of RGFP compound in DMSO stock. Add 10 µL of above DMSO stock to 2490 µL KHB buffer; final concentration of RGFP compound will be 10 µM. Pre-warm 45 ml InVitro HT Medium to 37° C. in a sterile 50 mL conical tube. Add 1.0 mL Torpedo Antibiotic Mix per 45 mL InVitro HT medium. Transfer 13 mL of warm HT medium with Antibiotic Mix into a 15 mL conical tube. Carefully remove the hepatocyte vials from liquid nitrogen (liquid phase). Immediately immerse the vial into a 37° C. water bath. Shake gently until the ice melts entirely. Do not keep the cells in 37° C. water bath longer than necessary. Immediately empty contents of the vial into 13 mL of pre-warmed InVitro HT Medium with antibiotics. Rinse the vial with the HT media that you have just transferred the hepatocytes to, in order to ensure complete transfer. Centrifuge the cell suspension at 600 RPM for 5 minutes at room temperature. Discard the supernatant by either pouring in one motion (do not pour partially and re-invert centrifuge tube) or aspirating using a vacuum pump. Add 1.0 mL of KHB (at room temperature) buffer to the tube of hepatocyte pellet. Loosen the cell pellet by gently swirling the centrifuge tube. Transfer 100 µL of above solution to a different tube and add 900 µL of KHB buffer to count the cells. Determine the total cell count and the number of viable cells using the Trypan Blue exclusion method. Once the cell count is obtained, multiply the number by 10 (attributing to the dilution factor). Now add required volume of KHB buffer to the tube containing hepatocytes such that the final count will be 2 million cells/mL. Dispense 50 µL of 2 million cells/ml to a 96 well plate and then add 50 µL of DMSO stock to respective wells (such that, the concentration of RGFP compounds is 5 µM and number of cells are 100000 in each well). Place the plates on a shaker in a 37° C. incubator with 5% $CO_2$. Separate plates for each time point are advisable (Time points: 0 h, 1 h, 2 h, and 6 h). After each time point, add 100 µL of quenching solution.

Quenching solution is an acetonitrile solution containing RGFP531 (10 µM) internal standard, 0.1% formic acid and phenylglyoxol (400 µM). The formic acid and phenylglyoxal is used for the identification and quantification of OPD as mentioned above. Pipette up and down a few times to ensure a complete stop of reaction. Transfer all the solution into a 1.5 mL tube, vortex thoroughly, and centrifuge at 14000 RPM at 4° C. for 5 minutes to precipitate cell debris. Transfer the 150 µL of supernatant to vials for analysis using HPLC.

Effect of Compounds on Long Term Memory for Object Recognition

Rats or C57BL/6J male mice are handled 1-2 min for 5 days and habituated to the experimental apparatus 5 min a day for 4 consecutive days in the absence of objects. During the training trial, rats or mice are placed in the experimental apparatus with two identical objects and allowed to explore these objects for 3 min, which does not result in short- or long-term memory (Stefanko, et al., 2009). Immediately following training, rats or mice receive subcutaneous injections of either vehicle (20% glycerol, 20% PEG 400, 20% propylene glycol, and 100 mM sodium acetate, pH 5.4), reference compound 1, RGFP109, class I HDAC inhibitor, (3, 10, 30 mg/kg), reference compound 2, RGFP136 (3, 10, 30 mg/kg), or a test compound disclosed herein (3, 10, 30 mg/kg). 24-h later rats or mice are tested for memory retention (5 min) using the object recognition memory task (ORM), in which a familiar object is replaced with a novel one. All training and testing trials are videotaped and analyzed by individuals blind to the treatment condition and the genotype of subjects. A rat or mouse is scored as exploring an object when its head was oriented toward the object within a distance of 1 cm or when the nose is touching the object. The relative exploration time is recorded and expressed by a discrimination index [DI=$(t_{novel}-t_{familiar})/(t_{novel}+t_{familiar})\times 100$].

A number of embodiments have been described. Nevertheless, it will be understood that various modifications may be made without departing from the spirit and scope of the disclosure. Accordingly, other embodiments are within the scope of the following claims.

What is claimed is:

1. A compound having a structure of formula (I), or a pharmaceutically acceptable salt thereof

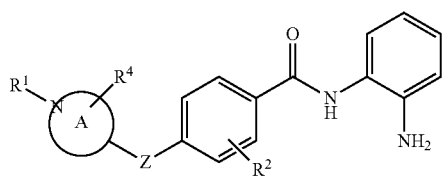

wherein
ring A is a 4-7 membered saturated heterocycle containing one nitrogen ring atom or a 7-9 membered saturated bicyclic heterocycle containing one nitrogen ring atom;
Z is O, $NR^3$, S, SO, or $SO_2$;
$R^1$ is H, $C_{1-6}$alkyl, $C_{1-6}$hydroxyalkyl, $C(O)C_{1-6}$alkyl, $C_{0-3}$alkylene-$C_{3-10}$cycloalkyl, or saturated $C_{0-3}$alkylene-$C_{2-5}$heterocycle having 1 or 2 heteroatoms selected from O, S, N, and $N(C_{1-4}$alkyl);
$R^2$ is H, F, Cl, or $CH_3$;
$R^3$ is H, $C_{1-6}$alkyl, $C_{1-6}$haloalkyl, $C_{0-3}$alkylene-$C_{3-7}$cycloalkyl, $C(O)C_{1-6}$-alkyl, or $C(O)C_{0-3}$alkylene-$C_{3-7}$cycloalkyl; and
$R^4$ is H or $C_{1-3}$alkyl.

2. The compound of claim 1, wherein ring A is a 4-7 membered saturated heterocycle containing one nitrogen ring atom or a 7-9 membered bicyclic saturated heterocycle containing one nitrogen ring atom; Z is O, $NR^3$, S, or $SO_2$; $R^1$ is $C_{1-6}$alkyl, $C_{1-6}$hydroxyalkyl, or $C_{0-3}$alkylene-$C_{3-7}$cycloalkyl; $R^2$ is H, F, Cl, or $CH_3$; $R^3$ is H, $C_{1-6}$-alkyl, $C_{1-6}$haloalkyl, $C_{0-3}$alkylene-$C_{3-7}$cycloalkyl, $C(O)C_{1-6}$-alkyl, or $C(O)C_{0-3}$alkylene-$C_{3-7}$cycloalkyl; and $R^4$ is H or $C_{1-3}$alkyl.

3. The compound or pharmaceutically acceptable salt of claim 1, wherein $R^1$ is H, $C_{1-6}$-alkyl, $C_{1-6}$hydroxyalkyl, $C_{0-3}$alkylene-$C_{3-10}$cycloalkyl, or saturated $C_{0-3}$alkylene-$C_{2-5}$heterocycle having 1 or 2 heteroatoms selected from O, S, N, and $N(C_{1-4}$alkyl).

4. The compound or pharmaceutically acceptable salt of claim 1, wherein $R^1$ is $C_{1-6}$alkyl, $C_{1-6}$hydroxyalkyl, or $C_{0-3}$alkylene-$C_{3-10}$cycloalkyl.

5. The compound or pharmaceutically acceptable salt of claim 1, wherein $R^1$ is methyl, isopropyl, sec-butyl, $CH_2C(CH_3)_3$, or

6. The compound or pharmaceutically acceptable salt of claim 1, wherein $R^1$ is cyclopropyl, cyclobutyl, cyclohexyl, adamantanyl, $CH_2$cyclopropyl, (1-methylcyclopropyl)methyl, $CH_2$cyclobutyl, $CH_2$cyclohexyl, $CH_2$-adamantanyl, azetidinyl, pyrrolidinyl, piperidinyl, piperazinyl, oxetanyl, tetrahydrofuranyl, tetrahydropyranyl, or morpholinyl.

7. The compound of claim 1, or a pharmaceutically acceptable salt thereof,
wherein
ring A is selected from the group consisting of:

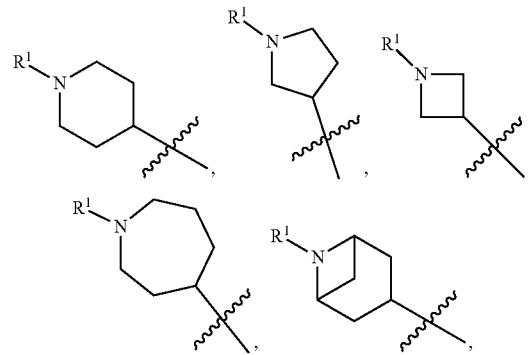

-continued

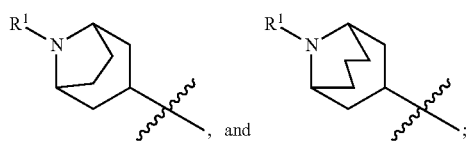

Z is O, NR³, S, SO, or SO₂;
R¹ is selected from the group consisting of H, CH₃, C(O)CH₃,

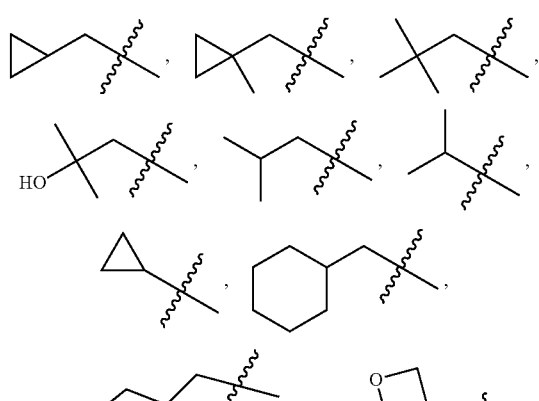

R² is H, F, Cl, or CH₃;
R³ is H, $C_{1-6}$-alkyl, $C_{1-6}$haloalkyl, $C_{0-3}$alkylene-$C_{3-7}$ cycloalkyl, C(O)$C_{1-6}$-alkyl, or C(O)$C_{0-3}$alkylene-$C_{3-7}$cycloalkyl; and
R⁴ is H or $C_{1-3}$alkyl.

8. The compound of claim 1, or a pharmaceutically acceptable salt thereof,
wherein ring A is selected from the group consisting of

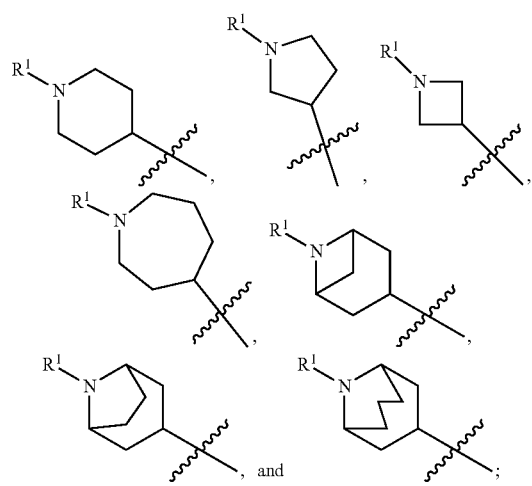

Z is O, NR³, S, SO, or SO₂; R¹ is selected from the group consisting of H, CH₃, C(O)CH₃,

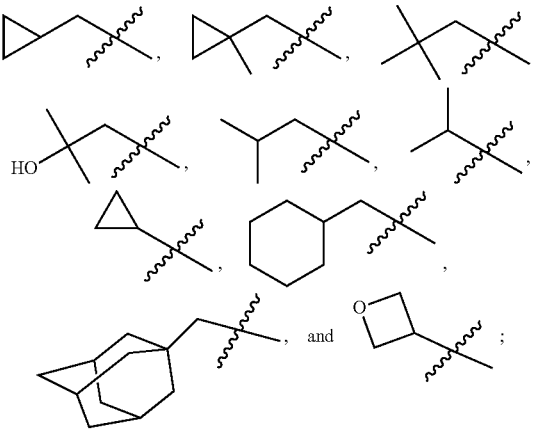

and R³ is H, $C_{1-6}$-alkyl, $C_{1-6}$haloalkyl, $C_{0-3}$alkylene-$C_{3-7}$ cycloalkyl, C(O)$C_{1-6}$alkyl, or C(O)$C_{0-3}$alkylene-$C_{3-7}$cycloalkyl.

9. The compound or pharmaceutically acceptable salt of claim 1, wherein ring A is selected from the group consisting of

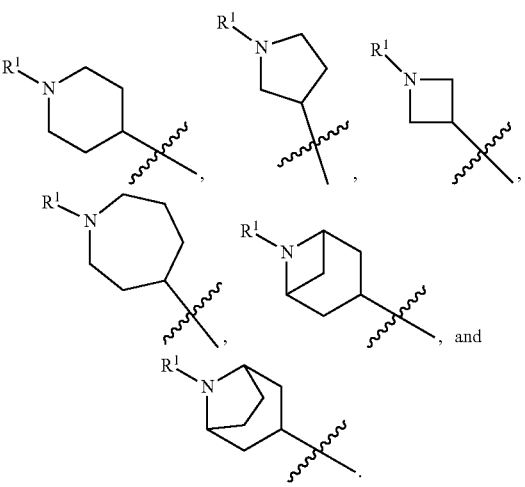

10. The compound or pharmaceutically acceptable salt of claim 1, wherein R² is H.

11. The compound or pharmaceutically acceptable salt of claim 1, wherein R¹ is selected from the group consisting of

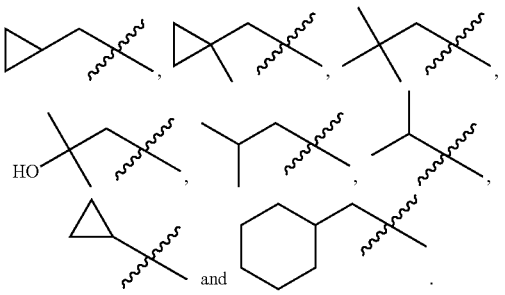

12. The compound or pharmaceutically acceptable salt of claim 1, wherein ring A is selected from the group consisting of

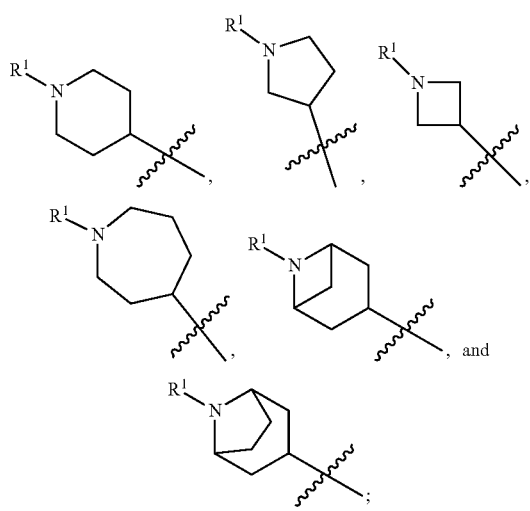

Z is O or NR³; and R¹ is selected from the group consisting of

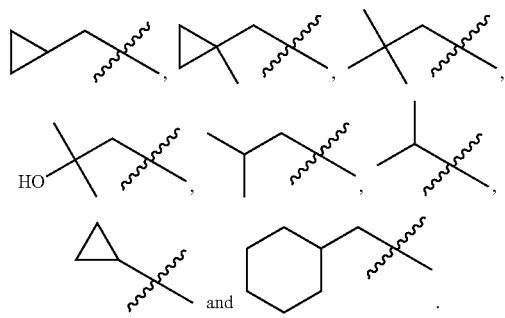

13. The compound of claim 1, wherein the compound of formula (I) is a compound of formula (III), or a pharmaceutically acceptable salt thereof

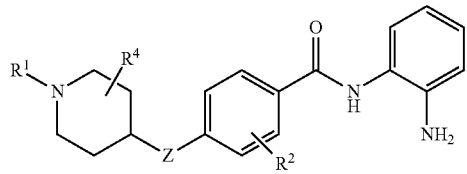

(III)

wherein Z is O, NR³, S, SO, or SO₂; R¹ is selected from the group consisting of

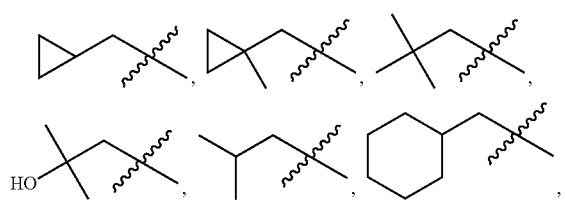

-continued

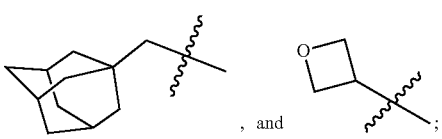

R² is H, F, Cl, or CH₃; R³ is H, $C_{1-6}$-alkyl, $C_{1-6}$haloalkyl, $C_{0-3}$alkylene-$C_{3-7}$cycloalkyl, C(O)$C_{1-6}$-alkyl, or C(O)$C_{0-3}$alkylene-$C_{3-7}$cycloalkyl; and R⁴ is H or $C_{1-3}$alkyl.

14. The compound or pharmaceutically acceptable salt of claim 1, wherein Z is O, NR³, S, or SO₂; and R¹ is selected from the group consisting of

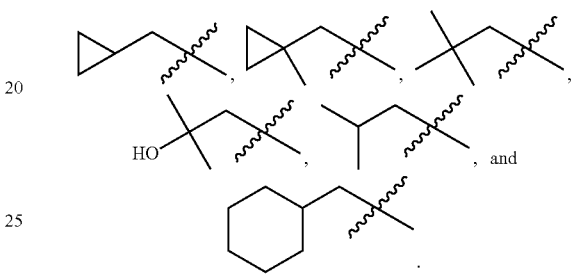

15. The compound of claim 1 having a structure selected from the group consisting of:

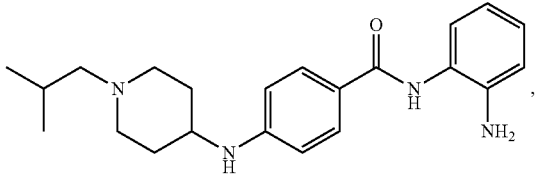

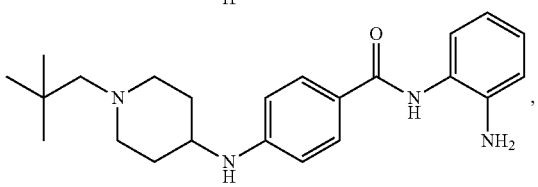

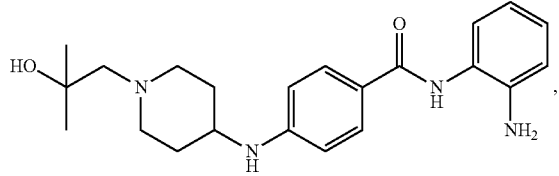

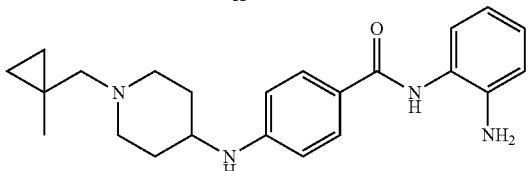

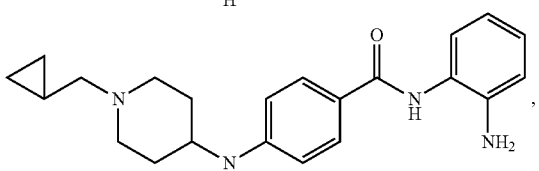

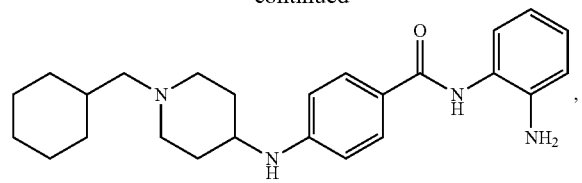
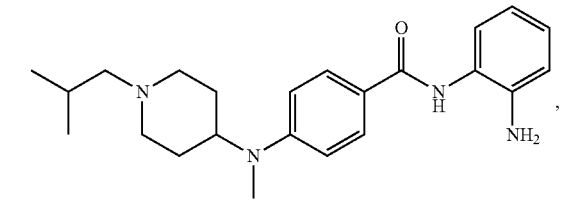
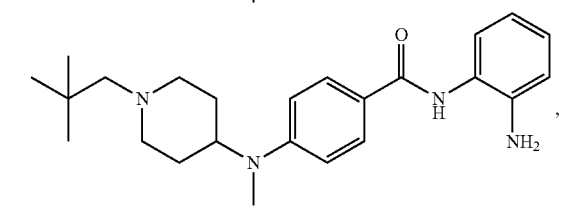
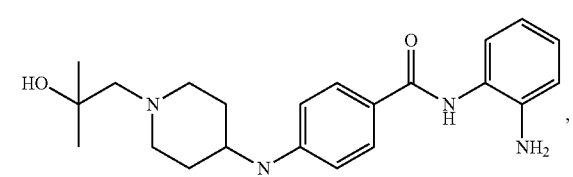
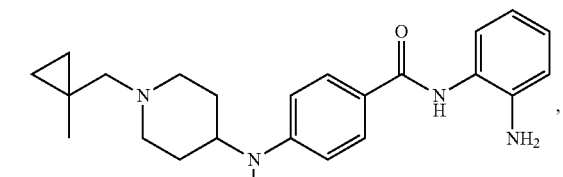
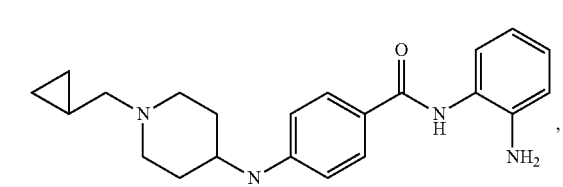
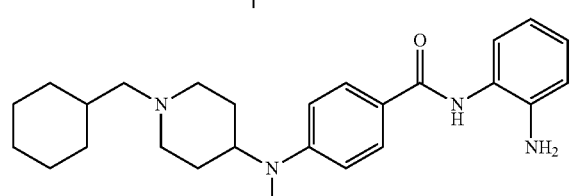
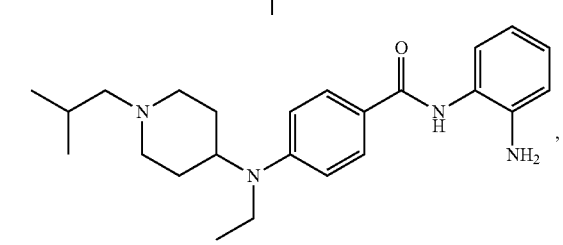
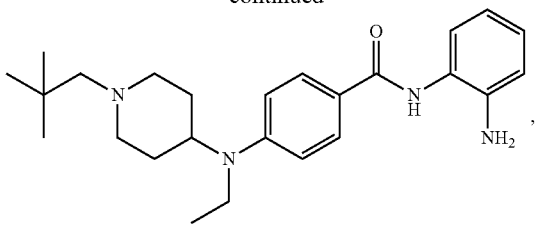
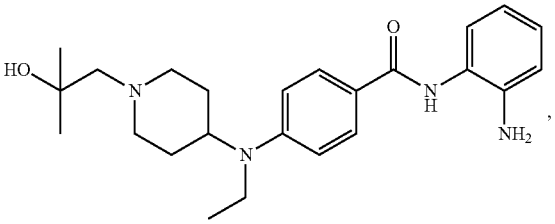
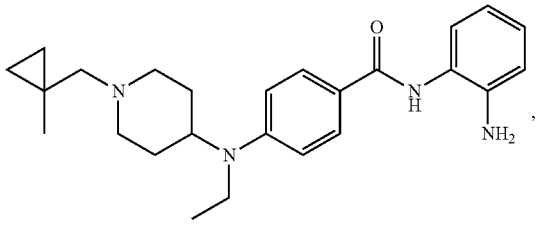
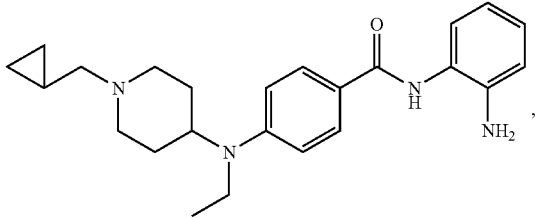
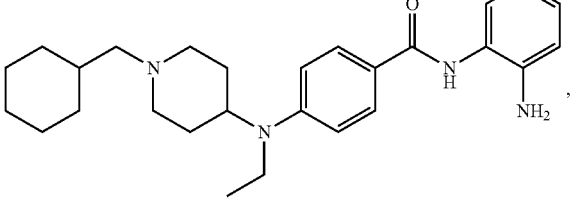
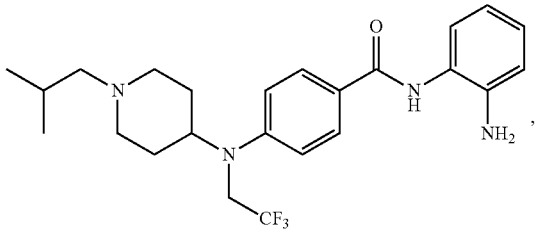
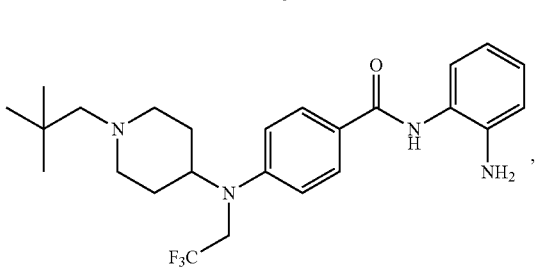

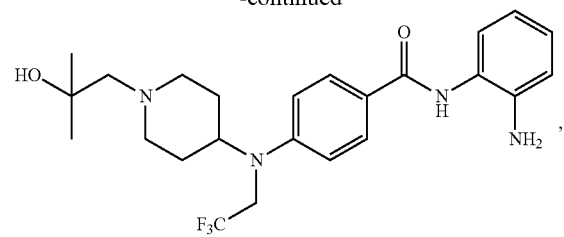
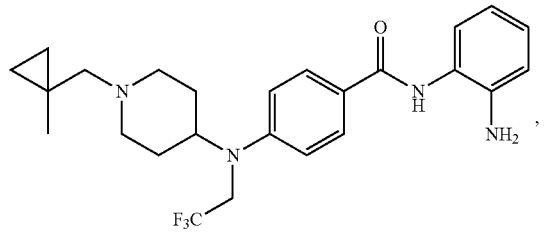
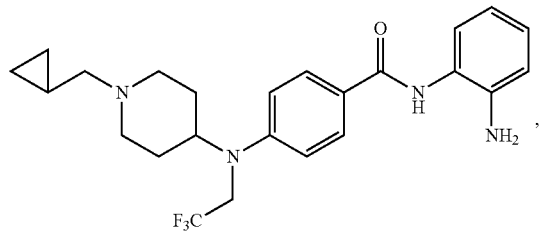
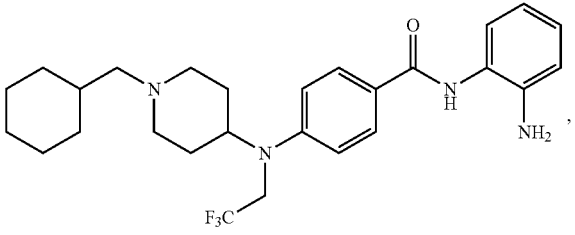
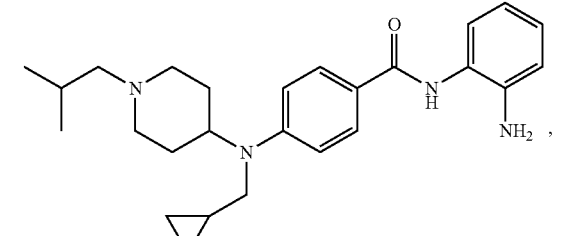
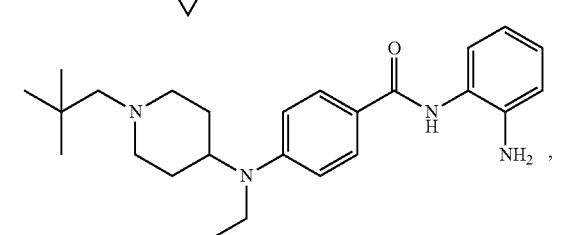
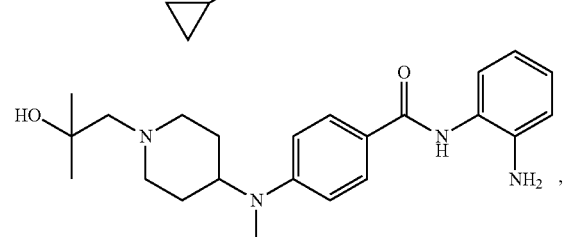
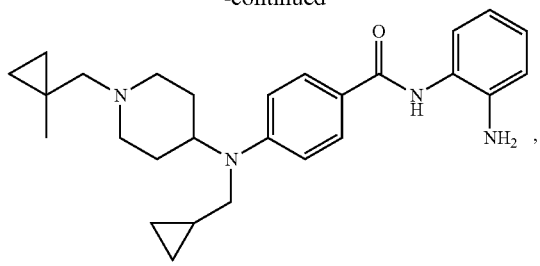
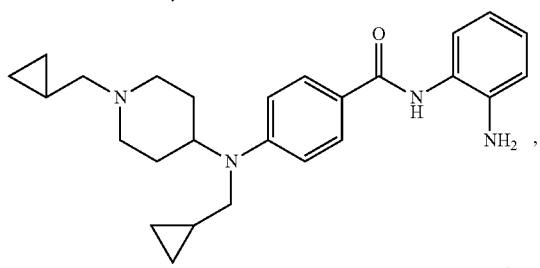
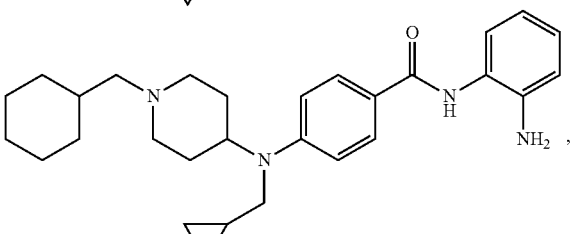
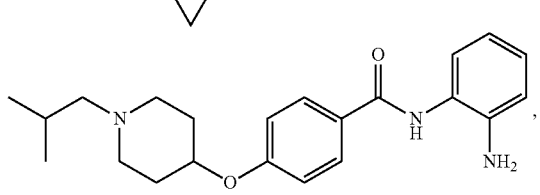
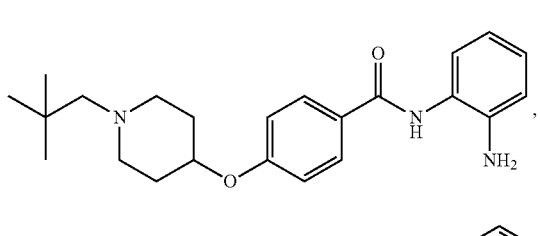
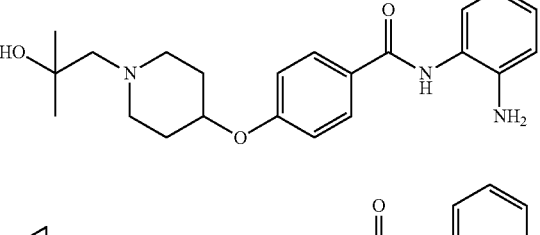
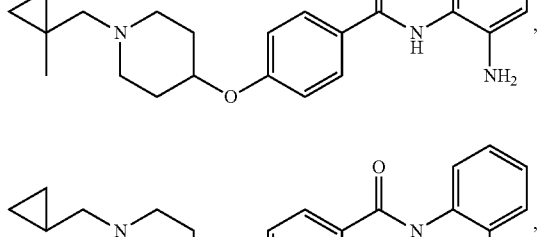

-continued
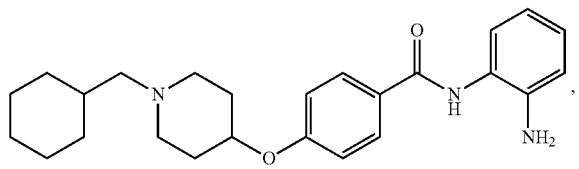,
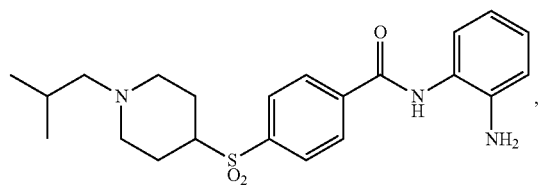,
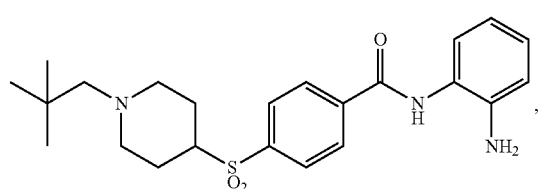,
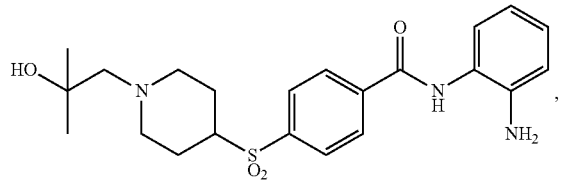,
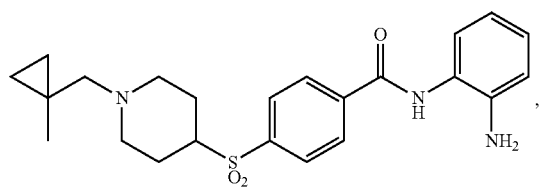,
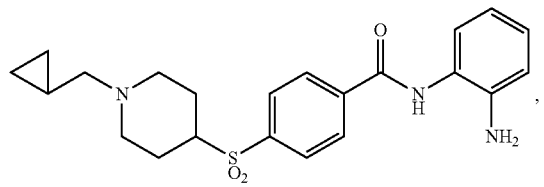,
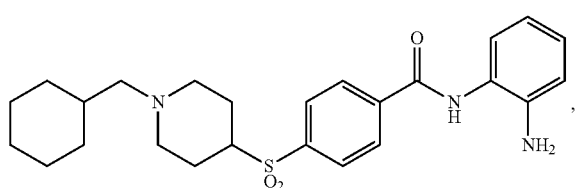,
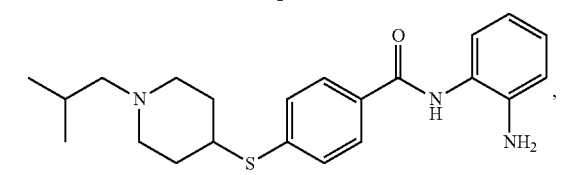,
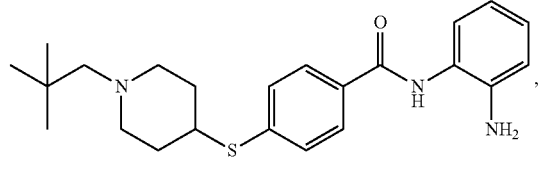,
-continued
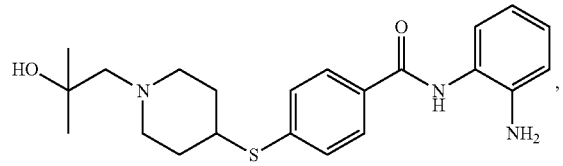,
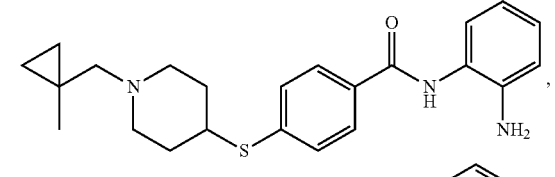,
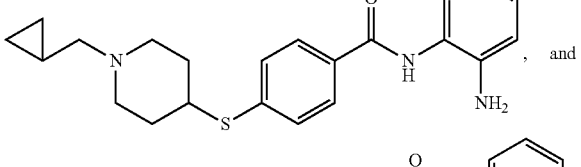, and
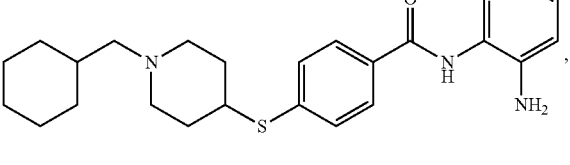,
or a pharmaceutically acceptable salt thereof.
16. The compound of claim 1 selected from the group consisting of
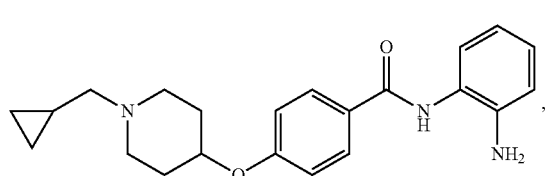,
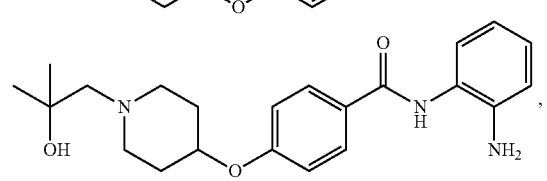,
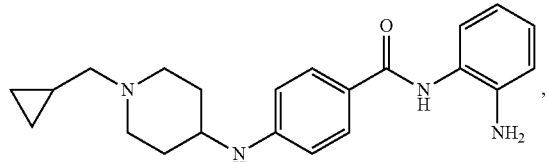,
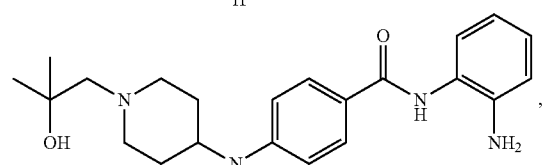,
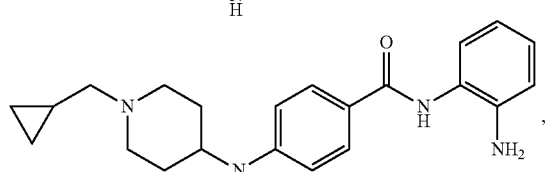,

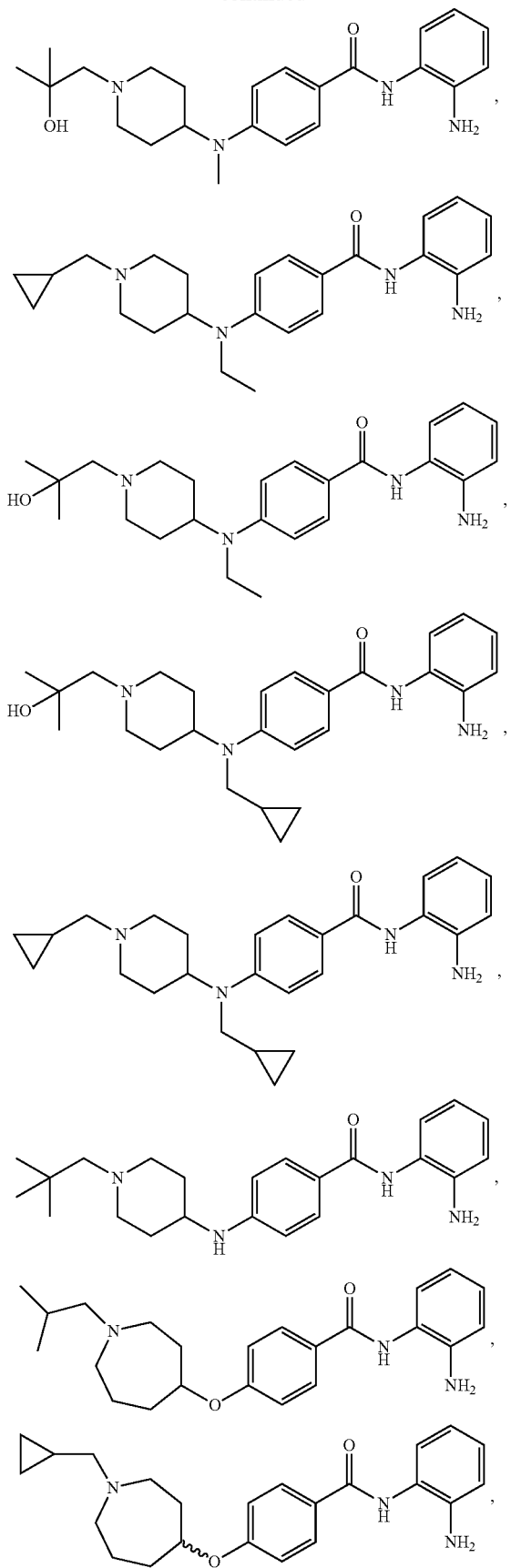

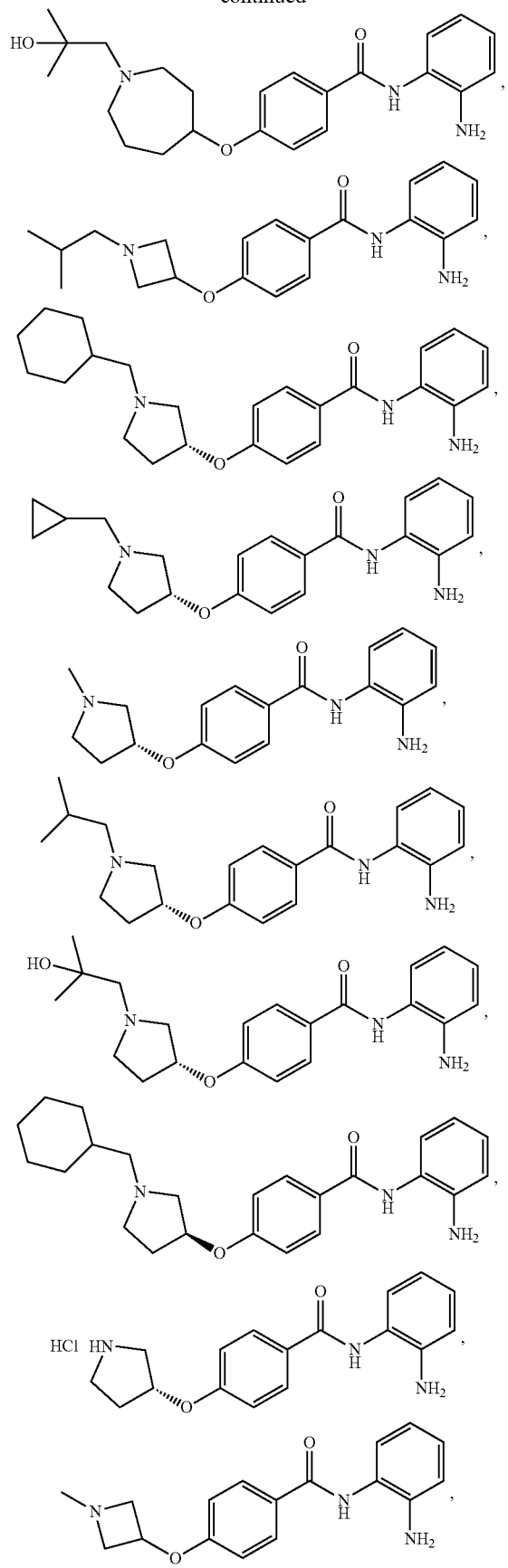
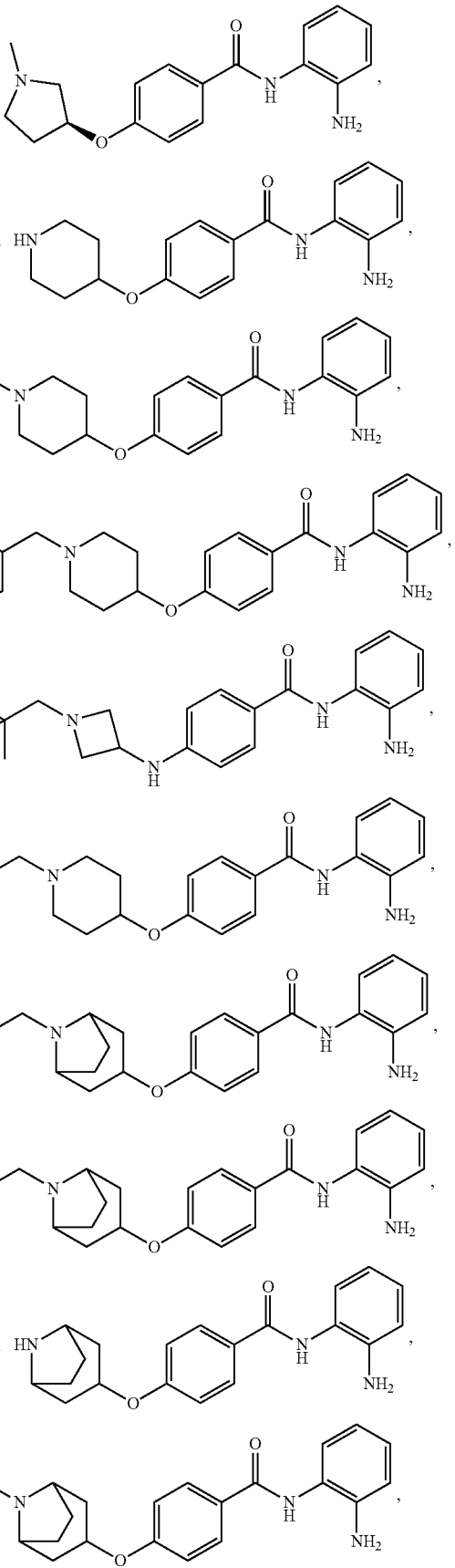

199
-continued
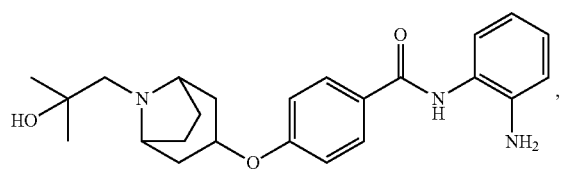,
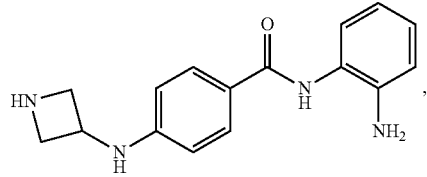,
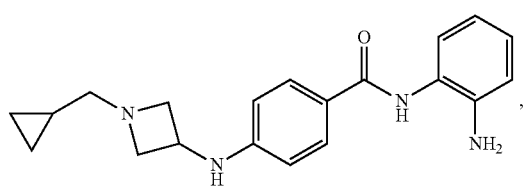,
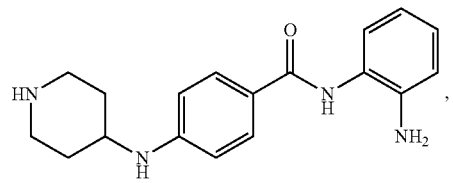,
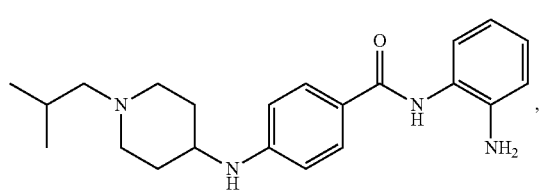,
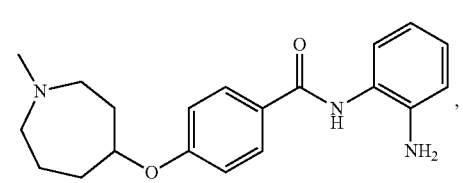,
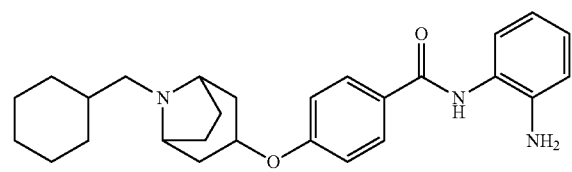,
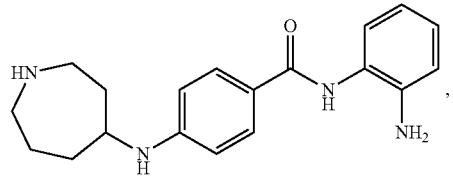,
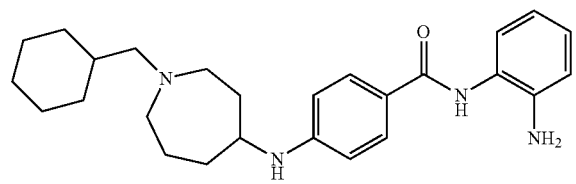,
200
-continued
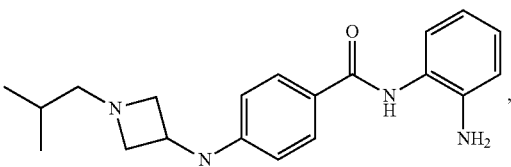,
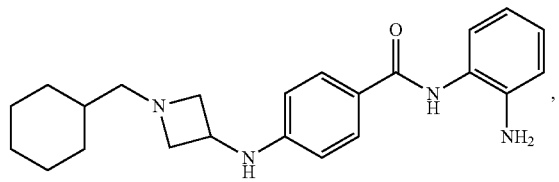,
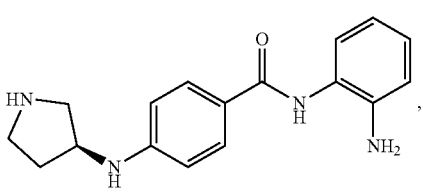,
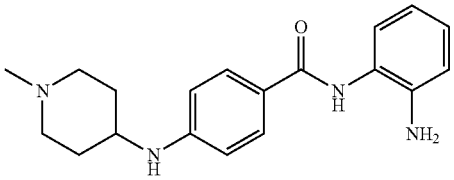,
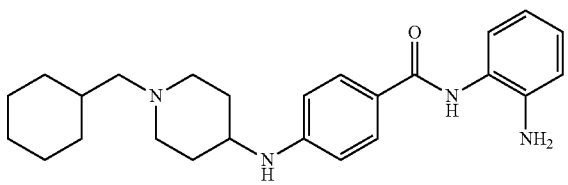,
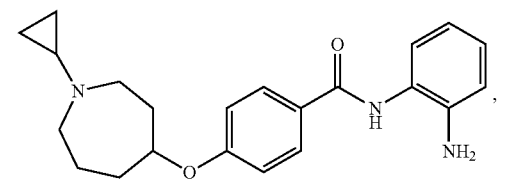,
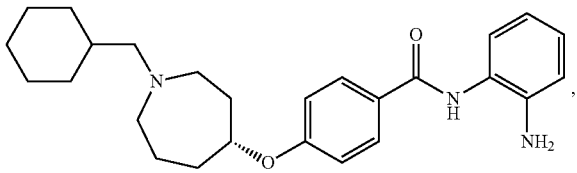,
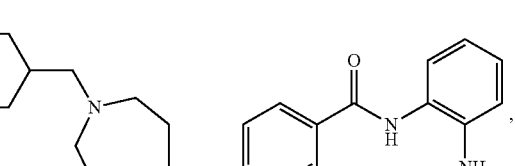,
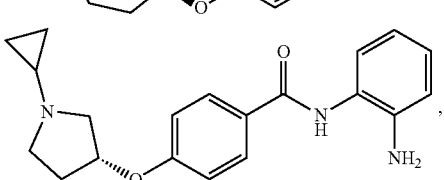,

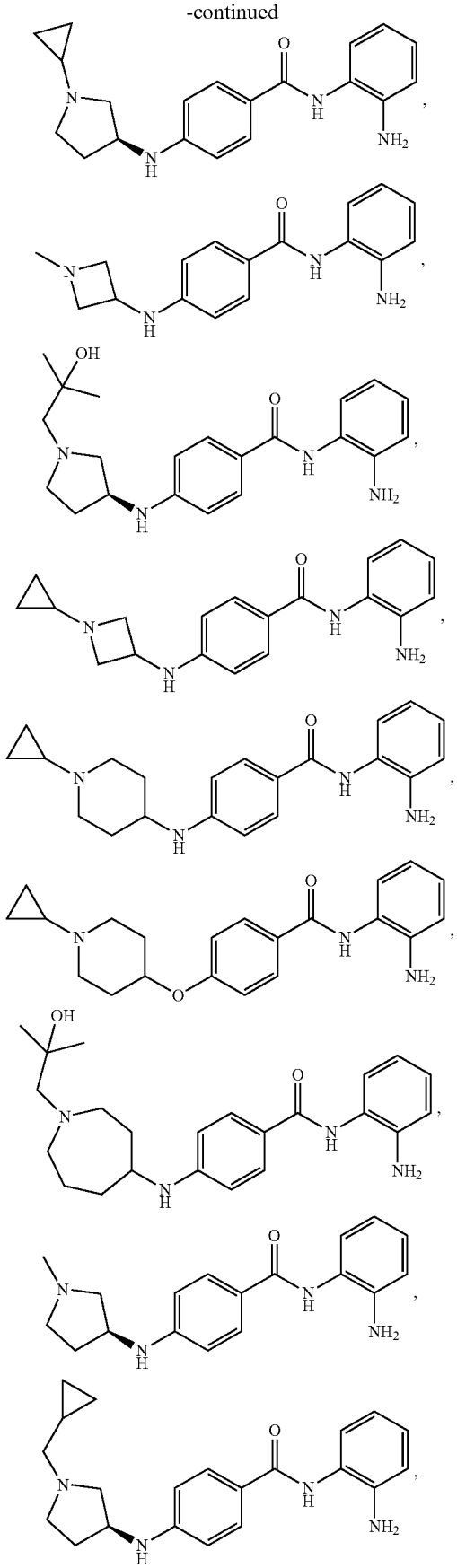

203
-continued
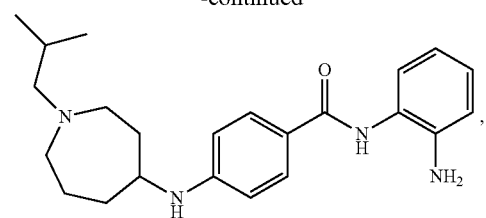
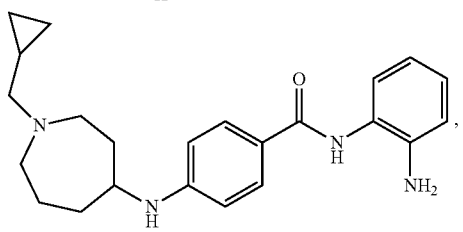
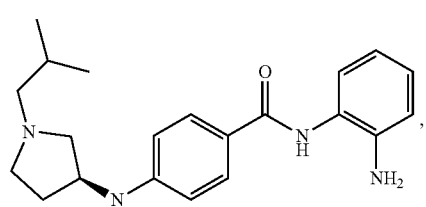
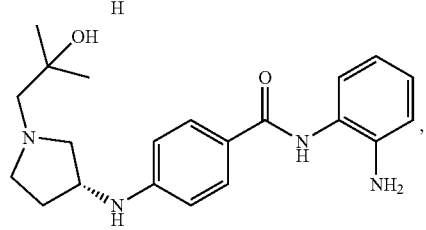
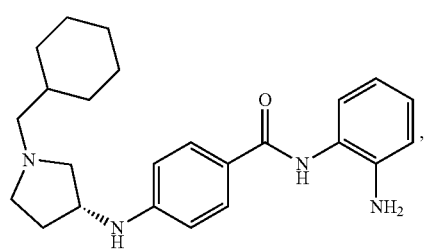
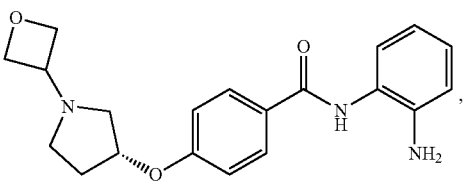
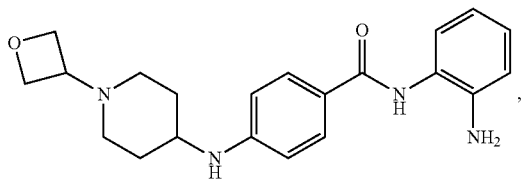
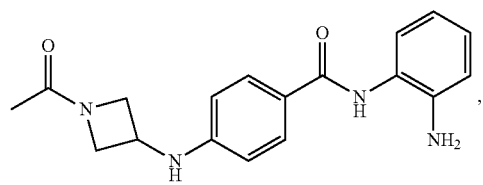
204
-continued
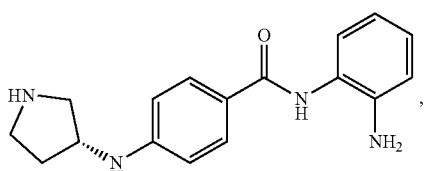
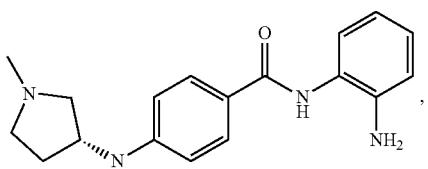
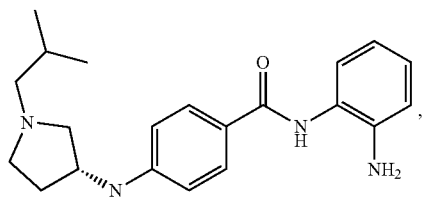
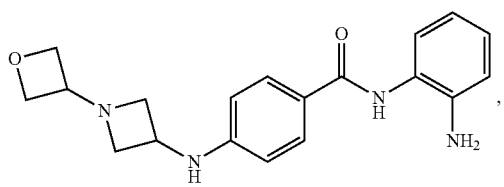
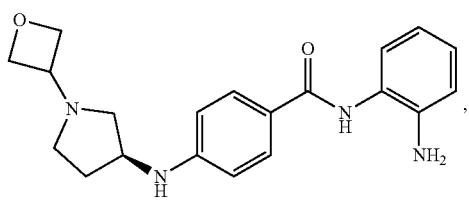
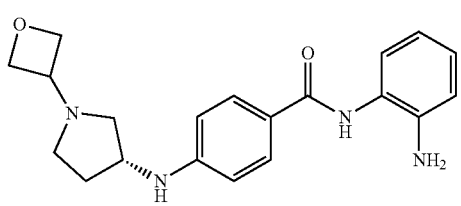
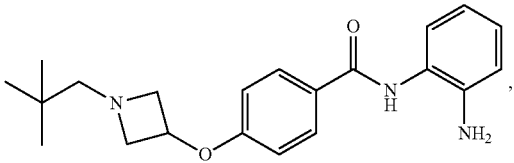
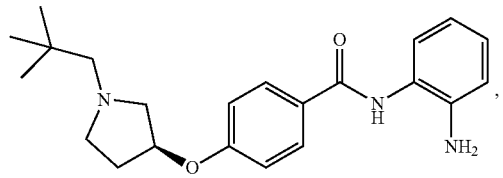
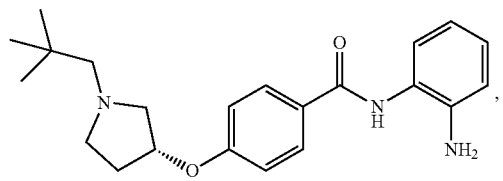

205
-continued
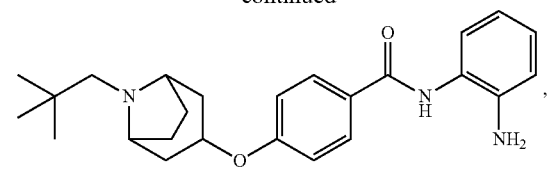
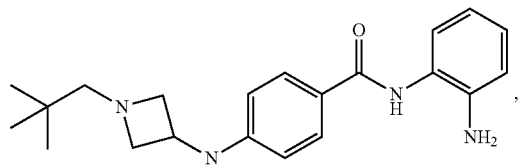
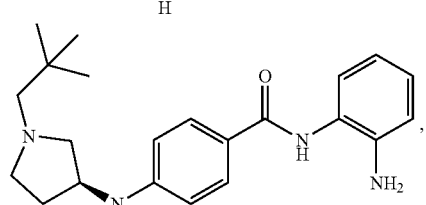
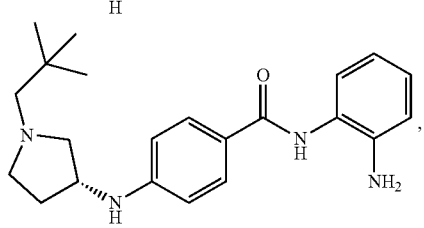
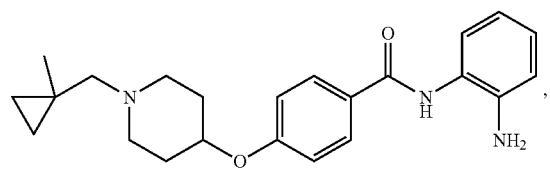
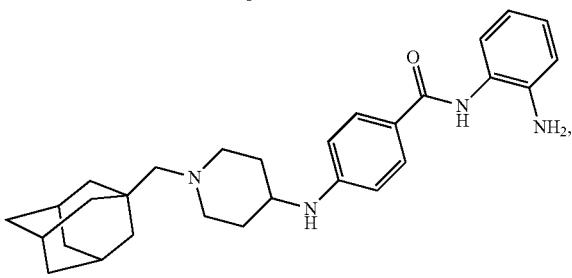
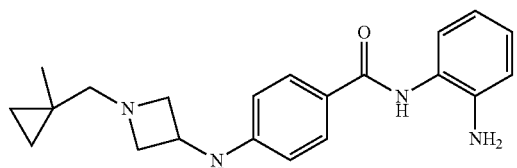
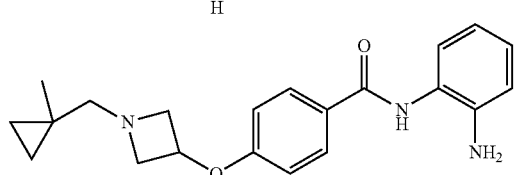
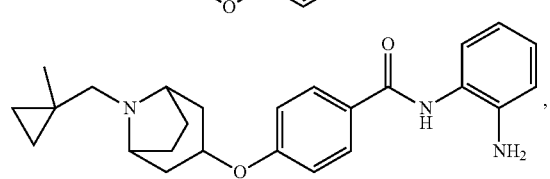
206
-continued
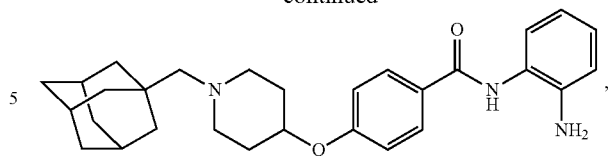
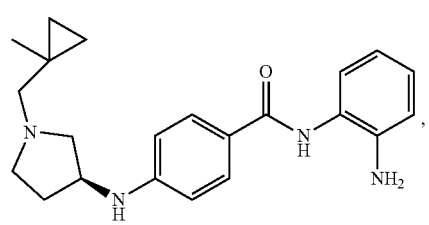
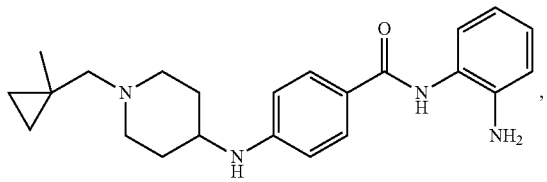
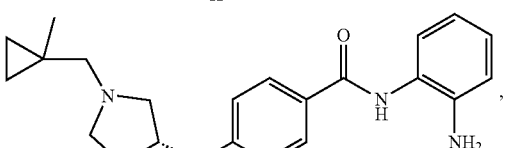
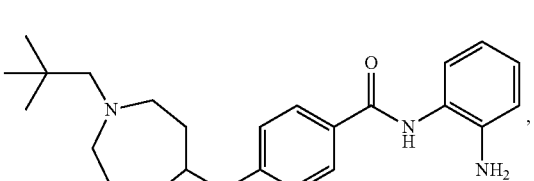
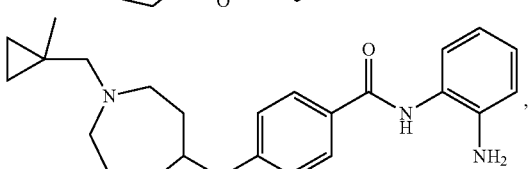
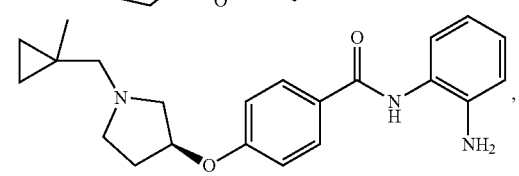
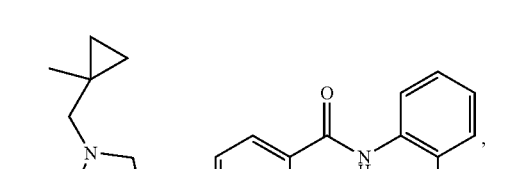
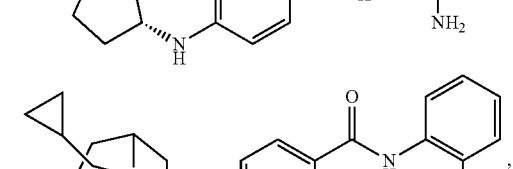
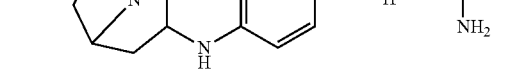

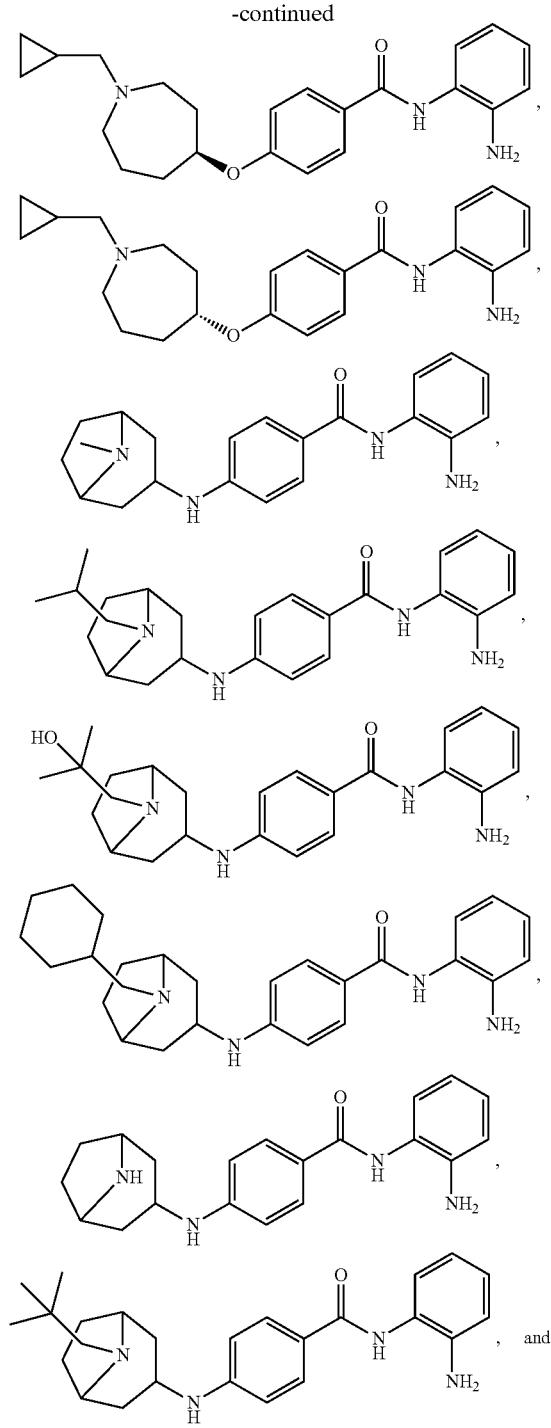
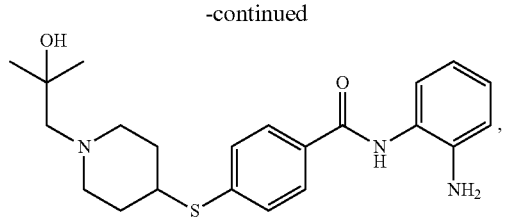
or a pharmaceutically acceptable salt thereof.
17. A pharmaceutical composition comprising the compound of claim 1, or pharmaceutically acceptable salt thereof, and a pharmaceutically acceptable carrier.
18. A compound selected from the group consisting of:
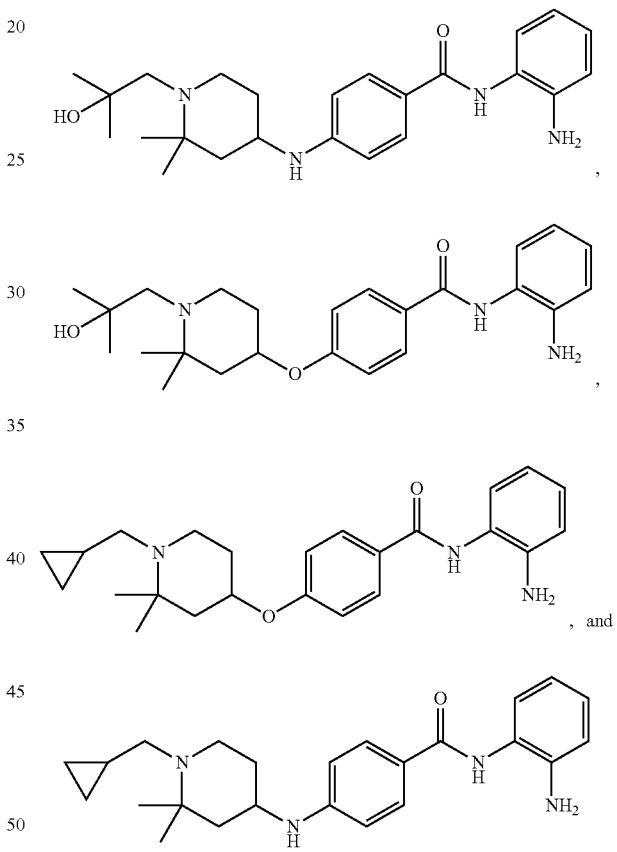
or a pharmaceutically acceptable salt thereof.
* * * * *